United States Patent
Du-Cuny et al.

(10) Patent No.: US 10,604,502 B2
(45) Date of Patent: Mar. 31, 2020

(54) SUBSTITUTED 5-CYANOINDOLE COMPOUNDS AND USES THEREOF

(71) Applicant: Novartis AG, Basel (CH)

(72) Inventors: Lei Du-Cuny, Kelkheim (DE); Qitao Xiao, Shanghai (CN); Guoliang Xun, Shanghai (CN); Qiangang Zheng, Shanghai (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/012,468

(22) Filed: Jun. 19, 2018

(65) Prior Publication Data

US 2019/0023684 A1  Jan. 24, 2019

(30) Foreign Application Priority Data

Jul. 19, 2017  (WO) ................ PCT/CN2017/089020

(51) Int. Cl.
| | |
|---|---|
| *C07D 401/04* | (2006.01) |
| *A61P 35/00* | (2006.01) |
| *A61P 35/02* | (2006.01) |
| *C07D 209/14* | (2006.01) |
| *C07D 409/14* | (2006.01) |
| *C07D 401/14* | (2006.01) |
| *C07D 405/14* | (2006.01) |
| *C07D 471/04* | (2006.01) |
| *C07D 498/04* | (2006.01) |
| *A61K 31/4439* | (2006.01) |
| *A61K 31/404* | (2006.01) |
| *A61K 31/4709* | (2006.01) |
| *A61K 31/437* | (2006.01) |
| *A61K 31/4375* | (2006.01) |
| *A61K 31/5383* | (2006.01) |
| *C07D 403/04* | (2006.01) |

(52) U.S. Cl.
CPC .......... *C07D 401/04* (2013.01); *A61K 31/404* (2013.01); *A61K 31/437* (2013.01); *A61K 31/4375* (2013.01); *A61K 31/4439* (2013.01); *A61K 31/4709* (2013.01); *A61K 31/5383* (2013.01); *A61P 35/00* (2018.01); *A61P 35/02* (2018.01); *C07D 209/14* (2013.01); *C07D 401/14* (2013.01); *C07D 403/04* (2013.01); *C07D 405/14* (2013.01); *C07D 409/14* (2013.01); *C07D 471/04* (2013.01); *C07D 498/04* (2013.01)

(58) Field of Classification Search
CPC .. C07D 401/04; C07D 209/14; C07D 401/14; C07D 403/04; C07D 405/14; C07D 409/14; C07D 471/04; C07D 498/04; A61P 35/02; A61P 35/00; A61K 31/404; A61K 31/437; A61K 31/4375; A61K 31/4439; A61K 31/4709; A61K 31/5383

USPC .................................................... 514/210.21
See application file for complete search history.

(56) References Cited

U.S. PATENT DOCUMENTS 5,621,002 A  4/1997  Bosslet

FOREIGN PATENT DOCUMENTS

| WO | WO 2004/078163 | 9/2004 |
| WO | WO 2015/134973 | 9/2015 |
| WO | WO 2017/149463 | 9/2017 |

OTHER PUBLICATIONS

Bai et al., "Inhibition enhancer of zeste homologue 2 promotes senescence and apoptosis induced by doxorubicin in p53 mutant gastric cancer cells" *Cell Prolif.* 47(3):211-8, 2014.
Chen et al., "Cyclin-dependent kinases regulate epigenetic gene silencing through phosphorylation of EZH2" *Nature Cell Biology* 12(11):1108-14, 2010.
Humphrey et al., "Stable Histone Deacetylase Complexes Distinguished by the Presence of SANT Domain Proteins CoREST/kiaa0071 and Mta-L1" *J. Biol. Chem.* 276:6817-6824, 2001.
Knutson et al., "Synergistic Anti-Tumor Activity of EZH2 Inhibitors and Glucocorticoid Receptor Agonists in Models of Germinal Center Non-Hodgkin Lymphomas" *PLoS One*, DOI:10.1371/journal.pone.0111840, 2014.
Mould et al., "Reversible Inhibitors of LSD1 as Therapeutic Agents in Acute Myeloid Leukemia: Clinical Significance and Progress to Date," *Med. Res. Rev.* 35(3):586-618, 2015.
Musch et al., "Nucleoside Drugs Induce Cellular Differentiation by Caspase-Dependent Degradation of Stem Cell Factors" *PLoS One* (5):e10726, 2010.
Shi et al., "Coordinated histone modifications mediated by a CtBP co-repressor complex" *Nature* 422:735-738, 2003.
Stazi et al., "LSD1 inhibitors: a patent review (2010-2015)" *Expert Opinion on Therapeutic Patents* 26(5):565-580, 2016.

(Continued)

*Primary Examiner* — Kristin A Vajda
(74) *Attorney, Agent, or Firm* — Daniel E. Raymond; Genomics Institute of the Novartis Research Foundation

(57) ABSTRACT

A compound of Formula (I), or a pharmaceutically acceptable salt thereof, is provided that has been shown to be useful for the treatment of lysine (K)-specific demethylase 1A (LSD1)-mediated diseases or disorders:

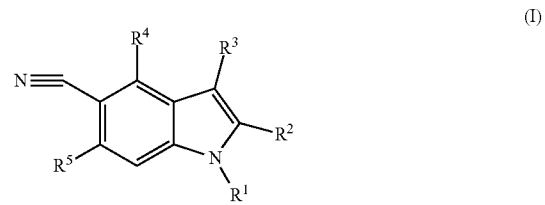

(I)

wherein $R^1$, $R^2$, $R^3$, $R^4$, and $R^5$ are as defined herein.

18 Claims, No Drawings

(56) References Cited

OTHER PUBLICATIONS

Wu et al., "Polycomb protein EZH2 regulates cancer cell fate decision in response to DNA damage" *Cell Death Differ.* 18(11):1771-9, 2011.
Yamaguchi et al., "Histone deacetylase inhibitor (SAHA) and repression of EZH2 synergistically inhibit proliferation of gallbladder carcinoma" *Cancer Sci.* 101(2):355-62, 2010.
Zeng et al., "Phosphorylation of EZH2 by CDK1 and CDK2" *Cell Cycle* 10(4):579-83, 2011.
Zheng et al., "A Systematic Review of Histone Lysine-Specific Demethylase 1 and Its Inhibitors" *Med. Res. Rev.* 35(5):1032-1071, 2015.

SUBSTITUTED 5-CYANOINDOLE COMPOUNDS AND USES THEREOF

CROSS-REFERENCE TO RELATED APPLICATIONS

This application claims the benefit of priority to International Application No. PCT/CN2017/089020, filed 19 Jun. 2017, the contents of which is incorporated herein by reference.

FIELD OF THE INVENTION

The present invention relates to cyano-substituted indole compounds, compositions comprising such compounds, and their use for the treatment of lysine (K)-specific demethylase 1A (LSD1)-mediated diseases or disorders.

BACKGROUND

Post-translational modifications on the lysine chains of histones are a major way by which chromatin structure is modified to regulate gene expression. Methylation and acetylation are examples of such chemical modifications. A number of enzymes that effect histone modifications have been discovered and, due to their effects on gene expression and cellular function, they have been targeted for therapeutic intervention. LSD1 is a histone demethylase that uses flavin adenine dinucleotide (FAD) as cofactor. Methylated histones H3K4 and H3K9 have been shown to be targets of LSD1. Other non-histone substrates include p53, E2F1, DNMT1 and STAT3.

LSD1 consists of three major domains: the N-terminal Swi3-Rsc8-Moira (SWIRM) domain which functions in nucleosome targeting, the tower domain which participates in protein-protein interactions, and the C-terminal catalytic domain that has similarity to the monoamine oxidases. LSD1 also shares homology with another lysine demethylase, LSD2, but it is very distinct from the Jumomji type histone demethylases. The enzymatic activity of LSD1 is dependent on the redox process of FAD and the protonated nitrogen in the methylated lysine is thought to limit its activity to mono- and di-methylated lysines in position 4 or 9 of histone H3 (H3K4 or H3K9).

LSD1 has been reported to be involved in a number of biological processes, including cell proliferation, epithelial-mesenchymal transition, stem cell biology and malignant transformation of cells. It has also been shown to be involved in cell differentiation. LSD1 has been implicated in a number of myeloproliferative and lymphoproliferative diseases, such as acute myeloid leukemia (AML) and acute lymphoblastic leukemia (ALL). It has also been shown to be linked to the aberrant function of the androgen receptor in prostate cancer as well as other cancers such as Small Cell Lung cancer. Reviews describing a variety of reversible and irreversible LSD1 inhibitors were published by Mould, Daniel P., et al., "Reversible Inhibitors of LSD1 as Therapeutic Agents in Acute Myeloid Leukemia: Clinical Significance and Progress to Date," Med. Res. Rev., 35, No. 3, 586-618, (2015); and Xheng, Yi-Choa, et. al., "A Systematic Review of Histone Lysine-Specific Demethylase 1 and Its Inhibitors" Med. Res. Rev., 35, No. 5, 1032-1071, (2015). Therefore, LSD1 has been recognized as a target for anti-cancer drug discovery.

As a drug discovery target, LSD1 has a fair degree of structural similarity to the Flavin-dependent Monoamine oxidases (MAOs). Both LSD1 and Monoamine oxidases utilize FAD as cofactor, e.g., as reported by G. W. Humphrey et. al., "Stable Histone Deacetylase Complexes Distinguished by the Presence of SANT Domain Proteins CoREST/kiaa0071 and Mta-L1" J. Biol. Chem, 276, 6817-6824 (2001) and Shi, et. al., "Coordinated histone modifications mediated by a CtBP co-repressor complex" Nature, 422, 735-738(2003). Thus a number of MAO inhibitors have been shown to inhibit LSD1 through irreversible interaction of FAD. Attempts have also been made to discover reversible inhibitors of LSD1.

In summary, LSD1 provides a pharmacological target for cancer and other disorders that associate with LSD1's activity. In particular, the need exists for novel small molecules that inhibit the activity of LSD1, which includes both irreversible and reversible inhibitors, for treating disorders associated with excessive LSD1 activity such as those described herein.

SUMMARY

The present invention provides a compound of Formula (I):

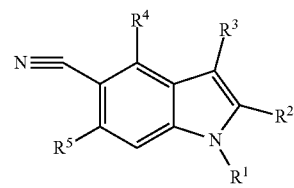

wherein $R^1$, $R^2$, $R^3$, $R^4$, and $R^5$ are as defined herein, including stereoisomers, tautomers, pharmaceutically acceptable salts, polymorphs, or solvates thereof, which are useful for the treatment of LSD1-mediated diseases or disorders.

The present invention also provides processes and intermediates for making the compounds of the present invention.

The present invention also provides pharmaceutical compositions comprising at least one of the compounds of the present invention and at least one pharmaceutically acceptable carrier, diluent or excipient. The pharmaceutical composition may further comprise at least one additional therapeutic agent. Of particular interest are additional therapeutic agents selected from: other anti-cancer agents, immunomodulators, anti-allergic agents, anti-nausea agents (or anti-emetics), pain relievers, cytoprotective agents, and combinations thereof.

The compounds of the present invention may be used in the treatment of diseases or disorders mediated by LSD1.

The compounds of the present invention may be used in therapy.

The compounds of the present invention may be used for the manufacture of a medicament for the treatment of diseases or disorders mediated by LSD1.

The present invention provides a method for the treatment of diseases or disorders mediated by LSD1, comprising administering to a patient in need thereof a therapeutically effective amount of a first therapeutic agent optionally with a second therapeutic agent, wherein the first therapeutic agent is a compound of the present invention and the second therapeutic agent is one other type of therapeutic agent.

Examples of diseases or disorders mediated by LSD1 include, but are not limited to, B cell lymphoma, acute myeloid leukemia, gastric cancer, hepatocellular carcinoma, prostate cancer, breast carcinoma, neuroblastoma, glioblastoma, nasopharyngeal carcinoma, colon cancer, gallbladder cancer, esophageal cancer, head and neck cancer, lung cancer, ovarian cancer, pancreatic cancer, endometrial carcinoma and soft tissue sarcomas such as rhabdomyosarcoma (RMS), chondrosarcoma, osteosarcoma, Ewing's sarcoma, liver fibrosis, and sickle cell disease.

The present invention provides a method for the treatment of diseases or disorders mediated by LSD1, comprising administering to a patient in need thereof a therapeutically effective amount of a first therapeutic agent optionally with a second therapeutic agent, wherein the first therapeutic agent is an LSD1 inhibitor and the second therapeutic agent is one other type of therapeutic agent; wherein the diseases or disorders are selected from diffused large B cell lymphoma (DLBCL), follicular lymphoma, other lymphomas, leukemia, multiple myeloma, gastric cancer, malignant rhabdoid tumor, prostate cancer and hepatocellular carcinoma.

The compounds of the present invention can be used alone, in combination with other compounds of the present invention, or in combination with one or more, preferably one to two other agent(s), simultaneously or sequentially.

Other features and advantages of the present invention will be apparent from the following detailed description and claims.

DETAILED DESCRIPTION

I. Compounds

In a first aspect, the present invention provides, inter alia, a compound of Formula (I):

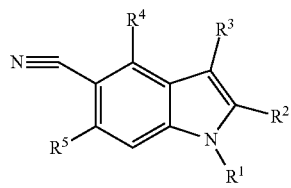

(I)

or a pharmaceutically acceptable salt thereof, wherein:
R$^1$ is selected from:
  C$_1$-C$_6$ alkyl substituted with one to two R$^a$;
  C$_3$-C$_6$ cycloalkyl substituted with at least one group selected from —C$_1$-C$_4$ alkyl, C$_1$-C$_4$ haloalkyl, halo, OH, CN, —C(O)R, —C(O)OR, —CONR$_2$, —NR—C(O)R, —NH$_2$, —NR'$_2$, —NR—C(O)OR', —NR—C(O)NR$_2$, —OC(O)NR$_2$, —NRSO$_2$R', —SO$_2$R', and —SO$_2$NR$_2$, and optionally further substituted with one to two R$^d$;
  7-11 membered spiro cyclyl optionally substituted with one or two R$^b$;
  7-11 membered spiro heterocyclyl comprising 1-2 heteroatoms selected from nitrogen, oxygen and sulfur, wherein the 7-11 membered spiroheterocyclyl is optionally substituted with one or two R$^b$;
  phenyl substituted with at least one group selected from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$, wherein the phenyl is further optionally substituted with one or two R$^b$;
  bicyclic heteroaryl comprising one to three heteroatoms selected from nitrogen, oxygen and sulfur, wherein the bicyclic heteroaryl is optionally substituted with one or two R$^b$;
  2-pyridone optionally substituted with one or two R$^b$;
  6-membered heteroaryl comprising one to two nitrogen atoms, wherein the 6-membered heteroaryl is substituted with at least one group selected from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$, and optionally further substituted with up to three R$^b$;

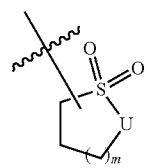

optionally substituted with one or two R$^d$; and

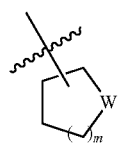

optionally substituted with one or two R$^d$;
R$^2$ is selected from: H, halogen, C$_1$-C$_4$ alkyl, C$_1$-C$_4$ haloalkyl, —C(O)OR, and —C(O)NR$_2$;
R$^3$ is selected from:

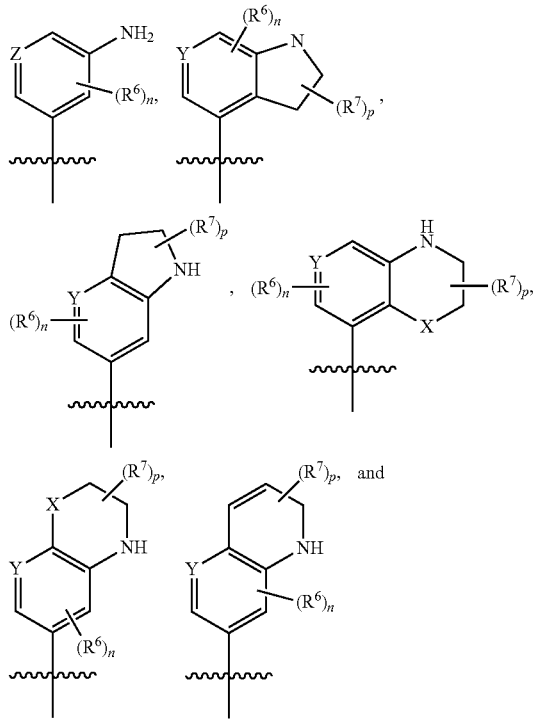

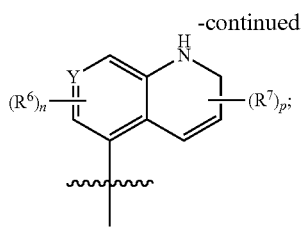

$R^4$ is selected from: H, halogen and $C_1$-$C_4$ alkyl;
$R^5$ is selected from: H, halogen, $C_1$-$C_4$ alkyl, $C_1$-$C_4$ haloalkyl, and $C_3$-$C_6$ cycloalkyl;
$R^6$ is independently at each occurrence selected from: halogen, CN, OH, $C_1$-$C_4$ alkyl, $C_1$-$C_4$ alkoxyl, and $C_1$-$C_4$ haloalkyl;
$R^7$ is independently at each occurrence selected from: oxo, halogen, CN, OH, $C_1$-$C_4$ alkyl, $C_1$-$C_4$ alkoxyl, and $C_1$-$C_4$ haloalkyl;
U is selected from: $CR_2$, NH, N—($C_{1-4}$ alkyl), N—C(O)—($C_{1-4}$ alkyl), N—C(O)—$NR_2$, and N—C(O)—O—($C_{1-4}$ alkyl);
W is selected from: O, NH, N—($C_{1-4}$ alkyl), N—$SO_2$—($C_{1-4}$ alkyl), N—C(O)—($C_{1-4}$ alkyl), N—C(O)—$NR_2$, N—$SO_2$—O—($C_{1-4}$ alkyl), N—$SO_2$—$NR_2$, and N—C(O)—O—($C_{1-4}$ alkyl);
X is independently at each occurrence selected from: $CR^eR^f$, $NR^f$ and O;
Y is independently at each occurrence selected from: $CR^e$ and N;
Z is selected from: CH, $CR^h$ and N;
R is independently at each occurrence selected from H and $C_1$-$C_4$ alkyl;
R' is independently at each occurrence $C_1$-$C_4$ alkyl;
$R^a$ is independently selected from: halogen, —OH, CN, —$SO_2R'$, —$SO_2NR_2$, —$NRSO_2R'$, —NR—$SO_2OR'$, —NR—$SO_2NR_2$, —$NR_2$, —NRC(O)R', —NR—C(O)$NR_2$, —NR—C(O)OR', and —$C_1$-$C_4$ alkoxy, wherein the —$C_1$-$C_4$ alkoxy is substituted with at least one group selected from —OH, halogen, and CN;
$R^b$ is independently selected from: halogen, $C_1$-$C_4$ haloalkoxy, OH, CN, —$CO_2R$, —C(O)$NR_2$, —CONRC(O)R', —CONR$SO_2R'$, —$NR_2$, —NRC(O)R, —NR—C(O)OR', —NR—C(O)$NR_2$, —$SO_2R'$, —$SO_2NR_2$, —$NRSO_2R'$, —NR—$SO_2OR'$, —NR—$SO_2NR_2$, $C_1$-$C_4$ alkyl substituted with zero to one $R^c$, and $C_1$-$C_4$ alkoxy substituted with zero to one $R^c$;
$R^c$ is independently selected from: OH, $C_1$-$C_4$ alkoxy, —$CO_2R$, —C(O)$NR_2$, —$NR_2$, and —NRC(O)R;
$R^d$ is independently selected from: OH, =O, —C(O)R, and —NH($C_1$-$C_4$ alkyl);
$R^e$ is independently at each occurrence selected from: H, halogen, CN, OH, $C_1$-$C_4$ alkyl, and $C_1$-$C_4$ haloalkyl;
$R^f$ is independently at each occurrence selected from: H, halogen, $C_1$-$C_4$ alkyl, and $C_1$-$C_4$ haloalkyl;
$R^h$ is independently at each occurrence selected from: halogen, CN, OH, $C_1$-$C_4$ alkyl, and $C_1$-$C_4$ haloalkyl;
m is independently selected from: 0, 1, and 2;
n, at each occurrence, is independently selected from: 0, 1, and 2; and
p, at each occurrence, is independently selected from: 0, 1, and 2;
provided that:
when $R^1$ is $C_1$-$C_6$ alkyl substituted with OH, $R^2$ is $C_1$-$C_4$ alkyl substituted with one or two halogen; and
when $R^1$ is $C_3$-$C_6$ cycloalkyl substituted with OH, $R^3$ is selected from:

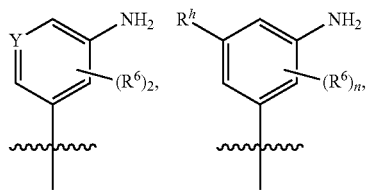

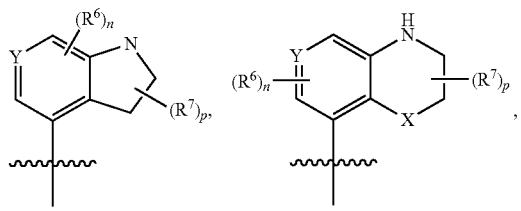

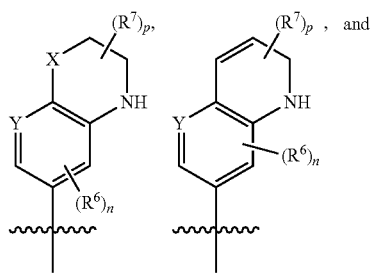

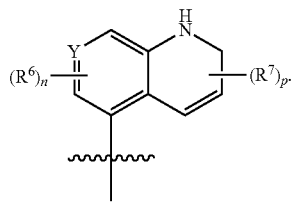

In a second aspect, the present invention provides a compound of Formula (I) or a pharmaceutically acceptable salt thereof, within the scope of the first aspect; wherein: $R^1$ is selected from cyclobutyl, cyclopentyl, and cyclohexyl, wherein each of the cyclobutyl, cyclopentyl, and cyclohexyl is independently substituted with one group selected from —OH, —C(O)OR, —$SO_2R'$, —$SO_2NR_2$, —$NRSO_2R'$, and —$CONR_2$.

In a third aspect, the present invention provides a compound of Formula (I) or a pharmaceutically acceptable salt thereof, within the scope of the first aspect or the second aspect; wherein $R^1$ is selected from cyclobutyl, cyclopentyl, and cyclohexyl, wherein each of cyclobutyl, cyclopentyl, and cyclohexyl is substituted with one group selected from —OH, —$SO_2CH_3$, —$SO_2NH_2$, —$NHSO_2CH_3$, —$COOCH_3$, and —$CONH_2$.

In a fourth aspect, the present invention provides a compound of Formula (I) or a pharmaceutically acceptable salt thereof, within the scope of the first aspect; wherein $R^1$ is 6-membered heteroaryl comprising one to two nitrogen atoms as ring members, substituted with at least one group selected from —NR—C(O)OR', —NR—C(O)$NR_2$, —NR—$SO_2R'$, —NR—$SO_2OR'$, —NR—$SO_2NR_2$, —C(O)OH, —$SO_2R'$, and —$SO_2NR_2$.

In a fifth aspect, the present invention provides a compound of Formula (I) or a pharmaceutically acceptable salt thereof, within the scope of the first aspect; wherein $R^1$ is phenyl substituted with at least one group selected from from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$.

In a sixth aspect, the present invention provides a compound of Formula (I) or a pharmaceutically acceptable salt thereof, within the scope of any of the above aspects; wherein $R^3$ is

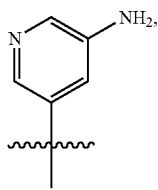 [SMILES: *c1cncc(N)c1]

further substituted with one or two $R^6$.

In a seventh aspect, the present invention provides a compound of Formula (I) or a pharmaceutically acceptable salt thereof, within the scope of the sixth aspect; wherein $R^6$ is halogen.

In an eighth aspect, the present invention provides a compound of Formula (I) or a pharmaceutically acceptable salt thereof, within the scope of the seventh aspect; wherein $R^6$ is chloro.

In a ninth aspect, the present invention provides a compound of Formula (I) or a pharmaceutically acceptable salt thereof, within the scope of any of the above aspects; wherein $R^4$ is H.

In a tenth aspect, the present invention provides a compound of Formula (I) or a pharmaceutically acceptable salt thereof, within the scope of any of the above aspects; wherein $R^5$ is —CH$_3$.

In an eleventh aspect, the present invention provides a compound of Formula (I) or a pharmaceutically acceptable salt thereof, within the scope of any of the above aspects; wherein the compound is selected from:

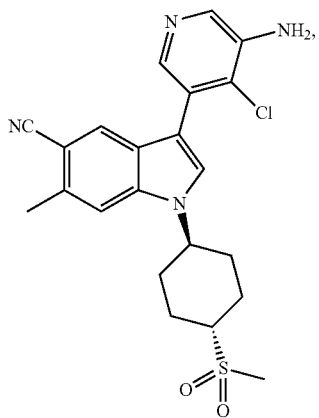

-continued

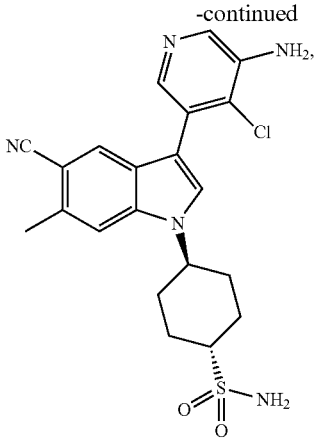

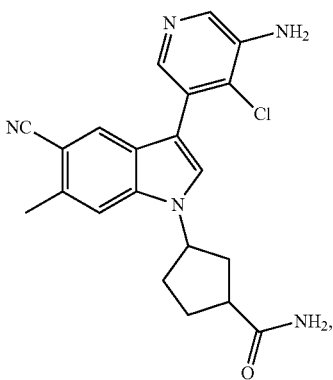

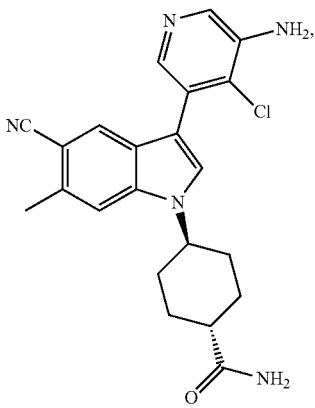

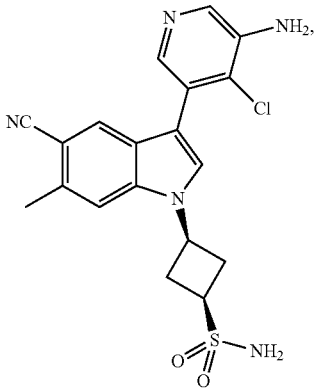

-continued
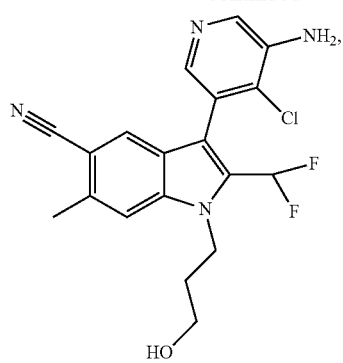
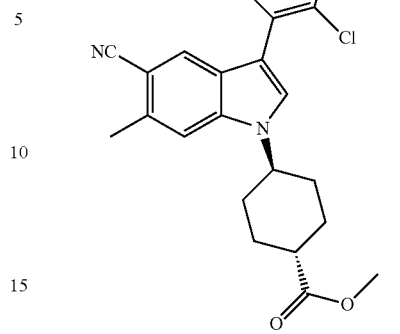
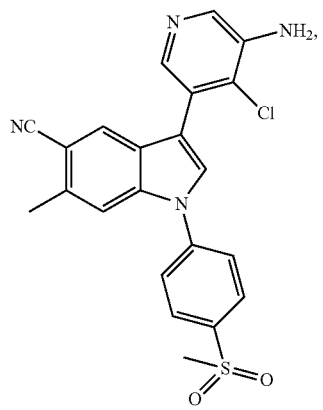
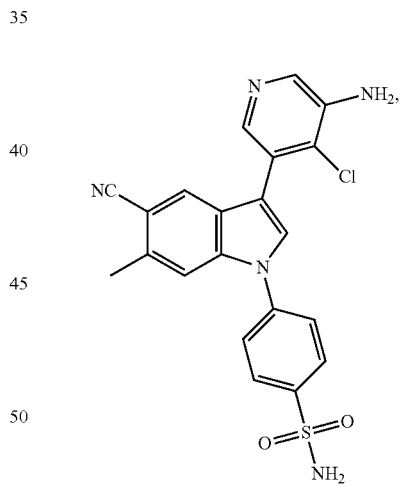
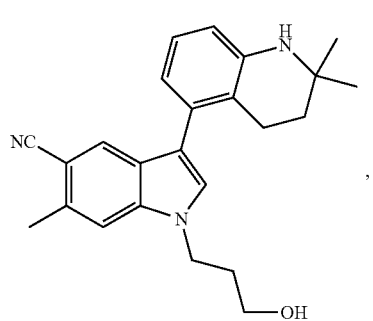
,

-continued
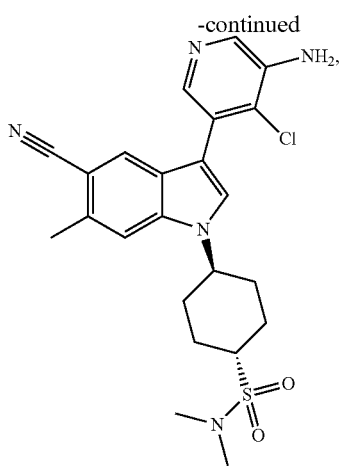
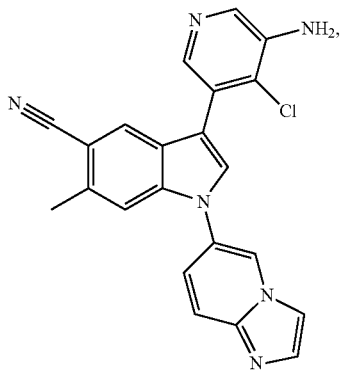
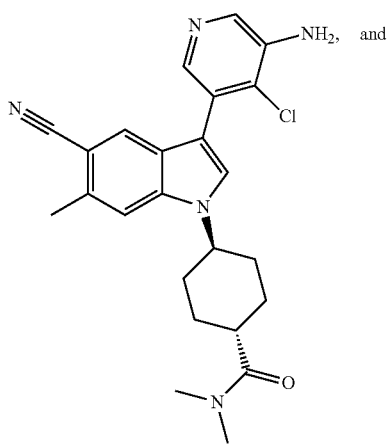, and
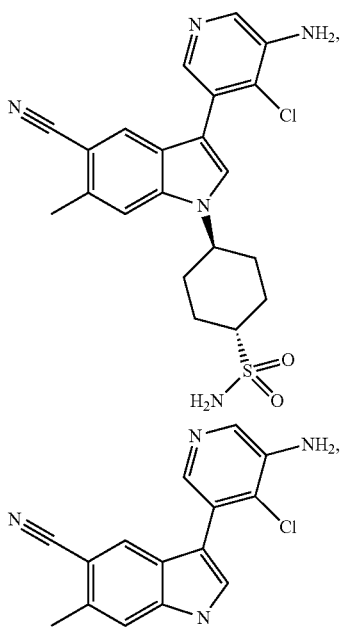
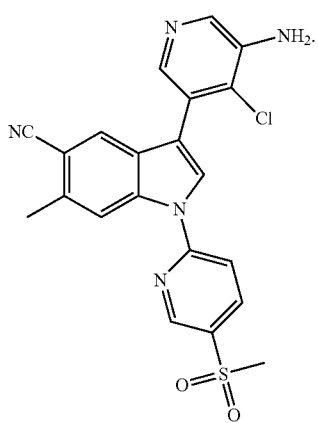
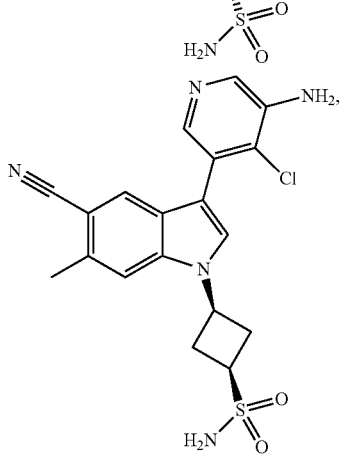
In a twelfth aspect, the present invention provides a compound of Formula (I) or a pharmaceutically acceptable salt thereof, within the scope of any of the above aspects; wherein the compound is selected from:

-continued
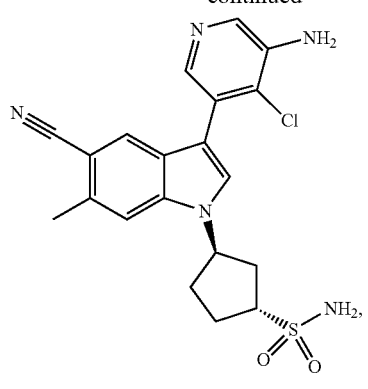
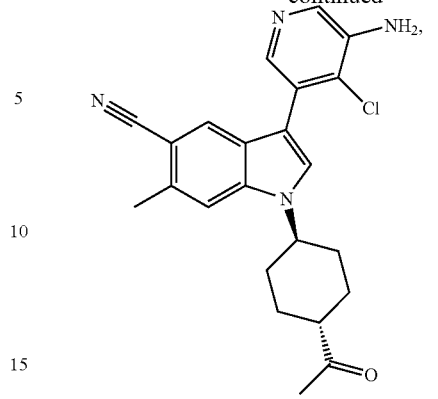
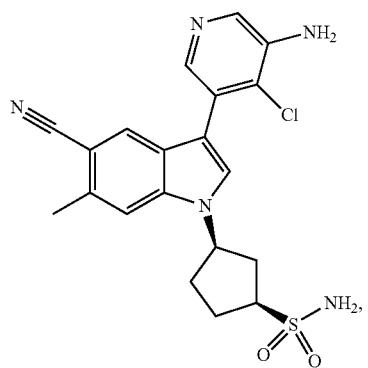 [SMILES: Cc1cc2c(cc1C#N)c(-c1cncc(N)c1Cl)cn2[C@@H]1CC[C@@H](S(N)(=O)=O)C1]
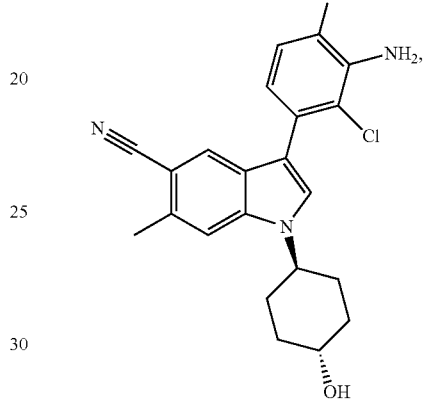
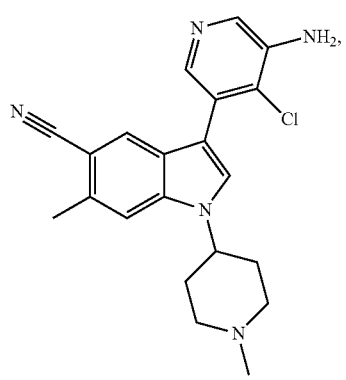
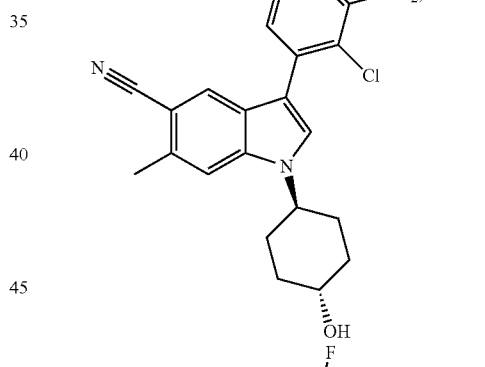
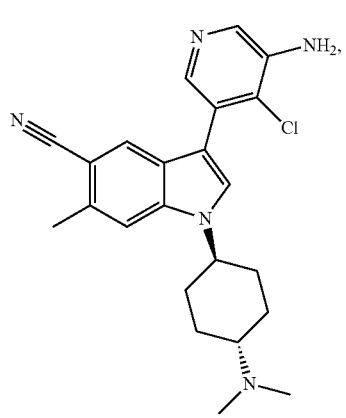 [SMILES: CN[C@H]1CC[C@@H](n2cc(-c3cncc(N)c3Cl)c3cc(C#N)c(C)cc32)CC1]
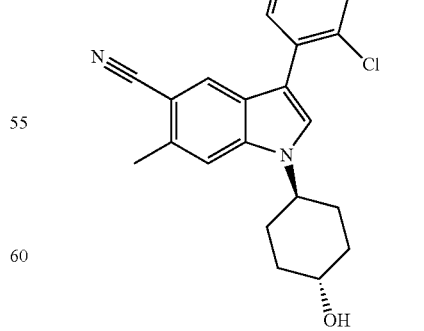
In a thirteenth aspect, the present invention provides compound, or a pharmaceutically acceptable salt, wherein the compound is selected from:

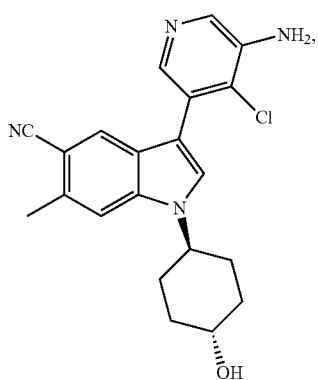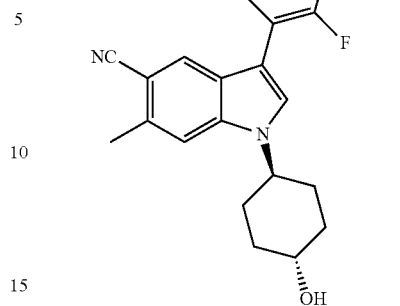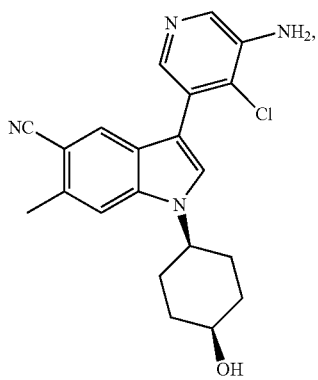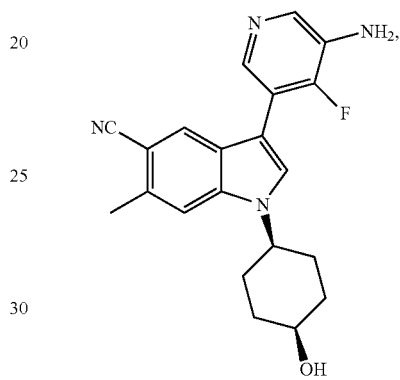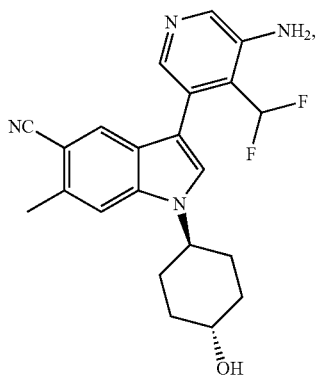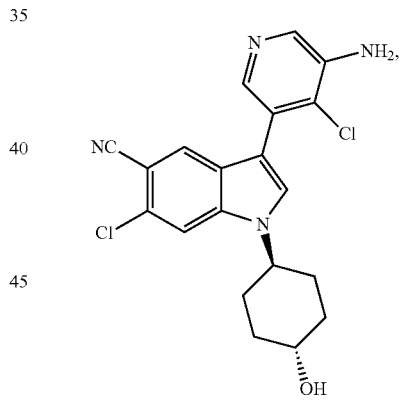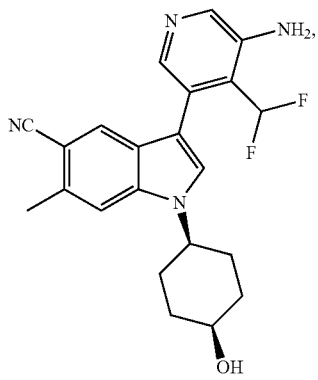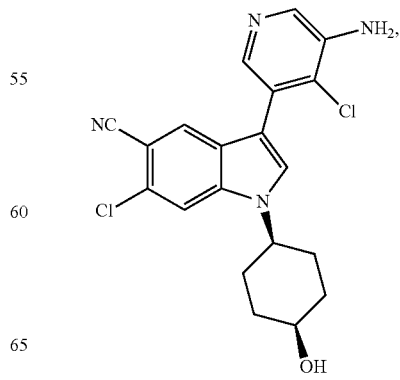

-continued
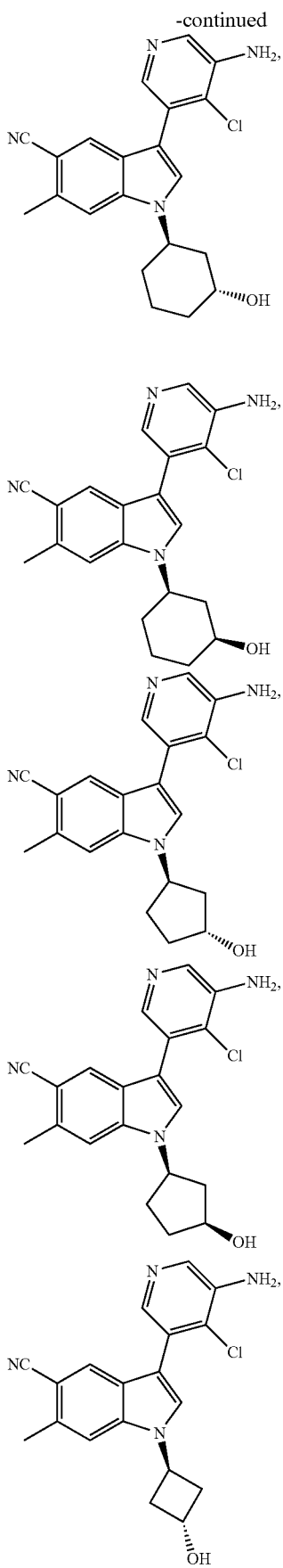
-continued
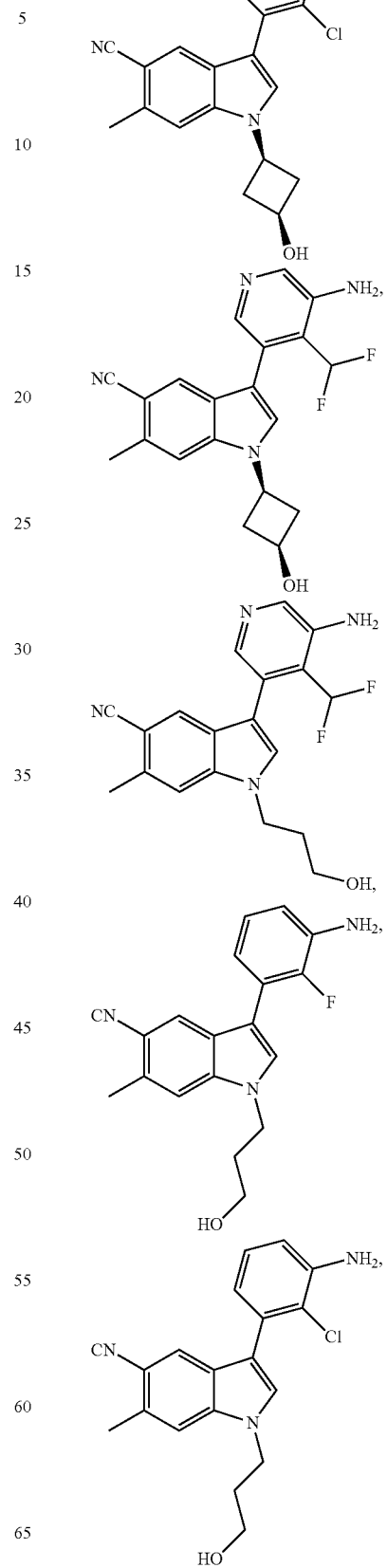

-continued
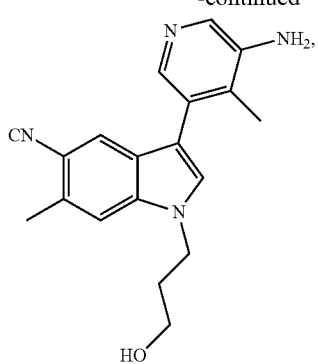
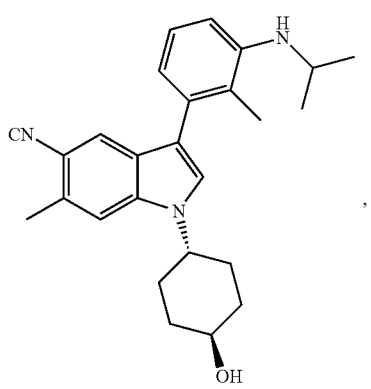
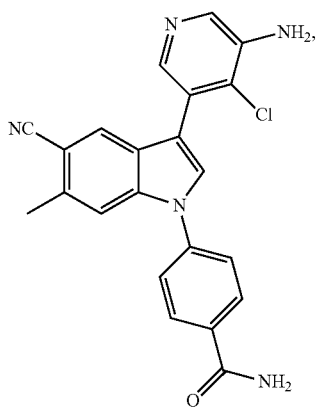
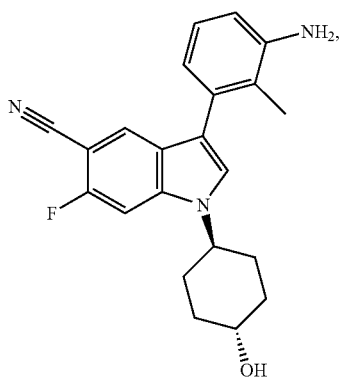
-continued
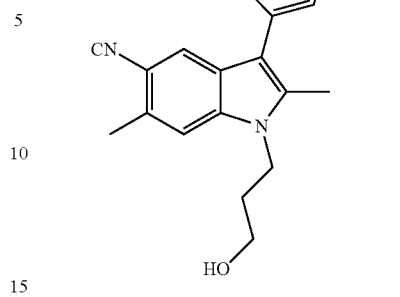
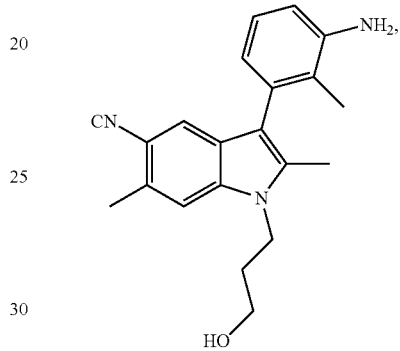
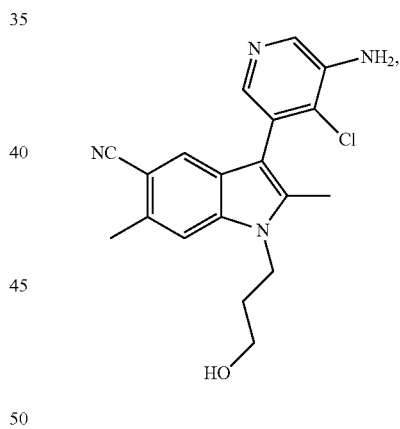
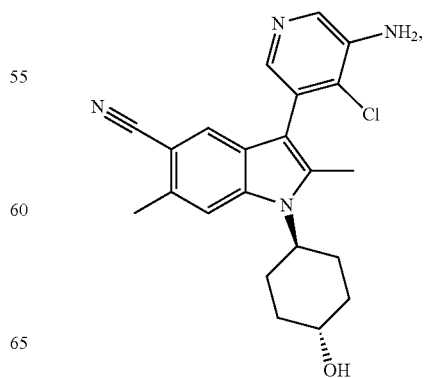

-continued

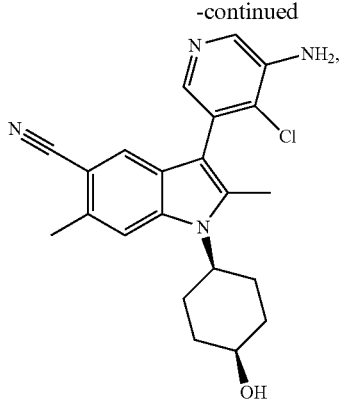

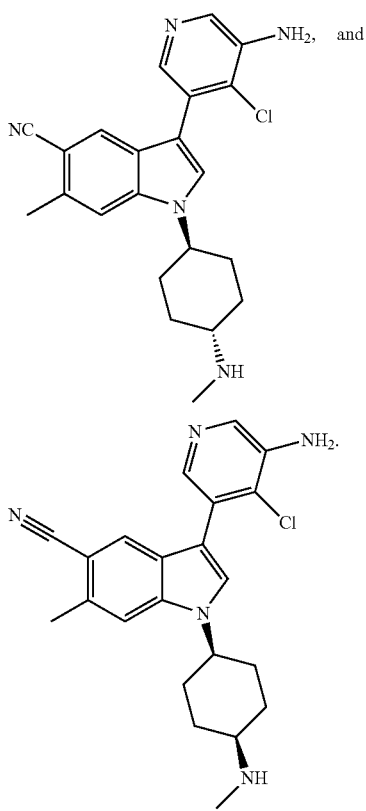

In a fourteenth aspect, the present invention provides a compound of Formula (I-1):

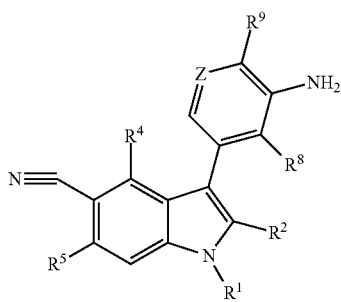

(I-1)

or a pharmaceutically acceptable salt thereof; wherein:
R¹ is selected from:
C₁-C₆ alkyl substituted with one to two R$^a$,
C₃-C₆ cycloalkyl substituted with at least one group selected from —C₁-C₄ alkyl, C₁-C₄ haloalkyl, halo, CN, —C(O)R, —C(O)OR, —CONR₂, —NR—C(O)R, —NH₂, —NR'₂, —NR—C(O)OR', —NR—C(O)NR₂, —OC(O)NR₂, —NRSO₂R', —SO₂R', and —SO₂NR₂, and optionally further substituted with one to two R$^d$;
7-11 membered spiro cyclyl optionally substituted with one or two R$^b$;
7-11 membered spiro heterocyclyl comprising 1-2 heteroatoms selected from nitrogen, oxygen and sulfur, wherein the 7-11 membered spiro heterocyclyl is optionally substituted with one or two R$^b$;
phenyl substituted with at least one group selected from —NR—C(O)OR', —NR—C(O)NR₂, —NR—SO₂R', —NR—SO₂OR', —NR—SO₂NR₂, —C(O)OH, —SO₂R', and —SO₂NR₂, wherein the phenyl is further optionally substituted with one or two R$^b$;
bicyclic heteroaryl comprising one to three heteroatoms selected from nitrogen, oxygen and sulfur, wherein the bicyclic heteroaryl is optionally substituted with one or two R$^b$;
2-pyridone optionally substituted with one or two R$^b$;
6-membered heteroaryl comprising one to two nitrogen atoms, wherein the 6-membered heteroaryl is substituted with at least one group selected from —NR—C(O)OR', —NR—C(O)NR₂, —NR—SO₂R', —NR—SO₂OR', —NR—SO₂NR₂, —C(O)OH, —SO₂R', and —SO₂NR₂, and optionally further substituted with up to three R$^b$;

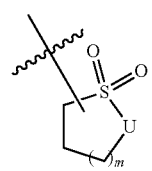

optionally substituted with one or two R$^d$; and

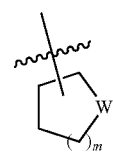

optionally substituted with one or two R$^d$;
R² is selected from: H, halogen, C₁-C₄ alkyl, C₁-C₄ haloalkyl, —C(O)OR, and —C(O)NR₂;
R⁴ is selected from: H, halogen and C₁-C₄ alkyl;
R⁵ is selected from: H, halogen, C₁-C₄ alkyl, C₁-C₄ haloalkyl, and C₃-C₆ cycloalkyl;
each of R⁸ and R⁹ is independently selected from H, halogen, CN, OH, C₁-C₄ alkyl, C₁-C₄ alkoxyl, and C₁-C₄ haloalkyl;
U is selected from: CR₂, NH, N—(C₁₋₄ alkyl), N—C(O)—(C₁₋₄ alkyl), N—C(O)—NR₂, and N—C(O)—O—(C₁₋₄ alkyl);
W is selected from: O, NH, N—(C₁₋₄ alkyl), N—SO₂—(C₁₋₄ alkyl), N—C(O)—(C₁₋₄ alkyl), N—C(O)—NR₂, N—SO₂—O—(C₁₋₄ alkyl), N—SO₂—NR₂, and N—C(O)—O—(C₁₋₄ alkyl);

Z is selected from: CH, CR$^h$ and N;

R is independently at each occurrence selected from H and C$_1$-C$_4$ alkyl;

R' is independently at each occurrence C$_1$-C$_4$ alkyl;

R$^a$ is independently selected from: halogen, CN, —SO$_2$R', —SO$_2$NR$_2$, —NRSO$_2$R', —NR—SO$_2$OR', —NR—SO$_2$NR$_2$, —NR$_2$, —NRC(O)R', —NR—C(O)NR$_2$, —NR—C(O)OR', and —C$_1$-C$_4$ alkoxy, wherein the —C$_1$-C$_4$ alkoxy is substituted with at least one group selected from —OH, halogen, and CN;

R$^b$ is independently selected from: halogen, C$_1$-C$_4$ haloalkoxy, OH, CN, —CO$_2$R, —C(O)NR$_2$, —CONRC(O)R', —CONRSO$_2$R', —NR$_2$, —NRC(O)R, —NR—C(O)OR', —NR—C(O)NR$_2$, —SO$_2$R', —SO$_2$NR$_2$, —NRSO$_2$R', —NR—SO$_2$OR', —NR—SO$_2$NR$_2$, C$_1$-C$_4$ alkyl substituted with zero to one R$^c$, and C$_1$-C$_4$ alkoxy substituted with zero to one R$^c$;

R$^c$ is independently selected from: OH, C$_1$-C$_4$ alkoxy, —CO$_2$R, —C(O)NR$^2$, —NR$_2$, and —NRC(O)R;

R$^d$ is independently selected from: OH, =O, —C(O)R, and —NH(C$_1$-C$_4$ alkyl);

R$^h$ is independently at each occurrence selected from: halogen, CN, OH, C$_1$-C$_4$ alkyl, and C$_1$-C$_4$ haloalkyl; and m is independently selected from: 0, 1, and 2.

In a fifteenth aspect, the present invention provides a compound of Formula (I) or (I-1), or a pharmaceutically acceptable salt thereof, within the scope of the fourteenth aspect; wherein: R$^1$ is selected from cyclobutyl, cyclopentyl, and cyclohexyl, wherein each of the cyclobutyl, cyclopentyl, and cyclohexyl is independently substituted with one group selected from —C(O)OR, —SO$_2$R', —SO$_2$NR$_2$, and —CONR$_2$.

In a sixteenth aspect, the present invention provides a compound of Formula (I) or (I-1), or a pharmaceutically acceptable salt thereof, within the scope of the fourteenth or fifteenth aspect; wherein: R$^1$ is selected from cyclobutyl, cyclopentyl, and cyclohexyl, wherein each of cyclobutyl, cyclopentyl, and cyclohexyl is independently substituted with one group selected from —SO$_2$CH$_3$, —SO$_2$NH$_2$, —NHSO$_2$CH$_3$, —COOCH$_3$, and —CONH$_2$.

In a seventeenth aspect, the present invention provides a compound of Formula (I) or (I-1), or a pharmaceutically acceptable salt thereof, within the scope of the fourteenth aspect; wherein: R$^1$ is 6-membered heteroaryl comprising one to two nitrogen atoms as ring members, substituted with at least one group selected from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$.

In an eighteenth aspect, the present invention provides a compound of Formula (I) or (I-1), or a pharmaceutically acceptable salt thereof, within the scope of the fourteenth or seventeenth aspect; wherein: R$^1$ is 6-membered heteroaryl comprising one to two nitrogen atoms as ring members, substituted with at least one group selected from —SO$_2$CH$_3$ and —SO$_2$NH$_2$.

In a nineteenth aspect, the present invention provides a compound of Formula (I) or (I-1), or a pharmaceutically acceptable salt thereof, within the scope of the fourteenth aspect; wherein: R$^1$ is phenyl substituted with at least one group selected from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$.

In a twentieth aspect, the present invention provides a compound of Formula (I) or (I-1), or a pharmaceutically acceptable salt thereof, within the scope of the fourteenth aspect; wherein: R$^1$ is phenyl substituted with at least one group selected from —SO$_2$CH$_3$ and —SO$_2$NH$_2$.

In a twenty-first aspect, the present invention provides a compound of Formula (I-1), or a pharmaceutically acceptable salt thereof, within the scope of the fourteenth to twentieth aspects, wherein Z is nitrogen.

In a twenty-second aspect, the present invention provides a compound of Formula (I-1), or a pharmaceutically acceptable salt thereof, within the scope of the fourteenth to twentieth aspects, wherein R$^8$ is halogen.

In a twenty-third aspect, the present invention provides a compound of Formula (I-1), or a pharmaceutically acceptable salt thereof, within the scope of the fourteenth to twenty-second aspects, wherein R$^9$ is H.

In a twenty-fourth aspect, the present invention provides a compound of Formula (I) or (I-1), or a pharmaceutically acceptable salt thereof, within the scope of the fourteenth to twenty-third aspects, wherein R$^4$ is H.

In a twenty-fifth aspect, the present invention provides a compound of Formula (I) or (I-1), or a pharmaceutically acceptable salt thereof, within the scope of the fourteenth to twenty-fourth aspects, R$^5$ is —CH$_3$.

In a twenty-sixth aspect, the present invention provides a compound of Formula (I-2):

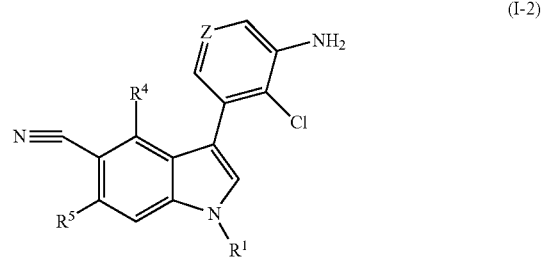

(I-2)

or a pharmaceutically acceptable salt thereof, wherein:

R$^1$ is selected from:

C$_1$-C$_6$ alkyl substituted with one to two R$^a$,

C$_3$-C$_6$ cycloalkyl substituted with at least one group selected from —C$_1$-C$_4$ alkyl, C$_1$-C$_4$ haloalkyl, halo, CN, —C(O)R, —C(O)OR, —CONR$_2$, —NR—C(O)R, —NH$_2$, —NR'$_2$, —NR—C(O)OR', —NR—C(O)NR$_2$, —OC(O)NR$_2$, —NRSO$_2$R', —SO$_2$R', and —SO$_2$NR$_2$, and optionally further substituted with one to two R$^d$;

7-11 membered spiro cyclyl optionally substituted with one or two R$^b$;

7-11 membered spiro heterocyclyl comprising 1-2 heteroatoms selected from nitrogen, oxygen and sulfur, wherein the 7-11 membered spiro heterocyclyl is optionally substituted with one or two R$^b$;

phenyl substituted with at least one group selected from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$;

bicyclic heteroaryl comprising one to three heteroatoms selected from nitrogen, oxygen and sulfur, wherein the bicyclic heteroaryl is optionally substituted with one or two R$^b$;

2-pyridone optionally substituted with one or two R$^b$;

6-membered heteroaryl comprising one to two nitrogen, wherein the 6-membered heteroaryl is substituted with at least one group selected from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$, and optionally further substituted with up to three R$^b$;

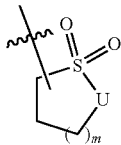

optionally substituted with one or two R$^d$; and

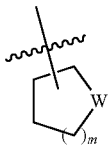

optionally substituted with one or two R$^d$;
R$^4$ is selected from: H, halogen and C$_1$-C$_4$ alkyl;
R$^5$ is selected from: H, halogen, C$_1$-C$_4$ alkyl, C$_1$-C$_4$ haloalkyl, and C$_3$-C$_6$ cycloalkyl;
U is selected from: CR$_2$, NH, N—(C$_{1-4}$ alkyl), N—C(O)—(C$_{1-4}$ alkyl), N—C(O)—NR$_2$, and N—C(O)—O—(C$_{1-4}$ alkyl);
W is selected from: O, NH, N—(C$_{1-4}$ alkyl), N—SO$_2$—(C$_{1-4}$ alkyl), N—C(O)—(C$_{1-4}$ alkyl), N—C(O)—NR$_2$, N—SO$_2$—O—(C$_{1-4}$ alkyl), N—SO$_2$—NR$_2$, and N—C(O)—O—(C$_{1-4}$ alkyl);
Z is selected from: CH, CR$^h$ and N;
R is independently at each occurrence selected from H and C$_1$-C$_4$ alkyl;
R' is independently at each occurrence C$_1$-C$_4$ alkyl;
R$^a$ is independently selected from: halogen, CN, —SO$_2$R', —SO$_2$NR$_2$, —NRSO$_2$R', —NR—SO$_2$OR', —NR—SO$_2$NR$_2$, —NR$_2$, —NRC(O)R', —NR—C(O)NR$_2$, —NR—C(O)OR', and —C$_1$-C$_4$ alkoxy, wherein the —C$_1$-C$_4$ alkoxy is at least substituted with one group selected from —OH, halogen, and CN;
R$^b$ is independently selected from: halogen, C$_1$-C$_4$ haloalkoxy, OH, CN, —CO$_2$R, —C(O)NR$_2$, —CONRC(O)R', —CONRSO$_2$R', —NR$_2$, —NRC(O)R, —NR—C(O)OR', —NR—C(O)NR$_2$, —SO$_2$R', —SO$_2$NR$_2$, —NRSO$_2$R', —NR—SO$_2$OR', —NR—SO$_2$NR$_2$, C$_1$-C$_4$ alkyl substituted with zero to one R$^c$, and C$_1$-C$_4$ alkoxy substituted with zero to one R$^c$;
R$^c$ is independently selected from: OH, C$_1$-C$_4$ alkoxy, —CO$_2$R, —C(O)NR$^2$, —NR$_2$, and —NRC(O)R;
R$^d$ is independently selected from: OH, =O, —C(O)R, and —NH(C$_1$-C$_4$ alkyl);
R$^h$ is independently at each occurrence selected from: halogen, CN, OH, C$_1$-C$_4$ alkyl, and C$_1$-C$_4$ haloalkyl; and
m is independently selected from: 0, 1, and 2;

In a twenty-seventh aspect, the present invention provides a compound of (I-2), or a pharmaceutically acceptable salt thereof, within the scope of the twenty-sixth aspect, wherein R$^4$ is H.

In a twenty-eighth aspect, the present invention provides a compound of Formula (I-2), or a pharmaceutically acceptable salt thereof, within the scope of the twenty-sixth or twenty-seventh aspects, wherein R$^5$ is —CH$_3$.

In a twenty-ninth aspect, the present invention provides a compound of Formula (I-2), or a pharmaceutically acceptable salt thereof, within the scope of the twenty-sixth to twenty-eighth aspects, wherein R$^1$ is selected from cyclobutyl, cyclopentyl, and cyclohexyl, wherein each of the cyclobutyl, cyclopentyl, and cyclohexyl is independently substituted with one group selected from —SO$_2$R', —SO$_2$NR$_2$, and —CONR$_2$.

In a thirtieth aspect, the present invention provides a compound of Formula (I-2), or a pharmaceutically acceptable salt thereof, within the scope of the twenty-sixth to twenty-ninth aspects, wherein R$^1$ is selected from cyclobutyl, cyclopentyl, and cyclohexyl, wherein each of cyclobutyl, cyclopentyl, and cyclohexyl is substituted with one group selected from —SO$_2$CH$_3$, —SO$_2$NH$_2$, and —CONH$_2$.

In a thirty-first aspect, the present invention provides a compound or a pharmaceutically acceptable salt thereof, wherein the compound is selected from Examples 1 to 113.

In a thirty-second aspect, the compounds of the present invention have IC$_{50}$ values ≤1 µM, using the LSD1 LC-MS assay disclosed herein, preferably, IC$_{50}$ values ≤0.5 µM, more preferably, IC$_{50}$ values ≤0.1 µM.

II. Other Embodiments

In another embodiment, the present invention provides a composition comprising at least one of the compounds of the present invention or a pharmaceutically acceptable salt thereof.

In another embodiment, the present invention provides a pharmaceutical composition comprising at least one of the compounds of the present invention or a pharmaceutically acceptable salt thereof and at least one pharmaceutically acceptable carrier, diluent or excipient.

In another embodiment, the present invention provides a pharmaceutical composition, comprising a therapeutically effective amount of at least one of the compounds of the present invention or a pharmaceutically acceptable salt thereof and at least one pharmaceutically acceptable carrier, diluent or excipient.

The pharmaceutical composition is useful in the treatment of diseases or disorders mediated by LSD1.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment of diseases or disorders mediated by LSD1, alone, or optionally in combination with another compound of the present invention and/or at least one other type of therapeutic agent.

In another embodiment, the present invention provides a method for the treatment of diseases or disorders mediated by LSD1, comprising administering to a patient in need of such treatment a therapeutically effective amount of at least one of the compounds of the present invention, alone, or optionally in combination with another compound of the present invention and/or at least one other type of therapeutic agent.

In another embodiment, the present invention provides a method for the treatment of diseases or disorders mediated by LSD1, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment of diseases or disorders mediated by LSD1, alone, or optionally in combination with another compound of the present invention and/or at least one other type of therapeutic agent.

In another embodiment, the present invention provides a combined preparation of a compound of the present invention and additional therapeutic agent(s) for use in therapy.

In another embodiment, the present invention provides a combination of a compound of the present invention and additional therapeutic agent(s) for simultaneous or separate use in therapy.

In another embodiment, the present invention provides a combined preparation of a compound of the present invention and additional therapeutic agent(s) for simultaneous, separate or sequential use in the treatment of diseases or disorders mediated by LSD1. The compound may be administered as a pharmaceutical composition described herein.

Examples of diseases or disorders mediated by LSD1 include, but are not limited to, B cell lymphoma, acute myeloid leukemia, gastric cancer, hepatocellular carcinoma, prostate cancer, breast carcinoma, neuroblastoma, glioblastoma, nasopharyngeal carcinoma, colon cancer, gallbladder cancer, esophageal cancer, head and neck cancer, lung cancer, ovarian cancer, pancreatic cancer, endometrial carcinoma and soft tissue sarcomas such as rhabdomyosarcoma (RMS), chondrosarcoma, osteosarcoma, Ewing's sarcoma, liver fibrosis, and sickle cell disease.

The present invention provides a method for the treatment of diseases or disorders mediated by LSD1, comprising administering to a patient in need thereof a therapeutically effective amount of a first therapeutic agent optionally with a second therapeutic agent, wherein the first therapeutic agent is an LSD1 inhibitor and the second therapeutic agent is one other type of therapeutic agent; wherein the diseases or disorders are selected from diffused large B cell lymphoma (DLBCL), follicular lymphoma, other lymphomas, leukemia, multiple myeloma, gastric cancer, malignant rhabdoid tumor, prostate cancer and hepatocellular carcinoma.

In another embodiment, additional therapeutic agent(s) used in combined pharmaceutical compositions or combined methods or combined uses, are selected from one or more, preferably one to three, of the following therapeutic agents: other anti-cancer agents, immunomodulators, anti-allergic agents, anti-nausea agents (or anti-emetics), pain relievers, cytoprotective agents, and combinations thereof.

In another embodiment, the present invention provides a method of treating a cancer in a subject, comprising administering to the subject an immunomodulator and a second therapeutic agent, wherein: (i) the immunomodulator is chosen from one or more of: an activator of a costimulatory molecule or an inhibitor of an immune checkpoint molecule, and (ii) the second therapeutic agent is chosen from a compound of the present invention thereby treating the cancer.

In another embodiment, a method of reducing growth, survival, or viability, or all, of a a cancer cell, comprising contacting the cell with an immunomodulator and a second therapeutic agent, wherein: (i) the immunomodulator is chosen from one or more of: an activator of a costimulatory molecule or an inhibitor of an immune checkpoint molecule, and ii) the second therapeutic agent is chosen from a compound of the present invention thereby reducing the growth, survival, or viability of the cancer cell.

Various (enumerated) embodiments of the invention are described herein. It will be recognized that features specified in each embodiment may be combined with other specified features to provide further embodiments of the present invention. It is also understood that each individual element of the embodiments is its own independent embodiment.

Other features of the present invention should become apparent in the course of the above descriptions of exemplary embodiments that are given for illustration of the invention and are not intended to be limiting thereof.

III. Definitions

The general terms used hereinbefore and hereinafter preferably have within the context of this invention the following meanings, unless otherwise indicated, where more general terms whereever used may, independently of each other, be replaced by more specific definitions or remain, thus defining more detailed embodiments of the invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "a," "an," "the" and similar terms used in the context of the present invention (especially in the context of the claims) are to be construed to cover both the singular and plural unless otherwise indicated herein or clearly contradicted by the context.

As used herein, the term "heteroatoms" refers to nitrogen (N), oxygen (O) or sulfur (S) atoms, in particular nitrogen or oxygen.

Unless otherwise indicated, any heteroatom with unsatisfied valences is assumed to have hydrogen atoms sufficient to satisfy the valences.

As used herein, the terms "alkyl" refers to a hydrocarbon radical of the general formula $C_nH_{2n+1}$. The alkane radical may be straight or branched. For example, the term "$C_1$-$C_{10}$ alkyl" or "$C_1$ to $C_{10}$ alkyl" refers to a monovalent, straight, or branched aliphatic group containing 1 to 10 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, heptyl, and the like).

The term "alkylene" refers to a divalent alkyl group. For example, the term "$C_1$-$C_6$ alkylene" or "C to $C_6$ alkylene" refers to a divalent, straight, or branched aliphatic group containing 1 to 6 carbon atoms (e.g., methylene (—$CH_2$—), ethylene (—$CH_2CH_2$—), n-propylene (—$CH_2CH_2CH_2$—), iso-propylene (—$CH(CH_3)CH_2$—), n-butylene, sec-butylene, iso-butylene, tert-butylene, n-pentylene, isopentylene, neopentylene, n-hexylene and the like).

The term "alkoxy" refers to an alkyl linked to an oxygen, which may also be represented as —O—R or —OR, wherein the R represents the alkyl group. "$C_1$-$C_6$ alkoxy" or "$C_1$ to $C_6$ alkoxy" is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halogen" or "halo" may be fluorine, chlorine, bromine or iodine (preferred halogens as substituents are fluorine and chlorine).

"Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" represents a haloalkyl group as defined above with the indicated number of carbon atoms attached through an oxygen bridge. For example, "$C_1$-$C_6$ haloalkoxy" or "$C_1$ to $C_6$ haloalkoxy" is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "oxo" or —C(O)— refers to a carbonyl group. For example, a ketone, aldehyde, or part of an acid, ester, amide, lactone, or lactam group.

The term "cycloalkyl" refers to nonaromatic carbocyclic ring that is fully hydrogenated ring, including mono-, bi- or poly-cyclic ring systems. "$C_3$-$C_8$ cycloalkyl" or "$C_3$ to $C_8$ cycloalkyl" is intended to include $C_3$, $C_4$, $C_5$, $C_6$, $C_7$ and $C_8$ cycloalkyl groups. Example cycloalkyl groups include, but are not limited to, cyclopropyl, cyclobutyl, cyclopentyl, cyclohexyl, and norbornyl.

The term "aryl" refers to 6- to 10-membered aromatic carbocyclic moieties having a single (e.g., phenyl) or a fused ring system (e.g., naphthalene.). A typical aryl group is phenyl group.

The term "benzyl", as used herein, refers to a methyl group on which one of the hydrogen atoms is replaced by a phenyl group.

"Heterocycloalkyl" means cycloalkyl, as defined in this application, provided that one or more of the ring carbons indicated, are replaced by a moiety selected from —O—, —N═, —NR—, —C(O)—, —S—, —S(O)— and —S(O)$_2$—, wherein R is hydrogen, $C_{1-4}$alkyl or a nitrogen protecting group (for example, carbobenzyloxy, p-methoxybenzyl carbonyl, t-butoxycarbonyl, acetyl, benzoyl, benzyl, p-methoxy-benzyl, p-methoxy-phenyl, 3,4-dimethoxybenzyl, and the like). For example, a 3 to 8 membered heterocycloalkyl includes epoxy, aziridinyl, azetidinyl, imidazolidinyl, pyrazolidinyl, tetrahydrofuranyl, tetrahydrothienyl, tetrahydrothienyl 1,1-dioxide, oxazolidinyl, thiazolidinyl, pyrrolidinyl, pyrrolidinyl-2-one, morpholino, piperazinyl, piperidinyl, piperidinylone, pyrazolidinyl, hexahydropyrimidinyl, 1,4-dioxa-8-aza-spiro[4.5]dec-8-yl, thiomorpholino, sulfanomorpholino, sulfonomorpholino, octahydropyrrolo[3,2-b]pyrrolyl, and the like.

The term "heteroaryl" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, isoxazolyl, imidazolyl, triazolyl, tetrazolyl, triazinyl, pyrimidinyl, pyrazinyl, thiazolyl, purinyl, benzimidazolyl, quinolinyl, isoquinolinyl, quinoxalinyl, benzopyranyl, benzothiophenyl, benzoimidazolyl, benzoxazolyl, 1H-benzo[d][1,2,3]triazolyl, and the like.). The heteroaromatic moiety may consist of a single or fused ring system. A typical single heteroaryl ring is a 5- to 6-membered ring containing one to four heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a heteroaryl fused to an aryl (e.g., phenyl).

"Bicyclic heteroaryl", as used herein, refers to an 8-10 membered bicycle, having 1 to 5 heteroatoms selected from N, O and S as ring atoms and the remaining ring atoms are carbon atoms. The nitrogen atoms of such heteroaryl rings can be optionally quaternerized and the sulfur atoms of such heteroaryl rings can be optionally oxidized. Bicyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, quinazolinyle, pteridinyl, indolizine, imidazo[1,2a]pyridine, quinoline, quinolinyl, isoquinoline, phthalazine, quinoxaline, naphthyridine, naphthyridinyl, quinolizine, indolyl, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, purinyl, carbazole, acridine, phenazine, phenothiazene, phenoxazine, 1,2-dihydropyrrolo[3,2,1-hi]indole, indolizine, pyrido[1,2-a]indole and 2(1H)-pyridinone.

The term "counter ion" is used to represent a negatively charged species such as chloride, bromide, hydroxide, acetate, and sulfate or a positively charged species such as sodium (Na+), potassium (K+), ammonium ($R_nNH_m$+, where n=0-4, m=0-4 and m+n=4) and the like.

As referred to herein, the term "substituted" means that at least one hydrogen atom is replaced with a non-hydrogen group, provided that normal valencies are maintained and that the substitution results in a stable compound. When a substituent is keto (i.e., ═O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C═C, C═N, or N═N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with zero to three R, then said group may be unsubstituted or substituted with up to three R, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, for example, a ketone (—CH—C=O) group in a molecule may tautomerize to its enol form (—C=C—OH). Thus, this invention is intended to cover all possible tautomers even when a structure depicts only one of them.

The phrase "pharmaceutically acceptable" indicates that the substance or composition must be compatible chemically and/or toxicologically, with the other ingredients comprising a formulation, and/or the mammal being treated therewith.

Unless specified otherwise, the term "compounds of the present invention" or "compounds of the present invention" refers to compounds of Formula (I) or (I-1), as well as isomers, such as stereoisomers (including diastereoisomers, enantiomers and racemates), geometrical isomers, conformational isomers (including rotamers and astropisomers), tautomers, isotopically labeled compounds (including deuterium substitutions), and inherently formed moieties (e.g., polymorphs, solvates and/or hydrates). When a moiety is present that is capable of forming a salt, then salts are included as well, in particular pharmaceutically acceptable salts.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms.

"Enantiomers" are a pair of stereoisomers that are non-superimposable mirror images of each other. A 1:1 mixture of a pair of enantiomers is a "racemic" mixture. The term is used to designate a racemic mixture where appropriate. When designating the stereochemistry for the compounds of the present invention, a single stereoisomer with known relative and absolute configuration of the two chiral centers is designated using the conventional RS system (e.g., (1S, 2S)); a single stereoisomer with known relative configuration but unknown absolute configuration is designated with stars (e.g., (1R*,2R*)); and a racemate with two letters (e.g, (1RS,2RS) as a racemic mixture of (1R,2R) and (1S,2S); (1RS,2SR) as a racemic mixture of (1R,2S) and (1S,2R)). "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Geometric isomers may occur when a compound contains a double bond or some other feature that gives the molecule a certain amount of structural rigidity. If the compound contains a double bond, the substituent may be E or Z configuration. If the compound contains a disubstituted cycloalkyl, the cycloalkyl substituent may have a cis- or trans-configuration.

Conformational isomers (or conformers) are isomers that can differ by rotations about one or more a bonds. Rotamers are conformers that differ by rotation about only a single a bond.

The term "atropisomer" refers to a structural isomer based on axial or planar chirality resulting from restricted rotation in the molecule.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation).

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers.

Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. For example, pharmaceutically acceptable salts include, but are not limited to, acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxymalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate or xinafoate salt form.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like, preferably hydrochloric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy,* 22nd Edition, Pharmaceutical Press, London, UK (2012), the invention of which is hereby incorporated by reference.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The present invention includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this present invention can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_{2}H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

"LSD1" refers to Lysine (K)-specific demethylase 1A.

The term "LSD1-mediated disease or disorder" refers to any disease or disorder which is directly or indirectly regulated by LSD1.

The term "diseases or disorders mediated by LSD1" refers to diseases or disorders which are directly or indirectly regulated by LSD1.

As used herein, the term "patient" encompasses all mammalian species.

As used herein, the term "subject" refers to an animal. Typically the animal is a mammal. A "subject" also refers to any human or non-human organism that could potentially benefit from treatment with a LSD1 inhibitor. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. Exemplary subjects include human beings of any age with risk factors for cancer disease.

As used herein, a subject is "in need of" a treatment if such subject would benefit biologically, medically or in quality of life from such treatment (preferably, a human).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease/disorder refers to the treatment of the disease/disorder in a mammal, particularly in a human, and includes: (a) ameliorating the disease/disorder, (i.e., slowing or arresting or reducing the development of the disease/disorder, or at least one of the clinical symptoms thereof); (b) relieving or modulating the disease/disorder, (i.e., causing regression of the disease/disorder, either physically, (e.g., stabilization of a discernible symptom), physiologically, (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a mammal, in particular, when such mammal is predisposed to the disease or disorder but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that will elicit the biological or medical response of a subject, for example, reduction or inhibition of LSD1, or ameliorate symptoms, alleviate conditions, slow or delay disease progression, or prevent a disease or disorder mediated by LSD1. When applied to a combination, the term refers to combined amounts of the active ingredients that result in the preventive or therapeutic effect, whether administered in combination, serially, or simultaneously.

Abbreviations as used herein, are defined as follows: "1×" for once, "2×" for twice, "3×" for thrice, "OC" for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for aqueous, "sat" or "sat'd" for saturated, "MW" for molecular weight, "mw" or "pwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, "ee" for "enantiomeric excess" and "a", "P", "R", "S", "E", and "Z" are stereochemical designations familiar to one skilled in the art.

The following abbreviations used herein below have the corresponding meanings:

ACN acetonitrile
Ac acetyl
AIBN azobisisobutyronitrile
Bn benzyl
Boc tert-butoxy carbonyl
Boc$_2$O di-tert-butyl dicarbonate
BOP bis(2-oxo-3-oxazolidinyl)phosphinic
Bu butyl
Cs$_2$CO$_3$ cesium carbonate anhydrous
CHCl$_3$ chloroform
DAST diethylaminosulfurtrifluoride
DBU 2,3,4,6,7,8,9,10-octahydropyrimido[1,2-a]azepine
DCM dichloromethane
DIAD diisopropyl azodicarboxylate
DMAP 4-dimethylaminopyridine
DME 1,2-dimethoxyethane
DMF dimethylformamide
DMSO dimethylsulfoxide
DPPA diphenylphosphoryl azide
EA ethyl acetate
Et ethyl
EtOH ethanol
EtOAc ethyl acetate HATU 2-(7-Aza-1H-benzotriazole-1-yl)-1,1,3,3-tetramethyluronium hexafluorophosphate
HCl hydrochloric acid
HOAc acetic acid
i-Bu isobutyl
i-Pr isopropyl
KOAc potassium acetate
LiAlH$_4$ lithium aluminium hydride
LiCl lithium chloride
LiHMDS lithium bis(trimethylsilyl)amide
mCPBA 3-Chloroperoxybenzoic acid
Me methyl
Me$_4$-t-BuXPhos di-tert-butyl(2',4',6'-triisopropyl-3,4,5,6-tetramethyl-[1,1'-biphenyl]-2-yl)phosphane
MeCN acetonitrile
MnO$_2$ manganese dioxide
N$_2$ nitrogen
NaBH$_4$ sodium borohydride
NaHCO$_3$ sodium bicarbonate
Na$_2$SO$_4$ sodium sulfate
NBS N-bromosuccinimide
NIS N-iodosuccinimide
PE petroleum ether
Ph phenyl
PPh$_3$ triphenylphosphine
Pd(dppf)Cl$_2$ [1,1'-bis(diphenylphosphino)ferrocene]dichloropalladium(II)
Pd(PPh$_3$)$_4$ palladium(0)tetrakis(triphenylphosphine)
Ph$_3$P=O triphenylphosphine oxide
t-Bu or Bu$^t$ tert-butyl
TBAB tetra-n-butylammonium bromide
TBAF tetra-n-butylammonium fluoride
TBS t-butyldimethylsilyl
TEA triethylamine
TFA trifluoroacetic acid
THF tetrahydrofuran
Ts-Cl p-toluenesulfonyl chloride
Zn(CN)$_2$ zinc cyanide IV. Synthesis The compounds of the present invention can be prepared in a number of ways known to one skilled in the art of organic synthesis in view of the methods, reaction schemes and examples provided herein. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transformations*, 2$^{nd}$-ed., Wiley-VCH Weinheim, Germany (1999), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this invention using conventional chemistry well known to those skilled in the art.

In the preparation of compounds of the present invention, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis*, 4th Ed., Wiley (2007). Protecting groups incorporated in making of the compounds of the present invention, such as the trityl protecting group, may be shown as one regioisomer but may also exist as a mixture of regioisomers.

Scheme 1 (below) describes potential routes for producing the compounds of the present invention which include compounds of Formula (I). Compounds of Formula (I) can be made substantially optically pure by either using substantially optically pure starting material or by separation chromatography, recrystallization or other separation techniques well-known in the art. For a more detailed description, see the Example section below.

Scheme 1

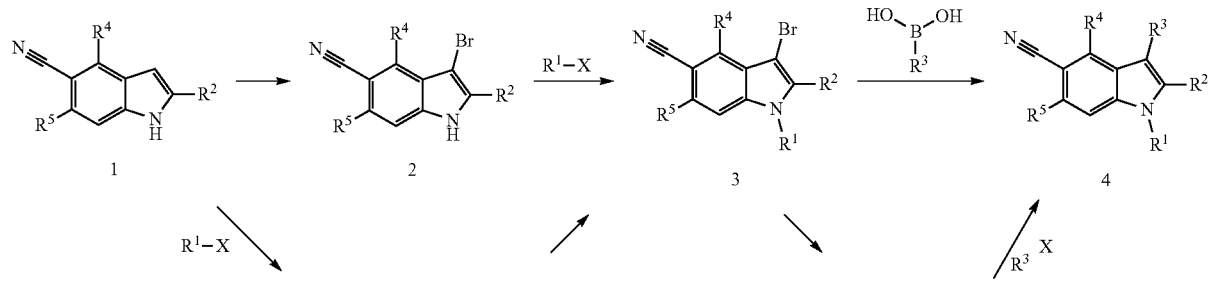

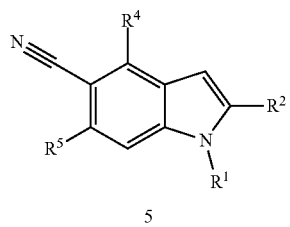

5

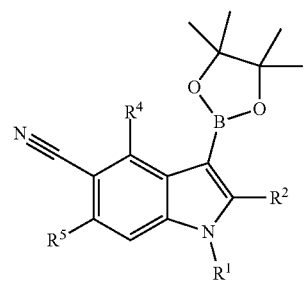

6

Under Scheme 1, substituted 1H-indole-5-carbonitrile 1 was treated with bromination reagents (such as NBS or $Br_2$) to form substituted 3-bromo-1H-indole-5-carbonitrile 2, which underwent alkylation with corresponding halide to give product 3. Compound 3 coupled with boronic acid or boronate under Suzuki reactions to yield compound 4. Alternatively, substituted 1H-indole-5-carbonitrile 1 was treated with halide first to give alkylation product 5, which reacted with boronic acid or boronate to generate coupled compound 4. In some other cases, 3 was treated with bis(pinacolato)diboron to generate corresponding boronate compound 6, which was alkylated with halide to generate compound 4.

General Methods

The following methods were used in the exemplified Examples, except where noted otherwise.

Purification of intermediates and final products was carried out via either normal or reverse phase chromatography. Normal phase chromatography was carried out using pre-packed $SiO_2$ cartridges eluting with either gradients of hexanes and ethyl acetate or DCM and MeOH unless otherwise indicated. For highly polar amines, gradients of DCM and 1M $NH_3$ in MeOH were used. Reverse phase preparative HPLC was carried out using C18 columns with UV 214 nm and 254 nm or prep LC-MS detection eluting with gradients of Solvent A (water with 0.1% TFA) and Solvent B (acetonitrile with 0.1% TFA) or with gradients of Solvent A (water with 0.05% TFA) and Solvent B (acetonitrile with 0.05% TFA) or with gradients of Solvent A (water with 0.05% ammonia) and Solvent B (acetonitrile with 0.05% ammonia).

LC/MS Methods Employed in Characterization of Examples

Reverse phase analytical HPLC/MS was performed on Agilent LC1200 systems coupled with 6110 (Methods A-D), or 6120 (Method E and F), or 6130 (Method G) Mass Spectrometer.

Method A: Linear gradient of 5% to 95% B over 1.2 min, with 1 min hold at 95% B;
 UV visualization at 214 nm and 254 nm
 Column: SunFire® C18 4.6×50 mm 3.5 μm
 Flow rate: 2 mL/min
 Solvent A: 0.1% trifluoroacetic acid, 99.9% water
 Solvent B: 0.1% trifluoroacetic acid, 99.9% acetonitrile.

Method B: Linear gradient of 5% to 95% B over 1.5 min, with 1 min hold at 95% B;
 UV visualization at 214 nm and 254 nm
 Column: XBridge® C18 4.6×50 mm 3.5 μm
 Flow rate: 2 mL/min
 Solvent A: water with 10 mM Ammonium hydrogen carbonate
 Solvent B: acetonitrile.

Method C: Linear gradient of 5% to 95% B over 1.2 min, with 1.3 min hold at 95% B,
 95% to 5% B over 0.01 min;
 UV visualization at 214 nm and 254 nm
 Column: SunFire® C18 4.6×50 mm 3.5 μm
 Flow rate: 2 mL/min
 Solvent A: 0.1% trifluoroacetic acid, 99.9% water
 Solvent B: 0.1% trifluoroacetic acid, 99.9% acetonitrile.

Method D: Linear gradient of 5% to 95% B over 1.4 min, with 1.6 min hold at 95% B,
 95% to 5% B over 0.01 min;
 UV visualization at 214 nm and 254 nm
 Column: XBridge® C18 4.6×50 mm 3.5 μm
 Flow rate: 1.8 mL/min
 Solvent A: water with 10 mM Ammonium hydrogen carbonate
 Solvent B: acetonitrile.

Method E: Linear gradient of 5% to 95% B over 1.5 min, with 1 min hold at 95% B;
 UV visualization at 214 nm and 254 nm
 Column: XBridge® C18 4.6×50 mm 3.5 μm
 Flow rate: 2 mL/min
 Solvent A: water with 10 mM Ammonium hydrogen carbonate
 Solvent B: acetonitrile.

Method F: Linear gradient of 5% to 95% B over 1.5 min, with 1 min hold at 95% B;
 UV visualization at 214 nm and 254 nm and 300 nm
 Column: XBridge® C18 4.6×30 mm 2.5 μm
 Flow rate: 1.8 mL/min
 Solvent A: water with 0.1% ammonia
 Solvent B: acetonitrile.

Method G: Linear gradient of 10% to 95% B over 2 min, with 1 min hold at 95% B;
 UV visualization at 214 nm, 254 nm and 300 nm
 Column: Sunfire® C18 4.6×30 mm 2.5 μm
 Flow rate: 1.8 mL/min
 Solvent A: water
 Solvent B: MeOH with 0.1% formic acid.

NMR Employed in Characterization of Examples $^1$H NMR spectra were obtained with Bruker Fourier transform spectrometers operating at frequencies as follows: $^1$H NMR: 400 MHz (Bruker). $^{13}$C NMR: 100 MHz (Bruker). Spectra data are reported in the format: chemical shift (multiplicity, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CDCl_3$, and which in $^{13}$C NMR spectra appear at 39.7 ppm for CD$_3$SOCD$_3$, 49.0 ppm for CD$_3$OD, and 77.0 ppm for CDCl$_3$. All $^{13}$C NMR spectra were proton decoupled.

V. Examples

The following Examples have been prepared, isolated and characterized using the methods disclosed herein. The following examples demonstrate a partial scope of the invention and are not meant to be limiting of the scope of the invention.

Unless specified otherwise, starting materials are generally available from a non-excluding commercial sources such as TCI Fine Chemicals (Japan), Shanghai Chemhere Co., Ltd. (Shanghai, China), Aurora Fine Chemicals LLC (San Diego, Calif.), FCH Group (Ukraine), Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), Chembridge Corporation (USA), Matrix Scientific (USA), Conier Chem & Pharm Co., Ltd (China), Enamine Ltd (Ukraine), Combi-Blocks, Inc. (San Diego, USA), Oakwood Products, Inc. (USA), Apollo Scientific Ltd. (UK), Allichem LLC. (USA) and Ukrorgsyntez Ltd (Latvia). PharmaBlock R&D Co. Ltd (Nanjing, China), Accela ChemBio Co. Ltd (Shanghai, China), Alputon Inc. (Shanghai, China), J&K Scientific Ltd. (Beijing, China).

INTERMEDIATES

Intermediate 2

3-bromo-1H-indole-5-carbonitrile

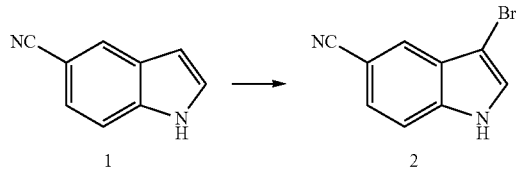 [SMILES: N#Cc1ccc2[nH]ccc2c1 ; N#Cc1ccc2[nH]cc(Br)c2c1]

To a solution of 1H-indole-5-carbonitrile (1) (1 g, 7.03 mmol) in DMF (5 mL) was added bromine (0.399 mL, 7.74 mmol). The mixture was stirred at 20° C. for 1 h. Water (15 mL) was added. The precipitate was collected and dried in high vacuum to afford the title compound (1.3 g, 71%) as a brown solid. $^1$H-NMR (400 MHz, DMSO-d$_6$) δ ppm 12.03 (s, 1H), 7.90 (s, 1H), 7.79 (s, 1H), 7.60 (d, 1H), 7.52 (d, 1H). LC-MS: [M+H]$^+$=221.0; 223.0.

Intermediate 4

3-bromo-6-methyl-1H-indole-5-carbonitrile

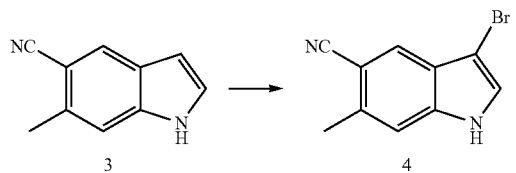

A mixture of compound 3 (2.8 g, 17.93 mmol) and NBS (3.5 g, 19.72 mmol) in DMF (60 mL) was stirred at rt for 1 h. EA and water were added to the mixture. The organic layer was separated and the aqueous layer was extracted with EA two times. The combined organic layers were washed with water and brine, dried over anhydrous Na$_2$SO$_4$, filtered and concentrated to give crude product which was purified by flash column chromatography (eluent: PE/EA, EA %=8%-20%) to give the title compound (3.1 g 74%). $^1$H NMR (300 MHz, CDCl$_3$) δ ppm 8.40 (s, 1H), 7.88 (s, 1H), 7.27 (d, 2H), 2.63 (s, 3H). LC-MS: [M+H]$^+$=235.2, 237.2.

Example 1

3-(5-amino-4-chloropyridin-3-yl)-1-((1R,4R)-4-hydroxycyclohexyl)-6-methyl-1H-indole-5-carbonitrile Example 2

3-(5-amino-4-chloropyridin-3-yl)-1-((1S,4S)-4-hydroxycyclohexyl)-6-methyl-1H-indole-5-carbonitrile Intermediate 1.2

3-bromo-6-methyl-1H-indole-5-carbonitrile

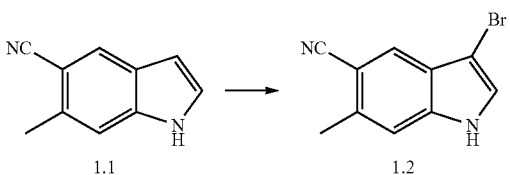

To a solution of 6-methyl-1H-indole-5-carbonitrile (4 g, 25.6 mmol) in DMF (30 mL) was added dropwise a solution of NBS (5.01 g, 28.2 mmol) in DMF (10 mL) under ice-bath. The mixture was stir at 0° C. for 30 min. Then the mixture was poured into cold water, collected the precipitate and dried in vacuum with toluene to afford the title compound (5 g, 83%) as off-white solid. $^1$H NMR (400 MHz, DMSO-d$_6$) δ 11.89 (s, 1H), 7.84 (s, 1H), 7.71 (d, J=2.6 Hz, 1H), 7.47 (s, 1H), 2.57-2.53 (m, 3H). LC-MS: [M+H]$^+$=235.9, 236.9.

Intermediate 1.3

1,4-dioxaspiro[4.5]decan-8-yl 4-methylbenzenesulfonate

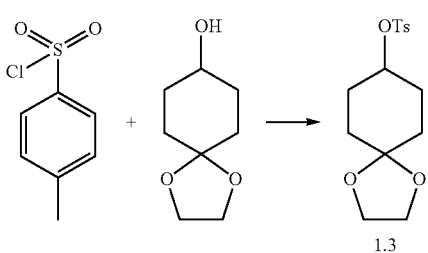 [SMILES: Cc1ccc(S(=O)(=O)Cl)cc1 ; OC1CCC2(CC1)OCCO2 ; Cc1ccc(S(=O)(=O)OC2CCC3(CC2)OCCO3)cc1]

To a solution of 1,4-dioxaspiro[4.5]decan-8-ol (3 g, 18.96 mmol), TEA (3.96 mL, 28.4 mmol), DMAP (0.232 g, 1.896 mmol) in DCM (50 mL) was added TsCl (4.34 g, 22.76 mmol). The mixture was stirred at rt for 20 hr. The mixture was washed with water, brine. The organic layer was dried over magnesium sulfate, filtered and concentrated; the residue was purified by CombiFlash, eluted with ethyl acetate in hexane (5-20%, 30 min). Collected the desired fraction, concentrated in vacuum to afford the title compound (4.5 g, 76%) as colorless syrup. $^1$H NMR (400 MHz, Chloroform-d) δ 7.80 (dd, J=8.3, 2.1 Hz, 2H), 7.33 (d, J=7.9 Hz, 2H), 4.65 (q, J=6.5, 5.1 Hz, 1H), 3.91 (tq, J=8.5, 5.7, 4.6 Hz, 4H), 2.45 (s, 3H), 1.94-1.72 (m, 6H), 1.55 (q, J=9.9, 9.0 Hz, 2H).

Intermediate 1.4

3-bromo-6-methyl-1-(1,4-dioxaspiro[4.5]decan-8-yl)-1H-indole-5-carbonitrile

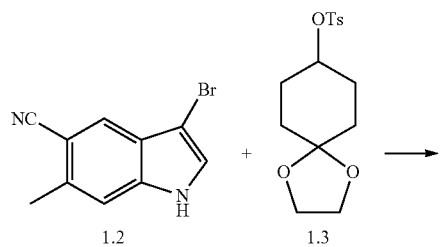

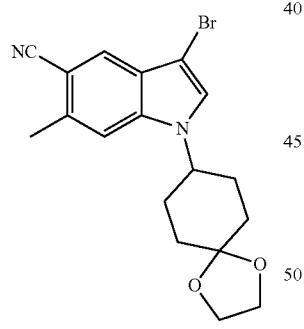

A mixture of 1.2 (6.6 g, 28.1 mmol), Cs$_2$CO$_3$ (27.4 g, 84 mmol) and 1.3 (9.65 g, 30.9 mmol) in DMF (60 mL) was stir at 60° C. for 2 days. Then the mixture was diluted with water, extracted with DCM twice. The organic layer was dried over magnesium sulfate, filtered and concentrated in vacuum. The residue was purified by CombiFlash, eluted with ethyl acetate in hexane (10-30%, 40 min). Collected the desired fraction to afford the title compound (7.8 g, 75%) as white solid. $^1$H NMR (400 MHz, DMSO-d$_6$) δ 7.88 (s, 1H), 7.83 (s, 1H), 7.77 (s, 1H), 4.69-4.50 (m, 1H), 4.04-3.85 (m, 4H), 2.58 (s, 3H), 2.08-1.87 (m, 4H), 1.88-1.69 (m, 4H). LC-MS: [M+H]$^+$=376.1, 377.2.

Intermediate 1.5

3-bromo-6-methyl-1-(4-oxocyclohexyl)-1H-indole-5-carbonitrile

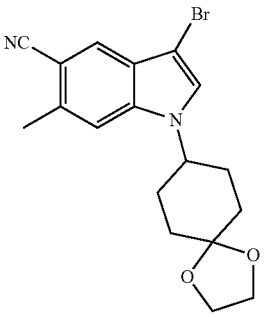

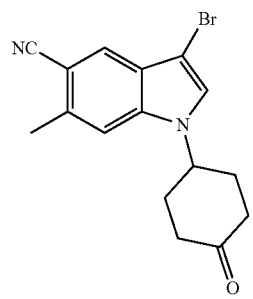

To solution of 1.4 (900 mg, 2.398 mmol) in THF (15 mL) was added hydrochloric acid (6 M, 3 mL). The mixture was stirred at 70° C. for 3 hr. Remove the most organic layer in vacuum, and the residue was extracted with DCM, the organic layer was dried over magnesium sulfate, filtered and concentrated in vacuum, the residue was purified by CombiFlash, eluted with DCM in hexane (20-50%, 30 min), collected the desired fraction to afford the title compound (500 mg, 62.9%) as white solid. $^1$H NMR (400 MHz, Chloroform-d) δ 7.88 (s, 1H), 7.30 (s, 1H), 7.24 (s, 1H), 4.81-4.62 (m, 1H), 2.68 (s, 3H), 2.67-2.55 (m, 4H), 2.43 (d, J=12.8 Hz, 2H), 2.31-2.13 (m, 2H).

Intermediate 1.6

3-bromo-1-(4-hydroxycyclohexyl)-6-methyl-1H-indole-5-carbonitrile

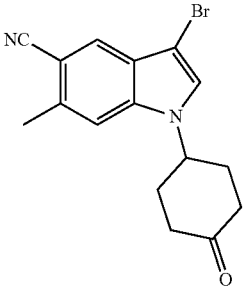

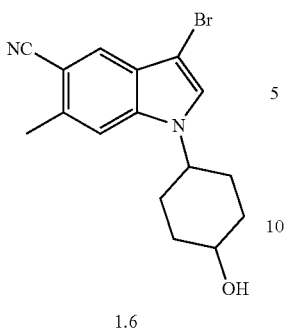

1.6

To a suspension of 1.5 (740 mg, 2.221 mmol) in Methanol (30 mL) was added NaBH$_4$ (126 mg, 3.33 mmol) under ice-bath. The mixture was stirred at 0° C. for 20 min, then most of methanol was removed in vacuum, the residue was re-dissolved in DCM, washed with water, brine. the organic layer was dried over magnesium sulfate, filtered and concentrated in vacuum to afford the title compound (720 mg, 97%) as white solid. $^1$H NMR (400 MHz, Methanol-d$_4$) δ 7.77 (s, 1H), 7.56 (d, J=5.9 Hz, 2H), 4.42 (ddt, J=12.0, 8.1, 3.8 Hz, 1H), 3.77-3.62 (m, 1H), 2.63 (s, 3H), 2.24-1.94 (m, 4H), 1.93-1.80 (m, 2H), 1.68-1.42 (m, 2H). LC-MS: [M+H]$^+$= 334.9, 335.9.

Intermediate 1.7

1-(4-hydroxycyclohexyl)-6-methyl-3-(4,4,5,5-tetramethyl-1,3,2-dioxaborolan-2-yl)-1H-indole-5-carbonitrile

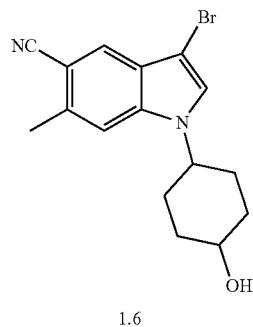

1.6

+

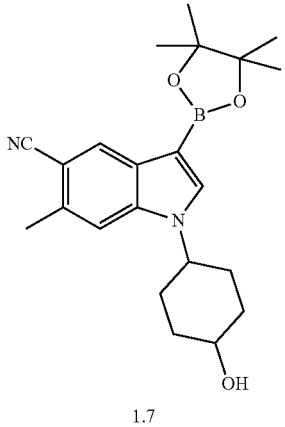

1.7

A solution of 1.6 (600 mg, 1.8 mmol), KOAc (265 mg, 2.7 mmol), Pin$_2$B$_2$(503 mg, 1.98 mmol) and PdCl$_2$(dppf) (132 mg, 0.18 mmol) in dioxane (20 mL) was stirred at 100° C. for 5 hr under nitrogen protection. The mixture was concentrated in vacuum to afford black syrup, it was used for the next directly. LC-MS: [M+H]$^+$=381.0.

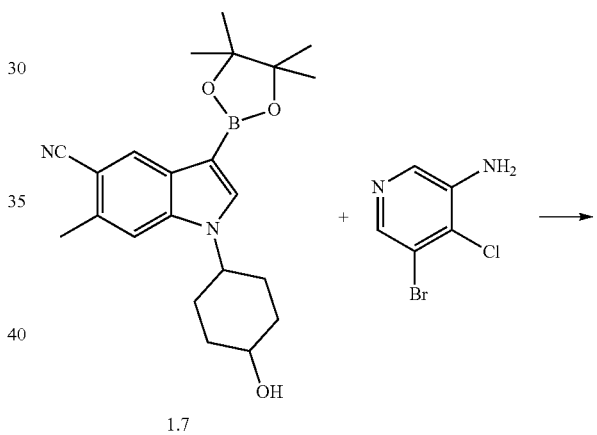

1.7

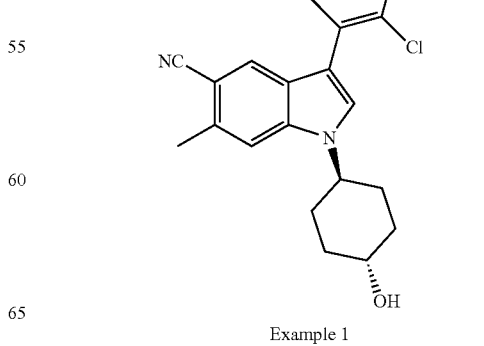

Example 1

47

-continued

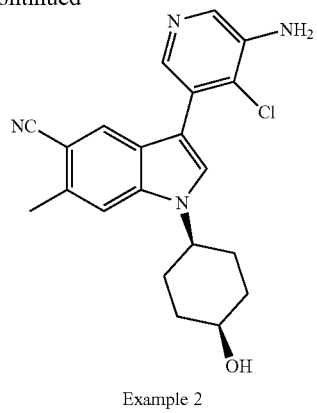

Example 2

To a solution of 1.7 (200 mg, 0.526 mmol), Na$_2$CO$_3$ (111 mg, 1.05 mmol), Pd(PPh$_3$)$_2$Cl$_2$ (36.9 mg, 0.053 mmol) and 5-bromo-4-chloropyridin-3-amine (109 mg, 0.526 mmol) in 2-propanol (5 mL) was added water (1.5 mL). The mixture was stirred at 100° C. for 3 hr under nitrogen protection. Removed the most organic solvents in vacuum, the residue was extracted with DCM twice, the organic layer was dried over magnesium sulfate, filtered and concentrated in vacuum. The residue was purified by CombiFlash, eluted with methanol in DCM (0-5%, 30 min). Collected the desired fraction to afford a brown solid, it was further purified by acidic prep-HPLC. Collected the desired fractions and lyophilized to afford the title compound Example 1 (36.7 mg, 13.4%) and the title compound Example 2 (5.3 mg, 1.9%) as pink powder.

Example 1

$^1$H NMR (400 MHz, Methanol-d$_4$) δ 8.14 (s, 1H), 8.08 (s, 1H), 7.94-7.86 (m, 2H), 7.66 (s, 1H), 4.51 (td, J=10.5, 9.4, 6.3 Hz, 1H), 3.83-3.61 (m, 1H), 2.66 (s, 3H), 2.21-2.06 (m, 4H), 2.04-1.87 (m, 2H), 1.63 (q, J=12.4, 11.9 Hz, 2H). LC-MS: [M+H]$^+$=380.9, 382.0.

Example 2

$^1$H NMR (400 MHz, Methanol-d$_4$) δ 8.11 (d, J=12.5 Hz, 2H), 7.91 (s, 2H), 7.67 (s, 1H), 4.53 (t, J=12.3 Hz, 1H), 4.11 (d, J=3.1 Hz, 1H), 2.66 (s, 3H), 2.38-2.19 (m, 2H), 2.00 (d, J=13.6 Hz, 2H), 1.94-1.81 (m, 4H). LC-MS: [M+H]$^+$=380.9, 382.0.

Example 3

3-(5-amino-4-(difluoromethyl)pyridin-3-yl)-1-((1R, 4R)-4-hydroxycyclohexyl)-6-methyl-1H-indole-5-carbonitrile

48

Example 4

3-(5-amino-4-(difluoromethyl)pyridin-3-yl)-1-((1S, 4S)-4-hydroxycyclohexyl)-6-methyl-1H-indole-5-carbonitrile Intermediate 3.1

1-ethyl 3-methyl 2-(3-bromo-5-nitropyridin-4-yl)malonate

To a suspension of sodium hydride (2.02 g, 60%, 50.5 mmol) in DMF (30 mL) was added diethyl malonate (7.71 mL, 50.5 mmol) under ice-bath. The mixture was stirred at 0° C. for 30 min, and then a solution of 3-bromo-4-chloro-5-nitropyridine (6 g, 25.3 mmol) in DMF (20 mL) was added. The mixture was stirred at 0° C. for 20 min, and then it was allowed to stir at rt for another 2 hours. The reaction was quenched by water (1000 mL), the mixture was extracted with DCM, the organic layer was dried over magnesium sulfate, filtered and concentrated in vacuum to afford brown oil, it was used for the next step directly. LC-MS: [M+H]$^+$=363.1, 364.0.

Intermediate 3.2

3-bromo-4-methyl-5-nitropyridine

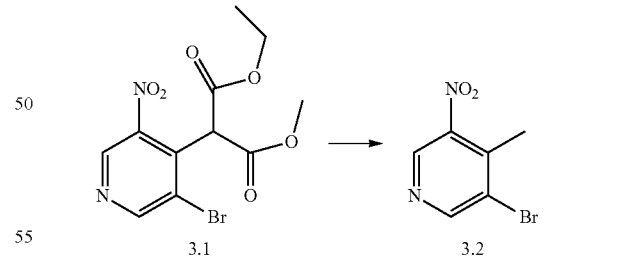

A mixture of 3.1 (8 g, 13.29 mmol) in hydrochloric acid (4M, 50 mL, 200 mmol) was stirred at rt for 20 h. The mixture was basified by aqueous of NaOH (10 M) to pH=10 under ice-bath. Then it was extracted with DCM, the organic layer was dried over magnesium sulfate, filtered and concentrated in vacuum, the residue was purified by Combi-Flash, eluted with ethyl acetate in hexane (5-15%, 30 min), collected the desired fraction to afford the title compound (2.1 g, 73.4%) as yellow solid. $^1$H NMR (400 MHz, DMSO-d$_6$) δ 9.06 (s, 1H), 9.02 (s, 1H), 2.56 (s, 3H).

Intermediate 3.3

3-bromo-5-nitroisonicotinaldehyde

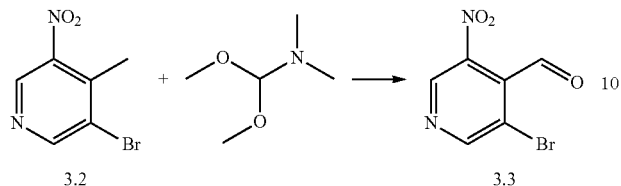

To a solution of 3.2 (2.1 g, 9.68 mmol) in DMF (10 mL) was added DMF-DMA (2.59 mL, 19.35 mmol). The mixture was stirred at 90° C. for 3 h. Then the mixture was cooled to rt, diluted with THF (25 mL). Then a solution of NaIO$_4$ (6.13 g, 28.7 mmol) in water (25 mL) was added. The mixture was stirred at rt for 20 hr. Then the mixture was concentrated in vacuum. The mixture was diluted with water, extracted with DCM. The organic layer was dried over magnesium sulfate, filtered and the filter was purified by CombiFlash, eluted with ethyl acetate in hexane (5-20%, 30 min), collected the desired fraction to afford the title compound (1.6 g, 72.5%) as white solid. $^1$H NMR (400 MHz, Chloroform-d) δ 10.27 (s, 1H), 9.30 (s, 1H), 9.11 (s, 1H).

Intermediate 3.4

3-bromo-4-(difluoromethyl)-5-nitropyridine

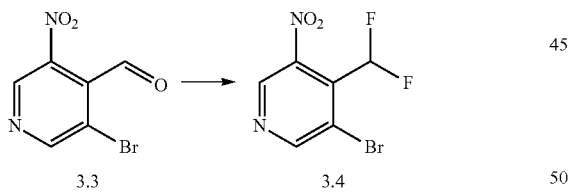

To a solution of 3.3 (200 mg, 0.866 mmol) in DCM (5 mL) was added DAST (0.343 mL, 2.60 mmol) under ice-bath. The mixture was stirred at 0° C. for 30 min, and then it was allowed to stir at rt for another 2 days. The mixture was quenched with water, the organic layer was dried over magnesium sulfate, filtered and concentrated, the residue was purified by CombiFlash, eluted with ethyl acetate in hexane (0-15%, 30 min), collected the desired fraction, and concentrated to afford the title compound (160 mg, 73%) as colorless syrup. $^1$H NMR (400 MHz, Chloroform-d) δ 9.05 (s, 1H), 8.97 (s, 1H), 7.07 (t, J=52.5 Hz, 1H).

Intermediate 3.5

5-bromo-4-(difluoromethyl)pyridin-3-amine

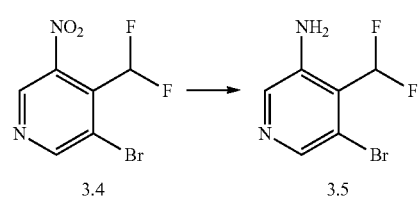 [SMILES: O=[N+]([O-])c1cncc(Br)c1C(F)F ; Nc1cncc(Br)c1C(F)F]

To a solution of 3.4 (180 mg, 0.711 mmol) and nickel (II) chloride hexahydrate (338 mg, 1.423 mmol) in methanol (6 mL) was added NaBH$_4$ (108 mg, 2.85 mmol) under ice-bath. The mixture was stirred at 0° C. for 20 min. Removed the methanol in vacuum, the residue was re-dissolved in DCM and water, the organic layer was dried over magnesium sulfate, filtered and concentrated to afford the title compound (100 mg, 63%) as yellow solid. It was used for the next step directly. $^1$H NMR (400 MHz, Chloroform-d) b 8.19-7.99 (m, 2H), 7.10 (t, J=53.4 Hz, 1H), 4.49 (s, 2H). LC-MS: [M+H]$^+$=225.0, 226.0.

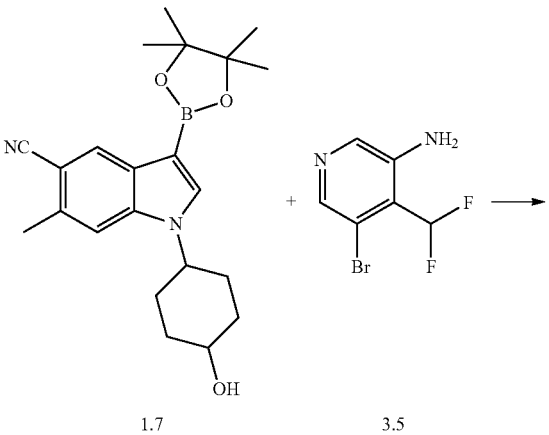

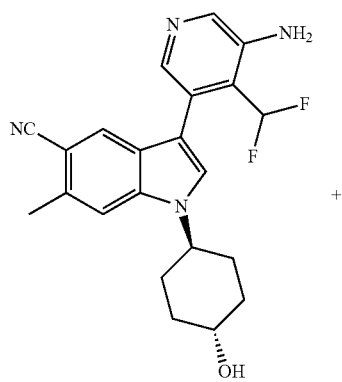

Example 3

-continued

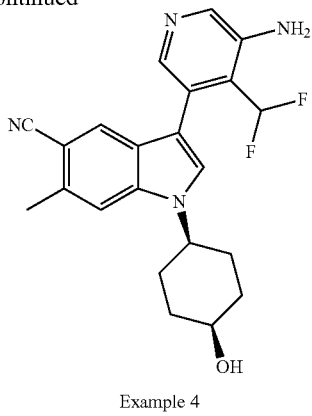

Example 4

The title compounds were prepared by using a procedure similar to that of Example 1 by replacing 5-bromo-4-chloropyridin-3-amine with intermediate 3.5.

Example 3

$^1$H NMR (400 MHz, Methanol-$d_4$) δ 8.21 (s, 1H), 7.97 (s, 1H), 7.83 (s, 1H), 7.68 (d, J=9.9 Hz, 2H), 6.77 (t, J=52.8 Hz, 1H), 4.50 (dq, J=12.0, 6.0, 3.8 Hz, 1H), 3.75 (td, J=11.2, 5.5 Hz, 1H), 2.65 (s, 3H), 2.15 (d, J=10.0 Hz, 4H), 2.06-1.86 (m, 2H), 1.72-1.52 (m, 2H). LC-MS: [M+H]$^+$=397.0, 398.0

Example 4

$^1$H NMR (400 MHz, Methanol-$d_4$) δ 8.17 (s, 1H), 7.91 (s, 1H), 7.81 (s, 1H), 7.66 (d, J=4.6 Hz, 2H), 6.73 (t, J=53.1 Hz, 1H), 4.52 (t, J=12.0 Hz, 1H), 4.10 (s, 1H), 2.66 (s, 3H), 2.26 (q, J=11.8 Hz, 2H), 2.02-1.83 (m, 6H). LC-MS: [M+H]$^+$= 397.0, 398.0.

Example 5

3-(5-amino-4-fluoropyridin-3-yl)-1-((1R,4R)-4-hydroxycyclohexyl)-6-methyl-1H-indole-5-carbonitrile Example 6

3-(5-amino-4-fluoropyridin-3-yl)-1-((1S,4S)-4-hydroxycyclohexyl)-6-methyl-1H-indole-5-carbonitrile Intermediate 5.1

3-bromo-4-fluoro-5-nitropyridine

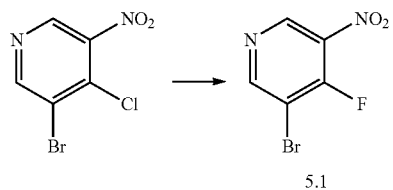 [SMILES: O=[N+]([O-])c1cncc(Br)c1Cl ; O=[N+]([O-])c1cncc(Br)c1F]

A suspension of 3-bromo-4-chloro-5-nitropyridine (3 g, 12.363 mmol) and KF (2.94 g, 50.5 mmol) in DMF (20 mL) was stirred at 50° C. for 2 hr. Then the mixture was filtered, and the filter was diluted with ethyl acetate, washed by water, brine. The organic layer was dried over magnesium sulfate, filtered and concentrated, the residue was purified by CombiFlash, eluted with ethyl acetate in hexane (0-10%, 40 min), collected the desired fraction to afford (250 mg, 8.4%) as yellow solid. LC-MS: [M–H]$^-$=219.8, 220.8.

Intermediate 5.2

5-bromo-4-fluoropyridin-3-amine

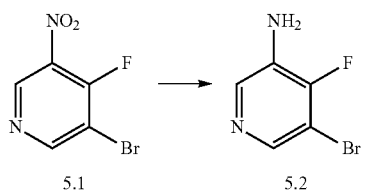 [SMILES: O=[N+]([O-])c1cncc(Br)c1F ; Nc1cncc(Br)c1F]

The title compound was prepared by using a procedure similar to that of intermediate 3.5 by replacing intermediate 3.4 with intermediate 5.1. $^1$H NMR (400 MHz, Chloroform-d) δ 8.36-7.80 (m, 2H), 3.85 (s, 2H). LC-MS: [M+H]$^+$= 192.8, 193.8.

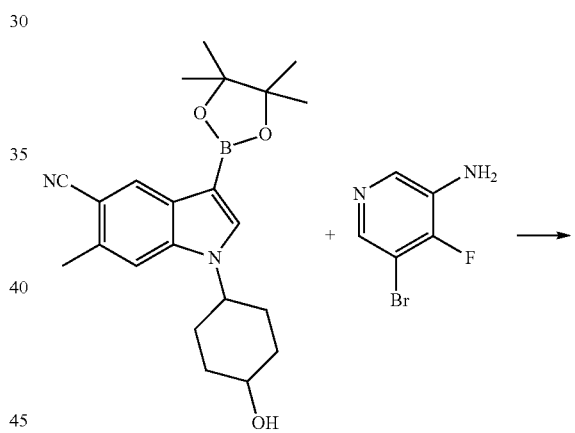

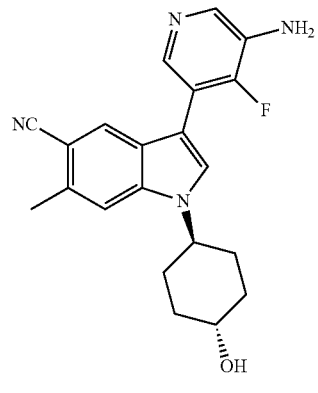

Example 5

-continued

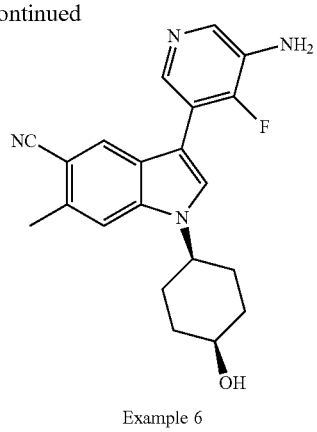

Example 6

The title compounds were prepared by using a procedure similar to that of Example 1 by replacing 5-bromo-4-chloropyridin-3-amine with intermediate 5.2.

Example 5

$^1$H NMR (400 MHz, Methanol-d$_4$) δ 8.08-7.90 (m, 3H), 7.77 (s, 1H), 7.60 (s, 1H), 4.48 (s, 1H), 3.74 (s, 1H), 2.65 (s, 3H), 2.25-2.07 (m, 4H), 2.06-1.90 (m, 2H), 1.62 (d, J=12.6 Hz, 2H). LC-MS: [M+H]$^+$=364.9, 365.9.

Example 6

$^1$H NMR (400 MHz, Methanol-d$_4$) δ 8.05 (d, J=2.5 Hz, 1H), 8.03 (d, J=0.8 Hz, 1H), 7.98 (d, J=1H), 7.79 (d, J=1.1 Hz, 1H), 7.61 (s, 1H), 4.48 (d, J=11.9 Hz, 1H), 4.09 (s, 1H), 2.65 (s, 3H), 2.27 (q, J=13.0, 12.4 Hz, 2H), 2.00 (d, J=14.2 Hz, 2H), 1.87 (t, J=11.7 Hz, 4H). LC-MS: [M+H]$^+$=364.9, 365.9.

Example 7

3-(5-amino-4-chloropyridin-3-yl)-6-chloro-1-((1R, 4R)-4-hydroxycyclohexyl)-1H-indole-5-carbonitrile Example 8

3-(5-amino-4-chloropyridin-3-yl)-6-chloro-1-((1S, 4S)-4-hydroxycyclohexyl)-1H-indole-5-carbonitrile Intermediate 7.2

3-bromo-6-chloro-1H-indole-5-carbonitrile

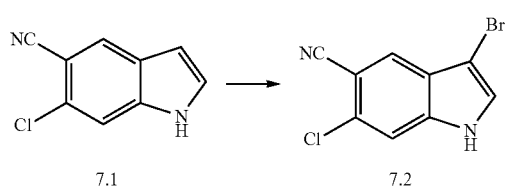 [SMILES: N#Cc1cc2cc[nH]c2cc1Cl ; N#Cc1cc2c(Br)c[nH]c2cc1Cl]

The title compound was prepared by using a procedure similar to that of intermediate 1.2 by intermediate 1.1 with intermediate 7.1. $^1$H NMR (400 MHz, DMSO-d$_6$) δ 12.17 (s, 1H), 8.07 (s, 1H), 7.84 (d, J=2.6 Hz, 1H), 7.77 (s, 1H). LC-MS: [M+H]$^+$=254.8, 256.8.

Intermediate 7.3

3-bromo-6-chloro-1-(1,4-dioxaspiro[4.5]decan-8-yl)-1H-indole-5-carbonitrile

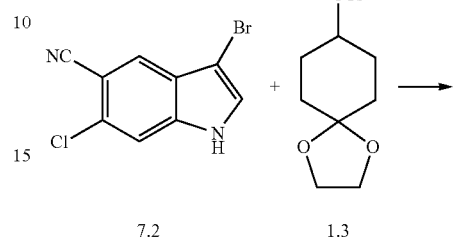

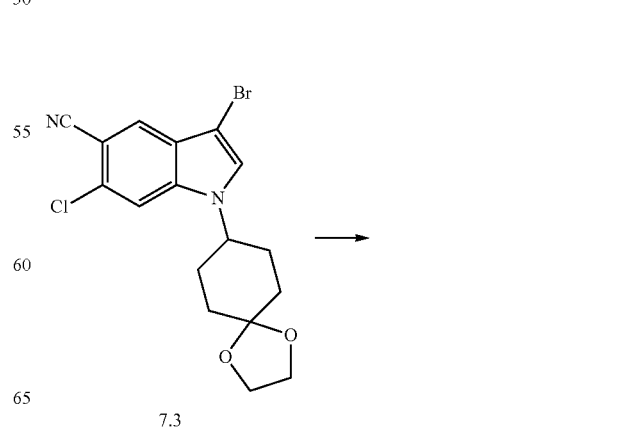

The title compound was prepared by using a procedure similar to that of intermediate 1.4 by replacing intermediate 1.2 with intermediate 7.2. $^1$H NMR (400 MHz, Chloroform-d) δ 7.90 (d, J=1.3 Hz, 1H), 7.50 (d, J=1.3 Hz, 1H), 7.36 (d, J=1.3 Hz, 1H), 4.24 (tt, J=10.8, 6.0 Hz, 1H), 4.01 (q, J=2.2 Hz, 4H), 3.91 (tt, J=6.4, 3.2 Hz, 1H), 2.16-2.00 (m, 4H), 1.94 (d, J=13.3 Hz, 2H), 1.80 (dd, J=11.7, 6.3 Hz, 2H). LC-MS: [M+H]$^+$=394.7, 396.7.

Intermediate 7.4

3-bromo-6-chloro-1-(4-oxocyclohexyl)-1H-indole-5-carbonitrile

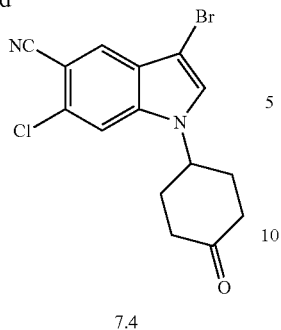

7.4

The title compound was prepared by using a procedure similar to that of intermediate 1.5 by replacing intermediate 1.4 with intermediate 7.3. LC-MS: [M−H]⁻=350.8, 352.8.

Intermediate 7.5

3-bromo-6-chloro-1-(4-hydroxycyclohexyl)-1H-indole-5-carbonitrile

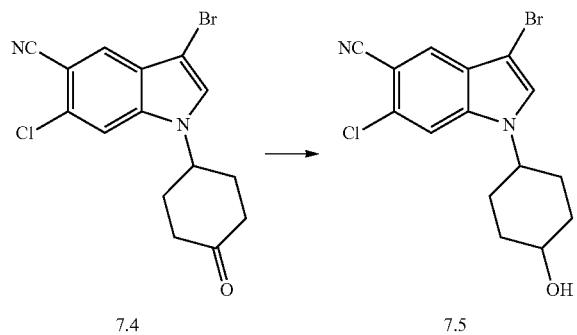 [SMILES: N#Cc1cc2c(Br)cn(C3CCC(=O)CC3)c2cc1Cl ; N#Cc1cc2c(Br)cn(C3CCC(O)CC3)c2cc1Cl]

The title compound was prepared by using a procedure similar to that of intermediate 1.6 by replacing intermediate 1.5 with intermediate 7.4. LC-MS: [M+H]⁺=352.8, 354.8.

Intermediate 7.6

6-chloro-1-(4-hydroxycyclohexyl)-3-(4,4,5,5-tetramethyl-1,3,2-dioxaborolan-2-yl)-1H-indole-5-carbonitrile

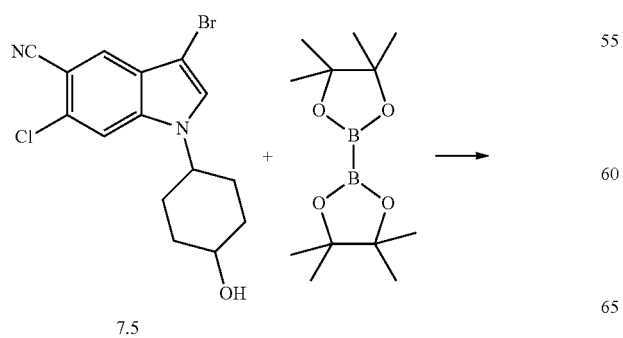

7.5

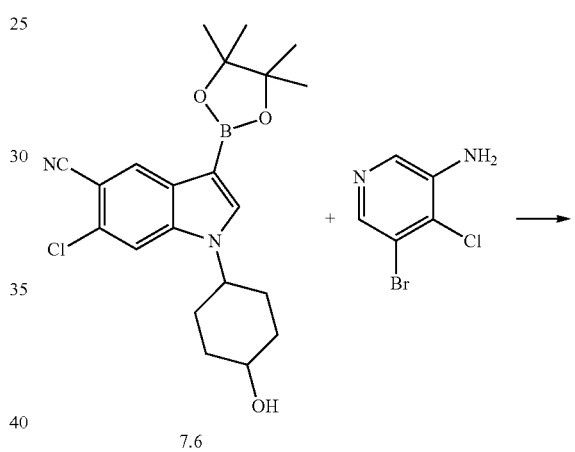

7.6

The title compound was prepared by using a procedure similar to that of intermediate 1.7 by replacing intermediate 1.6 with intermediate 7.5. LC-MS: [M+H]⁺=400.2, 402.2.

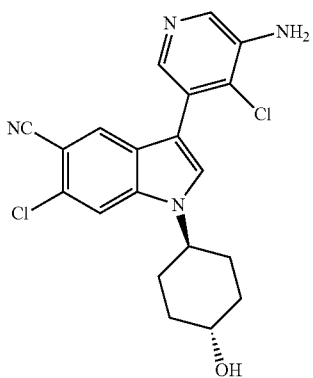

Example 7

-continued

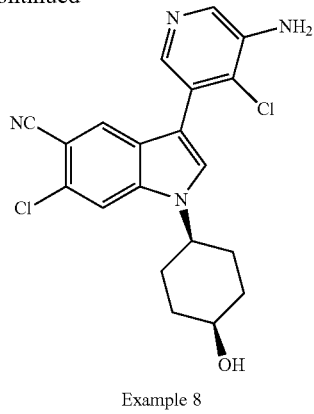

Example 8

The title compounds were prepared by using a procedure similar to that of Example 1 by replacing intermediate 1.7 with intermediate 7.6.

Example 7

$^1$H NMR (500 MHz, DMSO-d$_6$) δ 8.19 (s, 1H), 8.09 (s, 1H), 7.99 (s, 1H), 7.97 (s, 1H), 7.82 (s, 1H), 5.75 (s, 2H), 4.58 (s, 1H), 3.56 (s, 1H), 1.93 (q, J=13.3, 11.5 Hz, 6H), 1.49 (d, J=11.6 Hz, 2H). LC-MS: [M+H]$^+$=400.8, 402.8.

Example 8

$^1$H NMR (500 MHz, DMSO-d$_6$) δ 8.15 (s, 1H), 8.09 (s, 1H), 7.99 (s, 1H), 7.96 (s, 1H), 7.85 (s, 1H), 5.75 (s, 2H), 4.59 (s, 1H), 4.55 (d, J=3.8 Hz, 1H), 3.93 (s, 1H), 2.24-2.12 (m, 2H), 1.82 (d, J=13.0 Hz, 2H), 1.74 (t, J=12.0 Hz, 4H). LC-MS: [M+H]$^+$=400.8, 402.8.

Example 9

Trans-3-(5-amino-4-chloropyridin-3-yl)-1-((1R,3R)-3-hydroxycyclohexyl)-6-methyl-1H-indole-5-carbonitrile Intermediate 9.1

3-((tert-butyldimethylsilyl)oxy)cyclohexan-1-ol

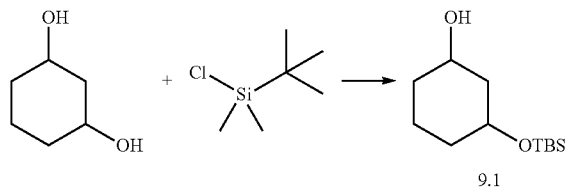

To a solution of cyclohexane-1,3-diol (5 g, 43.0 mmol) and imidazole (4.40 g, 64.6 mmol) in DMF (20 mL) was added TBSCl (7.79 g, 51.7 mmol). The mixture was stirred at rt for overnight. The mixture was diluted with water, extracted with DCM twice. The organic layer was dried over magnesium sulfate, filtered and concentrated in vacuum. The residue was purified by CombiFlash, eluted with methanol in DCM (0-5%, 30 min) to afford the title compound (7.5 g, 76%) as colorless syrup. $^1$H NMR (500 MHz, Chloroform-d) δ 4.19-3.92 (m, 1H), 3.83 (s, 1H), 2.22-1.07 (m, 8H), 0.89 (d, J=9.4 Hz, 9H), 0.08-0.00 (m, 6H). LC-MS: [M+H]$^+$=231.1.

Intermediate 9.2

3-((tert-butyldimethylsilyl)oxy)cyclohexyl 4-methylbenzenesulfonate

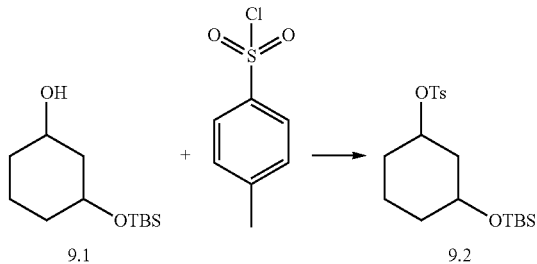 [SMILES: CC(C)(C)[Si](C)(C)OC1CCCC(O)C1 ; Cc1ccc(S(=O)(=O)Cl)cc1 ; Cc1ccc(S(=O)(=O)OC2CCCC(O[Si](C)(C)C(C)(C)C)C2)cc1]

To a solution of 9.1 (8.5 g, 85%, 31.4 mmol) and DMAP (7.66 g, 62.7 mmol) in DCM (150 mL) was added TsCl (7.17 g, 37.6 mmol) under ice-bath. The mixture was stirred at rt for 20 hr. The mixture was washed with water, brine. The organic layer was dried over magnesium sulfate, filtered and concentrated in vacuum. The residue was purified by CombiFlash, eluted with ethyl acetate in hexane (0-10%, 40 min), collected the desired fraction to afford 10.8 g colorless syrup. $^1$H NMR (400 MHz, DMSO-d$_6$) δ 7.95-7.74 (m, 2H), 7.65-7.44 (m, 2H), 4.72-4.36 (m, 1H), 4.10-3.52 (m, 1H), 2.46 (d, J=1.3 Hz, 3H), 1.82-1.09 (m, 8H), 0.83 (d, J=3.3 Hz, 9H), 0.05--0.05 (m, 6H). LC-MS: [M+H]$^+$=384.8.

Intermediate 9.3 & 9.4

3-bromo-1-((1R,3R)-3-((tert-butyldimethylsilyl)oxy) cyclohexyl)-6-methyl-1H-indole-5-carbonitrile (trans relative) & 3-bromo-1-((1R,3S)-3-((tert-butyldimethylsilyl)oxy)cyclohexyl)-6-methyl-1H-indole-5-carbonitrile (cis relative)

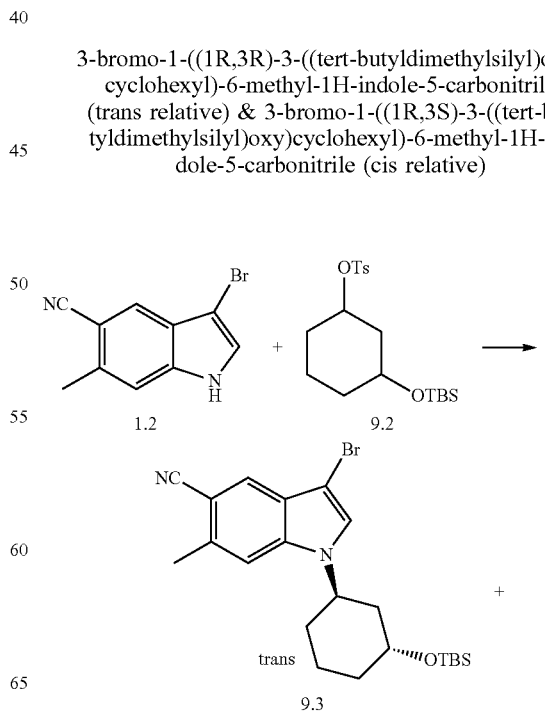

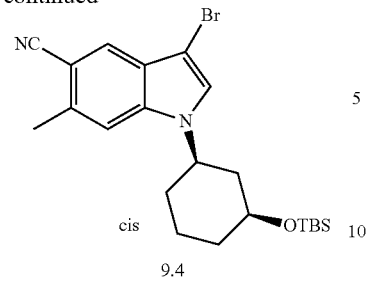

9.4

A mixture of 1.2 (2 g, 5.1 mmol), Cs₂CO₃ (3.33 g, 10.21 mmol) and 9.2 (2.16 g, 5.62 mmol) in DMF (20 mL) was stirred at 70° C. for 5 h. The mixture was diluted with DCM, washed with water, brine. The organic layer was dried over magnesium sulfate, filtered and concentrated in vacuum, then the residue was purified by CombiFlash, eluted with ethyl acetate in hexane (5-15%, 30 min). Collected the desired fraction to afford the titled compound 9.3 (760 mg) and compound 9.4 (250 mg) as white solid. The structure was confirmed after removing the TBS protecting group in the next step.

Intermediate 9.5

3-bromo-1-((1R,3R)-3-hydroxycyclohexyl)-6-methyl-1H-indole-5-carbonitrile (trans relative)

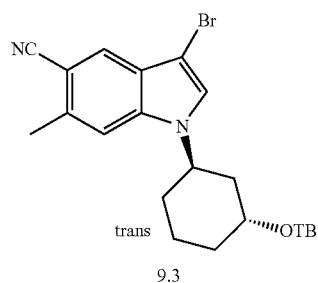

9.3

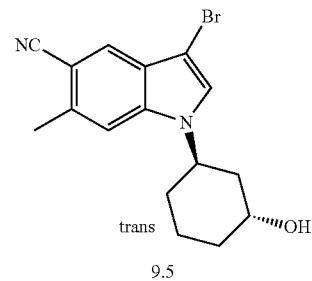

9.5

To a solution of 9.3 (760 mg, 1.698 mmol) in THF (20 mL) was added a solution of a solution of TBAF in THF (1M, 6.79 mL, 6.79 mmol). The mixture was stirred at rt for 1 hr. The mixture was diluted with DCM, washed with water, brine. The organic layer was dried over magnesium sulfate, filtered and concentrated in vacuum. Then the residue was purified by CombiFlash, eluted with methanol in DCM (0-5%, 30 min) collected the desired fraction to afford the title compound (440 mg, 78%) as white solid. ¹H NMR (400 MHz, Chloroform-d) δ 7.84 (s, 1H), 7.30 (s, 1H), 7.25 (s, 1H), 4.74 (tt, J=12.1, 3.8 Hz, 1H), 4.40 (p, J=3.0 Hz, 1H), 2.70-2.58 (m, 3H), 2.19 (ddq, J=12.9, 3.9, 1.9 Hz, 1H), 2.12 (dtd, J=12.6, 3.7, 1.8 Hz, 1H), 2.08-1.93 (m, 1H), 1.87 (dt, J=12.6, 2.8 Hz, 5H). LC-MS: [M+H]⁺=332.8, 335.8.

Intermediate 9.6

1-((1R,3R)-3-hydroxycyclohexyl)-6-methyl-3-(4,4,5,5-tetramethyl-1,3,2-dioxaborolan-2-yl)-1H-indole-5-carbonitrile (trans relative)

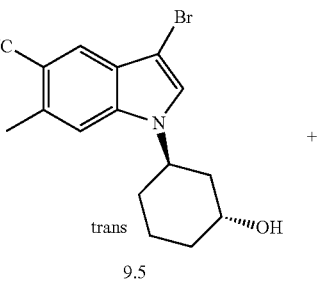

9.5

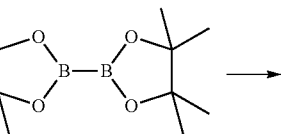

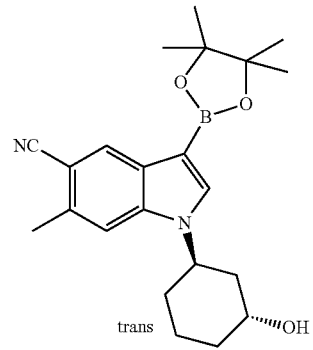

9.6

The title compound was prepared by using a procedure similar to that of intermediate 1.7 by replacing intermediate 1.6 with intermediate 9.5. LC-MS: [M+H]⁺=381.3.

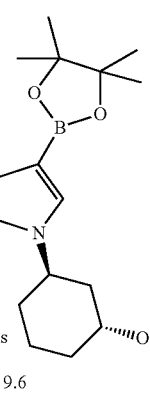

9.6

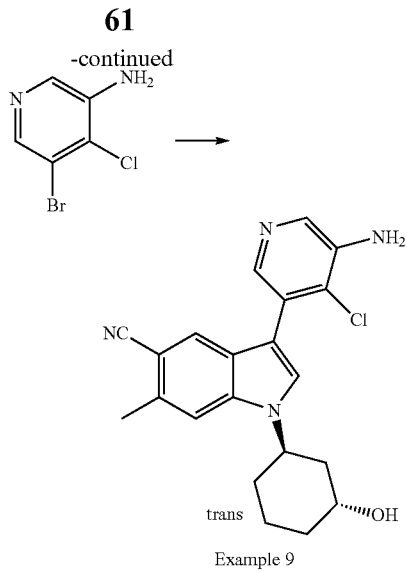

Example 9

The title compound was prepared by using a procedure similar to that of Example 1 by replacing intermediate 1.7 with intermediate 9.6. $^1$H NMR (400 MHz, Methanol-$d_4$) δ 8.04 (s, 1H), 7.84 (s, 1H), 7.77 (s, 1H), 7.71 (s, 1H), 7.60 (s, 1H), 4.84 (ddd, J=12.1, 8.2, 3.7 Hz, 1H), 4.30 (p, J=3.0 Hz, 1H), 2.64 (s, 3H), 2.20-1.97 (m, 4H), 1.96-1.81 (m, 2H), 1.81-1.72 (m, 1H), 1.62 (tdd, J=13.5, 4.3, 2.6 Hz, 1H). LC-MS: [M+H]$^+$=381.2, 382.2.

Example 10

Cis-3-(5-amino-4-chloropyridin-3-yl)-1-((1R, 3S)-3-hydroxycyclohexyl)-6-methyl-1H-indole-5-carbonitrile Intermediate 10.1

3-bromo-1-((1R,3S)-3-hydroxycyclohexyl)-6-methyl-1H-indole-5-carbonitrile (cis relative)

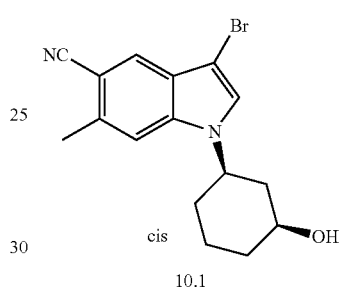

The title compound was prepared by using a procedure similar to that of intermediate 9.5 by replacing intermediate 9.3 with intermediate 9.4. $^1$H NMR (400 MHz, Chloroform-d) δ 7.86 (s, 1H), 7.26 (s, 1H), 7.23 (s, 1H), 4.25 (tt, J=12.0, 3.7 Hz, 1H), 3.86 (tt, J=10.9, 4.2 Hz, 1H), 2.66 (d, J=0.8 Hz, 3H), 2.41 (ddt, J=9.8, 4.0, 2.0 Hz, 1H), 2.22-1.94 (m, 3H), 1.71 (q, J=11.7 Hz, 1H), 1.64 (d, J=3.4 Hz, 1H), 1.49 (tt, J=13.1, 3.1 Hz, 1H), 1.40-1.26 (m, 1H). LC-MS: [M+H]$^+$= 332.8, 335.8.

Intermediate 10.2

1-((1R,3S)-3-hydroxycyclohexyl)-6-methyl-3-(4,4,5,5-tetramethyl-1,3,2-dioxaborolan-2-yl)-1H-indole-5-carbonitrile(cis relative)

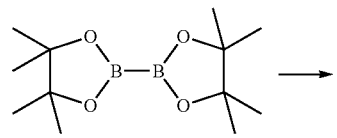

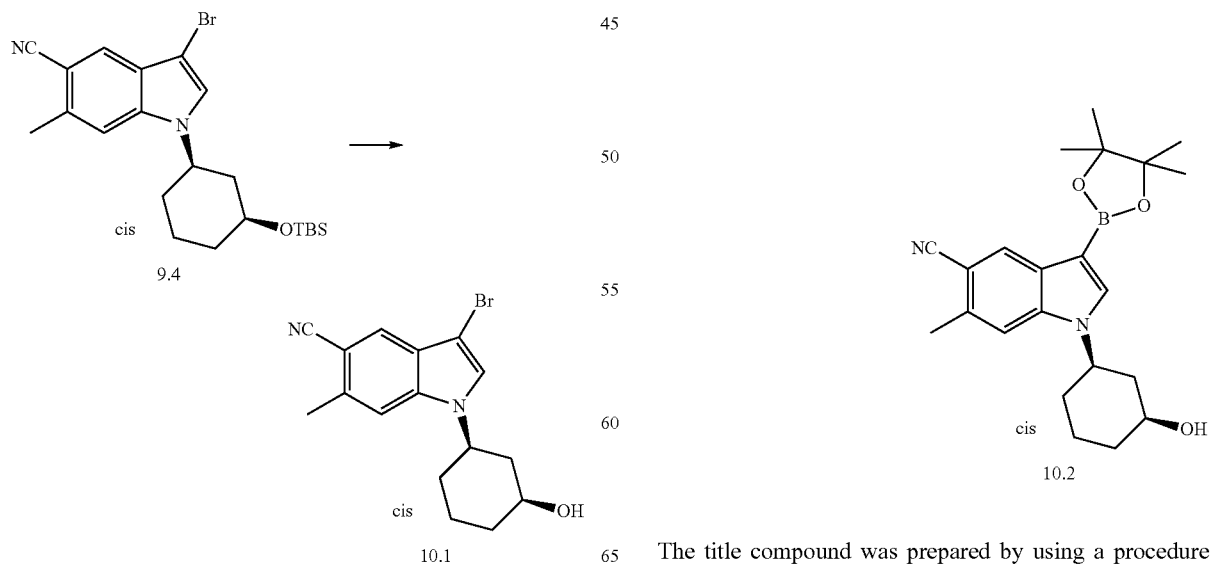

The title compound was prepared by using a procedure similar to that of intermediate 1.7 by replacing intermediate 1.6 with intermediate 10.1. LC-MS: [M+H]$^+$=381.3.

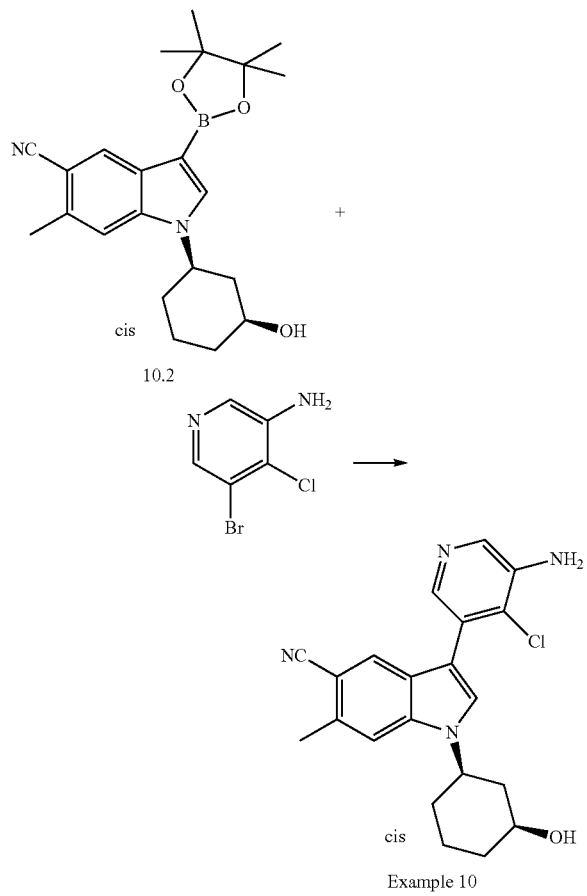

10.2

+

Example 10

The title compound was prepared by using a procedure similar to that of Example 1 by replacing intermediate 1.7 with intermediate 10.2. ¹H NMR (400 MHz, Methanol-d₄) δ 8.05 (s, 1H), 7.84 (s, 1H), 7.77 (s, 1H), 7.72 (s, 1H), 7.59 (s, 1H), 4.64-4.39 (m, 1H), 3.83 (tt, J=11.0, 4.2 Hz, 1H), 2.64 (s, 3H), 2.36 (ddq, J=11.6, 4.1, 1.9 Hz, 1H), 2.14-2.00 (m, 2H), 1.96 (dt, J=13.2, 3.2 Hz, 1H), 1.91-1.68 (m, 2H), 1.61 (ddt, J=16.6, 13.2, 6.5 Hz, 1H), 1.47-1.21 (m, 1H). LC-MS: [M+H]⁺=380.2, 382.2.

Example 11

Trans-3-(5-amino-4-chloropyridin-3-yl)-1-((1R,3R)-3-hydroxycyclopentyl)-6-methyl-1H-indole-5-carbonitrile Intermediate 11.1

3-((tert-butyldimethylsilyl)oxy)cyclopentan-1-ol

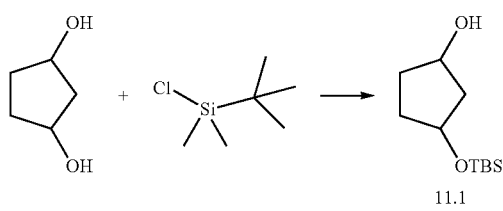

11.1

To a solution of cyclopentane-1,3-diol (3.2 g, 31.3 mmol) and imidazole (4.27 g, 62.7 mmol) in DMF (30 mL) was added TBSCl (5.19 g, 34.5 mmol). The mixture was stirred at rt for 2 days. The mixture was diluted with water (200 mL), extracted with DCM twice, the organic layer was dried over magnesium sulfate, filtered and concentrated, the residue was purified by CombiFlash, eluted with methanol in DCM (0-5%, 40 min) to afford the title compound (2.5 g, 40%) as colorless oil. ¹H NMR (400 MHz, Chloroform-d) δ 4.40 (dt, J=15.9, 4.6 Hz, 2H), 2.00 (dtd, J=29.1, 16.0, 14.5, 8.0 Hz, 2H), 1.78 (q, J=5.2 Hz, 2H), 1.49 (td, J=11.9, 9.6, 4.6 Hz, 2H), 0.83 (s, 9H), 0.08--0.04 (m, 6H).

Intermediate 11.2

3-((tert-butyldimethylsilyl)oxy)cyclopentyl 4-methylbenzenesulfonate

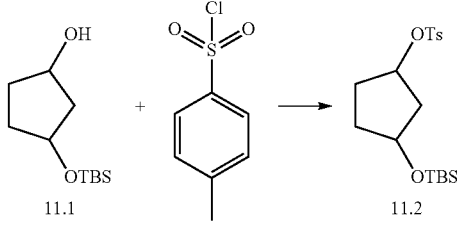 [SMILES: CC(C)(C)[Si](C)(C)OC1CCC(O)C1 ; Cc1ccc(S(=O)(=O)Cl)cc1 ; Cc1ccc(S(=O)(=O)OC2CCC(O[Si](C)(C)C(C)(C)C)C2)cc1]

11.1    11.2

To a solution of 11.1 (2 g, 9.24 mmol) DMAP (1.36 g, 11.09 mmol) in DCM (40 mL) was added TsCl (2.12 g, 11.09 mmol) under ice-bath. The mixture was allowed to stir at rt for another 20 hr. The mixture was washed with water, brine. The organic layer was dried over magnesium sulfate, filtered and the filter was concentrated in vacuum, the residue was purified by CombiFlash, eluted with ethyl acetate in hexane (0-10%, 30 min). Collected the desired fraction and concentrated to afford the title compound (2.95 g, 86%) as colorless syrup. ¹H NMR (400 MHz, Chloroform-d) δ 7.84-7.68 (m, 2H), 7.42-7.29 (m, 2H), 5.02 (tt, J=6.6, 3.3 Hz, 1H), 4.34 (ddd, J=5.9, 4.1, 1.9 Hz, 1H), 2.45 (s, 3H), 2.13-1.73 (m, 6H), 0.83 (s, 9H), -0.00 (d, J=2.1 Hz, 6H).

Intermediate 11.3

3-bromo-1-((1R,3R)-3-((tert-butyldimethylsilyl)oxy)cyclopentyl)-6-methyl-1H-indole-5-carbonitrile (trans relative)

Intermediate 11.4

3-bromo-1-((1R,3S)-3-((tert-butyldimethylsilyl)oxy)cyclopentyl)-6-methyl-1H-indole-5-carbonitrile (cis relative)

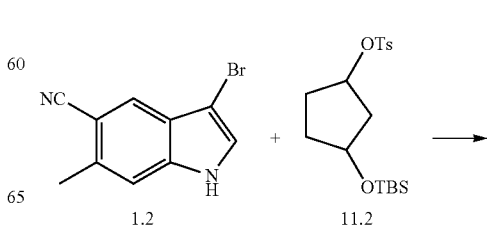

1.2    11.2

-continued

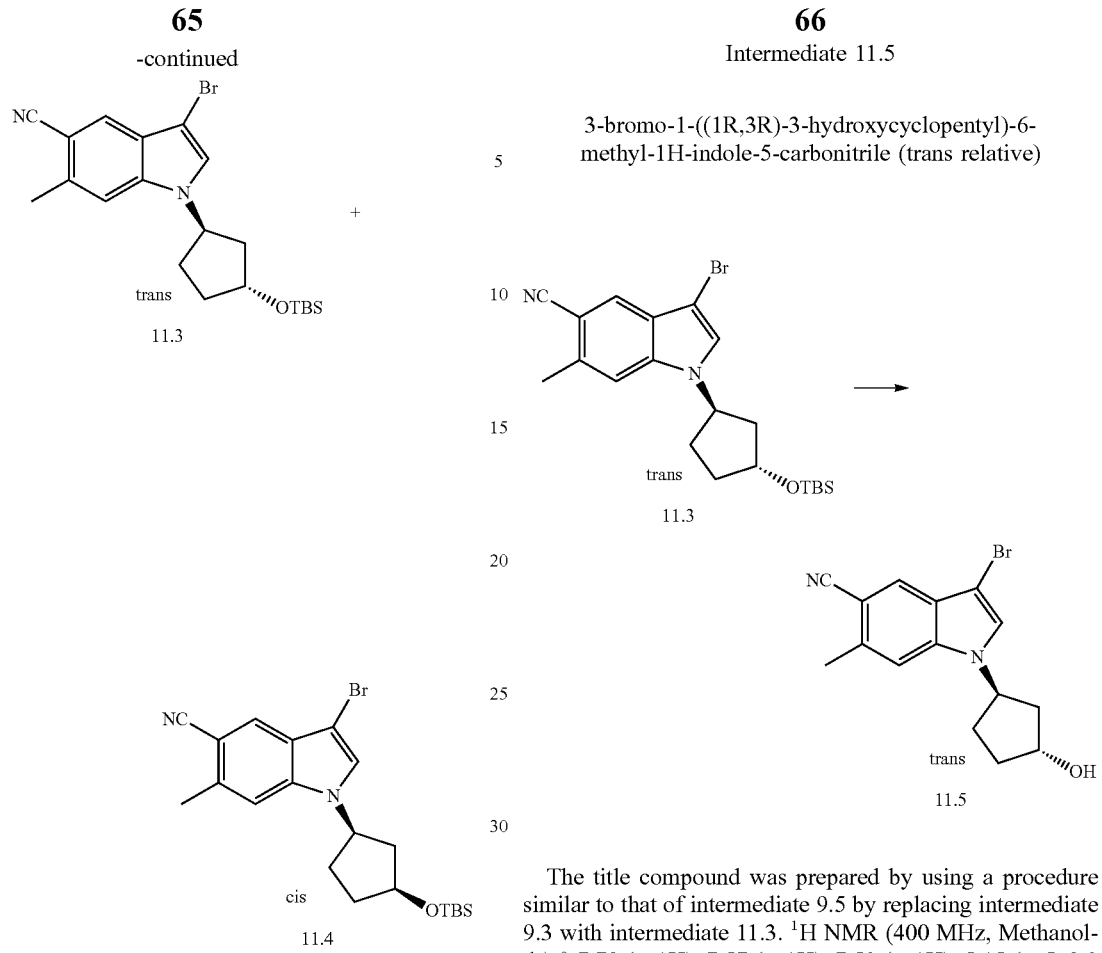

A mixture of 1.2 (1.8 g, 7.66 mmol), Cs₂CO₃ (3.74 g, 11.45 mmol) and 11.2 (2.84 g, 7.66 mmol) in DMF (30 mL) was stirred at 80° C. for 3 h. Then the mixture was cooled to rt, water was added, extracted with DCM twice, the organic layer was dried over magnesium sulfate, filtered and concentrated in vacuum. The residue was purified by CombiFlash, eluted with ethyl acetate in hexane (0-5%, 30 min), collected the desired fractions to afford the title compound 11.3 (150 mg, 4.52% yield) and the title compound 11.4 (2.1 g, 63.3%).

Intermediate 11.3

$^1$H NMR (400 MHz, Chloroform-d) δ 7.75 (s, 1H), 7.17 (s, 1H), 7.12 (s, 1H), 4.93 (p, J=7.9 Hz, 1H), 4.41 (dt, J=5.5, 2.8 Hz, 1H), 2.57 (d, J=0.9 Hz, 3H), 2.44-2.28 (m, 1H), 2.16-2.10 (m, 1H), 2.04 (dtd, J=13.1, 6.2, 3.2 Hz, 1H), 1.91 (ddd, J=13.7, 8.8, 5.5 Hz, 1H), 1.79-1.64 (m, 2H), 0.83 (s, 9H), 0.00 (s, 6H).

Intermediate 11.4

$^1$H NMR (400 MHz, Chloroform-d) δ 7.72 (s, 1H), 7.53 (s, 1H), 7.16 (s, 1H), 4.75 (dtd, J=11.9, 7.7, 4.1 Hz, 1H), 4.33 (dt, J=5.2, 2.6 Hz, 1H), 2.53 (d, J=0.7 Hz, 3H), 2.32 (ddd, J=15.0, 9.7, 5.5 Hz, 1H), 2.15 (dtd, J=13.1, 7.9, 3.3 Hz, 1H), 2.05-1.94 (m, 1H), 1.86-1.72 (m, 3H), 0.83 (s, 9H), −0.00 (d, J=2.7 Hz, 6H).

Intermediate 11.5

3-bromo-1-((1R,3R)-3-hydroxycyclopentyl)-6-methyl-1H-indole-5-carbonitrile (trans relative)

The title compound was prepared by using a procedure similar to that of intermediate 9.5 by replacing intermediate 9.3 with intermediate 11.3. $^1$H NMR (400 MHz, Methanol-d₄) δ 7.78 (s, 1H), 7.57 (s, 1H), 7.53 (s, 1H), 5.15 (p, J=8.0 Hz, 1H), 4.50 (tt, J=5.7, 2.9 Hz, 1H), 2.63 (d, J=0.8 Hz, 3H), 2.43 (dtd, J=13.6, 8.0, 5.9 Hz, 1H), 2.31-2.17 (m, 2H), 2.11 (ddd, J=13.9, 8.8, 5.7 Hz, 1H), 1.88 (ddt, J=13.0, 9.0, 7.0 Hz, 1H), 1.78-1.65 (m, 1H). LC-MS: [M+H]⁺=318.9, 320.9.

Intermediate 11.6

1-((1R,3R)-3-hydroxycyclopentyl)-6-methyl-3-(4,4,5,5-tetramethyl-1,3,2-dioxaborolan-2-yl)-1H-indole-5-carbonitrile (trans relative)

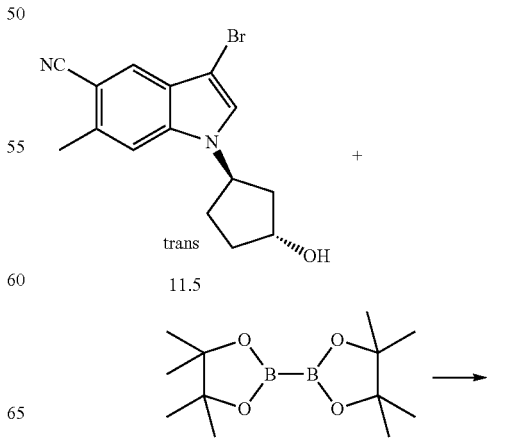

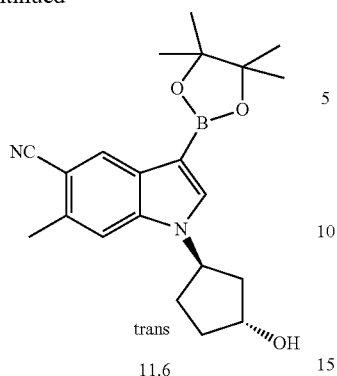

11.6

The title compound was prepared by using a procedure similar to that of intermediate 1.7 by replacing intermediate 1.6 with intermediate 11.5. LC-MS: [M+H]⁺=366.9.

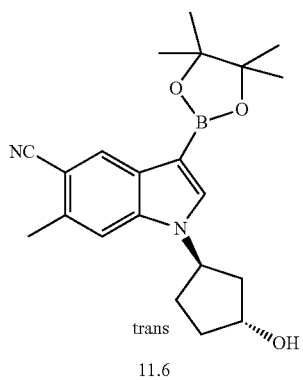

11.6

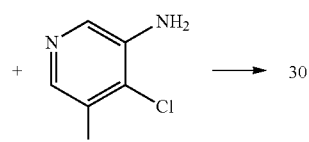

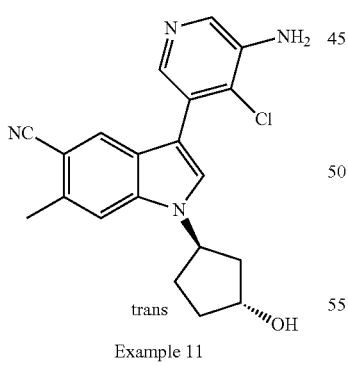

Example 11

The title compound was prepared by using a procedure similar to that of Example 1 by replacing intermediate 1.7 with intermediate 11.6. ¹H NMR (400 MHz, Methanol-d₄) δ 8.05 (s, 1H), 7.84 (s, 1H), 7.77 (s, 1H), 7.68 (s, 1H), 7.57 (s, 1H), 5.21 (p, J=8.0 Hz, 1H), 4.54 (dt, J=5.7, 2.8 Hz, 1H), 2.64 (s, 3H), 2.49 (dtd, J=14.1, 8.2, 6.0 Hz, 1H), 2.36-2.20 (m, 3H), 2.07-1.88 (m, 1H), 1.81 (m, 1H). LC-MS: [M+H]⁺= 366.9, 368.9.

Example 12

Cis-3-(5-amino-4-chloropyridin-3-yl)-1-((1R,3S)-3-hydroxycyclopentyl)-6-methyl-1H-indole-5-carbonitrile Intermediate 12.1

3-bromo-1-((1R,3S)-3-hydroxycyclopentyl)-6-methyl-1H-indole-5-carbonitrile (cis relative)

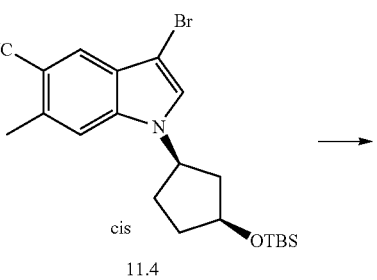

11.4

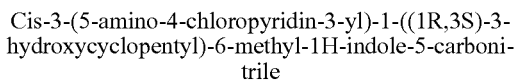

12.1

The title compound was prepared by using a procedure similar to that of intermediate 9.5 by replacing intermediate 9.3 with intermediate 11.4. ¹H NMR (400 MHz, Methanol-d4) δ 7.77 (s, 1H), 7.71 (s, 1H), 7.58 (s, 1H), 5.20-4.95 (m, 1H), 4.41 (dq, J=5.5, 3.8 Hz, 1H), 2.62 (d, J=0.8 Hz, 3H), 2.55 (ddd, J=14.8, 9.4, 5.8 Hz, 1H), 2.39-2.19 (m, 1H), 2.10 (tt, J=12.8, 8.5 Hz, 1H), 2.00-1.67 (m, 3H). LC-MS: [M+H]⁺= 318.9, 320.9.

Intermediate 12.2

1-((1R,3S)-3-hydroxycyclopentyl)-6-methyl-3-(4,4,5,5-tetramethyl-1,3,2-dioxaborolan-2-yl)-1H-indole-5-carbonitrile (cis relative)

12.1

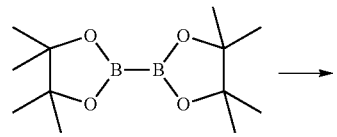

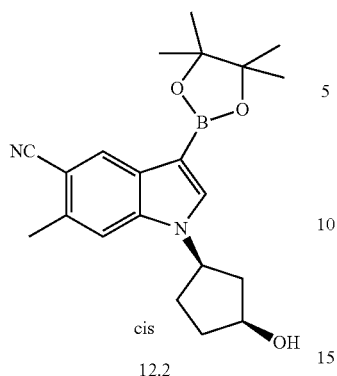

12.2

The title compound was prepared by using a procedure similar to that of intermediate 1.7 by replacing intermediate 1.6 with intermediate 12.1. LC-MS: [M+H]⁺=366.9.

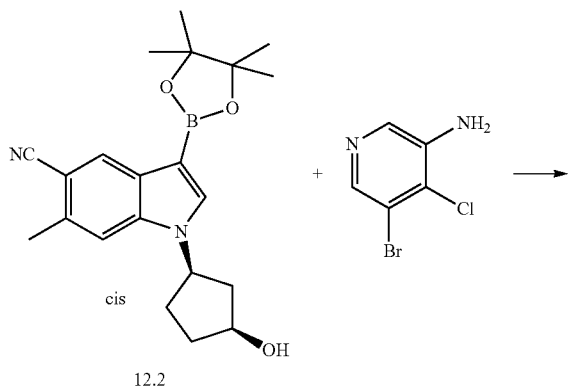

Example 12

The title compound was prepared by using a procedure similar to that of Example 1 by replacing intermediate 1.7 with intermediate 12.2. ¹H NMR (400 MHz, Methanol-d₄) δ 8.04 (s, 1H), 7.87 (s, 1H), 7.86 (s, 1H), 7.78 (s, 1H), 7.63 (s, 1H), 5.18-5.00 (m, 1H), 4.44 (dq, J=8.1, 3.8 Hz, 1H), 2.64 (m, 4H), 2.33 (dtd, J=14.6, 7.1, 4.7 Hz, 1H), 2.19 (m, 1H), 1.95 (ddd, J=8.9, 7.0, 4.2 Hz, 3H). LC-MS: [M+H]⁺=366.9, 368.9.

Example 13

3-(5-amino-4-chloropyridin-3-yl)-1-((1R,3R)-3-hydroxycyclobutyl)-6-methyl-1H-indole-5-carbonitrile Intermediate 13.1

(1S,3S)-3-(benzyloxy)cyclobutyl 4-methylbenzenesulfonate

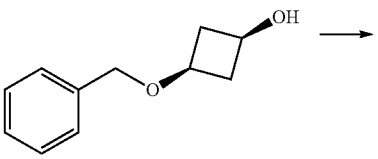

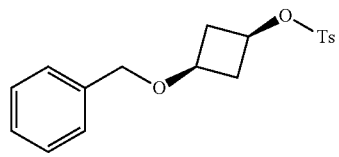

13.1

To a solution of (1s,3s)-3-(benzyloxy)cyclobutan-1-ol (4 g, 22.44 mmol) in DCM (50 mL) was added DMAP (4.11 g, 33.36 mmol). The mixture was cooled to 0° C. and the solution of TsCl (4.71 g, 24.69 mmol) in DCM (30 mL) was added dropwise to the mixture at 0° C. The mixture was warmed to rt and stirred at rt overnight. The mixture was washed with 1 N HCl (2×50 mL) and the aqueous layer was extracted with DCM (2×50 mL). The combined organic layers were washed with water and brine, dried over Na₂SO₄ and concentrated to give the title compound (7.3 g, 98%). ¹H NMR (300 MHz, DMSO-d₆) δ ppm 7.83 (d, 2H), 7.56-7.50 (m, 2H), 7.38-7.30 (m, 5H), 4.55 (p, 1H), 4.37 (s, 2H), 3.69 (p, 1H), 2.61 (ddd, 2H), 2.48 (s, 3H), 2.07-1.93 (m, 2H). LC-MS: [M+H]⁺=333.4.

Intermediate 13.2

1-((1R,3R)-3-(benzyloxy)cyclobutyl)-3-bromo-6-methyl-1H-indole-5-carbonitrile

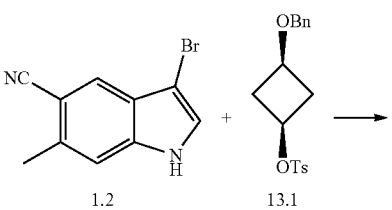

1.2      13.1

-continued

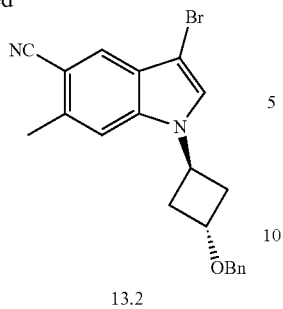

13.2

The title compound was prepared by using a procedure similar to that of intermediate 1.4 by replacing intermediate 1.3 with intermediate 13.1. LC-MS: [M+H]⁺=396.7, 397.7.

Intermediate 13.3

3-bromo-1-((1R,3R)-3-hydroxycyclobutyl)-6-methyl-1H-indole-5-carbonitrile

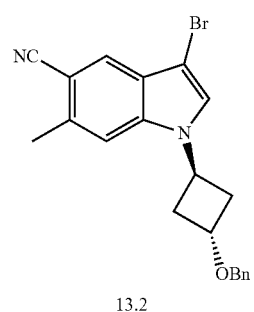 → 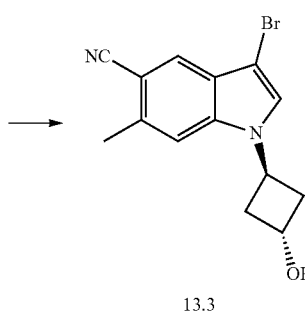

13.2    13.3

To a solution of 13.2 (1 g, 2.53 mmol) in DCM (25 mL) was added a solution of BBr₃ in DCM (2.78 mL, 2.78 mmol) under ice-bath. The mixture was stirred at 0° C. for 1 hr. Then the mixture was washed with water, brine. The organic layer was dried over magnesium sulfate, filtered and concentrated in vacuum. The residue was purified by Combi-Flash, eluted with methanol in DCM (0-5%, 30 min), collected the desired fraction to afford the title compound (620 mg, 80%) as white solid. LC-MS: [M+H]⁺=304.8, 306.8.

Intermediate 13.4

1-((1R,3R)-3-hydroxycyclobutyl)-6-methyl-3-(4,4,5,5-tetramethyl-1,3,2-dioxaborolan-2-yl)-1H-indole-5-carbonitrile

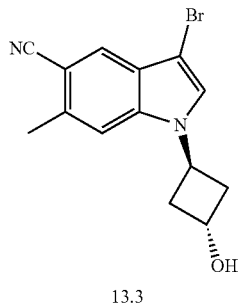 +

13.3

-continued

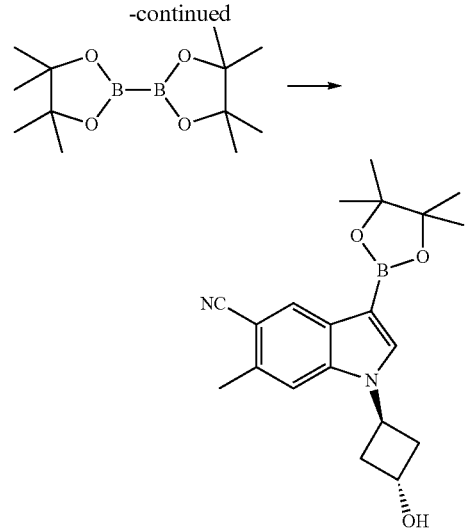

13.4

The title compound was prepared by using a procedure similar to that of intermediate 1.7 by replacing intermediate 1.6 with intermediate 13.3. LC-MS: [M+H]⁺=350.9.

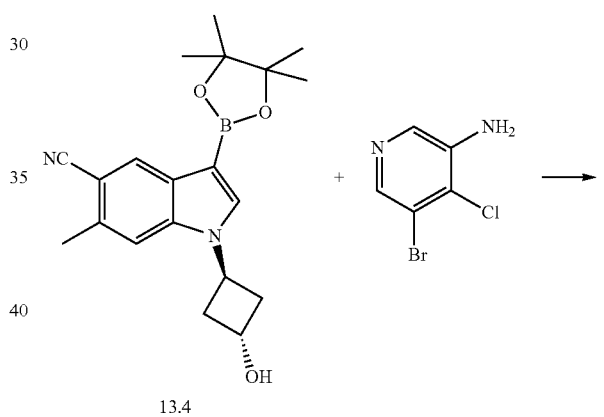

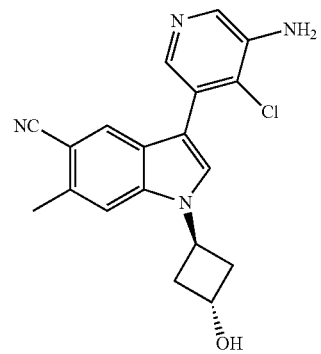

Example 13

The title compound was prepared by using a procedure similar to that of Example 1 by replacing intermediate 1.7 with intermediate 13.4. ¹H NMR (400 MHz, Methanol-d₄) δ 8.06 (s, 1H), 7.86 (s, 1H), 7.79 (s, 1H), 7.78 (s, 1H), 7.47 (s, 1H), 5.27 (p, J=7.2 Hz, 1H), 4.59 (dt, J=6.8, 3.3 Hz, 1H), 2.85-2.72 (m, 2H), 2.71-2.53 (m, 5H). LC-MS: [M+H]⁺= 352.9, 354.9.

Example 14

3-(5-amino-4-chloropyridin-3-yl)-1-((1S,3S)-3-hydroxycyclobutyl)-6-methyl-1H-indole-5-carbonitrile

Intermediate 14.1

(1R,3R)-3-(benzyloxy)cyclobutyl 4-nitrobenzoate

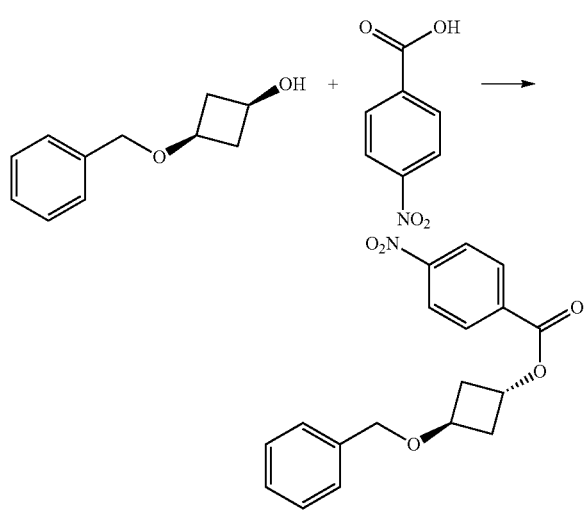

14.1

To a solution of (1s,3s)-3-(benzyloxy)cyclobutan-1-ol, (500 mg, 2.8 mmol), 4-nitrobenzoic acid (935 mg, 5.6 mmol) and PPh$_3$ (2.2 g, 8.4 mmol) in dry THF (25 mL) was added DIAD (1.7 g, 8.4 mmol) dropwise at 0° C. under N$_2$ atmosphere. After addition was completed, the mixture was stirred at 0° C. for 15 min and then allowed to room temperature overnight. The mixture was concentrated and then purified by CombiFlash, eluted with ethyl acetate in hexane (0-15%, 30 min) to give the title compound (900 mg, 98%) as a yellow solid. $^1$H NMR (300 MHz, CDCl$_3$) δ ppm 8.31-8.26 (m, 2H), 8.23-8.18 (m, 2H), 7.39-7.27 (m, 5H), 5.44 (dq, 1H), 4.47 (d, 2H), 4.37 (tt, 1H), 2.67-2.56 (m, 2H), 2.55-2.44 (m, 2H).

Intermediate 14.2

(1R,3R)-3-(benzyloxy)cyclobutan-1-ol

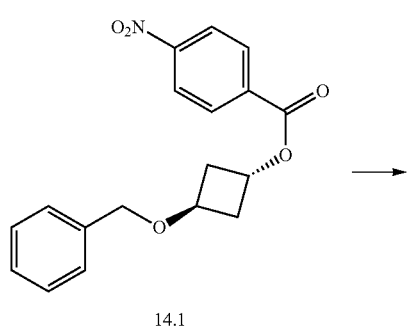

14.1

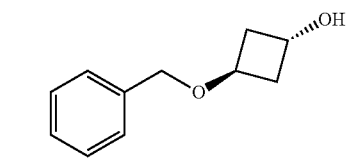

14.2

To a solution of compound 14.1 (850 mg, 2.5968 mmol) in dioxane (18 mL) was added 0.4 N NaOH (13 mL, 5.1935 mmol). The mixture was stirred at rt for 1 h. HOAc (234 mg, 3.8952 mmol) was added and the mixture was concentrated. EA (15 mL) and saturated NaHCO$_3$ (30 mL) was added to the residue. The organic layer was washed with saturated NaHCO$_3$ and separated. The aqueous layer was extracted with EA (2×10 mL). The combined organic layers were washed with water and brine, dried over Na$_2$SO$_4$ and concentrated to give the title compound (435 mg, 94%). $^1$H NMR (300 MHz, CDCl$_3$) δ ppm 7.37-7.28 (m, 5H), 4.56 (tt, 1H), 4.43 (s, 2H), 4.34-4.26 (m, 1H), 2.44-2.33 (m, 2H), 2.24-2.16 (m, 2H), 2.12 (s, 1H). LC-MS: [M+Na]$^+$=201.2.

Intermediate 14.3

(1r,3r)-3-(benzyloxy)cyclobutyl 4-methylbenzenesulfonate

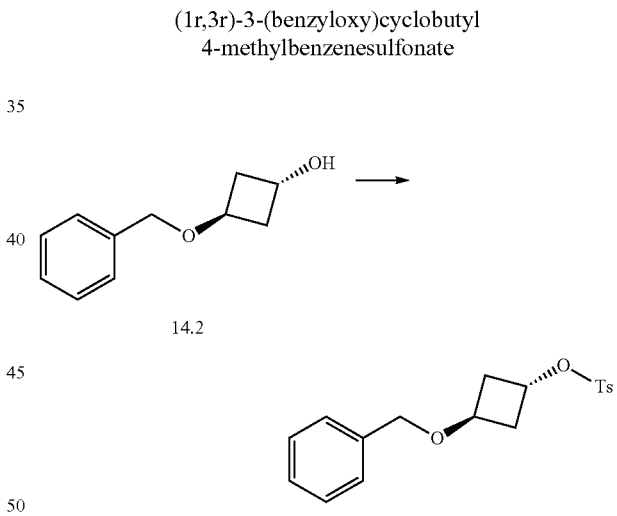

14.3

The title compound was prepared by using a procedure similar to that of intermediate 13.1 by replacing (1s,3s)-3-(benzyloxy)cyclobutan-1-ol with intermediate 14.2.

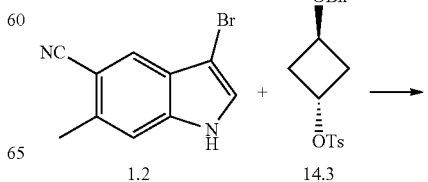

1.2      14.3

-continued

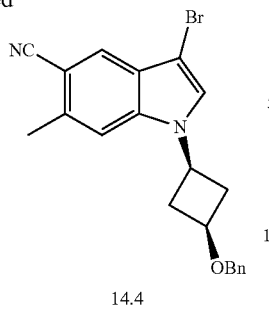

14.4

The title compound was prepared by using a procedure similar to that of intermediate 1.4 by replacing intermediate 1.3 with intermediate 14.3. $^1$H NMR (400 MHz, Chloroform-d) δ 7.84 (s, 1H), 7.42-7.28 (m, 6H), 7.19 (s, 1H), 4.51 (s, 2H), 4.43 (p, J=8.3 Hz, 1H), 4.02 (p, J=7.0 Hz, 1H), 3.11-2.83 (m, 2H), 2.63 (s, 3H), 2.49-2.30 (m, 2H). LC-MS: [M+H]$^+$=394.9, 397.9.

Intermediate 14.5

1-((1s,3s)-3-(benzyloxy)cyclobutyl)-6-methyl-3-(4,4,5,5-tetramethyl-1,3,2-dioxaborolan-2-yl)-1H-indole-5-carbonitrile

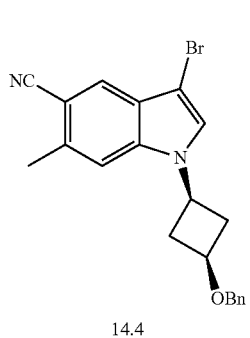

14.4

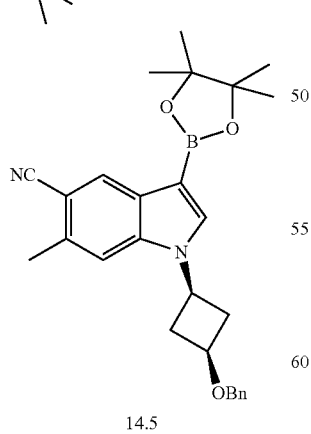

14.5

The title compound was prepared by using a procedure similar to that of intermediate 1.7 by replacing intermediate 1.6 with intermediate 14.4. LC-MS: [M+H]$^+$=443.3.

Intermediate 14.6

3-(5-amino-4-chloropyridin-3-yl)-1-((1S,3S)-3-(benzyloxy)cyclobutyl)-6-methyl-1H-indole-5-carbonitrile

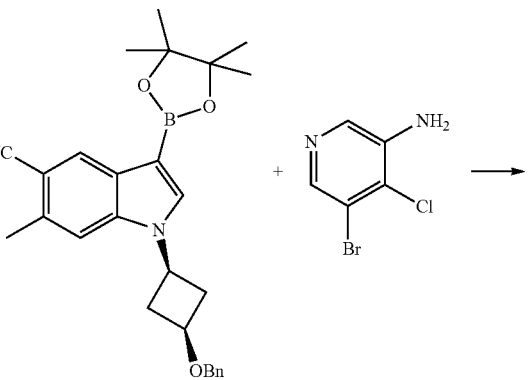

14.5

14.6

The title compound was prepared by using a procedure similar to that of Example 1 by replacing intermediate 1.7 with intermediate 14.5. LC-MS: [M+H]$^+$=442.9, 443.9.

14.6

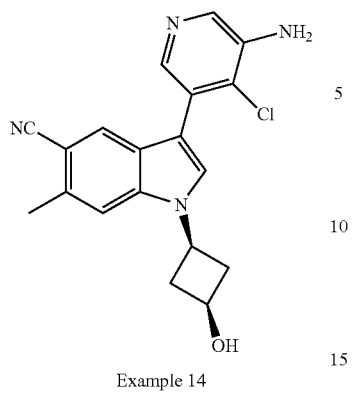

Example 14

To a solution of 14.6 (85 mg, 0.192 mmol) in DCM (10 mL) was added a solution BBr$_3$ in DCM (1M, 0.216 mL, 0.216 mmol), the mixture was stirred at 0° C. for 30 min. Then the mixture was quenched by water, washed by brine. The organic layer was dried over magnesium sulfate, filtered and concentrated; the residue was further purified by basic Prep-HPLC (0.1% NH$_4$OH/ACN/H$_2$O). Collected the desired fraction, lyophilized to afford the title compound (6.5 mg, 8.2%) as white powder. $^1$H NMR (400 MHz, Methanol-d$_4$) δ 8.06 (s, 1H), 7.86 (s, 1H), 7.78 (s, 1H), 7.75 (s, 1H), 7.52 (s, 1H), 4.66-4.55 (m, 1H), 4.27-4.16 (m, 1H), 3.06 (d, J=8.4 Hz, 2H), 2.64 (s, 3H), 2.39 (d, J=9.8 Hz, 2H). LC-MS: [M+H]$^+$=352.9, 353.9.

Example 15

3-(5-amino-4-(difluoromethyl)pyridin-3-yl)-1-((1S, 3S)-3-hydroxycyclobutyl)-6-methyl-1H-indole-5-carbonitrile Intermediate 15.1

3-(5-amino-4-(difluoromethyl)pyridin-3-yl)-1-((1S, 3S)-3-(benzyloxy)cyclobutyl)-6-methyl-1H-indole-5-carbonitrile

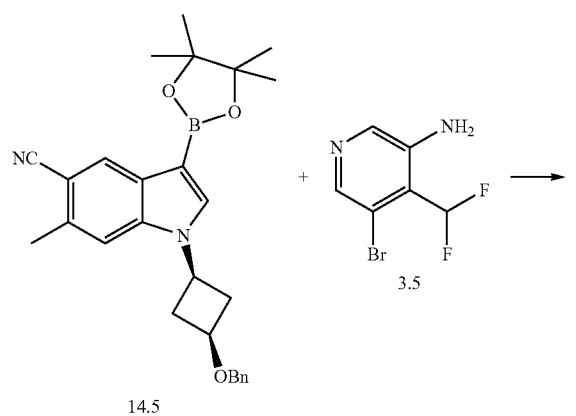

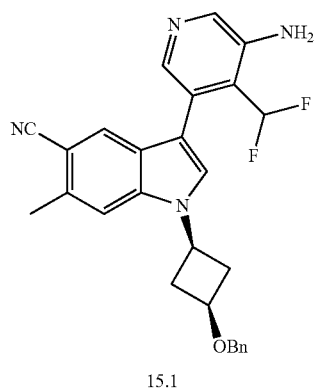

15.1

The title compound was prepared by using a procedure similar to that of Example 1 by replacing intermediate 1.7 and 5-bromo-4-chloropyridin-3-amine with intermediate 14.5 and intermediate 3.5. LC-MS: [M+H]$^+$=459.0.

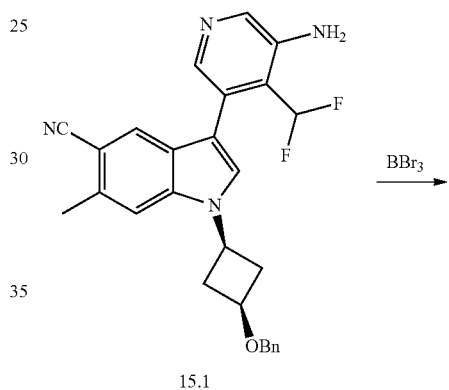

15.1

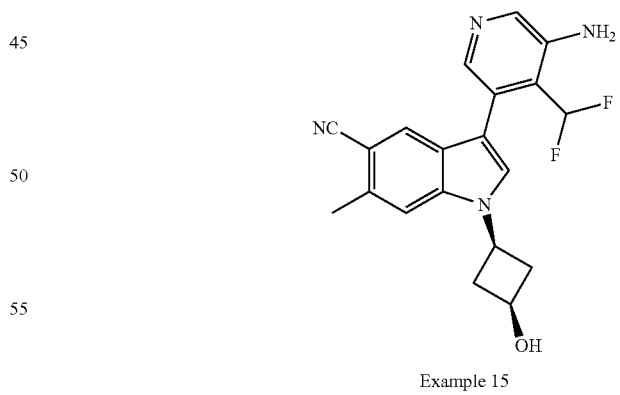

Example 15

The title compound was prepared by using a procedure similar to that of Example 14 by replacing intermediate 14.6 with intermediate 15.1. $^1$H NMR (400 MHz, Methanol-d$_4$) δ 8.13 (s, 1H), 7.79 (s, 1H), 7.72 (s, 1H), 7.61 (s, 1H), 7.54 (s, 1H), 6.65 (t, J=53.5 Hz, 1H), 4.61 (p, J=8.2 Hz, 1H), 4.22 (p, J=7.3 Hz, 1H), 3.13-2.95 (m, 2H), 2.64 (s, 3H), 2.39 (q, J=9.6 Hz, 2H). LC-MS: [M+H]$^+$=369.0.

Example 16

3-(5-amino-4-(difluoromethyl)pyridin-3-yl)-1-(3-hydroxypropyl)-6-methyl-1H-indole-5-carbonitrile

Intermediate 16.1

3-bromo-1-(3-hydroxypropyl)-6-methyl-1H-indole-5-carbonitrile

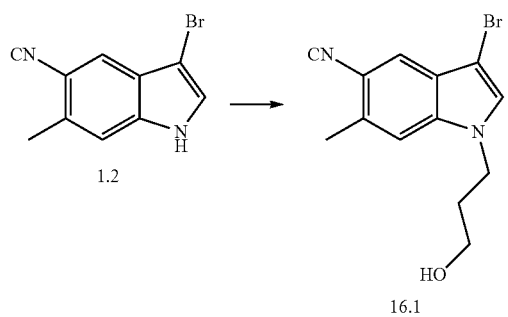

To a solution of 1.2 (2.0 g, 8.51 mmol) in DMF (20 mL) was added NaH (0.235 g, 9.78 mmol). After 10 min stirring, 3-bromopropan-1-ol (1.478 g, 10.63 mmol) was added dropwise over 10 min. After stirring at r.t. for 12 h, LC-MS showed starting material still remains, 1 eq of $Cs_2CO_3$ was added, and then heated to 50° C. for 2 h. The mixture was diluted with water (20 mL), and then extracted with EA (20 mL×2). The organic layer was dried over $Na_2SO_4$, filtered and concentrated; the residue was purified by silica column to afford the title compound (1000 mg, 40%) as brown oil. LC-MS: $[M+H]^+$=293.1, 295.1.

Intermediate 16.2

1-(3-hydroxypropyl)-6-methyl-3-(4,4,5,5-tetramethyl-1,3,2-dioxaborolan-2-yl)-1H-indole-5-carbonitrile

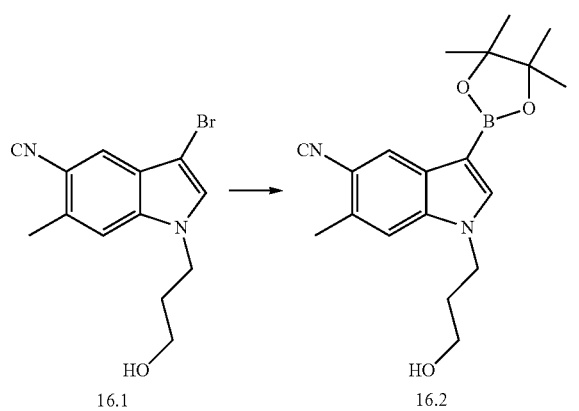

The title compound was prepared by using a procedure similar to that of intermediate 1.7 by replacing intermediate 1.6 with intermediate 16.1. LC-MS: $[M+H]^+$=341.3.

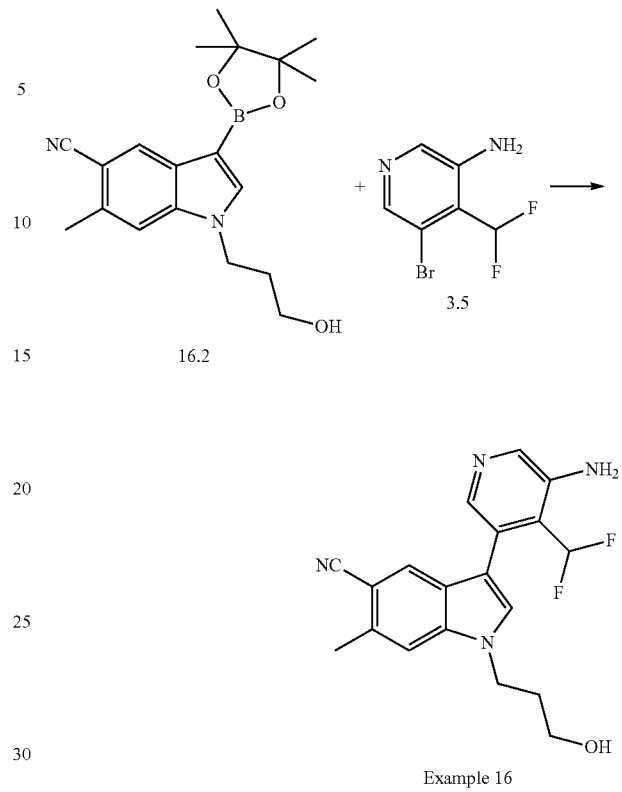

The title compound was prepared by using a procedure similar to that of Example 1 by replacing intermediate 1.7 and 5-bromo-4-chloropyridin-3-amine with intermediate 16.2 and intermediate 3.5. $^1H$ NMR (400 MHz, Methanol-$d_4$) δ 8.17 (s, 1H), 7.94 (s, 1H), 7.84 (s, 1H), 7.63 (s, 1H), 7.57 (s, 1H), 6.79 (t, J=52.9 Hz, 1H), 4.41 (t, J=6.9 Hz, 2H), 3.57 (t, J=5.9 Hz, 2H), 2.66 (s, 3H), 2.20-1.93 (m, 2H). LC-MS: $[M+H]^+$=357.3.

Example 17

3-(3-amino-2-fluorophenyl)-1-(3-hydroxypropyl)-6-methyl-1H-indole-5-carbonitrile

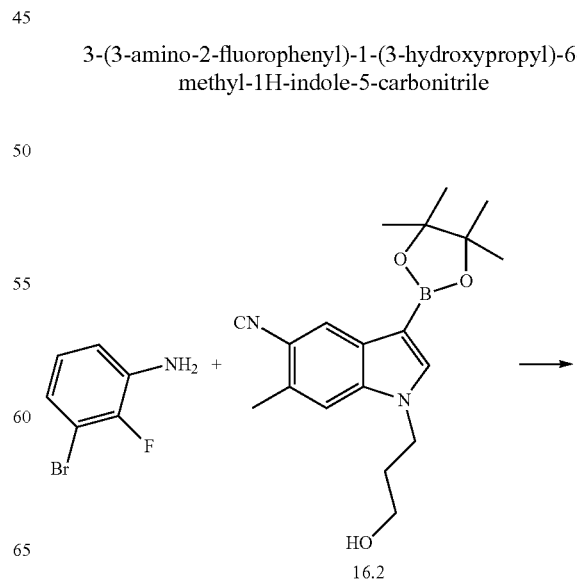

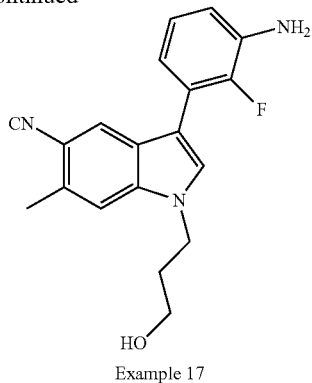

Example 17

The title compound was prepared by using a procedure similar to that of example 1 by replacing intermediate 1.7 and 5-bromo-4-chloropyridin-3-amine with 16.2 and 3-bromo-2-fluoroaniline. $^1$H NMR (400 MHz, Methanol-$d_4$) 5: 8.01 (s, 1H), 7.57 (s, 1H), 7.2 (s, 1H), 6.97-7.01 (m, 1H), 6.87-6.93 (m, 1H), 6.77-6.83 (m, 1H), 4.33-4.39 (t, 2H), 3.53-3.59 (t, 2H), 2.63 (s, 3H), 2.01-2.10 (m, 2H), LC-MS: [M+H]$^+$=324.2.

Example 18

3-(3-amino-2-chlorophenyl)-1-(3-hydroxypropyl)-6-methyl-1H-indole-5-carbonitrile The title compound was prepared by using a procedure similar to that of example 1 by replacing intermediate 1.7 and 5-bromo-4-chloropyridin-3-amine with 16.2 and 3-bromo-2-chloroaniline. $^1$H NMR (400 MHz, Methanol-$d_4$) δ:7.77 (s, 1H), 7.45-7.53 (m, 2H), 7.07-7.14 (m, 1H), 6.75-6.88 (m, 2H), 4.31-4.40 (m, 2H), 3.53-3.59 (m, 2H), 2.60 (s, 3H), 1.99-2.10 (m, 2H). LC-MS: [M+H]$^+$=340.2.

Example 19

3-(5-amino-4-methylpyridin-3-yl)-1-(3-hydroxypropyl)-6-methyl-1H-indole-5-carbonitrile

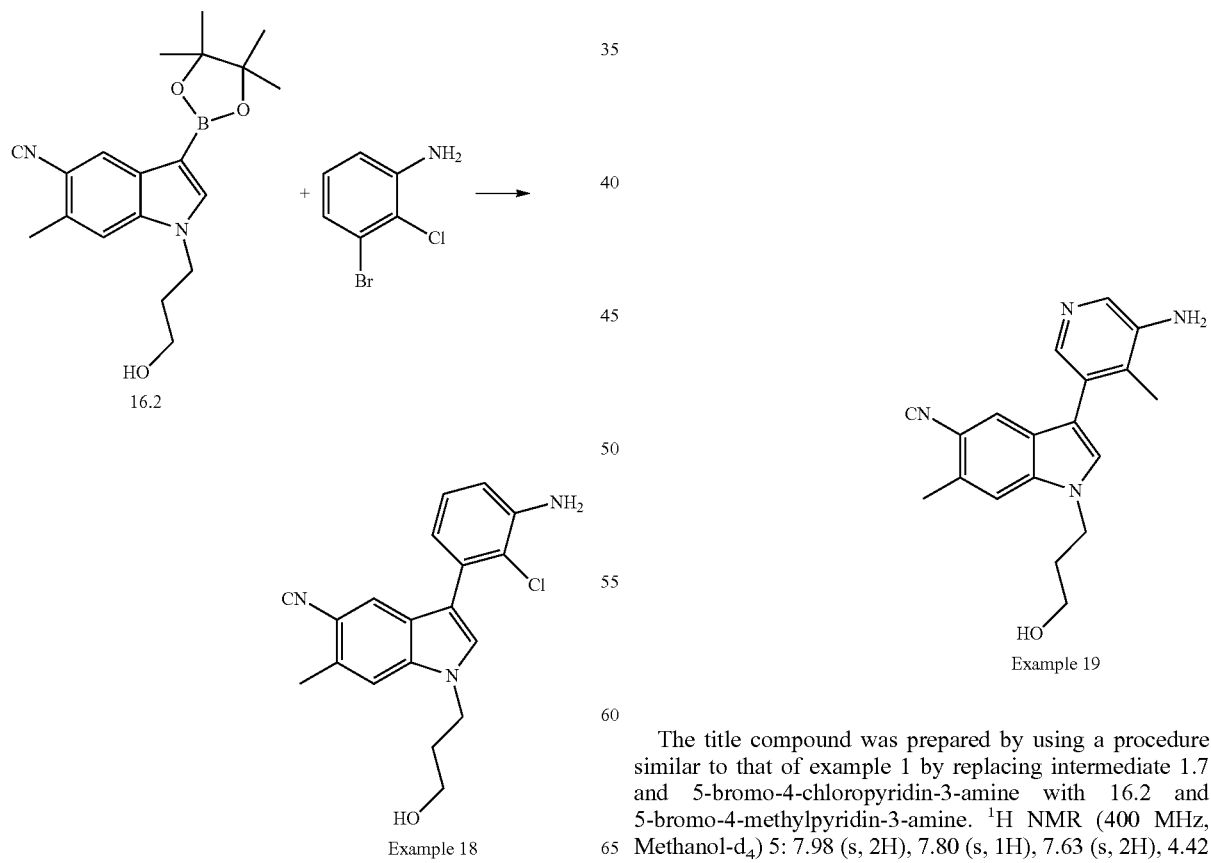

Example 19

The title compound was prepared by using a procedure similar to that of example 1 by replacing intermediate 1.7 and 5-bromo-4-chloropyridin-3-amine with 16.2 and 5-bromo-4-methylpyridin-3-amine. $^1$H NMR (400 MHz, Methanol-$d_4$) 5: 7.98 (s, 2H), 7.80 (s, 1H), 7.63 (s, 2H), 4.42 (t, J=4.7 Hz, 2H), 3.57 (m, J=5.9 Hz, 2H), 2.66 (s, 3H), 2.31 (s, 3H), 2.01-2.15 (m, 2H). LC-MS: [M+H]$^+$=321.3

Example 20

1-((1R,4R)-4-hydroxycyclohexyl)-3-(3-(isopropylamino)-2-methylphenyl)-6-methyl-1H-indole-5-carbonitrile

Intermediate 20.1

3-bromo-N-isopropyl-2-methylaniline

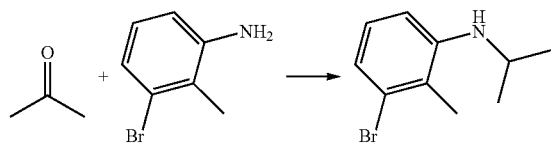

In a 50 mL round-bottomed flask was acetone (937 mg, 16.12 mmol) and 3-bromo-2-methylaniline (2000 mg, 10.75 mmol) in MeOH (15 mL) to give a yellow solution. After 1 h stirring, NaCNBH$_3$ (878 mg, 13.97 mmol) was added. The reaction was kept stirring for 12 h. The reaction was quenched with NH$_4$Cl (aq). The reaction was extracted with EA. The combined organic phase was washed with brine and dried over Na$_2$SO$_4$, concentrated and purified by column chromatography on silica gel (eluent: PE/EA=10:1~2:1) to give the title compound (858 mg, 35%) as a yellow solid. LC-MS: [M+H]$^+$=228.1, 230.4.

Intermediate 20.2

N-isopropyl-2-methyl-3-(4,4,5,5-tetramethyl-1,3,2-dioxaborolan-2-yl)aniline

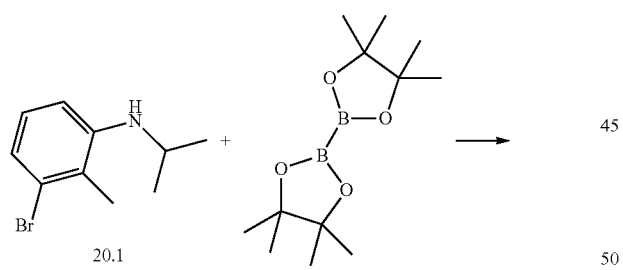

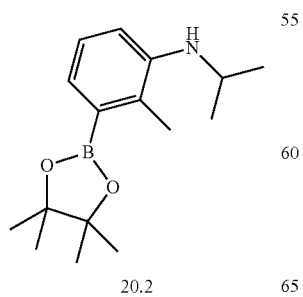

The title compound was prepared by using a procedure similar to that of intermediate 1.7 by replacing intermediate 1.6 with 20.1. LC-MS: [M+H]$^+$=276.3.

Intermediate 20.3

3-(3-(isopropylamino)-2-methylphenyl)-6-methyl-1-(1,4-dioxaspiro[4.5]decan-8-yl)-1H-indole-5-carbonitrile

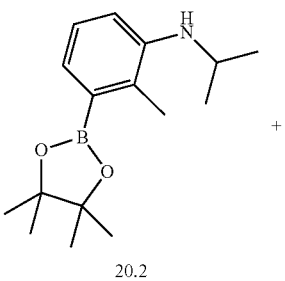

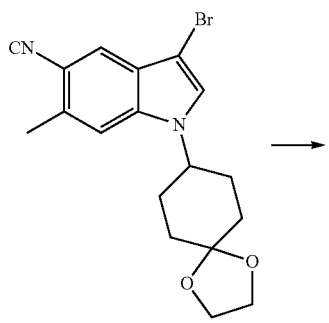

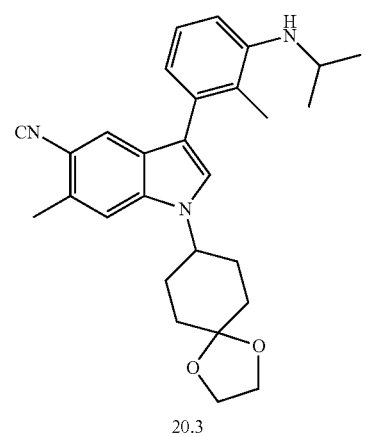

The title compound was prepared by using a procedure similar to that of example 1 by replacing intermediate 1.7 and 5-bromo-4-chloropyridin-3-amine with 20.2 and 1.4. LC-MS: [M+H]$^+$=444.3.

Intermediate 20.4

3-(3-(isopropylamino)-2-methylphenyl)-6-methyl-1-(4-oxocyclohexyl)-1H-indole-5-carbonitrile

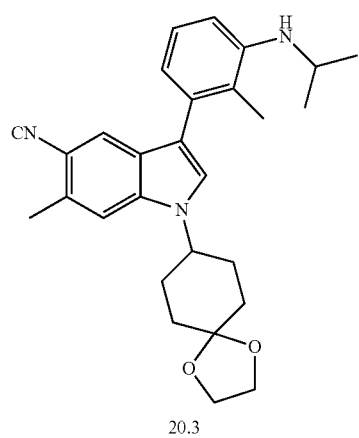

20.3

→

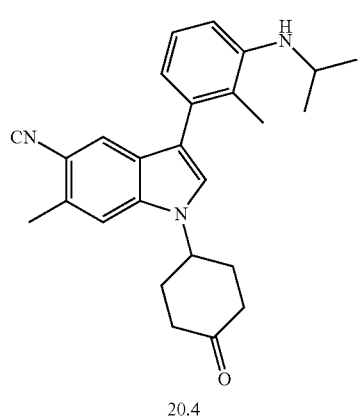

20.4

The title compound was prepared by using a procedure similar to that of intermediate 1.5 by replacing intermediate 1.4 with 20.3 LC-MS: [M+H]$^+$=400.3.

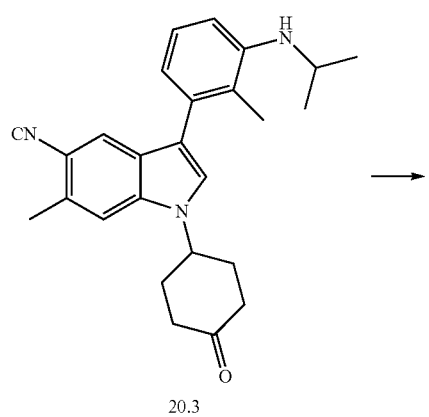

20.3

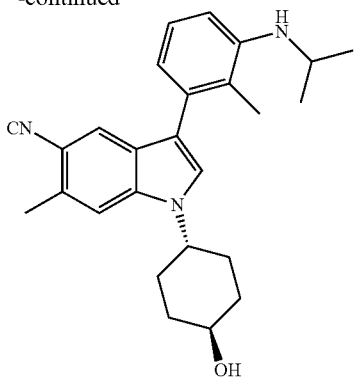

Example 20

In a 10 mL flask 20.3 (40 mg, 0.100 mmol) was dissolved in MeOH (2 mL) to give a yellow solution. NaBH$_4$ (3.79 mg, 0.100 mmol) was added. After stirring at r.t. for 2 h, the reaction was quenched with NH$_4$Cl (aq). The reaction was extracted with EA. The organic layer dried Na$^2$SO$^4$, filtered and concentrated. The residue was purified via by prep-HPLC (0.1% TFA/ACN/H$_2$O) to deliver title compound (25 mg, 50%). $^1$H NMR (METHANOL-d$_4$) δ: 7.64 (s, 1H), 7.61 (s, 1H), 7.56 (s, 1H), 7.43-7.47 (m, 2H), 7.29-7.34 (m, 1H), 4.43-4.54 (m, 1H), 3.80-3.89 (m, 1H), 3.68-3.79 (m, 1H), 2.65 (s, 3H), 2.31 (s, 3H), 2.09-2.17 (m, 4H), 1.92-2.06 (m, 2H), 1.56-1.68 (m, 2H), 1.43 (d, J=6.5 Hz, 6H). LC-MS: [M+H]$^+$=402.4.

Example 21

4-(3-(5-amino-4-chloropyridin-3-yl)-5-cyano-6-methyl-1H-indol-1-yl)benzamide

Intermediate 21.1

4-(5-cyano-6-methyl-1H-indol-1-yl)benzamide

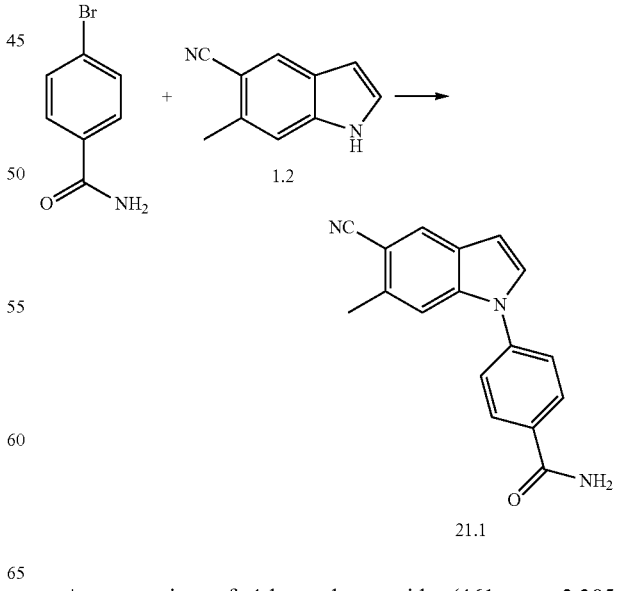

A suspension of 4-bromobenzamide (461 mg, 2.305 mmol), 1.2 (300 mg, 1.921 mmol), 1,10-phenanthroline (69.2 mg, 0.384 mmol), Cu$_2$O (27.5 mg, 0.192 mmol), and TBAF THF solution (8 mL, 8.00 mmol) was concentrated to remove organic solvent before heating up at 150° C. for 2 hr under nitrogen protection. The mixture was re-dissolved in DCM, filtered and the filter was purified by CombiFlash, eluted with ethyl acetate in hexane (40-80%, 30 min). Collected the desired fraction and concentrated in vacuum to afford the title compound (420 mg, 79%) as brown solid. LC-MS: [M+H]$^+$=276.2.

Intermediate 21.2

4-(3-bromo-5-cyano-6-methyl-1H-indol-1-yl)benzamide

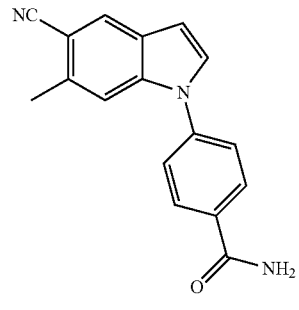

21.1

To a solution of 21.1 (420 mg, 1.526 mmol) in DMF (Volume: 10 mL) was added NBS (299 mg, 1.678 mmol), the mixture was stir at 0° C. for 1 hr. Then water (30 mL) was added, filtered and dried in vacuum to afford the title compound (370 mg, 69%) as brown solid. $^1$H NMR (400 MHz, DMSO-d$_6$) δ 8.15 (d, J=5.2 Hz, 2H), 8.11-8.06 (m, 2H), 8.00 (s, 1H), 7.75-7.71 (m, 2H), 7.69 (s, 1H), 7.53 (s, 1H), 2.58 (s, 3H). LC-MS: [M+H]$^+$=353.1, 355.1.

Intermediate 21.3

4-(5-cyano-6-methyl-3-(4,4,5,5-tetramethyl-1,3,2-dioxaborolan-2-yl)-1H-indol-1-yl)benzamide

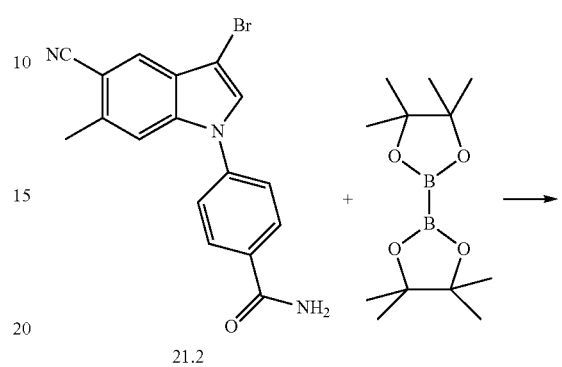

21.2

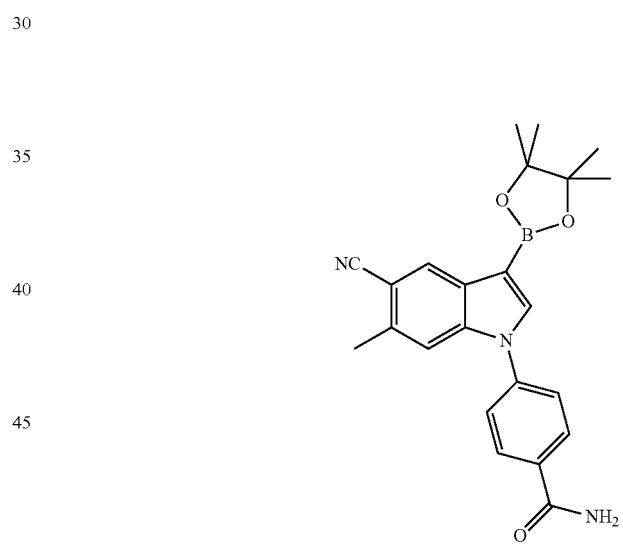

21.3

A solution of 21.2 (150 mg, 0.423 mmol), Pin$_2$B$_2$(323 mg, 1.270 mmol), KOAc (83 mg, 0.847 mmol), tricyclohexylposphine (24 mg, 0.085 mmol) and Pd$_2$(dba)$_3$ (20 mg, 0.021 mmol) in 1,4-dioxane (5 mL) was heated at 100° C. for 2 hr under nitrogen protection. The mixture was diluted with DCM, washed with water; the organic layer was dried over magnesium sulfate, filtered and concentrated in vacuum to afford black syrup. The residue was purified by CombiFlash, eluted with methanol in DCM (0-5%, 30 min). Collected the desired fraction to afford the title compound (140 mg, 66%) as off-white solid. $^1$H NMR (400 MHz, DMSO-d$_6$) δ 8.18 (s, 1H), 8.14 (s, 1H), 8.13-8.04 (m, 3H), 7.77-7.72 (m, 2H), 7.63 (s, 1H), 7.52 (s, 1H), 2.56 (s, 3H), 1.35 (s, 9H). LC-MS: [M+H]$^+$=402.0.

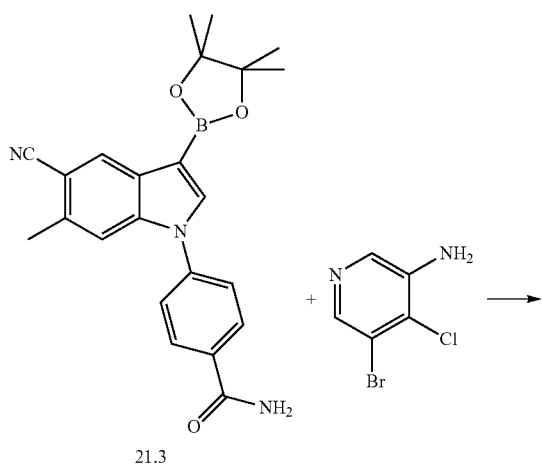

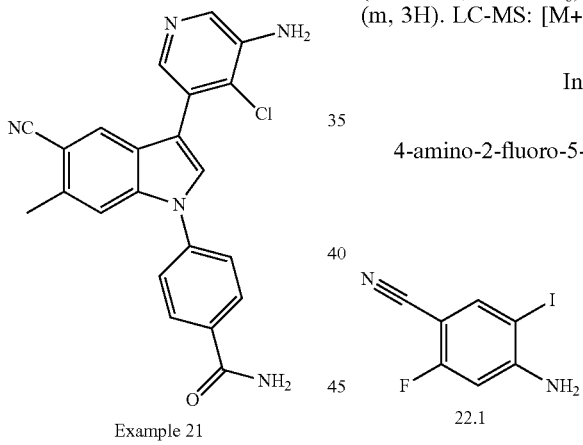

Example 21

To a solution of 21.3 (70 mg, 0.174 mmol), 5-bromo-4-chloropyridin-3-amine (36.2 mg, 0.174 mmol), Na$_2$CO$_3$ (37.0 mg, 0.349 mmol), Pd$_2$(dba)$_3$ (8 mg, 8.72 μmol) and tricyclophexylphosphine (10 mg, 0.035 mmol) in 2-Propanol (10 mL) was added water (3 mL). The mixture was stir at 100° C. for 2 hr under nitrogen protection. Remove most organic solvent in vacuum, then the residue was re-dissolved in DCM, washed with water; the organic layer was dried over magnesium sulfate, filtered and concentrated in vacuum. The residue was purified by CombiFlash, eluted with methanol in DCM (0-5%, 30 min). Collected the desired fraction to afford 40 mg brown syrup, it was further purified by basic Prep-HPLC (0.1% NH$_4$OH/ACN/H$_2$O). Collected the desired fraction and lyophilized to afford 10 mg title compound as off-white powder. $^1$H NMR (400 MHz, Methanol-d$_4$) δ 8.22-8.05 (m, 3H), 7.96 (d, J=15.9 Hz, 1H), 7.87 (s, 2H), 7.79-7.71 (m, 2H), 7.65 (d, J=0.9 Hz, 1H), 2.63 (d, J=0.8 Hz, 3H). LC-MS: [M+H]$^+$=401.8, 402.8.

Example 22

3-(3-amino-2-methylphenyl)-6-fluoro-1-((1R,4R)-4-hydroxycyclohexyl)-1H-indole-5-carbonitrile Intermediate 22.1

4-amino-2-fluoro-5-iodobenzonitrile

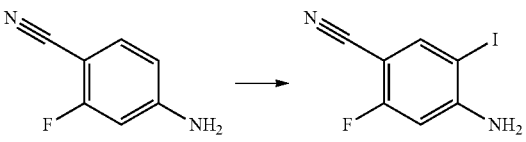

The aniline 4-amino-2-fluorobenzonitrile (500 mg, 3.7 mmol) was dissolved in AcOH (8 mL) and cooled in an ice bath. NIS (827 mg, 3.7 mmol) was added, and the reaction mixture was stirred for 3 h at ambient temperature. The reaction mixture was then concentrated to about one-quarter of the volume, and the solid that formed was collected by filtration. The solid was washed with petroleum ether and dried to give compound 22.1 (1.2 g) as a tan solid. $^1$H NMR (300 MHz, DMSO-d$_6$) δ 8.01 (d, J) 7.7 Hz, 1H), 6.61-6.55 (m, 3H). LC-MS: [M+H]$^+$=263.3.

Intermediate 22.2

4-amino-2-fluoro-5-((trimethylsilyl)ethynyl)benzonitrile

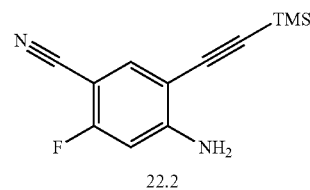

To a solution of compound 22.1 (730 mg, 2.79 mmol), Et$_3$N (7 mL), Pd(PPh$_3$)$_2$Cl$_2$ (20 mg, 0.028 mmol), and CuI (4 mg, 0.021 mmol) in THF (17 mL), trimethylsilylacetylene (329 mg, 3.35 mmol) was added. The resulting mixture was stirred for 24 h at room temperature. Then 70 mL of EA was added and the mixture was washed with brine (50 mL*2). The organic phase was dried and filtered. The solvent is removed under vacuum, and the residue was purified by column chromatography on silica gel (PE/EA=20:1) to obtain title compound (460 mg 71%). $^1$H NMR (300 MHz, DMSO-d$_6$) δ 7.65 (d, J=7.4 Hz, 1H), 6.64-6.60 (m, 3H), 0.24 (s, 9H). LC-MS: [M+H]$^+$=233.4.

Intermediate 22.3

4-amino-5-ethynyl-2-fluorobenzonitrile

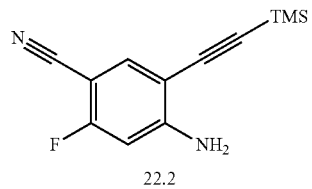

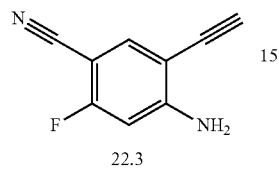

A mixture of compound 22.2 (510 mg, 2.20 mmol) and K$_2$CO$_3$ (1500 mg, 10.85 mmol) in 10 mL of MeOH was stirred at room temperature for 1 hour. Then the mixture was diluted with EA (80 mL) and washed with brine (40 mL*3). The organic phase was dried and concentrated to give (340 mg, 97%). $^1$H NMR (300 MHz, DMSO-d$_6$) δ 7.69 (d, 1H), 6.73 (s, 2H), 6.61 (d, 1H), 4.47 (s, 1H). LC-MS: [M+H]$^+$=161.2.

Intermediate 22.4

6-fluoro-1H-indole-5-carbonitrile

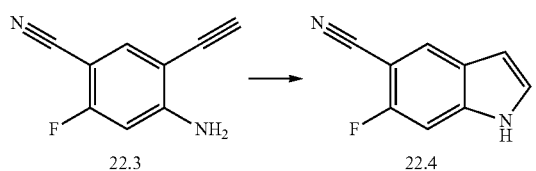

A mixture of intermediate 22.3 (340 mg, 2.12 mmol) and CpRu(PPh$_3$)$_2$Cl (154 mg, 0.21 mmol) in pyridine (12 mL) was stirred under nitrogen at 98° C. for 3 hours. The mixture was diluted with EA (100 mL) and washed with saturated NH$_4$Cl (50 mL*3). The organic phase were dried over anhydrous Na2SO4, filtered and evaporated under vacuum. Purification by flash column chromatography through silica gel provided title compound (240 mg, 70%). $^1$H NMR (300 MHz, DMSO-d$_6$) δ 11.71 (s, 1H), 8.11 (d, 1H), 7.54 (s, 1H), 7.44 (d, 1H), 6.58 (s, 1H). LC-MS: [M+H]$^+$=161.29.

Intermediate 22.5

3-bromo-6-fluoro-1H-indole-5-carbonitrile

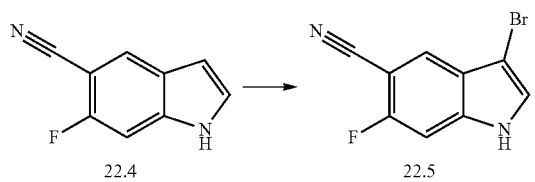 [SMILES: N#Cc1cc2cc[nH]c2cc1F ; N#Cc1cc2c(Br)c[nH]c2cc1F]

To a solution of intermediate 22.4 (200 mg, 1.25 mmol) in DMF (4 mL) was added NBS (245 mg, 1.38 mmol) in several portions. After addition, it was stirred at that temperature for 1 h. Then it was diluted with EA and washed with brine for 3 times. The organic layer was dried over anhydrous Na$_2$SO$_4$, filtered and concentrated to give product (300 mg, 100%). $^1$H NMR (301 MHz, DMSO-d$_6$) δ 12.01 (s, 1H), 7.89 (d, 1H), 7.70 (d, 1H), 7.45 (d, 1H). LC-MS: [M+H]$^+$=239.3.

Intermediate 22.6

3-bromo-6-fluoro-1-(1,4-dioxaspiro[4.5]decan-8-yl)-1H-indole-5-carbonitrile

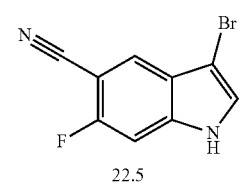

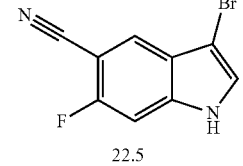

The title compound was prepared by using a procedure similar to that of intermediate 1.4 by replacing intermediate 1.2 with 22.5. $^1$H NMR (300 MHz, CDCl$_3$) δ 7.81 (d, 1H), 7.34 (s, 1H), 7.18 (d, 1H), 4.31-4.08 (m, 1H), 4.00 (s, 4H), 2.12-2.04 (m, 4H), 1.95-1.91 (m, 2H), 1.84-1.78 (m, 2H). LC-MS: [M+H]$^+$=379.1.

Intermediate 22.7

3-bromo-6-fluoro-1-(4-oxocyclohexyl)-1H-indole-5-carbonitrile

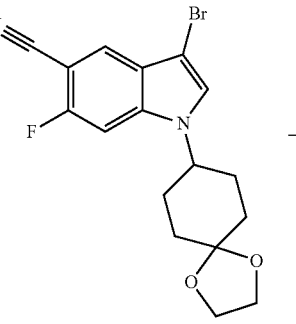

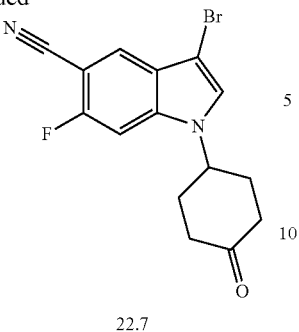

22.7

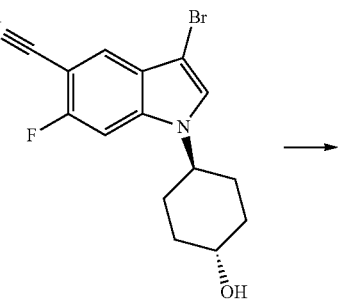

22.8

The title compound was prepared by using a procedure similar to that of intermediate 1.5 by replacing intermediate 1.4 with 22.6. ¹H NMR (300 MHz, CDCl₃) δ 7.85 (d, 1H), 7.29 (s, 1H), 7.23 (d, 1H), 5.15-4.34 (m, 1H), 2.86-2.54 (m, 4H), 2.50-2.35 (m, 2H), 2.30-2.17 (m, 2H). LC-MS: [M+H]⁺ =335.1.

Intermediate 22.8

3-bromo-6-fluoro-1-(4-hydroxycyclohexyl)-1H-indole-5-carbonitrile

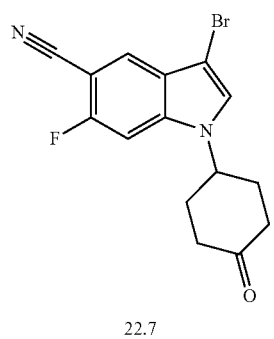

22.7

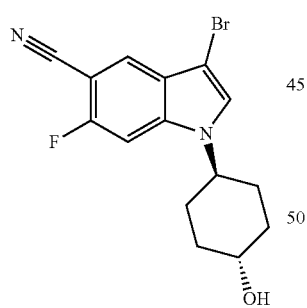

22.8

To a solution of compound 22.7 (85 mg, 0.25 mmol) in MeOH (1.5 mL) was added NaBH₄ (38 mg, 1.0 mmol) under ice-cold. After addition, it was stirred at that temperature for 1 h. Then it was diluted with DCM and washed with water for 2 times. The aqueous phase was extracted with EA. The combined organic layer was dried over anhydrous Na₂SO₄, filtered and concentrated to give title compound (85 mg, 100%). ¹H NMR (301 MHz, DMSO-d₆) δ ppm 8.16-7.90 (m, 3H), 4.91-4.67 (m, 1H), 4.61-4.35 (m, 1H), 3.75-3.49 (m, 1H), 2.10-1.80 (m, 6H), 1.60-1.38 (m, 2H). LC-MS: [M+H]⁺=339.2.

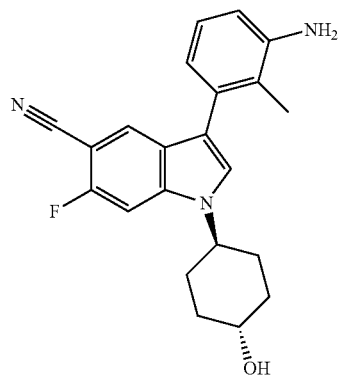

Example 22

To a mixture of 22.8 (85 mg, 0.25 mmol) and compound 2-methyl-3-(4,4,5,5-tetramethyl-1,3,2-dioxaborolan-2-yl) aniline (88 mg, 0.38 mmol) in the co-solvent of i-PrOH/H₂O (5 mL, 10:1) was added 2N Na₂CO₃ aq. (1.2 mL) and Pd(PPh₃)₂Cl₂ (18 mg, 0.026 mmol). The mixture was stirred at 100° C. for 30 min under N₂ atmosphere. Then the mixture was diluted with brine and extracted with EA for three times. The combined organic phase was washed with brine and dried over Na₂SO₄, concentrated and purified by Pre-HPLC (ACN/H₂O) to give title compound (33.2 mg, 36%). ¹H NMR (400 MHz, DMSO-d₆) δ ppm 7.90 (d, 1H), 7.71 (d, 1H), 7.68 (s, 1H), 6.96 (t, 1H), 6.66 (d, 1H), 6.54 (d, 1H), 4.92 (s, 2H), 4.72 (d, 1H), 4.62-4.30 (m, 1H), 3.72-3.42 (m, 1H), 2.04-1.76 (m, 9H), 1.64-1.38 (m, 2H). LC-MS: [M+H]⁺=364.1.

Example 24

3-(3-amino-2-methylphenyl)-1-(3-hydroxypropyl)-2,6-dimethyl-1H-indole-5-carbonitrile Intermediate 24.1

6-methyl-1-(phenylsulfonyl)-1H-indole-5-carbonitrile

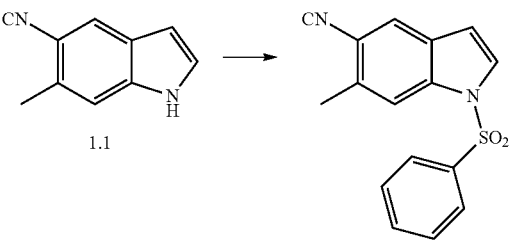

In a 100 mL round-bottomed flask was added intermediate 1.1 (1.5 g, 9.60 mmol) in MeCN (30 mL) to give a colorless solution. NaH (0.291 g, 11.52 mmol) was added, the reaction turned white suspension and then stirred for 10 min, phenylsulfonyl chloride (2.036 g, 11.52 mmol) in THF (5 mL) was added dropwise. The reaction was quenched with NH$_4$Cl (aq). The reaction was extracted with EA. The combined organic phase was washed with brine and dried over Na$_2$SO$_4$, concentrated and purified by column chromatography on silica gel (eluent: PE/EA=10:1~1:2) to give the light brown solid (2.4 g, 85%). LC-MS: [M+H]$^+$=296.9.

Intermediate 24.2

2,6-dimethyl-1-(phenylsulfonyl)-1H-indole-5-carbonitrile

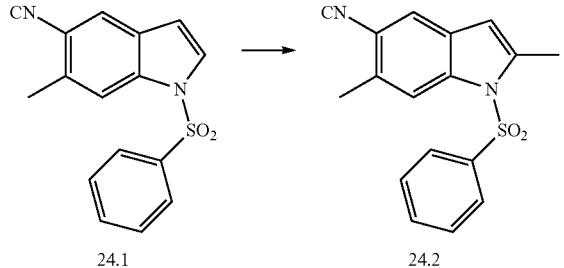

To a solution of intermediate 24.1 (2200 mg, 7.42 mmol) in THF (20 mL) was added LDA (4.45 mL, 8.91 mmol) at −78° C. After 30 min stirring at this temperature, the reaction was warmed to r.t. for additional 10 min stirring, and then cooled to −78° C., MeI (0.650 mL, 10.39 mmol) in THF (3 mL) was added dropwise. Then the reaction was warmed to r.t. gradually, and kept stirring at r.t. for 12 h. The reaction was cooled to r.t. and quenched with NH$_4$Cl (aq). The combined organic phase was washed with brine and dried over Na$_2$SO$_4$, concentrated and purified by column chromatography on silica gel (eluent: DCM/MeOH=10:1~2:1) to give the title compound (0.75 g, 33%). LC-MS: [M+H]$^+$=311.2.

Intermediate 24.3

2,6-dimethyl-1H-indole-5-carbonitrile

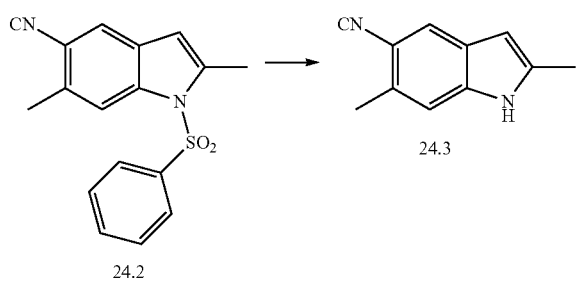

In a 50 mL round-bottomed flask was added intermediate 24.2 (1.6 g, 5.16 mmol) in MeOH (30 mL) to give a colorless solution. NaOH solution in water (8.25 mL, 41.2 mmol) is added. The reaction was heated to 80° C. for 2 h. The reaction was cooled to 0° C., and then quenched with NH$_4$Cl (aq). The mixture was extracted with EA for three times. The combined organic phase was washed with brine and dried over Na$_2$SO$_4$, concentrated and purified by column chromatography on silica gel (eluent: DCM/MeOH=10:1~2:1) to give the title compound (640 mg, 72%). LC-MS: [M+H]$^+$=171.0.

Intermediate 24.4

3-bromo-2,6-dimethyl-1H-indole-5-carbonitrile

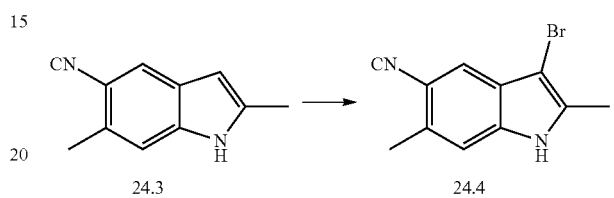

In a 25 mL round-bottomed flask was added intermediate 24.3 (300 mg, 1.763 mmol) in DMF (7 mL) to give a yellow solution. The reaction was cooled to 0° C., NBS (376 mg, 2.115 mmol) was added. The reaction was kept stirring for 3 h at this temperature. The reaction was quenched with NH$_4$Cl (aq). The mixture was extracted with EA for three times. The combined organic phase was washed with brine and dried over Na$_2$SO$_4$, concentrated and purified by column chromatography on silica gel (eluent: DCM/MeOH=10:1~2:1) to give the title compound (340 mg, 77%). $^1$H NMR (METHANOL-d$_4$) δ: 7.64 (s, 1H), 7.27 (s, 1H), 2.55-2.59 (s, 3H), 2.38-2.43 (s, 3H). LC-MS: [M+H]$^+$=248.9.

Intermediate 24.5

3-(3-amino-2-methylphenyl)-2,6-dimethyl-1H-indole-5-carbonitrile

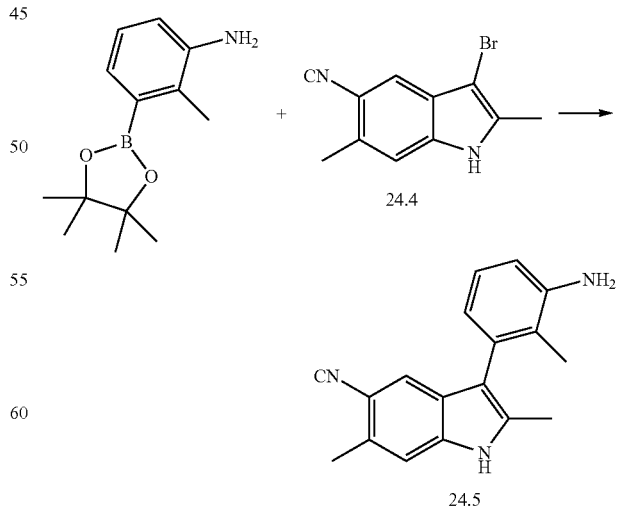

The title compound was prepared by using a procedure similar to that of example 1 by replacing intermediate 1.7 and 5-bromo-4-chloropyridin-3-amine with 2-methyl-3-(4,4,5,5-tetramethyl-1,3,2-dioxaborolan-2-yl)aniline and 24.4 LC-MS: [M+H]⁺=276.0.

Example 24

3-(3-amino-2-methylphenyl)-1-(3-hydroxypropyl)-2,6-dimethyl-1H-indole-5-carbonitrile

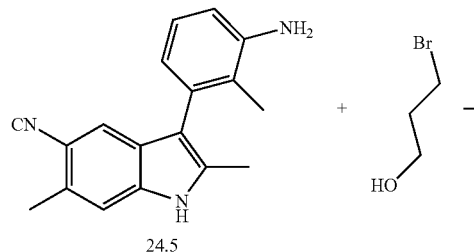
24.5

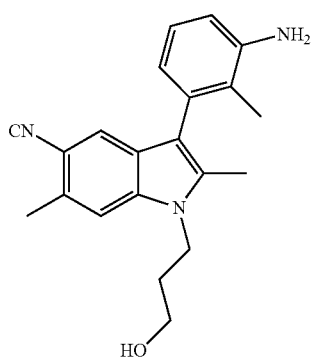
Example 24

In a 10 mL round-bottomed flask was added intermediate 24.5 (17 mg, 0.062 mmol) and Cs₂CO₃ (40.2 mg, 0.123 mmol) in DMF (1.2 mL) to give a yellow solution. 3-bromopropan-1-ol (8.58 mg, 0.062 mmol) was added. The reaction was kept stirring at r.t. for 4 h. The reaction was quenched with NH₄Cl (aq). The combined organic phase was washed with brine and dried over Na₂SO₄, concentrated and purified by prep-HPLC (0.1% NH₃.H₂O/ACN/H₂O) to give the title compound (5 mg, 25%) as a white solid. ¹H NMR (METHANOL-d₄) δ: 7.44 (s, 1H), 7.40 (s, 1H), 7.02-7.07 (m, 1H), 6.80 (d, J=7.8 Hz, 1H), 6.61 (d, J=6.7 Hz, 1H), 4.33 (t, J=7.2 Hz, 2H), 3.60 (t, J=5.9 Hz, 2H), 2.61 (s, 3H), 2.29 (s, 3H), 1.99 (quin, J=6.6 Hz, 2H), 1.91 (s, 3H). LC-MS: [M+H]⁺=334.0.

Example 25

3-(5-amino-4-chloropyridin-3-yl)-1-(3-hydroxypropyl)-2,6-dimethyl-1H-indole-5-carbonitrile Intermediate 25.1

3-bromo-2,6-dimethyl-1-(phenylsulfonyl)-1H-indole-5-carbonitrile

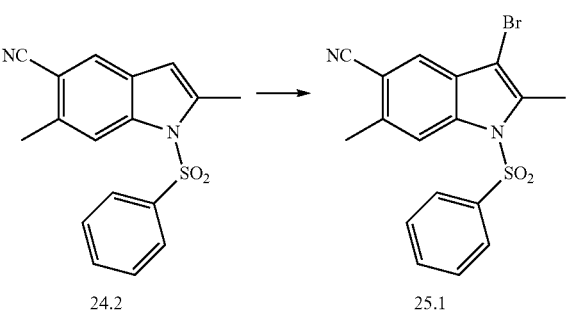
24.2    25.1

In a 10 mL round-bottomed flask was added intermediate 24.2 (150 mg, 0.483 mmol) in DMF (2 mL) to give a colorless solution. The reaction was cooled to 0° C., NBS (112 mg, 0.628 mmol) in DMF (0.5 mL) was added dropwise. The reaction was quenched with NH₄Cl (aq). The mixture was extracted with EA for three times. The combined organic phase was washed with brine and dried over Na₂SO₄, concentrated and purified by column chromatography on silica gel (eluent: PE/EA=10:1~2:1) to give the title compound (60 mg, 32%) as a yellow solid. LC-MS: [M+H]⁺=388.8.

Intermediate 25.2

2,6-dimethyl-1-(phenylsulfonyl)-3-(4,4,5,5-tetramethyl-1,3,2-dioxaborolan-2-yl)-1H-indole-5-carbonitrile

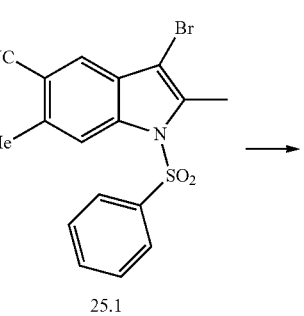
25.1

-continued

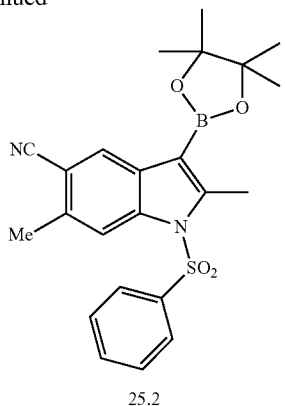

25.2

The title compound was prepared by using a procedure similar to that of intermediate 21.3 by replacing intermediate 21.2 with 25.1. LC-MS: [M+H]$^+$=437.0.

Intermediate 25.3

3-(5-amino-4-chloropyridin-3-yl)-2,6-dimethyl-1-(phenylsulfonyl)-1H-indole-5-carbonitrile

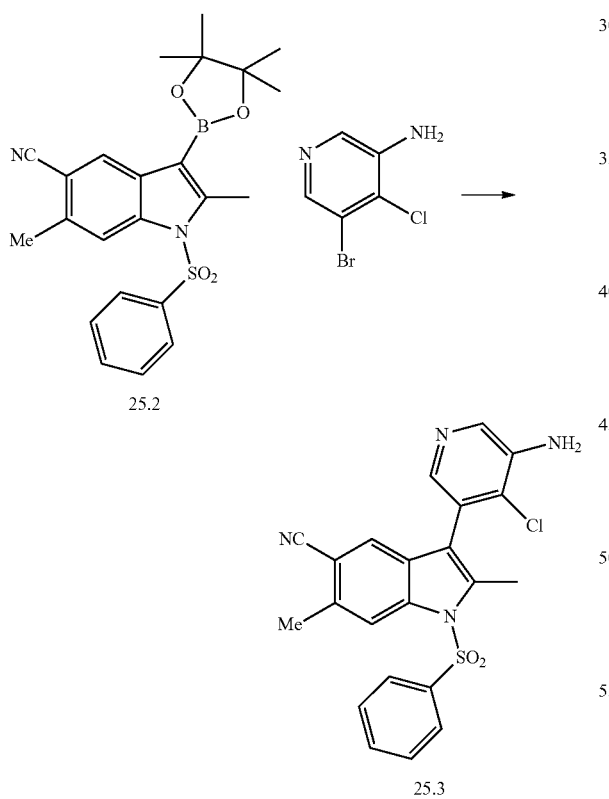

In a 25 mL round-bottomed flask were added K$_3$PO$_4$ (63.2 mg, 0.298 mmol), 25.2 (65 mg, 0.149 mmol), xphos Pd G2(20 mg, 0.025 mmol) and R1 (30.9 mg, 0.149 mmol). The reaction was evacuated and filled with N$_2$ for three times. Dioxane (4 mL) and water (1 mL) were added. The reaction was heated to 80° C. for 5 h under N$_2$ protection. The reaction was cooled to r.t. and quenched with NH$_4$Cl (aq). The combined organic phase was washed with brine and dried over Na$_2$SO$_4$, concentrated and purified by column chromatography on silica gel (eluent: PE/EA=10:1~2:1) to give the title compound (30 mg, 46%) as a yellow solid. LC-MS: [M+H]$^+$=436.9.

Intermediate 25.4

3-(5-amino-4-chloropyridin-3-yl)-2,6-dimethyl-1H-indole-5-carbonitrile

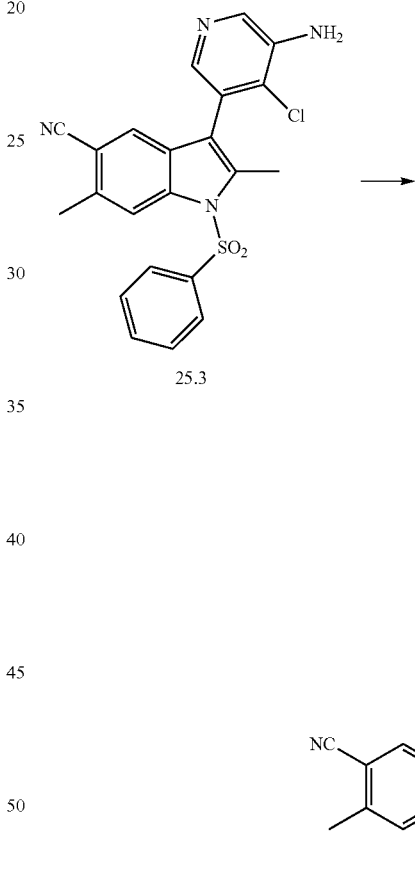

In a 10 mL round-bottomed flask were added 25.3 (30 mg, 0.069 mmol) and 2N NaOH (0.343 mL, 0.687 mmol) solution in MeOH (2 mL) to give a yellow solution. The reaction was heated to 70° C. for 2 h. The reaction was cooled to r.t. and quenched with NH$_4$Cl (aq). The combined organic phase was washed with brine and dried over Na$_2$SO$_4$, concentrated and purified by column chromatography on silica gel (eluent: DCM/MeOH=10:1~2:1) to give the title compound (15 mg, 75%) as a yellow solid. $^1$H NMR (METHANOL-d$_4$) δ: 8.08 (s, 1H), 7.75 (s, 1H), 7.48 (s, 1H), 7.32 (s, 1H), 2.58 (s, 3H), 2.33 (s, 3H). LC-MS: [M+H]$^+$= 297.0.

Example 25

3-(5-amino-4-chloropyridin-3-yl)-1-(3-hydroxypropyl)-2,6-dimethyl-1H-indole-5-carbonitrile

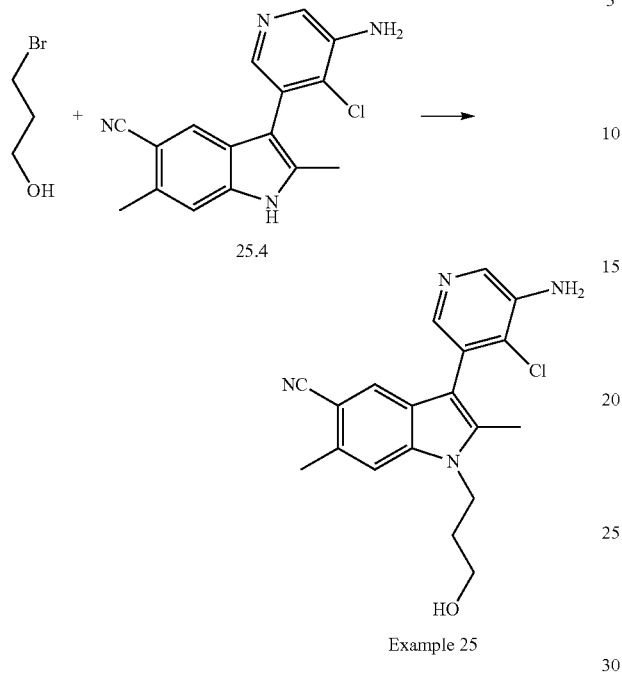

The title compound was prepared by using a procedure similar to that of example 24 by replacing intermediate 24.5 with 25.4. $^1$H NMR (400 MHz, Methanol-d$_4$)δ: 8.08 (s, 1H), 7.72 (s, 1H), 7.48-7.51 (m, 2H), 4.33-4.39 (m, 2H), 3.58-3.62 (m, 2H), 2.62 (s, 3H), 2.36 (s, 3H), 2.18-2.22 (m, 2H). LC-MS: [M+H]$^+$=355.0.

Example 26

3-(3-amino-6-fluoro-2-methylphenyl)-1-((1R,4R)-4-hydroxycyclohexyl)-6-methyl-1H-indole-5-carbonitrile

Example 27

3-(3-amino-6-fluoro-2-methylphenyl)-1-((1S,4S)-4-hydroxycyclohexyl)-6-methyl-1H-indole-5-carbonitrile

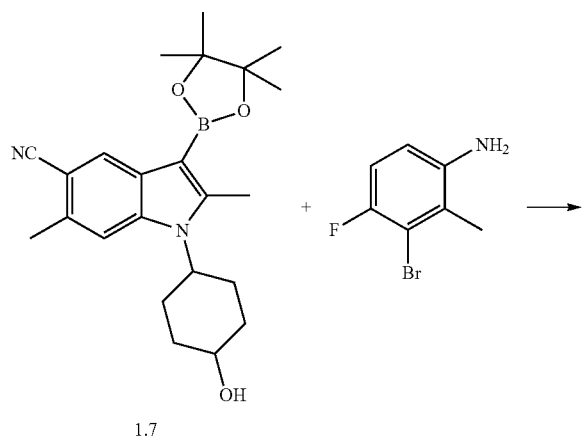

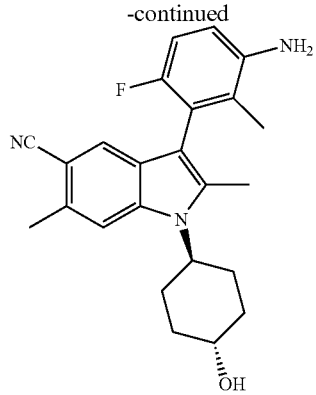

Example 26

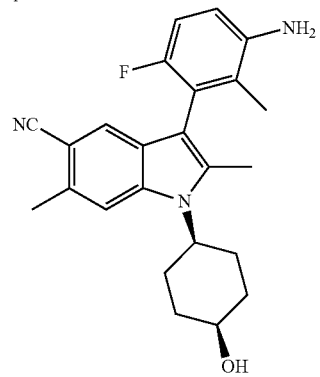

Example 27

To a solution of 1.7 (200 mg, 0.526 mmol), Na$_2$CO$_3$ (111 mg, 1.05 mmol), Pd(PPh$_3$)$_2$Cl$_2$ (36.9 mg, 0.053 mmol) and 3-bromo-4-fluoro-2-methylaniline (204 mg, 0.526 mmol) in 2-Propanol (5 mL) was added water (1.5 mL). The mixture was stirred at 100° C. for 3 hr under nitrogen protection. Removed the most organic solvents in vacuum, the residue was extracted with DCM twice, the organic layer was dried over magnesium sulfate, filtered and concentrated in vacuum. The residue was purified by CombiFlash, eluted with methanol in DCM (0-5%, 30 min). Collected the desired fraction to afford a brown solid, it was further purified by acidic Prep-HPLC (0.1% TFA/ACN/H$_2$O). The desired fraction was lyophilized to give the title compounds Example 26 (32 mg, 15.3%) and Example 27 (5.6 mg, 2.7%) as pink powder.

Example 26

$^1$H NMR (400 MHz, Methanol-d$_4$) δ 7.61 (s, 1H), 7.55 (s, 1H), 7.50 (s, 1H), 7.36 (dd, J=8.9, 4.8 Hz, 1H), 7.19 (t, J=8.7 Hz, 1H), 4.49 (dd, J=13.7, 10.1 Hz, 1H), 3.73 (td, J=10.8, 5.5 Hz, 1H), 2.65 (s, 3H), 2.16 (d, J=24.8 Hz, 7H), 1.96 (q, J=12.2 Hz, 2H), 1.75-1.50 (m, 2H). LC-MS: [M+H]$^+$=378.0.

Example 27

$^1$H NMR (400 MHz, Methanol-d$_4$) δ 7.62 (s, 1H), 7.54 (s, 1H), 7.51 (s, 1H), 7.34 (dd, J=9.0, 4.8 Hz, 1H), 7.18 (t, J=8.7 Hz, 1H), 4.51 (t, J=12.1 Hz, 1H), 4.10 (s, 1H), 2.65 (s, 3H), 2.36-2.15 (m, 5H), 1.99 (d, J=13.7 Hz, 2H), 1.87 (q, J=13.8 Hz, 4H). LC-MS: [M+H]$^+$=378.0.

Example 28

3-(3-amino-2,6-difluorophenyl)-1-((1R,4R)-4-hydroxycyclohexyl)-6-methyl-1H-indole-5-carbonitrile

Example 29

3-(3-amino-2,6-difluorophenyl)-1-((1S,4S)-4-hydroxycyclohexyl)-6-methyl-1H-indole-5-carbonitrile

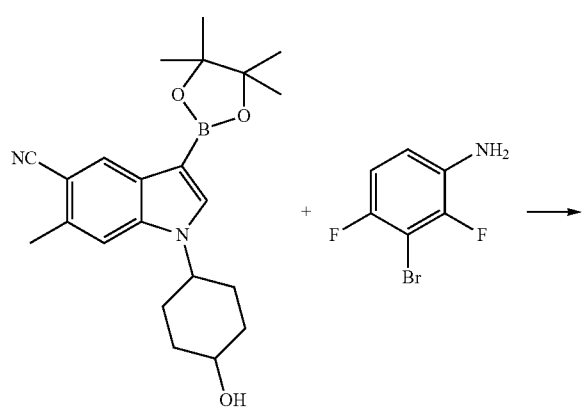

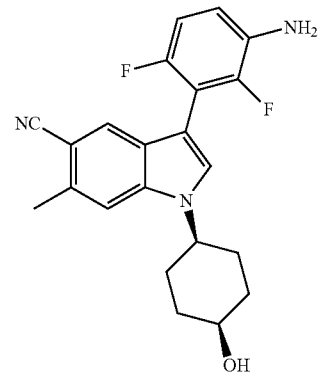

Example 28

Example 29

The title compounds were prepared by using a procedure similar to that of Example 1 by replacing 3-bromo-4-fluoro-2-methylaniline with 3-bromo-2,4-difluoroaniline.

$^1$H NMR (400 MHz, Methanol-d$_4$) δ 7.74 (t, J=2.0 Hz, 1H), 7.59 (d, J=4.8 Hz, 1H), 7.53 (d, J=4.0 Hz, 1H), 6.96-6.69 (m, 2H), 4.43 (ddt, J=12.0, 8.3, 3.7 Hz, 1H), 3.71 (ddt, J=11.0, 6.8, 4.0 Hz, 1H), 2.62 (s, 3H), 2.10 (tt, J=8.4, 3.8 Hz, 4H), 1.90 (qd, J=13.3, 12.6, 3.9 Hz, 2H), 1.71-1.50 (m, 2H). LC-MS: [M+H]$^+$=381.2.

Example 29

$^1$H NMR (400 MHz, Methanol-d$_4$) δ 7.77 (d, J=2.4 Hz, 1H), 7.69 (s, 1H), 7.59 (s, 1H), 7.11-6.87 (m, 2H), 4.50 (t, J=12.1 Hz, 1H), 4.09 (s, 1H), 2.65 (d, J=4.2 Hz, 3H), 2.26 (q, J=12.6, 11.4 Hz, 2H), 1.91 (dq, J=39.8, 14.0 Hz, 6H). LC-MS: [M+H]$^+$=381.2.

Example 30

3-(3-amino-2-chloro-4-fluorophenyl)-1-((1R,4R)-4-hydroxycyclohexyl)-6-methyl-1H-indole-5-carbonitrile

Example 31

3-(3-amino-2-chloro-4-fluorophenyl)-1-((1S,4S)-4-hydroxycyclohexyl)-6-methyl-1H-indole-5-carbonitrile

Intermediate 30.1

3-bromo-2-chloro-6-fluoroaniline

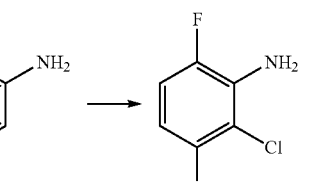

To a solution of 5-bromo-2-fluoroaniline (5 g, 26.3 mmol) in DMF (30 mL) was added NCS (3.69 g, 27.6 mmol). The mixture was stirred at 60° C. for 2 hr. The mixture was diluted with water, extracted with ethyl acetate twice. Then the organic layer was dried over magnesium sulfate, filtered and concentrated in vacuum. The residue was purified by CombiFlash, eluted with ethyl acetate in hexane (0-5%, 40 min), collected the desired fraction to afford the title compound (1.2 g, 5.35 mmol, 20.32% yield). 1H NMR (400 MHz, DMSO-d6) δ 7.03 (dd, J=10.8, 8.7 Hz, 1H), 6.90 (dd, J=8.8, 5.1 Hz, 1H), 5.77 (s, 2H). LC-MS: [M+H]$^+$=223.9, 226.0, 228.3.

Intermediate 30.2

2-chloro-6-fluoro-3-(4,4,5,5-tetramethyl-1,3,2-di-oxaborolan-2-yl)aniline

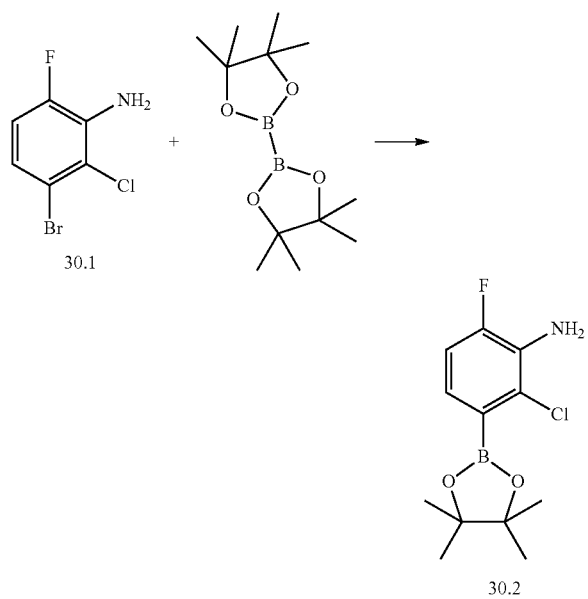

A solution of 30.1 (300 mg, 1.337 mmol), Pin$_2$B$_2$(441 mg, 1.738 mmol), KOAc (262 mg, 2.67 mmol) and PdCl2(dppf) (109 mg, 0.134 mmol) in dioxane (5 mL) was stirred at 100° C. for 10 hr under nitrogen protection. The mixture was diluted with DCM, washed with water, brine. The organic layer was dried over magnesium sulfate, filtered and concentrated in vacuum. The residue was purified by Combi-Flash, eluted with ethyl acetate in hexane (0-30%, 30 min). Collected the desired fraction to afford the title compound (150 mg, 41.3%) as white solid. $^1$H NMR (400 MHz, DMSO-d6) δ 7.02 (dd, J=10.8, 8.2 Hz, 1H), 6.83 (dd, J=8.1, 6.2 Hz, 1H), 5.33 (s, 2H), 1.29 (s, 12H). LC-MS: [M+H]$^+$= 272.2

Intermediate 30.3

3-(3-amino-2-chloro-4-fluorophenyl)-6-methyl-1-(1,4-dioxaspiro[4.5]decan-8-yl)-1H-indole-5-carbonitrile

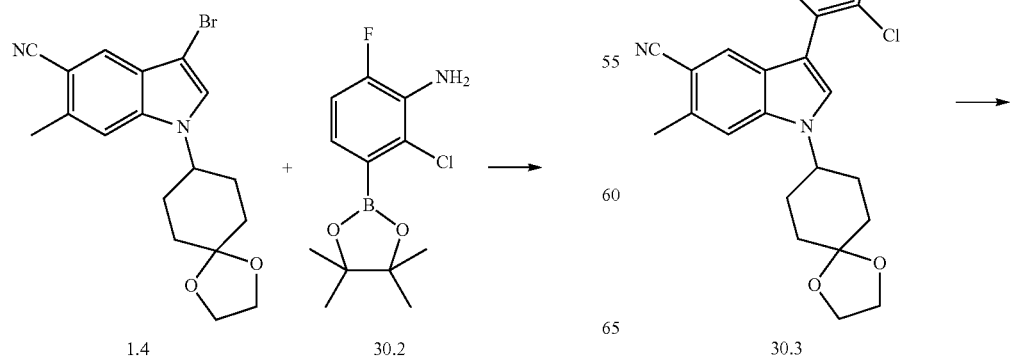

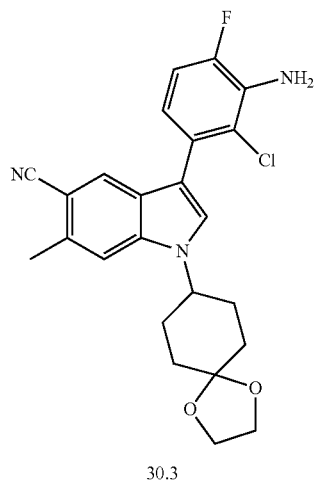

To a solution of 30.2 (181 mg, 0.666 mmol), 1.4 (250 mg, 0.666 mmol), PdCl$_2$(PPh$_3$)$_2$(46.8 mg, 0.067 mmol) and Na$_2$CO$_3$ (141 mg, 1.332 mmol) in 2-Propanol (9 mL) was added water (3 mL). The mixture was stirred at 100° C. for 5 hr under nitrogen protection. Then the mixture was diluted with water, extracted with DCM twice, and then organic layer was dried over magnesium sulfate, filtered and concentrated in vacuum. The residue was purified by Combi-Flash, eluted with methanol in DCM (0-2%, 30 min), collected the desired fraction to afford the title compound (100 mg, 34.1% yield) as grey solid. LC-MS: [M+H]$^+$= 439.2, 441.2.

Intermediate 30.4

3-(3-amino-2-chloro-4-fluorophenyl)-6-methyl-1-(4-oxocyclohexyl)-1H-indole-5-carbonitrile

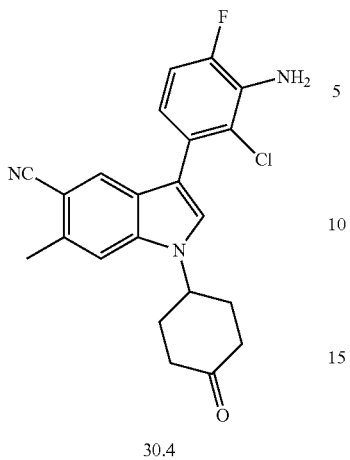

30.4

To a solution of 30.3 (100 mg, 0.227 mmol) in DCM (2 mL) was added TFA (2 mL, 26.0 mmol). The mixture was stirred at rt for 2 hr. Then the mixture was concentrated in vacuum, the residue was re-dissolved in DCM, washed with water, brine. The organic layer was dried over magnesium sulfate, filtered and concentrated in vacuum to afford 90 mg colorless syrup. It was used for the next step directly. LC-MS: [M+H]$^+$=382.0, 383.0.

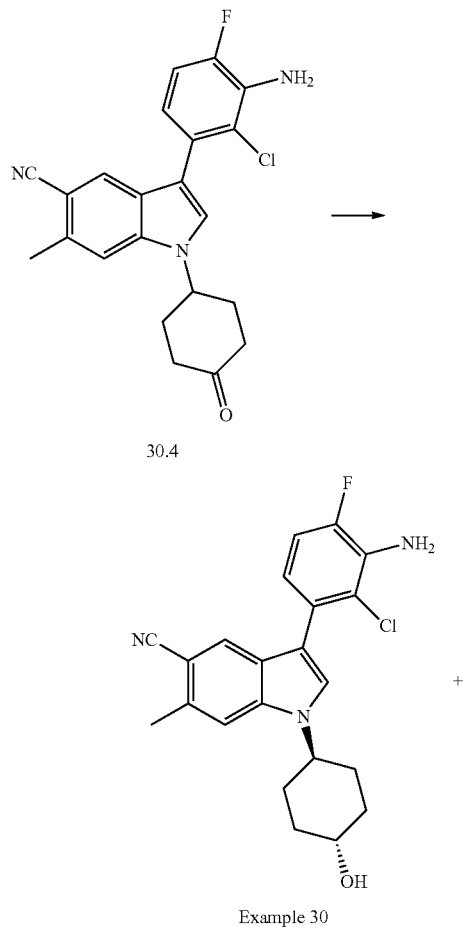

30.4

Example 30

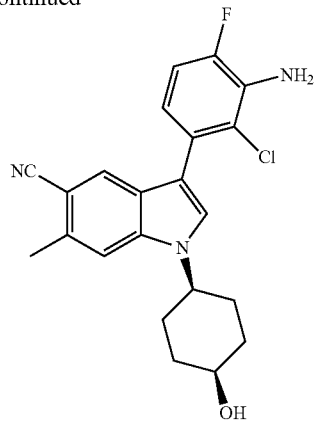

Example 31

To a solution of 30.4 (90 mg, 0.227 mmol) in methanol (2 mL) was added NaBH$_4$ (17.20 mg, 0.455 mmol) under ice-bath. The mixture was stirred at 0° C. for 10 min. Then the mixture was diluted with DCM, washed with water, the organic layer was dried over magnesium sulfate, filtered and concentrated in vacuum, the residue was further purified by basic Prep-HPLC (0.1% NH$_4$OH/ACN/H$_2$O), collected the desired fractions and lyophilized to afford the title compound Example 30 (29.8 mg, 31.3%) and the title compound Example 31 (1.6 mg, 1.59%) as white powder.

Example 30 ZGW428

$^1$H NMR (400 MHz, Methanol-d4) δ 7.72 (s, 1H), 7.54 (d, J=2.6 Hz, 2H), 7.02 (dd, J=10.6, 8.4 Hz, 1H), 6.73 (dd, J=8.4, 5.6 Hz, 1H), 4.44 (tt, J=12.1, 3.6 Hz, 1H), 3.73 (tt, J=11.0, 4.0 Hz, 1H), 2.68-2.55 (m, 3H), 2.18-2.05 (m, 4H), 2.02-1.83 (m, 2H), 1.72-1.46 (m, 2H). LC-MS: [M+H]$^+$= 398.1, 399.1

Example 31 JRY432

$^1$H NMR (400 MHz, Methanol-d4) δ 7.74 (s, 1H), 7.56 (d, J=8.4 Hz, 2H), 7.04 (dd, J=10.6, 8.5 Hz, 1H), 6.81-6.69 (m, 1H), 4.46 (ddt, J=12.1, 7.6, 3.7 Hz, 1H), 4.09 (t, J=2.9 Hz, 1H), 2.72-2.57 (m, 3H), 2.42-1.73 (m, 8H). LC-MS: [M+H]$^+$= 398.1, 399.1

Example 32

3-(3-amino-5-cyanophenyl)-1-((1R,4R)-4-hydroxy-cyclohexyl)-6-methyl-1H-indole-5-carbonitrile Intermediate 32.1

3-amino-5-(4,4,5,5-tetramethyl-1,3,2-dioxaborolan-2-yl)benzonitrile

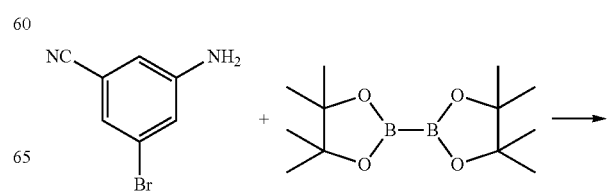

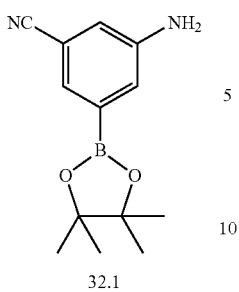

32.1

The title compound was prepared by using a procedure similar to that of intermediate 30.2 by replacing intermediate 30.1 with 3-amino-5-bromobenzonitrile. $^1$H NMR (400 MHz, Methanol-$d_4$) δ 7.27 (dd, J=2.4, 0.9 Hz, 1H), 7.20 (t, J=1.2 Hz, 1H), 6.99 (dd, J=2.5, 1.6 Hz, 1H), 1.32 (s, 12H). LC-MS: [M+H]$^+$=245.1.

Intermediate 32.2

3-(3-amino-5-cyanophenyl)-6-methyl-1-(1,4-dioxaspiro[4.5]decan-8-yl)-1H-indole-5-carbonitrile

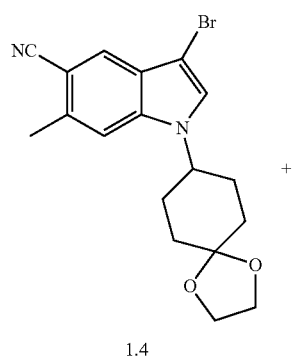

1.4

+

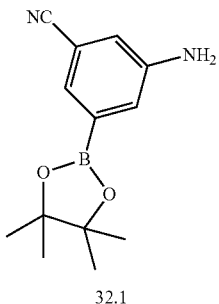 

32.1

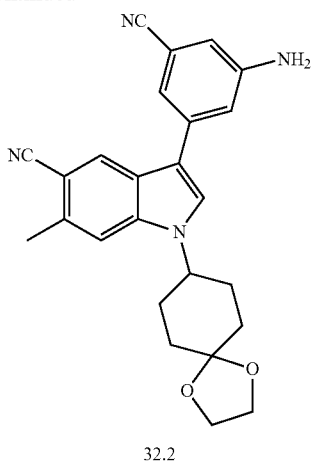

32.2

The title compound was prepared by using a procedure similar to that of intermediate 30.3 by replacing intermediate 30.2 with intermediate 32.1. $^1$H NMR (400 MHz, DMSO-$d_6$) δ 8.33 (s, 1H), 8.13 (s, 1H), 7.76 (s, 1H), 7.36 (t, J=1.5 Hz, 1H), 7.33 (t, J=1.9 Hz, 1H), 6.73 (t, J=1.7 Hz, 1H), 5.66 (s, 2H), 4.73-4.47 (m, 1H), 3.97-3.78 (m, 4H), 2.59 (s, 3H), 2.13-2.00 (m, 2H), 1.94 (d, J=12.3 Hz, 2H), 1.88-1.76 (m, 4H). LC-MS: [M+H]$^+$=412.9.

Intermediate 32.3

3-(3-amino-5-cyanophenyl)-6-methyl-1-(4-oxocyclohexyl)-1H-indole-5-carbonitrile

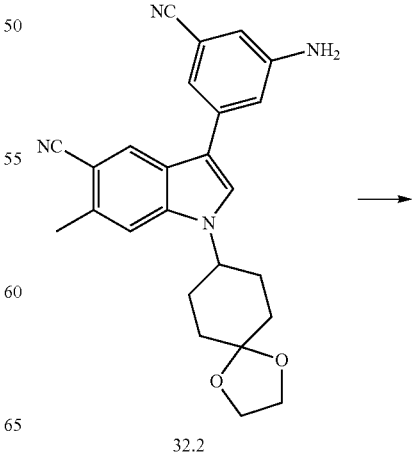

32.2

-continued

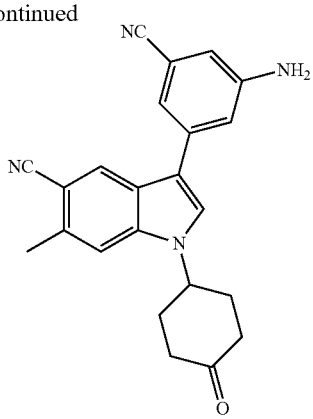

32.3

To a solution of 32.2 (120 mg, 0.291 mmol) in THF (10 mL) was added HCl (6M, 2 mL, 12.00 mmol). The mixture was stir at 60° C. for 2 hr. The mixture was basified by aqueous sodium hydroxide (1M) to pH=9, then extracted with DCM twice, the organic layer was dried over magnesium sulfate, filtered and concentrated in vacuum to afford the title compound (100 mg, 93%) as white solid. It was used for the next step directly. LC-MS: [M+H]$^+$=368.9.

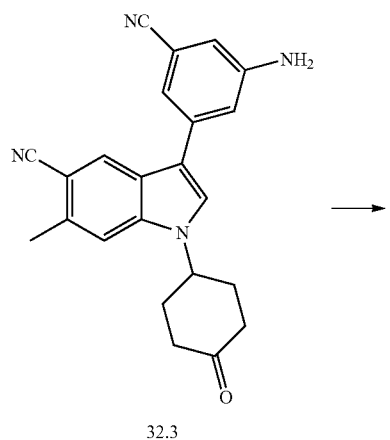

Example 32

To a solution of 32.3 (130 mg, 0.353 mmol) in methanol (10 mL) was added NaBH$_4$ (20 mg, 0.529 mmol). The mixture was stirred at 0° C. for 10 min. The mixture was concentrated in vacuum, and then the residue was re- dissolved in DCM, washed with water. The organic layer was dried over magnesium sulfate, filtered and concentrated in vacuum. The residue was loaded in silica and purified by CombiFlash, eluted with methanol in DCM (0-3%, 30 min), collected the desired fraction to afford the title compound (15 mg, 11.4%) as dried powder. $^1$H NMR (400 MHz, Methanol-d$_4$) δ 8.18 (s, 1H), 7.76 (s, 1H), 7.57 (s, 1H), 7.29-7.22 (m, 1H), 7.17 (t, J=1.5 Hz, 1H), 6.84 (dd, J=2.2, 1.4 Hz, 1H), 4.44 (ddd, J=11.8, 8.0, 3.8 Hz, 1H), 3.74 (ddd, J=15.2, 10.9, 4.2 Hz, 1H), 2.70-2.57 (m, 3H), 2.17-2.0 (m, 4H), 1.97 (qd, J=13.2, 12.7, 3.5 Hz, 2H), 1.73-1.55 (m, 2H). LC-MS: [M+H]$^+$=371.0, 372.0.

Example 33

3-(3-amino-2,6-difluorophenyl)-1-(3-hydroxypropyl)-6-methyl-1H-indole-5-carbonitrile

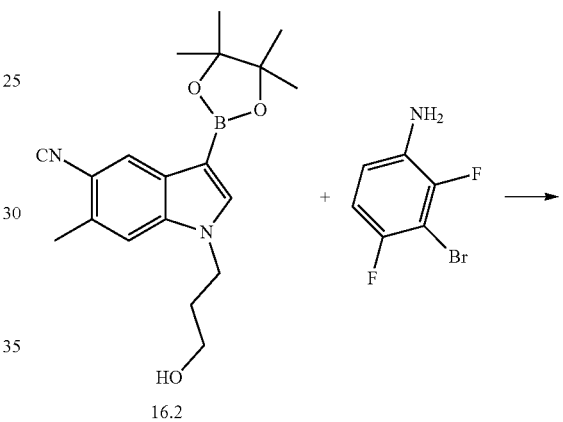

16.2

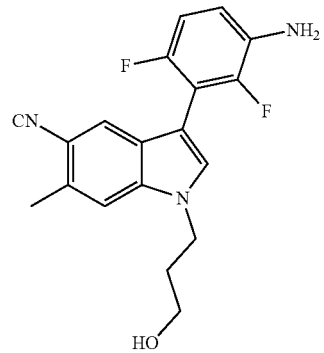

Example 33

The title compound was prepared by using a procedure similar to that of example 1 by replacing intermediate 1.7 and 5-bromo-4-chloropyridin-3-amine with 16.2 and 3-bromo-2,4-difluoroaniline. $^1$H NMR (DMSO-d$_6$) δ: 7.69-7.79 (m, 2H), 7.66 (s, 1H), 6.87-6.99 (m, 1H), 6.69-6.82 (m, 1H), 4.62-4.74 (m, 1H), 4.28-4.37 (m, 2H), 3.38-3.43 (m, 2H), 2.59 (s, 3H), 1.92-1.98 (m, 2H). LC-MS: [M+H]$^+$= 342.2.

Example 34

3-(2,2-dimethyl-1,2,3,4-tetrahydroquinolin-5-yl)-1-(3-hydroxypropyl)-6-methyl-1H-indole-5-carbonitrile

Intermediate 34.1

2-methylbut-3-yn-2-yl acetate

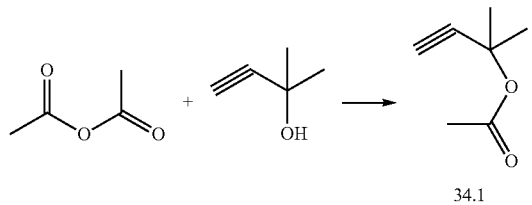

To a solution of 2-methylbut-3-yn-2-ol (34.6 mL, 357 mmol), DMAP (2.179 g, 17.83 mmol), TEA (59.7 mL, 428 mmol) in DCM (200 mL) was added acetic anhydride (33.7 mL, 357 mmol) under ice-bath. The mixture was stirred at rt for 20 hr. The mixture was washed with water, then HCl (1 M, 200 mL), followed by NaOH (0.1 N, 100 mL), the organic layer was dried over magnesium sulfate, filtered and concentrated to afford the title compound (45 g, 80%) as colorless oil. It was used for the next step directly. $^1$H NMR (400 MHz, Chloroform-d) δ 2.54 (d, J=1.0 Hz, 1H), 2.04 (d, J=1.1 Hz, 3H), 1.68 (d, J=1.0 Hz, 6H).

Intermediate 34.3

5-bromo-2,2-dimethyl-1,2-dihydroquinoline

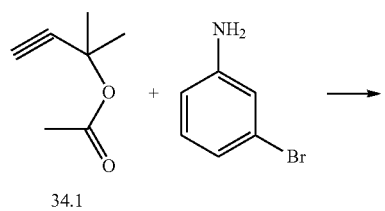

To a solution of 34.1 (22 g, 70%, 122 mmol) and 3-bromoaniline (13.29 mL, 122 mmol) in THF (200 mL) was added CuCl (1.209 g, 12.21 mmol). The mixture was stirred at 70° C. for 20 hr. Filtered and concentrated, the residue was purified by CombiFlash, eluted with ethyl acetate in hexane (0-1%, 60 min) to afford the title compound 34.3 (11.8 g, 40.6%) as brown syrup and 5.2 g compound 34.2 as by-product. $^1$H NMR (400 MHz, Methanol-d$_4$) δ 6.67 (d, J=7.9 Hz, 1H), 6.61-6.51 (m, 2H), 6.18 (d, J=9.8 Hz, 1H), 5.46 (d, J=9.7 Hz, 1H), 1.25 (s, 6H). LC-MS: [M+H]$^+$=240.1.

Intermediate 34.4

2,2-dimethyl-5-(4,4,5,5-tetramethyl-1,3,2-dioxaborolan-2-yl)-1,2-dihydroquinoline

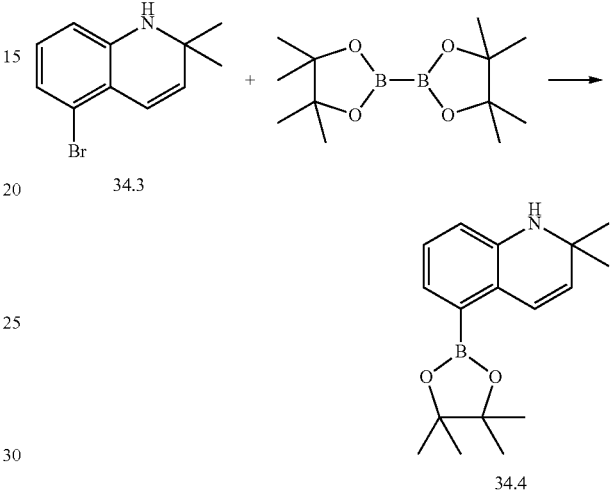

The title compound was prepared by using a procedure similar to that of intermediate 30.2 by replacing intermediate 30.1 with intermediate 34.3. $^1$H NMR (400 MHz, DMSO-d$_6$) δ 6.98-6.70 (m, 3H), 6.52 (d, J=7.8 Hz, 1H), 5.76 (s, 1H), 5.45 (d, J=10.2 Hz, 1H), 1.27 (s, 12H), 1.19 (s, 6H). LC-MS: [M+H]$^+$=286.2.

Intermediate 34.5

2,2-dimethyl-5-(4,4,5,5-tetramethyl-1,3,2-dioxaborolan-2-yl)-1,2,3,4-tetrahydroquinoline

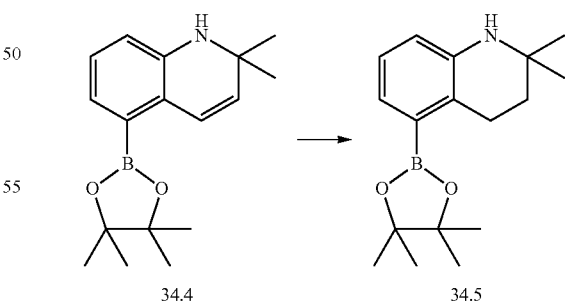

To a solution of 34.4 (220 mg, 0.771 mmol) in methanol (5 mL) was added Pd—C (5%, wet) (82 mg, 0.771 mmol). The mixture was stirred at rt under a hydrogen balloon for 2 h. Filtered and concentrated to afford 205 mg brown solid. It was used for the next step directly. LC-MS: [M+H]$^+$=374.3.

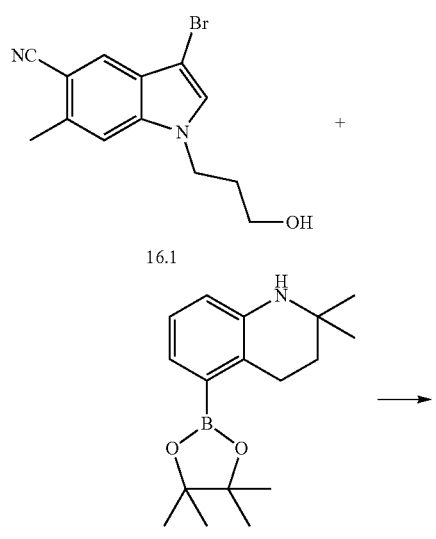

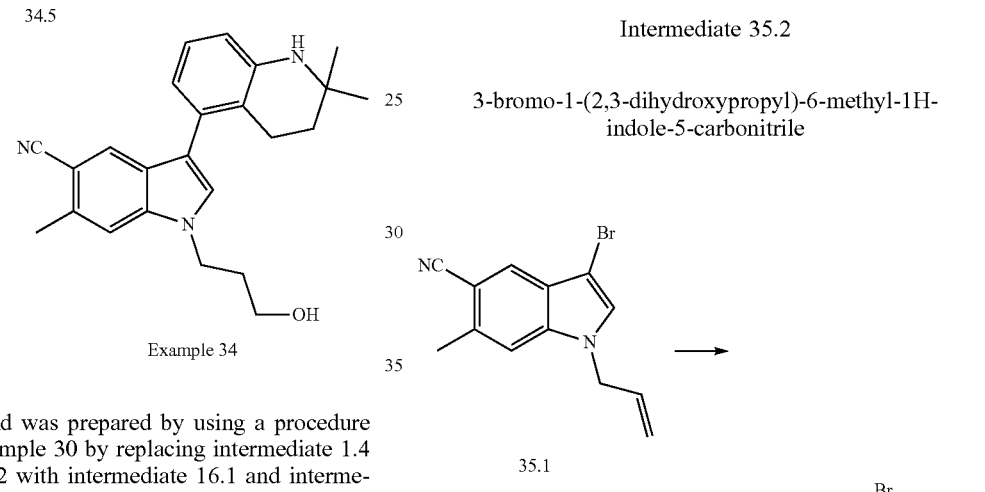

Example 34

The title compound was prepared by using a procedure similar to that of example 30 by replacing intermediate 1.4 and intermediate 30.2 with intermediate 16.1 and intermediate 34.5. $^1$H NMR (400 MHz, Methanol-$d_4$) δ 7.67 (s, 1H), 7.48 (s, 1H), 7.31 (s, 1H), 6.99 (t, J=7.7 Hz, 1H), 6.58 (dd, J=25.2, 7.7 Hz, 2H), 4.33 (t, J=6.9 Hz, 2H), 3.55 (t, J=6.0 Hz, 2H), 2.62 (d, J=4.0 Hz, 5H), 2.10-1.98 (m, 2H), 1.58 (t, J=6.7 Hz, 2H), 1.21 (s, 6H). LC-MS: [M+H]$^+$=374.3, 375.3.

Example 35

1-(2,3-dihydroxypropyl)-3-(2,2-dimethyl-1,2,3,4-tetrahydroquinolin-5-yl)-6-methyl-1H-indole-5-carbonitrile Intermediate 35.1

1-allyl-3-bromo-6-methyl-1H-indole-5-carbonitrile

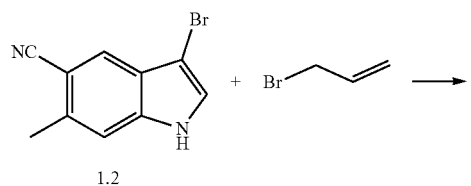

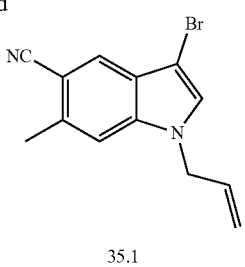

The title compound was prepared by using a procedure similar to that of intermediate 1.4 by replacing intermediate 1.3 with intermediate 3-bromoprop-1-ene. $^1$H NMR (400 MHz, DMSO-$d_6$) δ 7.86 (d, J=5.2 Hz, 1H), 7.73 (s, 1H), 7.61 (s, 1H), 6.11-5.86 (m, 1H), 5.17 (d, J=10.4 Hz, 1H), 5.02 (d, J=17.0 Hz, 1H), 4.86 (d, J=5.5 Hz, 2H), 2.56 (d, J=4.7 Hz, 3H). LC-MS: [M+H]$^+$=275.1, 277.1.

Intermediate 35.2

3-bromo-1-(2,3-dihydroxypropyl)-6-methyl-1H-indole-5-carbonitrile

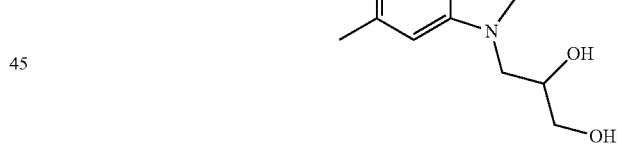

To a suspension of 35.1 (170 mg, 0.618 mmol), $K_2CO_3$ (256 mg, 1.854 mmol), potassium ferrocyanide (683 mg, 1.854 mmol), (DHQ)$_2$PHAL (9.63 mg, 0.012 mmol) and in t-BuOH (3 mL) and water (3.00 mL) was added potassium osmate dihydrate (2.270 mg, 6.18 μmol) under ice-bath. The mixture was stirred at 0° C. for 30 min, and then it was allowed to stir at rt for another 20 hr. Then the mixture was quenched with $Na_2SO_3$, Then the most organic solvents were removed in vacuum, then DCM was added to the mixture, filtered and the filter was separated, the aqueous layer was extracted with DCM, the organic layer was dried over magnesium sulfate, filtered and concentrated, the residue was purified by silica gel, eluted with methanol in DCM (0-3%, 30 min), collected the desired fraction to afford the title compound (150 mg, 83%) as white solid. LC-MS: [M+H]$^+$=308.1, 310.1.

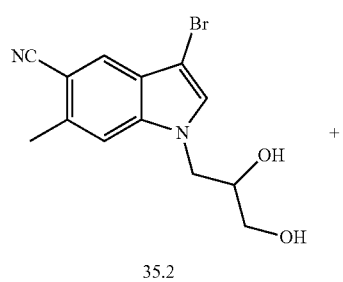

35.2

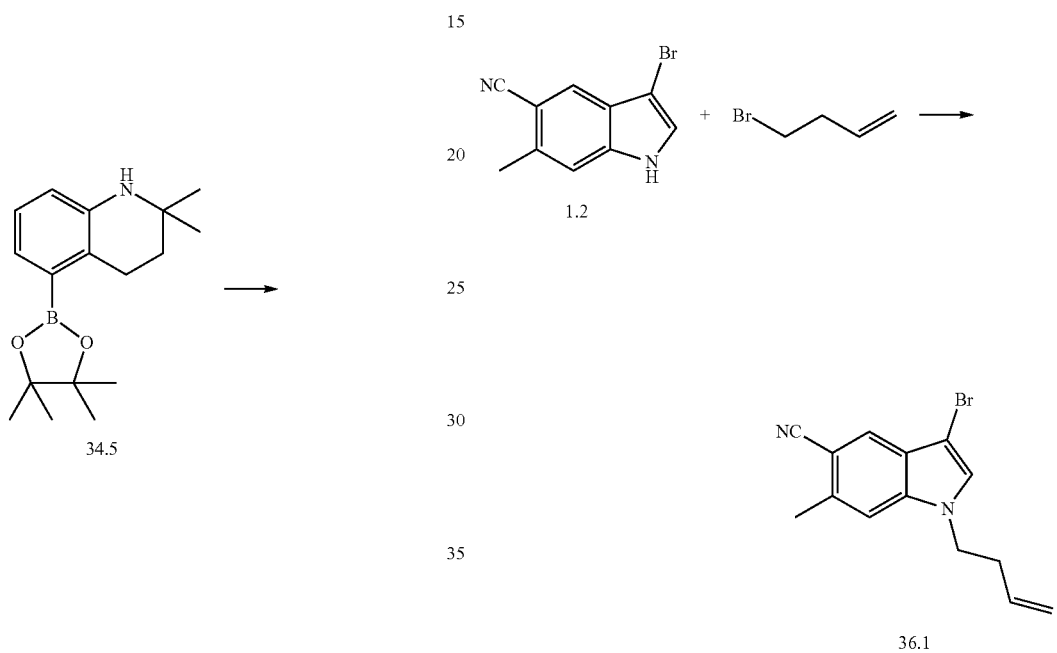

34.5

Example 35

The title compound was prepared by using a procedure similar to that of intermediate 30.3 by replacing intermediate 1.4 and intermediate 30.2 with intermediate 35.2 and intermediate 34.5. ¹H NMR (400 MHz, Methanol-d₄) δ 7.67 (s, 1H), 7.51 (s, 1H), 7.33 (s, 1H), 6.99 (t, J=7.7 Hz, 1H), 6.62 (d, J=7.4 Hz, 1H), 6.56 (d, J=8.0 Hz, 1H), 4.40 (dd, J=14.5, 4.2 Hz, 1H), 4.19 (dd, J=14.5, 7.2 Hz, 1H), 3.99 (dq, J=9.8, 5.3 Hz, 1H), 3.54 (d, J=5.4 Hz, 2H), 2.63 (d, J=12.2 Hz, 5H), 1.59 (t, J=6.7 Hz, 2H), 1.22 (s, 6H). LC-MS: [M+H]⁺= 390.3.

Example 36

1-(3,4-dihydroxybutyl)-3-(2,2-dimethyl-1,2,3,4-tetrahydroquinolin-5-yl)-6-methyl-1H-indole-5-carbonitrile Intermediate 36.1

3-bromo-1-(but-3-en-1-yl)-6-methyl-1H-indole-5-carbonitrile

The title compound was prepared by using a procedure similar to that of intermediate 1.4 by replacing intermediate 1.3 with 4-bromobut-1-ene. ¹H NMR (400 MHz, DMSO-d₆) δ 7.83 (s, 1H), 7.76 (s, 1H), 7.70 (s, 1H), 5.76 (dt, J=17.7, 8.3 Hz, 1H), 4.98 (q, J=12.7, 9.3 Hz, 2H), 4.27 (q, J=6.6 Hz, 2H), 2.57 (d, J=5.2 Hz, 3H), 2.46 (m, 2H).

Intermediate 36.2

3-bromo-1-(3,4-dihydroxybutyl)-6-methyl-1H-indole-5-carbonitrile

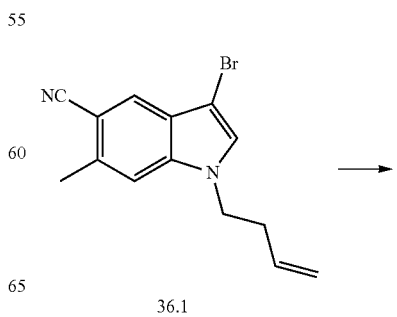

36.1

-continued

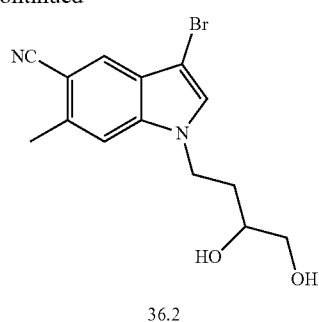

36.2

The title compound was prepared by using a procedure similar to that of intermediate 35.2 by replacing intermediate 35.1 with intermediate 36.1. LC-MS: [M+H]⁺=322.1, 324.1.

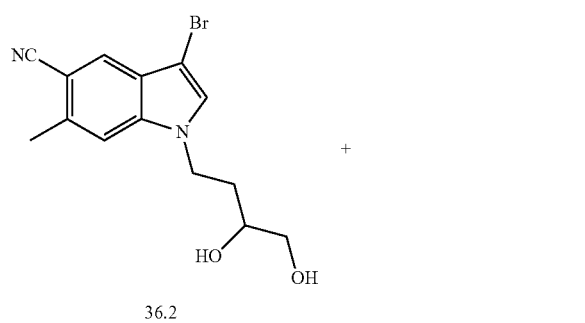

36.2

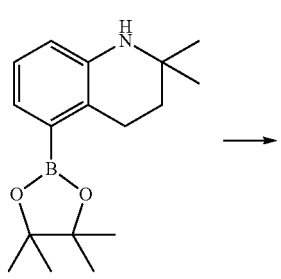

34.5

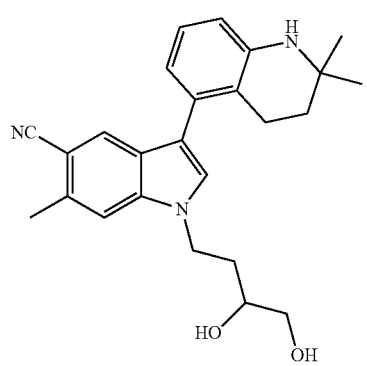

Example 36

The title compound was prepared by using a procedure similar to that of example 30 by replacing intermediate 1.4 and intermediate 30.2 with intermediate 36.2 and intermediate 34.5. ¹H NMR (400 MHz, Methanol-d₄) δ 7.67 (s, 1H), 7.51 (s, 1H), 7.33 (s, 1H), 6.98 (t, J=7.7 Hz, 1H), 6.62 (d, J=7.4 Hz, 1H), 6.55 (d, J=8.0 Hz, 1H), 4.40 (dd, J=14.5, 4.2 Hz, 2H), 3.44-3.55 (m, 3H), 2.62 (s, 5H), 2.12 (m, 1H), 2.08 (m, 1H), 1.59 (t, J=6.8 Hz, 2H), 1.21 (s, 6H). LC-MS: [M+H]⁺=404.3.

Example 37

Trans-3-(5-amino-4-chloropyridin-3-yl)-6-methyl-1-((1R,3R)-3-(methylsulfonyl)cyclopentyl)-1H-indole-5-carbonitrile Intermediate 37.1

(1S,3R)-3-(3-bromo-5-cyano-6-methyl-1H-indol-1-yl)cyclopentyl methanesulfonate (cis relative)

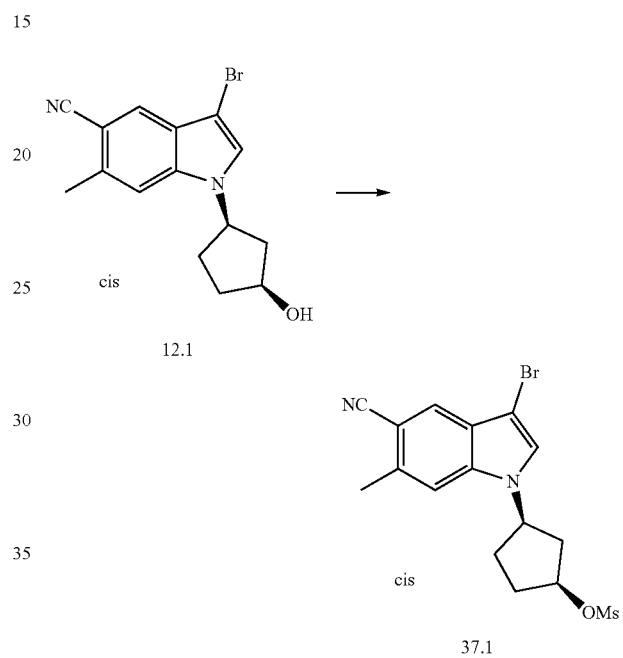

To a solution of 12.1 (300 mg, 0.940 mmol) and TEA (0.196 mL, 1.410 mmol) in DCM (10 mL) was added Ms-Cl (0.088 mL, 1.128 mmol). The mixture was stir at rt for 2 hr. Then the mixture was washed with water, the organic layer was dried over magnesium sulfate, filtered and concentrated in vacuum to afford 400 mg white solid, it was used for the next step directly.

Intermediate 37.2

3-bromo-6-methyl-1-((1R,3R)-3-(methylthio)cyclopentyl)-1H-indole-5-carbonitrile (trans relative)

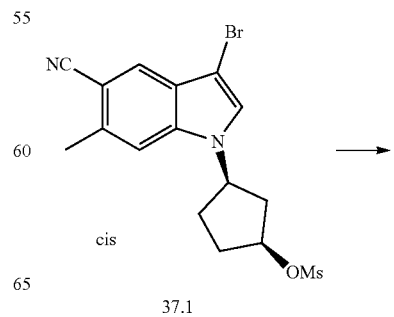

37.1

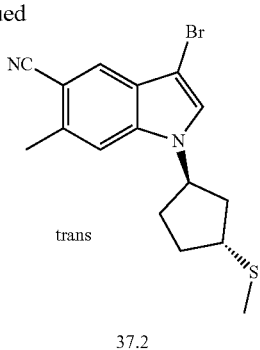

37.2

To a solution of 37.1 (320 mg, 0.805 mmol) in ethanol (5 mL) was added sodium thiomethoxide (141 mg, 2.014 mmol). The mixture was stirred at 70° C. for 2 hr. Then the mixture was diluted with water, extracted with DCM twice. The organic layer was dried over magnesium sulfate, filtered and concentrated in vacuum. The residue was purified by CombiFlash, eluted with ethyl acetate in hexane (10-20%, 30 min). Collected the desired structure to afford the title compound (260 mg, 92%) as colorless syrup. 1H NMR (400 MHz, Methanol-$d_4$) δ 7.78 (s, 1H), 7.60 (s, 1H), 7.52 (s, 1H), 5.11 (p, J=7.4 Hz, 1H), 3.42 (dq, J=7.9, 6.3 Hz, 1H), 2.63 (d, J=0.8 Hz, 3H), 2.50-2.19 (m, 4H), 2.14 (s, 3H), 2.06-1.88 (m, 1H), 1.83-1.66 (m, 1H). LC-MS: [M+H]$^+$=348.8, 350.8.

Intermediate 37.3

3-bromo-6-methyl-1-((1R,3R)-3-(methylsulfonyl)cyclopentyl)-1H-indole-5-carbonitrile (trans relative)

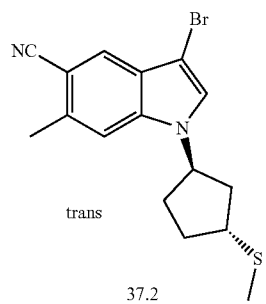

37.2

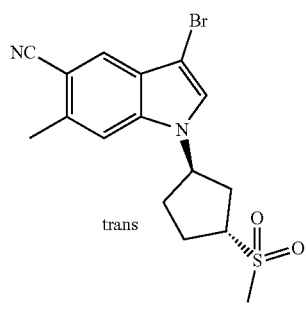

37.3

To a solution of 37.2 (270 mg, 0.773 mmol) in DCM (15 mL) was added m-CPBA (75%, 356 mg, 1.546 mmol), the mixture was stir at 0° C. for 1 hr. Then aqueous of sodium thiosulfate was added to get rid of the excess m-CPBA. Then the mixture was washed with aqueous NaOH (0.1M). The organic layer was dried over magnesium sulfate, filtered and concentrated in vacuum. Then the residue was purified by CombiFlash, eluted with ethyl acetate in hexane (20-40%, 30 min). Collected the desired fraction to afford the title compound (270 mg, 92%) as white solid. 1H NMR (400 MHz, Methanol-$d_4$) δ 7.80 (s, 1H), 7.63 (s, 1H), 7.54 (s, 1H), 5.10 (p, J=7.5 Hz, 1H), 3.96 (tt, J=9.8, 6.8 Hz, 1H), 3.00 (s, 3H), 2.70 (ddd, J=13.9, 7.9, 5.7 Hz, 1H), 2.64 (d, J=0.8 Hz, 3H), 2.47-2.06 (m, 5H).

Intermediate 37.4

6-methyl-1-((1R,3R)-3-(methylsulfonyl)cyclopentyl)-3-(4,4,5,5-tetramethyl-1,3,2-dioxaborolan-2-yl)-1H-indole-5-carbonitrile (trans relative)

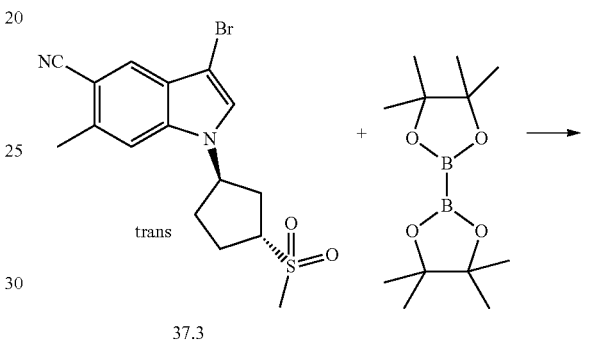

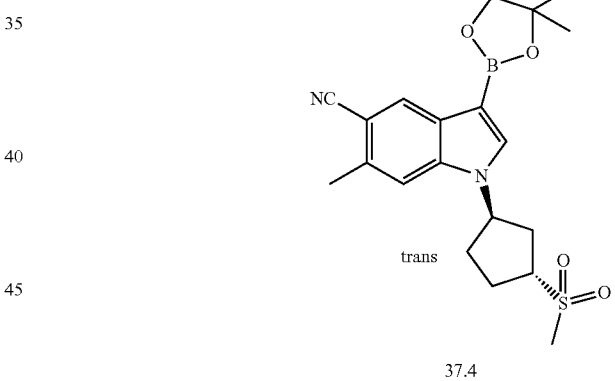

37.4

A solution of 37.3 (240 mg, 0.629 mmol), B$_2$pin$_2$ (256 mg, 1.007 mmol), KOAc (124 mg, 1.259 mmol) in dioxane (5 mL) was bubbled with nitrogen for 2 minutes, then Pd$_2$(dba)$_3$ (28.8 mg, 0.031 mmol) and tricyclohexyphosphine (35.3 mg, 0.126 mmol) was added. The mixture was degassed with nitrogen three times. Then the mixture was stirred at 100° C. for 3 hr in a sealed tube. The mixture was diluted with ethyl acetate, washed with water; the organic layer was dried over magnesium sulfate, filtered and concentrated in vacuum. The residue was purified by CombiFlash, eluted with ethyl acetate in hexane (0-20%, 30 min). Collected the desired fraction and concentrated in vacuum to afford the title compound (170 mg, 50.4%) as a pale yellow solid. 1H NMR (400 MHz, DMSO-$d_6$) δ 8.08 (s, 1H), 7.99 (s, 1H), 7.64 (s, 1H), 5.06 (q, J=7.1 Hz, 1H), 4.17-3.88 (m, 1H), 3.02 (d, J=2.2 Hz, 3H), 2.57-2.42 (m, 4H), 2.43-2.03 (m, 5H), 1.32 (s, 9H).

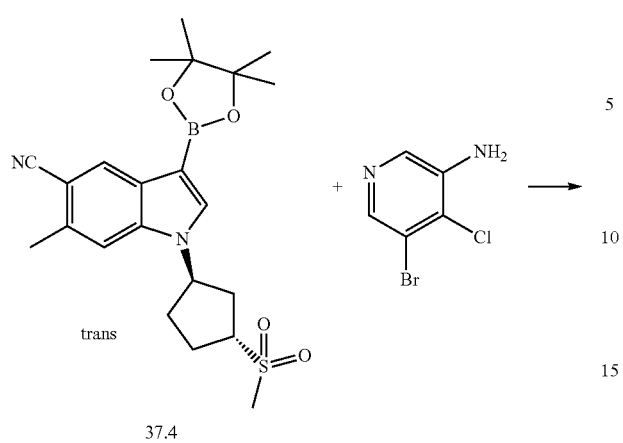

37.4

Example 37

A solution of 37.4 (170 mg, 0.278 mmol), Na₂CO₃ (58.9 mg, 0.556 mmol) 5-bromo-4-chloropyridin-3-amine (57.6 mg, 0.278 mmol), Pd(PPh₃)₂Cl₂ (19.50 mg, 0.028 mmol) in 2-Propanol (3 mL) was added water (1 mL). The mixture was degassed with nitrogen three times. Then the mixture was stirred at 100° C. for 1 hr under nitrogen protection. The mixture was diluted with ethyl acetate, washed with water; the organic layer was dried over magnesium sulfate, filtered and concentrated in vacuum. The residue purified with basic Prep-HPLC (0.1% NH₄OH/ACN/H₂O). Collected the desired fraction and lyophilized to afford the title compound (8.2 mg, 6.8%) as white powder. ¹H NMR (400 MHz, Methanol-d₄) δ 8.06 (s, 1H), 7.86 (s, 1H), 7.78 (s, 1H), 7.73 (s, 1H), 7.59 (s, 1H), 5.17 (p, J=7.4 Hz, 1H), 4.08-3.87 (m, 1H), 3.01 (s, 3H), 2.76 (ddd, J=13.8, 7.8, 5.4 Hz, 1H), 2.65 (s, 3H), 2.53-2.12 (m, 5H). LC-MS: [M+H]⁺=428.9, 430.9.

Example 38

3-(5-amino-4-chloropyridin-3-yl)-6-methyl-1-((1R,3S)-3-(methylsulfonyl)cyclopentyl)-1H-indole-5-carbonitrile (cis relative)

Intermediate 38.1

(1R,3R)-3-(3-bromo-5-cyano-6-methyl-1H-indol-1-yl)cyclopentyl methanesulfonate (trans relative)

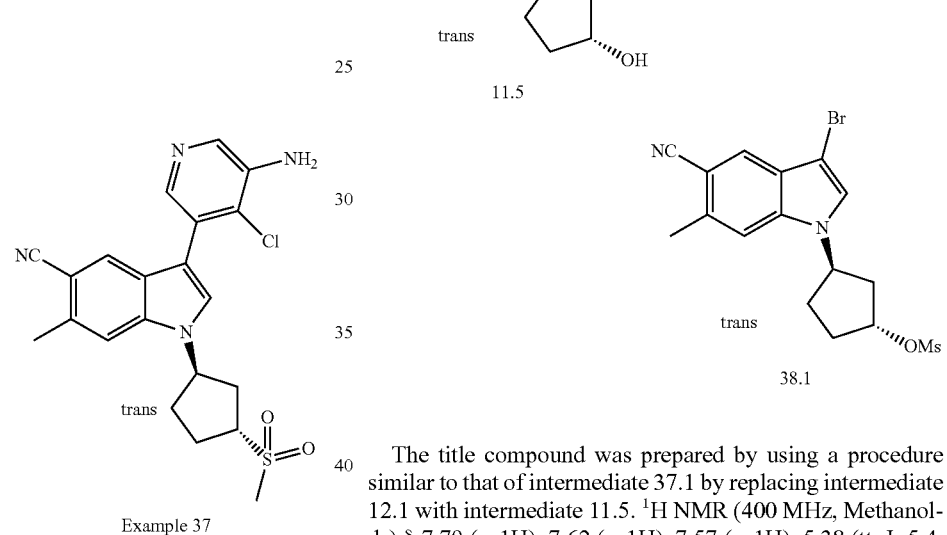

The title compound was prepared by using a procedure similar to that of intermediate 37.1 by replacing intermediate 12.1 with intermediate 11.5. ¹H NMR (400 MHz, Methanol-d₄) δ 7.79 (s, 1H), 7.62 (s, 1H), 7.57 (s, 1H), 5.38 (tt, J=5.4, 2.5 Hz, 1H), 5.29-5.11 (m, 1H), 3.12 (s, 3H), 2.63 (d, J=0.8 Hz, 3H), 2.61-2.51 (m, 1H), 2.52-2.29 (m, 3H), 2.21-2.08 (m, 1H), 1.96 (td, J=6.9, 2.9 Hz, 1H).

Intermediate 38.2

3-bromo-6-methyl-1-((1R,3S)-3-(methylthio)cyclopentyl)-1H-indole-5-carbonitrile (cis relative)

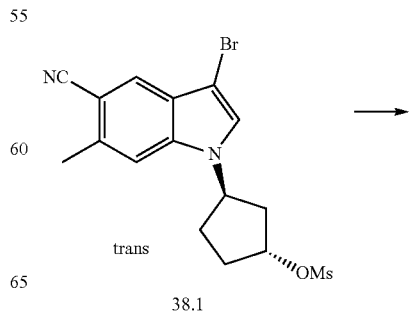

38.1

125
-continued

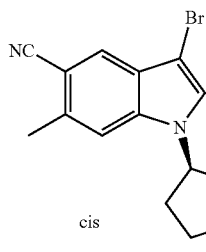

38.2

The title compound was prepared by using a procedure similar to that of intermediate 37.2 by replacing intermediate 37.1 with intermediate 38.1. $^1$H NMR (400 MHz, Methanol-$d_4$) δ 7.78 (s, 1H), 7.65 (s, 1H), 7.56 (s, 1H), 5.01 (p, J=7.9 Hz, 1H), 3.27 (d, J=7.2 Hz, 1H), 2.63 (d, J=0.8 Hz, 3H), 2.38-2.06 (m, 5H), 1.97-1.71 (m, 2H). LC-MS: [M+H]$^+$= 348.8, 350.8.

Intermediate 38.3

6-methyl-1-((1R,3S)-3-(methylsulfonyl)cyclopentyl)-3-(4,4,5,5-tetramethyl-1,3,2-dioxaborolan-2-yl)-1H-indole-5-carbonitrile (cis relative)

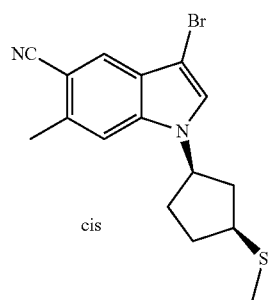

38.2

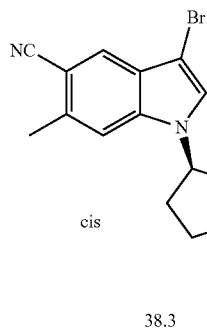

38.3

The title compound was prepared by using a procedure similar to that of intermediate 37.3 by replacing intermediate 37.2 with intermediate 38.2. $^1$H NMR (400 MHz, Methanol-$d_4$) δ 7.80 (s, 1H), 7.67 (s, 1H), 7.60 (s, 1H), 5.09 (p, J=8.4 Hz, 1H), 3.92-3.71 (m, 1H), 3.00 (s, 3H), 2.74 (dt, J=13.6, 8.2 Hz, 1H), 2.63 (d, J=0.8 Hz, 3H), 2.47-2.11 (m, 5H). LC-MS: [M+H]$^+$=380.8, 382.8.

126
Intermediate 38.4

6-methyl-1-((1R,3S)-3-(methylsulfonyl)cyclopentyl)-3-(4,4,5,5-tetramethyl-1,3,2-dioxaborolan-2-yl)-1H-indole-5-carbonitrile (cis Relative)

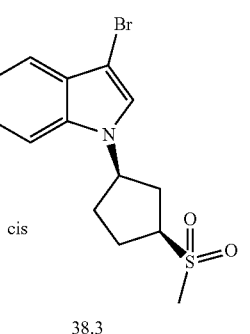

38.3

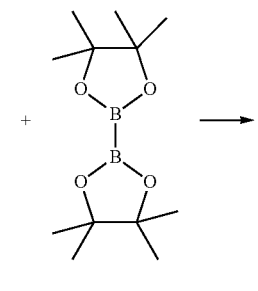

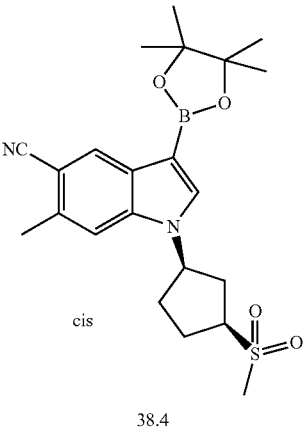

38.4

The title compound was prepared by using a procedure similar to that of intermediate 37.4 by replacing intermediate 37.3 with intermediate 38.3. $^1$H NMR (400 MHz, Methanol-$d_4$) δ 8.15 (s, 1H), 7.88 (s, 1H), 7.56 (s, 1H), 5.05 (p, J=8.8, 8.3 Hz, 1H), 3.97-3.71 (m, 1H), 3.00 (d, J=1.8 Hz, 3H), 2.75 (dt, J=13.6, 8.2 Hz, 1H), 2.62 (d, J=2.7 Hz, 3H), 2.49-2.18 (m, 5H), 1.37 (s, 9H).

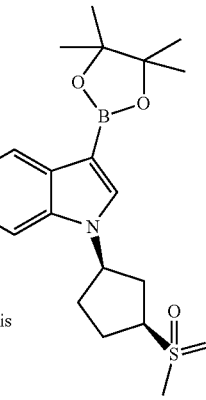

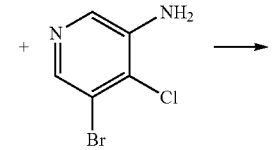

38.4

-continued

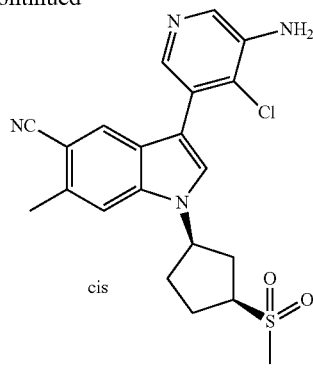

Example 38

The title compound was prepared by using a procedure similar to that of Example 37 by replacing intermediate 37.4 with intermediate 38.4. $^1$H NMR (400 MHz, Methanol-$d_4$) δ 8.05 (s, 1H), 7.85 (s, 1H), 7.80 (s, 1H), 7.78 (s, 1H), 7.65 (s, 1H), 5.15 (p, J=8.2 Hz, 1H), 3.98-3.73 (m, 1H), 3.01 (s, 3H), 2.80 (dt, J=13.6, 8.2 Hz, 1H), 2.65-2.62 (m, 3H), 2.50-2.12 (m, 5H). LC-MS: [M+H]$^+$=428.9, 430.9.

Example 39

3-(5-amino-4-chloropyridin-3-yl)-1-((1R,3R)-3-cyanocyclobutyl)-6-methyl-1H-indole-5-carbonitrile Intermediate 38.2

(1R,3R)-3-cyanocyclobutyl 4-methylbenzenesulfonate & (1S,3S)-3-cyanocyclobutyl 4-methylbenzenesulfonate

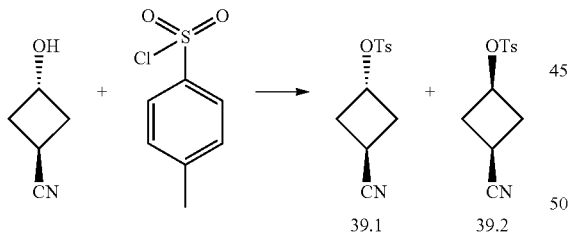

To a solution of 3-hydroxycyclobutanecarbonitrile (500 mg, 5.15 mmol) and DMAP (943 mg, 7.72 mmol) in DCM (20 mL) was added Ts-Cl (1178 mg, 6.18 mmol). The mixture was stirred at rt for 20 hr. The mixture was washed with water, brine. The organic layer was dried over magnesium sulfate, filtered and concentrated in vacuum. Then the residue was purified by CombiFlash, eluted with ethyl acetate in hexane (10-30%, 30 min) to afford titled compound 39.1 (120 mg, 0.478 mmol, 9.27%) and titled compound 39.2 (920 mg, 3.66 mmol, 71.1%).

Trans $^1$H NMR (400 MHz, Methanol-$d_4$) δ 7.79 (dd, J=8.6, 2.2 Hz, 2H), 7.46 (d, J=8.1 Hz, 2H), 5.03 (pd, J=6.9, 1.2 Hz, 1H), 3.28-3.19 (m, 1H), 2.67-2.52 (m, 4H), 2.46 (s, 3H).

Cis $^1$H NMR (400 MHz, Methanol-$d_4$) δ 7.84-7.74 (m, 2H), 7.45 (d, J=8.1 Hz, 2H), 4.77 (p, J=7.4 Hz, 1H), 2.86 (tt, J=9.7, 7.9 Hz, 1H), 2.64 (ddq, J=12.2, 7.2, 2.4 Hz, 2H), 2.52-2.29 (m, 5H).

Intermediate 38.3

3-bromo-1-((1R,3R)-3-cyanocyclobutyl)-6-methyl-1H-indole-5-carbonitrile

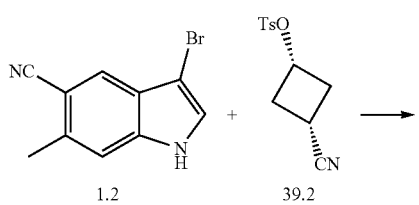

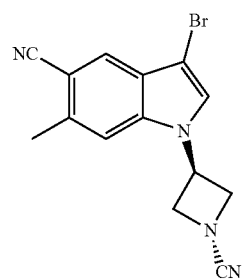

The title compound was prepared by using a procedure similar to that of intermediate 1.4 by replacing intermediate 1.3 with intermediate 39.2. $^1$H NMR (400 MHz, DMSO-$d_6$) δ 8.20 (s, 1H), 7.86 (s, 1H), 7.64 (s, 1H), 5.21-4.96 (m, 1H), 3.31-3.10 (m, 1H), 3.01-2.74 (m, 4H), 2.57 (s, 3H). LC-MS: [M+H]$^+$=313.3, 315.3.

Intermediate 38.4

1-((1R,3R)-3-cyanocyclobutyl)-6-methyl-3-(4,4,5,5-tetramethyl-1,3,2-dioxaborolan-2-yl)-1H-indole-5-carbonitrile

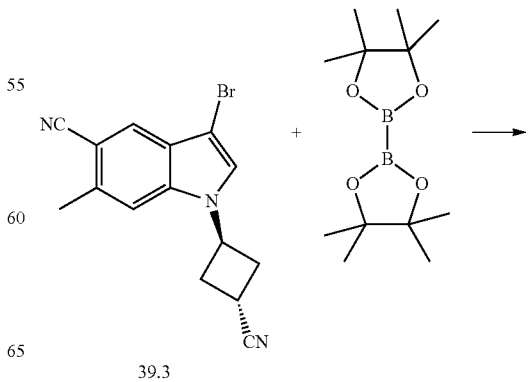

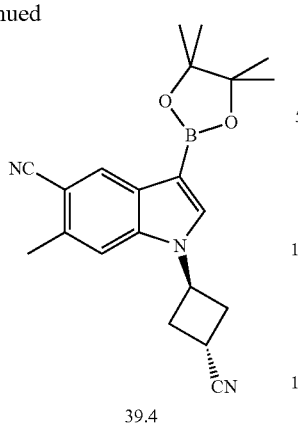

39.4

The title compound was prepared by using a procedure similar to that of intermediate 1.7 by replacing intermediate 1.6 with intermediate 39.3. LC-MS: [M−H]⁻=361.2.

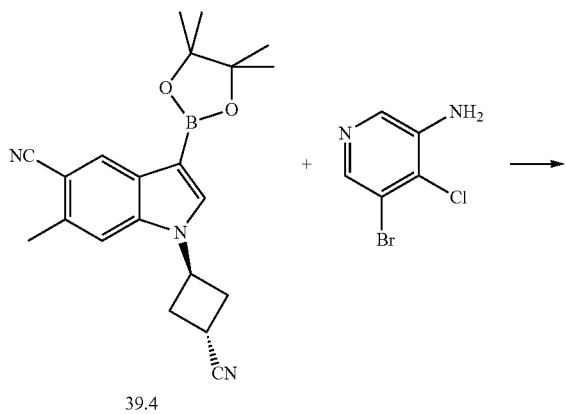

39.4

Example 39

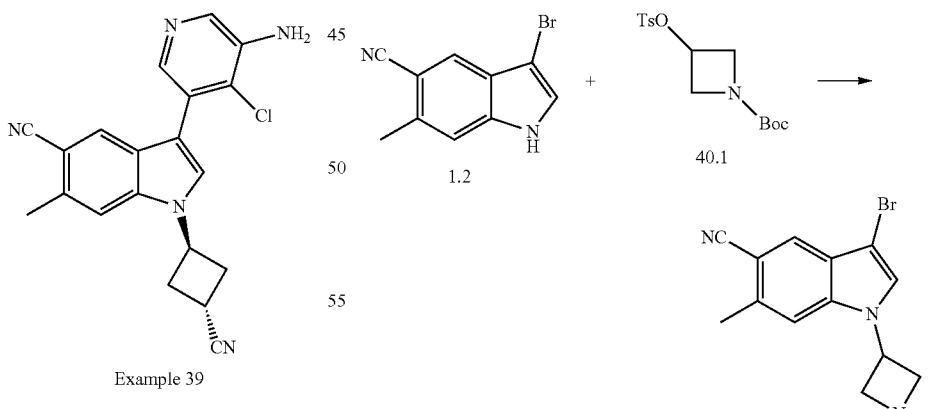

The title compound was prepared by using a procedure similar to that of Example 26 by replacing intermediate 1.7 with intermediate 39.4. ¹H NMR (400 MHz, Methanol-d₄) δ 8.13-7.99 (m, 1H), 7.96-7.80 (m, 2H), 7.78 (q, J=2.8 Hz, 1H), 7.54 (d, J=5.1 Hz, 1H), 5.12 (s, 1H), 3.25 (s, 1H), 3.16-3.01 (m, 2H), 2.91 (t, J=8.0 Hz, 2H), 2.64 (q, J=3.0 Hz, 3H). LC-MS: [M+H]⁺=361.2, 363.1.

Example 40

1-(azetidin-3-yl)-3-(2,2-dimethyl-1,2,3,4-tetrahydro-quinolin-5-yl)-6-methyl-1H-indole-5-carbonitrile Intermediate 40.1 tert-butyl 3-(tosyloxy)azetidine-1-carboxylate

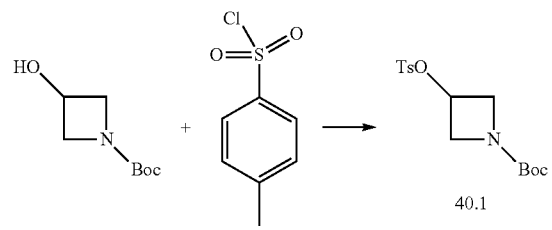 [SMILES: CC(C)(C)OC(=O)N1CC(O)C1 ; Cc1ccc(S(=O)(=O)Cl)cc1 ; Cc1ccc(S(=O)(=O)OC2CN(C(=O)OC(C)(C)C)C2)cc1]

To a solution of tert-butyl 3-hydroxyazetidine-1-carboxylate (500 mg, 2.89 mmol), DIPEA (1.008 mL, 5.77 mmol), DMAP (17.63 mg, 0.144 mmol) in THF (10 mL) was added TsCl (826 mg, 4.33 mmol). The mixture was stirred at rt for 20 h. Then the mixture washed with water, brine. The organic layer was dried over magnesium sulfate, filtered and concentrated, the residue was purified by CombiFlash, eluted with ethyl acetate in hexane (10-40, 30 min), collected the desired fraction to afford the title compound (700 mg, 74%) as white solid. LC-MS: [M+H−100]⁺=228.0.

Intermediate 40.2 tert-butyl 3-(3-bromo-5-cyano-6-methyl-1H-indol-1-yl)azetidine-1-carboxylate

The title compound was prepared by using a procedure similar to that of intermediate 1.4 by replacing intermediate 1.3 with intermediate 40.1. LC-MS: [M+H]⁺=389.1, 391.1.

Intermediate 40.3 tert-butyl 3-(5-cyano-3-(2,2-dimethyl-1,2,3,4-tetra-hydroquinolin-5-yl)-6-methyl-1H-indol-1-yl)azetidine-1-carboxylate

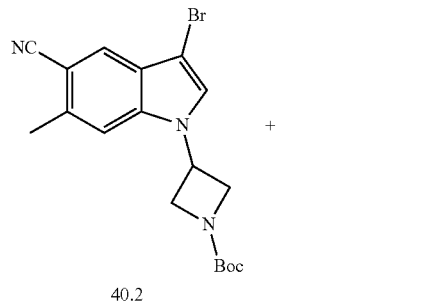

40.2

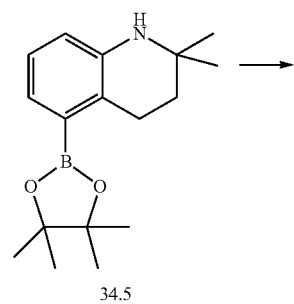

34.5

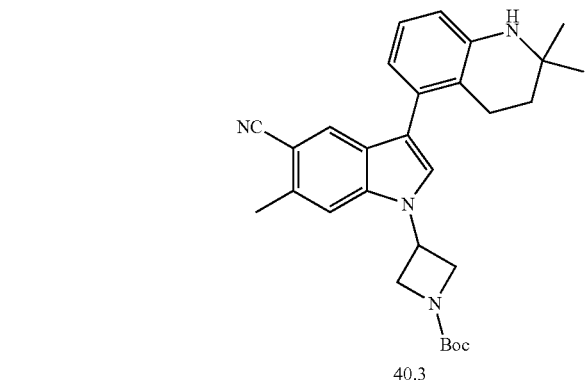

40.3

The title compound was prepared by using a procedure similar to that of intermediate 30.3 by replacing intermediate 1.4 and intermediate 30.2 with intermediate 40.2 and intermediate 34.5. LC-MS: [M+H]⁺=471.3.

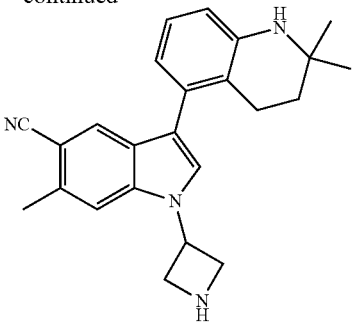

Example 40

To a solution of 40.3 (95 mg, 0.202 mmol) in DCM (10 mL) was added TFA (2 mL, 26.0 mmol). The mixture was stirred at rt for 2 hr. Then the mixture was concentrated in vacuum and the residue was further purified by acidic Prep-HPLC (0.1% TFA/ACN/H₂O), collected the desired fraction and lyophilized to afford the title compound (38 mg, 50.7%) as white powder. ¹H NMR (400 MHz, Methanol-d₄) δ 7.92 (s, 1H), 7.70 (s, 1H), 7.60 (s, 1H), 7.41 (t, J=7.8 Hz, 1H), 7.32 (d, J=7.1 Hz, 1H), 7.16 (d, J=7.9 Hz, 1H), 5.81 (p, J=8.1 Hz, 1H), 4.65 (d, J=8.1 Hz, 4H), 2.84 (t, J=6.7 Hz, 2H), 2.65 (s, 3H), 1.89 (t, J=6.7 Hz, 2H), 1.43 (s, 6H). LC-MS: [M+H]⁺=370.2.

Example 41

3-(3-amino-2-fluorophenyl)-1-(3-(3-hydroxy-propoxy)propyl)-6-methyl-1H-indole-5-carbonitrile

Intermediate 41.1

3-bromo-1-(3-(3-hydroxypropoxy)propyl)-6-methyl-1H-indole-5-carbonitrile

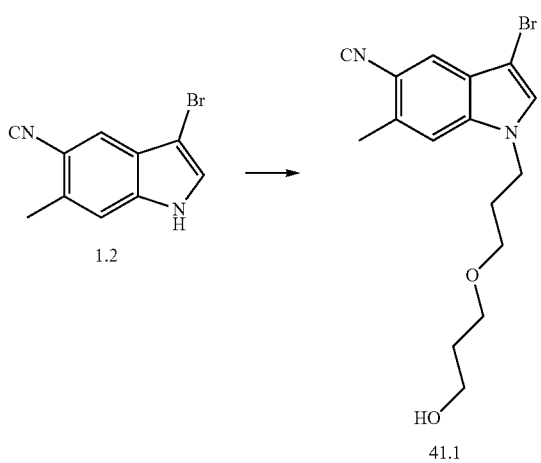

To a solution of 1.2 (2.0 g, 8.51 mmol) in DMF (20 mL) was added NaH (0.235 g, 9.78 mmol). After 10 min stirring, 3-bromopropan-1-ol (3.0 g, 21.0 mmol) was added dropwise over 10 min. After stirring at r.t. for 12 h, LC-MS showed s.m. still remains, 1 eq of Cs₂CO₃ was added, and then heated to 50° C. for 2 h. The mixture was diluted with water (20 mL), and then extracted with EA (20 mL×2). The organic layer was dried over Na₂SO₄, filtered and concentrated; the residue was purified by silica column to afford the title compound (975 mg, 30%) as brown oil. LC-MS: $[M+H]^+=351.1$.

Intermediate 41.2

1-(3-(3-hydroxypropoxy)propyl)-6-methyl-3-(4,4,5,5-tetramethyl-1,3,2-dioxaborolan-2-yl)-1H-indole-5-carbonitrile

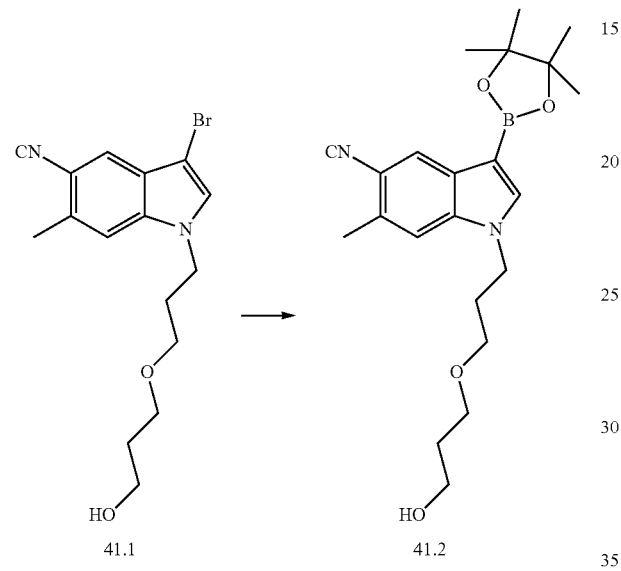

The title compound was prepared by using a procedure similar to that of intermediate 1.7 by replacing intermediate 1.6 with intermediate 41.1. LC-MS: $[M+H]^+=399.3$.

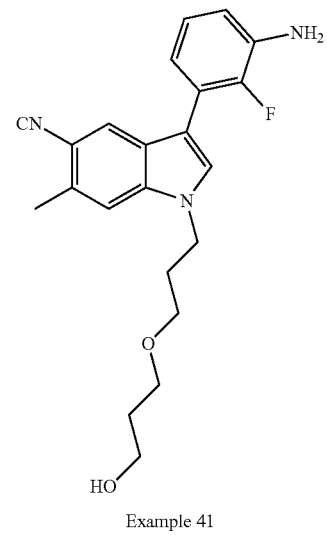

Example 41

The title compound was prepared by using a procedure similar to that of example 1 by replacing intermediate 1.7 and 5-bromo-4-chloropyridin-3-amine with 41.2 and 3-bromo-2-fluoroaniline. ¹H NMR (400 MHz, Methanol-d₄) δ: 8.01 (s, 1H), 7.55 (s, 1H), 7.50 (s, 1H), 6.96-7.04 (m, 1H), 6.87-6.94 (m, 1H), 6.80 (t, J=8.0 Hz, 1H), 4.36 (s, 2H), 3.66 (t, J=6.4 Hz, 2H), 3.49 (t, J=6.3 Hz, 2H), 3.33-3.39 (m, 2H), 2.64 (s, 3H), 2.04-2.15 (m, 2H), 1.76-1.87 (m, 2H). LC-MS: $[M+H]^+=382.2$.

Example 42

3-(3-amino-2-cyanophenyl)-1-(3-hydroxypropyl)-6-methyl-1H-indole-5-carbonitrile

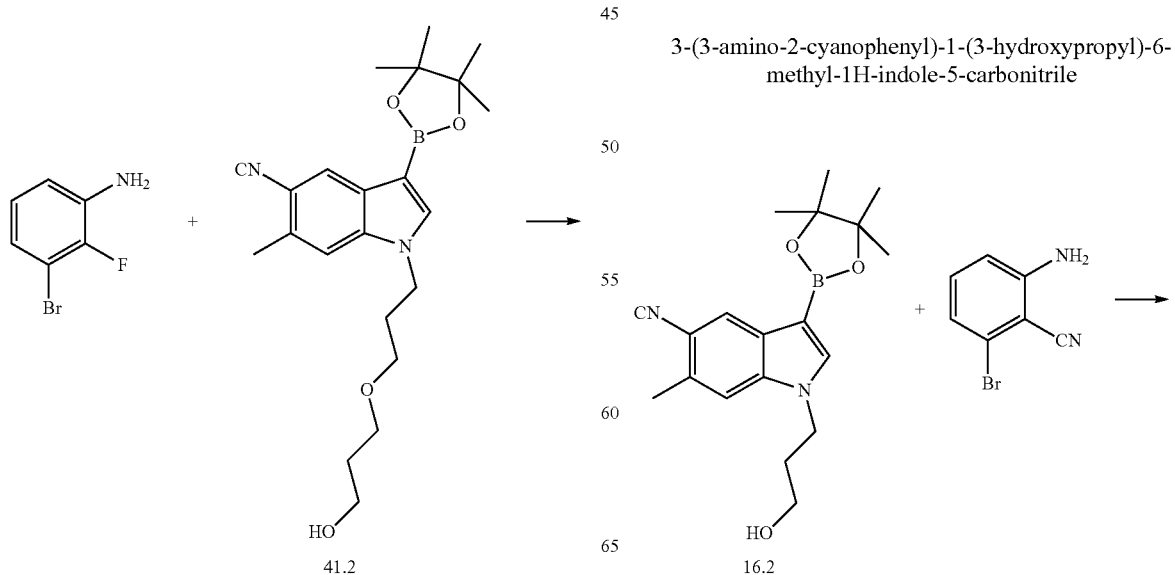

-continued

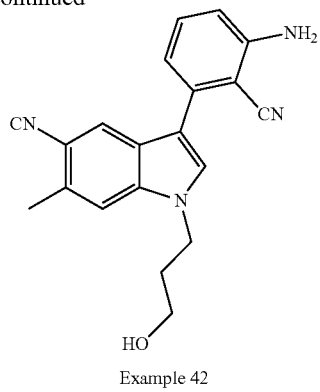

Example 42

The title compound was prepared by using a procedure similar to that of example 1 by replacing intermediate 1.7 and 5-bromo-4-chloropyridin-3-amine with 16.2 and 2-amino-6-bromobenzonitrile. $^1$H NMR (400 MHz, Methanol-$d_4$) δ: 7.95 (s, 1H), 7.68 (s, 1H), 7.55 (s, 1H), 7.43-7.44 (m, 1H), 6.73-6.88 (m, 2H), 4.37 (m, 2H), 3.57 (m, 2H), 2.64 (s, 3H), 2.06 (m, 2H). LC-MS: [M+H]$^+$=331.2.

Example 43

3-(5-amino-4-chloropyridin-3-yl)-1-(1,1-dioxidothietan-3-yl)-6-methyl-1H-indole-5-carbonitrile Intermediate 43.1

6-methyl-3-(4,4,5,5-tetramethyl-1,3,2-dioxaborolan-2-yl)-1H-indole-5-carbonitrile

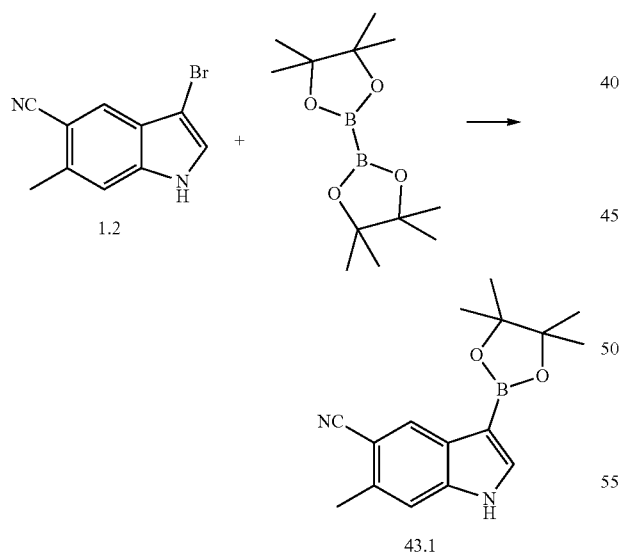

A solution of 1.2 (500 mg, 2.127 mmol), Pin$_2$B$_2$(864 mg, 3.40 mmol), KOAc (417 mg, 4.25 mmol) in dioxane (15 mL) was bubbled with nitrogen for 2 min, then Pd$_2$(dba)$_3$ (97 mg, 0.106 mmol) and tricyclohexylphosphine (119 mg, 0.425 mmol) was added, the mixture was degassed with nitrogen for three times. Then the mixture was heated to 110° C. for 3 hr. Then most dioxane was removed in vacuum, the residue was diluted with ethyl acetate, washed with water, brine. The organic layer was dried over magnesium sulfate, filtered and concentrated in vacuum. The residue was purified by CombiFlash, eluted with ethyl acetate in hexane (0-20%, 35 min). Collected the desired fraction and concentrated in vacuum to afford the title compound (580 mg, 72.5%) as brown solid. $^1$H NMR (400 MHz, DMSO-$d_6$) δ 11.91 (s, 1H), 8.06 (s, 1H), 7.81 (d, J=2.5 Hz, 1H), 7.45 (t, J=0.9 Hz, 1H), 2.59-2.52 (m, 3H), 1.31 (s, 12H). LC-MS: [M+H]$^+$=283.0.

Intermediate 43.2

3-(5-(bis(4-methoxybenzyl)amino)-4-chloropyridin-3-yl)-6-methyl-1H-indole-5-carbonitrile

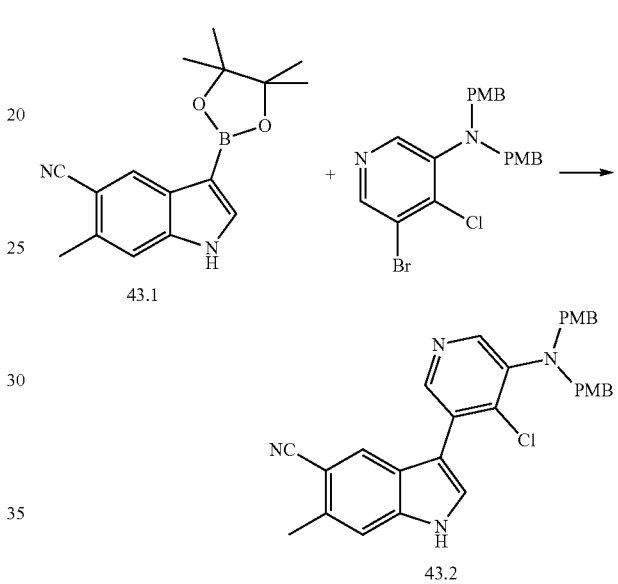

The title compound was prepared by using a procedure similar to that of example 1 by replacing intermediate 1.7 and 5-bromo-4-chloropyridin-3-amine with 43.1 and 5-bromo-4-chloro-N,N-bis(4-methoxybenzyl)pyridin-3-amine. $^1$H NMR (400 MHz, DMSO-$d_6$) δ ppm 11.94 (s, 1H), 8.26 (s, 1H), 8.24 (s, 1H), 7.85 (s, 1H), 7.77 (s, 1H), 7.50 (s, 1H), 7.30 (d, 4H), 6.88 (d, 4H), 4.26 (s, 4H), 3.72 (s, 6H), 2.56 (s, 3H). LC-MS: [M+H]$^+$=522.9, 523.9.

Intermediate 43.3

3-(5-(bis(4-methoxybenzyl)amino)-4-chloropyridin-3-yl)-1-(1,1-dioxidothietan-3-yl)-6-methyl-1H-indole-5-carbonitrile

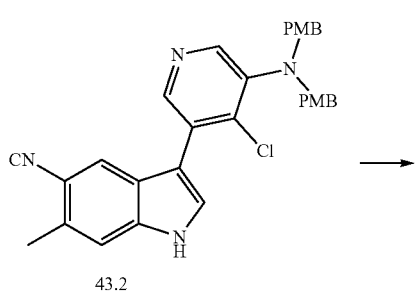

-continued

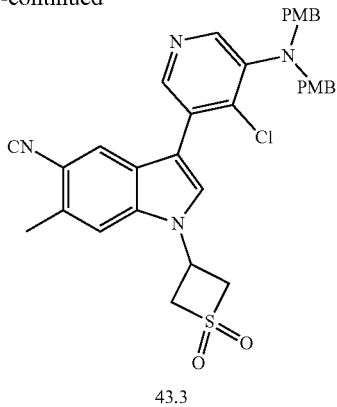

43.3

To a solution of compound 43.2 (150 mg, 0.28 mmol, 1.0 eq) and compound 3-bromothietane 1,1-dioxide (172.6 mg, 0.56 mmol, 2.0 eq, w=60%) in DMF (8.0 mL, anhydrous) was added Cs₂CO₃ (182.4 mg, 0.56 mmol, 2.0 eq) and the mixture was stirred at 60° C. for 16 hours. LCMS showed the reaction was completed. The mixture was quenched with H₂O and extracted with EA. The combined organic phase was washed with H₂O (40 mL*3), dried over anhydrous sodium sulfate, filtered and concentrated to give the crude (0.375 mmol) as a yellow oil, which was used to next step without further purification. LC-MS: [M+H]⁺=627.0.

Example 43

3-(5-amino-4-chloropyridin-3-yl)-1-(1,1-dioxidothietan-3-yl)-6-methyl-1H-indole-5-carbonitrile

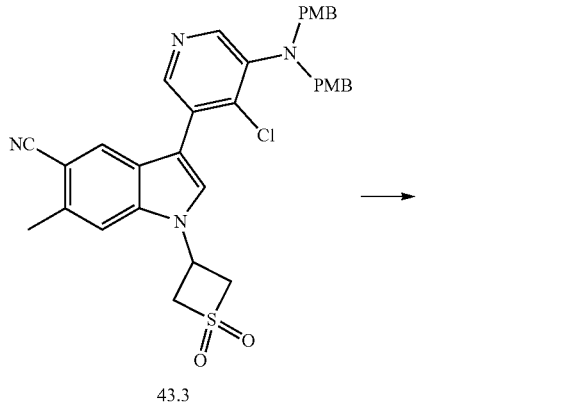

Example 43

To a solution of compound 43.1 (crude, 0.375 mmol, 1.0 eq) in CH₂Cl₂ (2.0 mL, anhydrous) was added TFA (1.0 mL) and the mixture was stirred at 7-15° C. for 1 hour. LCMS showed the reaction was completed. The mixture was concentrated and the residue was dissolved in DMF (3.5 mL) and basified by NH₃H₂O (25% 28%) until the pH=9.0. Then the mixture was purified by prep-HPLC (0.1% NH₃H₂O/ACN/H₂O) to deliver title compound (51.2 mg, 35.3%) as a white solid. ¹H NMR (400 MHz, CDCl₃): δ 8.17 (s, 1H), 8.04 (s, 1H), 7.90 (s, 1H), 7.70 (s, 1H), 7.35 (s, 1H), 5.41-5.38 (m, 1H), 4.92-4.86 (m, 2H), 4.63-4.58 (m, 2H), 4.25 (brs, 2H), 2.69 (s, 3H). LC-MS: [M+H]⁺=387.0.

Example 44 methyl (1R,4R)-4-(3-(5-amino-4-chloropyridin-3-yl)-5-cyano-6-methyl-1H-indol-1-yl)cyclohexane-1-carboxylate Intermediate 44.1

3-(5-amino-4-chloropyridin-3-yl)-6-methyl-1H-indole-5-carbonitrile

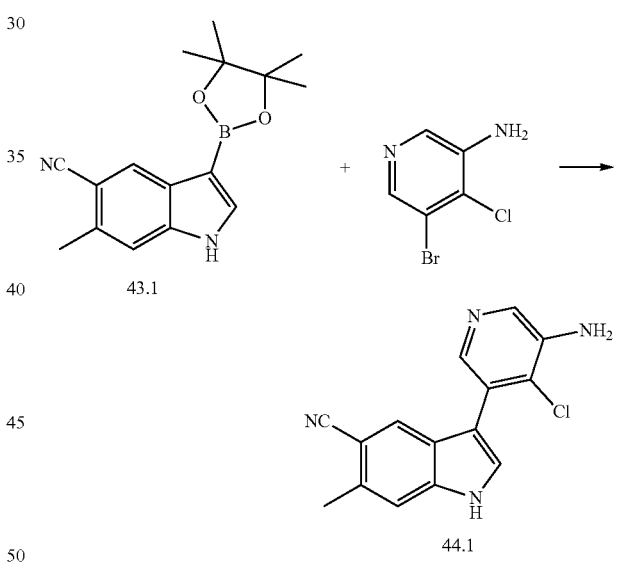

To a solution of 43.1 (1.3 g, 4.61 mmol), 5-bromo-4-chloropyridin-3-amine (1.004 g, 4.84 mmol), Na₂CO₃ (0.977 g, 9.22 mmol), Pd(PPh₃)₂Cl₂ (0.323 g, 0.461 mmol) in 2-Propanol (25 mL) was added water (8 mL). The mixture was stir at 100° C. for 2 hr under nitrogen protection. Then the mixture was diluted with DCM, washed with water, brine. The organic layer was dried over magnesium sulfate, filtered and concentrated in vacuum. The residue was purified by CombiFlash, eluted with methanol in DCM (0-5%, 30 min). Collected the desired fraction and concentrated in vacuum to afford the title compound (1.1 g, 84%) as off-white solid. ¹H NMR (400 MHz, DMSO-d6) δ 11.89 (d, J=2.6 Hz, 1H), 8.07 (s, 1H), 7.84 (s, 1H), 7.81 (s, 1H), 7.72 (d, J=2.5 Hz, 1H), 7.49 (s, 1H), 5.73 (s, 2H), 2.56 (s, 3H). LC-MS: [M+H]⁺=283.1, 285.1.

139

Intermediate 44.2 methyl 4-(tosyloxy)cyclohexane-1-carboxylate

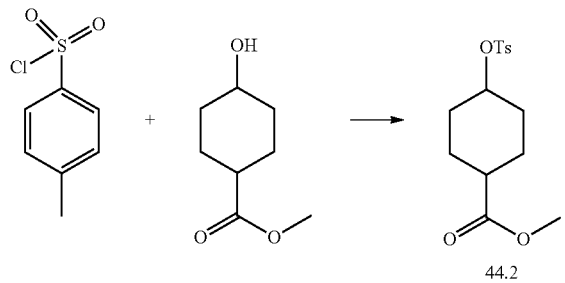 [SMILES: Cc1ccc(S(=O)(=O)Cl)cc1 ; COC(=O)C1CCC(O)CC1 ; COC(=O)C1CCC(OS(=O)(=O)c2ccc(C)cc2)CC1]

44.2

The title compound was prepared by using a procedure similar to that of intermediate 40.1 by replacing tert-butyl 3-hydroxyazetidine-1-carboxylate with methyl 4-hydroxy-cyclohexanecarboxylate. $^1$H NMR (400 MHz, DMSO-$d_6$) δ 7.93-7.68 (m, 2H), 7.56-7.33 (m, 2H), 4.83-4.27 (m, 1H), 3.57 (d, J=10.4 Hz, 3H), 2.50 (p, J=1.9 Hz, 3H), 2.40-2.23 (m, 1H), 1.90-1.71 (m, 2H), 1.71-1.32 (m, 6H).

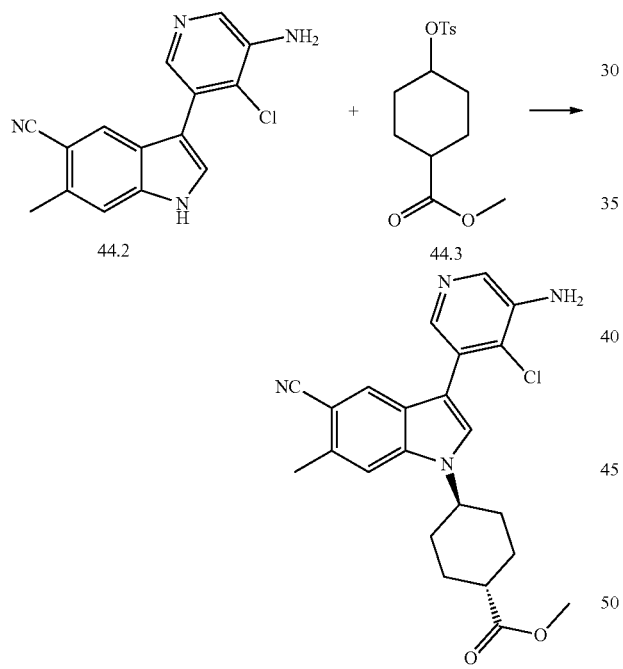

Example 44

A mixture of 44.2 (100 mg, 0.354 mmol), 44.3 (133 mg, 0.424 mmol) and Cs$_2$CO$_3$ (230 mg, 0.707 mmol) in DMF (2 mL) was stirred at 70° C. for 20 hr. The mixture was filtered and the filter was further purified by basic Prep-HPLC (0.1% NH$_4$OH/ACN/H$_2$O). Collected the desired fraction and lyophilized to afford the title compound (40 mg, 26.7%) as white powder. $^1$HNMR indicated we only get the trans product. $^1$H NMR (400 MHz, Methanol-$d_4$) δ 8.05 (s, 1H), 7.84 (s, 1H), 7.77 (s, 1H), 7.71 (s, 1H), 7.60 (s, 1H), 4.49 (t, J=12.0 Hz, 1H), 3.70 (s, 3H), 2.65 (s, 3H), 2.56-2.42 (m, 1H), 2.19 (d, J=11.8 Hz, 4H), 2.04-1.86 (m, 2H), 1.86-1.65 (m, 2H). LC-MS: [M+H]$^+$=422.2, 424.2.

140

Example 45

(1R,4R)-4-(3-(5-amino-4-chloropyridin-3-yl)-5-cyano-6-methyl-1H-indol-1-yl)cyclohexane-1-carboxamide

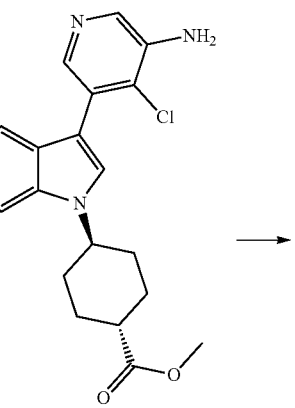

Example 44

Example 45

A solution of methyl Example 44 (40 mg, 0.095 mmol) in an ammonia methanol solution (7M, 4 mL, 8.00 mmol) was sealed and heated at 100° C. for 20 hr. The mixture was purified by basic Prep-HPLC (0.1% NH$_4$OH/ACN/H$_2$O), Collected the desired fraction and lyophilized to afford the title compound (14 mg, 36.1%) as white powder. $^1$H NMR (400 MHz, Methanol-$d_4$) δ 8.05 (s, 1H), 7.84 (s, 1H), 7.77 (s, 1H), 7.70 (s, 1H), 7.61 (s, 1H), 4.50 (ddd, J=11.7, 7.9, 3.8 Hz, 1H), 2.65 (s, 3H), 2.41 (tt, J=11.9, 3.6 Hz, 1H), 2.28-2.15 (m, 2H), 2.15-2.05 (m, 2H), 2.05-1.71 (m, 4H). LC-MS: [M+H]$^+$=407.1, 409.1.

Example 46

(1R,4R)-4-(3-(5-amino-4-chloropyridin-3-yl)-5-cyano-6-methyl-1H-indol-1-yl)cyclohexane-1-carboxylic acid

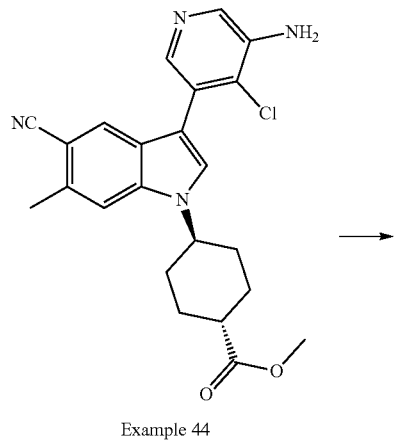

Example 44

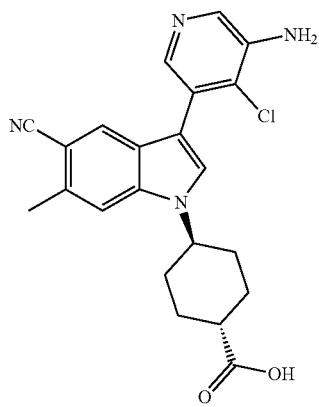

Example 46

To a solution of methyl Example 44 (50 mg, 0.118 mmol) in mixture of THF (3 mL) and water (1 mL) was added LiOH (10 mg, 0.418 mmol). The mixture was stir at rt for 2 hr. The mixture was acidified to pH=7-9, then the mixture was purified by basic Prep-HPLC (0.1% NH$_4$OH/ACN/H$_2$O). Collected the desired fraction and lyophilized to afford the title compound (25 mg, 51.9%) as yellow powder. $^1$H NMR (400 MHz, Methanol-d$_4$) δ 8.04 (s, 1H), 7.85 (s, 1H), 7.77 (s, 1H), 7.72 (s, 1H), 7.62 (s, 1H), 4.57-4.36 (m, 1H), 2.74-2.55 (m, 3H), 2.31 (dd, J=14.0, 10.7 Hz, 1H), 2.21-2.09 (m, 4H), 1.99-1.86 (m, 2H), 1.86-1.67 (m, 2H). LC-MS: [M+H]$^+$=408.9, 410.9.

Example 47

3-(5-amino-4-chloropyridin-3-yl)-6-methyl-1-((1R,4R)-4-(methylsulfonyl)cyclohexyl)-1H-indole-5-carbonitrile

Intermediate 47.1

(1R,4R)-4-((tert-butyldimethylsilyl)oxy)cyclohexan-1-ol

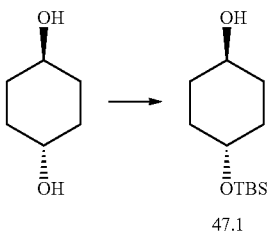 [SMILES: O[C@H]1CC[C@H](O)CC1 ; CC(C)(C)[Si](C)(C)O[C@H]1CC[C@H](O)CC1]

47.1

To a solution of (1r,4r)-cyclohexane-1,4-diol (3 g, 25.8 mmol) and imidazole (2.64 g, 38.7 mmol) in DMF (30 mL) was added TBS-Cl (4.28 g, 28.4 mmol). The mixture was stirred at rt for 3 day. The mixture was diluted with water (150 mL), extracted with DCM three times. The organic layers were combined, dried over magnesium sulfate, filtered and concentrated in vacuum (high vacuum at 70° C. to remove most DMF) to afford a light oil. The residue was loaded purified by CombiFlash, eluted with methanol in DCM (0-5%, 30 min). Collected the desired fraction and concentrated in vacuum to afford the title compound (6 g, 80%) as colorless syrup. 1H NMR (400 MHz, DMSO-d6) δ 3.72-3.35 (m, 2H), 1.80-1.58 (m, 4H), 1.37-1.06 (m, 4H), 0.82 (s, 9H), 0.00 (s, 6H).

Intermediate 47.2

(1R,4R)-4-((tert-butyldimethylsilyl)oxy)cyclohexyl methanesulfonate

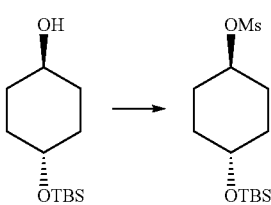

47.1      47.2

To a solution of 47.1 (6 g, 18.23 mmol) and TEA (3.56 mL, 25.5 mmol) in DCM (20 mL) was added MsCl (1.704 mL, 21.87 mmol) under ice-bath. The mixture was stir at rt for 3 hr. Then the mixture was washed with water, the organic layer was dried over magnesium sulfate, filtered and concentrated in vacuum. The residue was purified by CombiFlash, eluted with ethyl acetate in hexane (5-20%, 30 min), Collected the desired fraction and concentrated in vacuum to afford the title compound (4.3 g, 76%) as colorless syrup. $^1$H NMR (400 MHz, Methanol-d4) δ 4.66 (tt, J=7.8, 3.6 Hz, 1H), 3.85-3.75 (m, 1H), 2.98 (s, 3H), 2.10-1.96 (m, 2H), 1.87-1.75 (m, 2H), 1.62 (dtd, J=12.7, 8.5, 3.8 Hz, 2H), 1.50-1.30 (m, 2H), 0.83 (s, 9H), 0.00 (s, 6H).

Intermediate 47.3 tert-butyldimethyl(((1S,4S)-4-(methylthio)cyclohexyl)oxy)silane

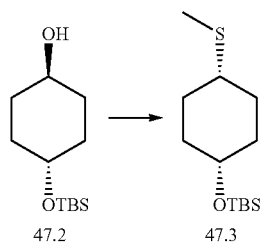 [SMILES: CC(C)(C)[Si](C)(C)O[C@H]1CC[C@H](O)CC1 ; CS[C@H]1CC[C@@H](O[Si](C)(C)C(C)(C)C)CC1]

A solution of 47.2 (4.8 g, 15.64 mmol) and sodium thiomethoxide (2.181 g, 31.1 mmol) in ethanol (30 mL) was stirred at 70° C. for 20 hr. Then the mixture was diluted with water, extracted with DCM twice. The organic layer was dried over magnesium sulfate, filtered and concentrated in vacuum. The residue was purified by CombiFlash, eluted with ethyl acetate in hexane (0-10%, 30 min). Collected the desired fraction and concentrated in vacuum to afford the title compound (3.3 g, 81%) as brown syrup. $^1$H NMR (400 MHz, Methanol-$d_4$) δ 3.85 (q, J=3.5, 2.5 Hz, 1H), 2.55 (qd, J=7.8, 6.9, 3.3 Hz, 1H), 2.00 (s, 3H), 1.73-1.62 (m, 6H), 1.52-1.45 (m, 2H), 0.85 (s, 9H), −0.00 (s, 6H).

Intermediate 47.4 tert-butyldimethyl(((1S,4S)-4-(methylsulfonyl)cyclohexyl)oxy)silane

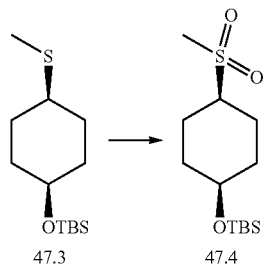 [SMILES: CS[C@H]1CC[C@@H](O[Si](C)(C)C(C)(C)C)CC1 ; CC(C)(C)[Si](C)(C)O[C@H]1CC[C@@H](S(C)(=O)=O)CC1]

To a solution of 47.3 (3.3 g, 10.13 mmol, 80%) in DCM (30 mL) was added m-CPBA (4.66 g, 20.27 mmol, 75%) under ice-bath. The mixture was stir at 0° C. for 1 hr. Aqueous sodium thiosulfate was added to get rid of the excess m-CPBA. Then the mixture was washed with 0.1N sodium hydroxide. The organic layer was dried over magnesium sulfate, filtered and concentrated in vacuum. The residue was purified by CombiFlash, eluted with ethyl acetate in hexane (30-80%, 30 min). Collected the desired fraction to afford the title compound (3 g, 96%) as white solid. $^1$H NMR (400 MHz, DMSO-d6) δ 3.97 (d, J=4.1 Hz, 1H), 3.00 (tt, J=10.1, 4.8 Hz, 1H), 2.85 (s, 3H), 1.84-1.60 (m, 6H), 1.55-1.39 (m, 2H), 0.83 (s, 9H), 0.00 (s, 6H).

Intermediate 47.5

(1s,4s)-4-(methylsulfonyl)cyclohexan-1-ol

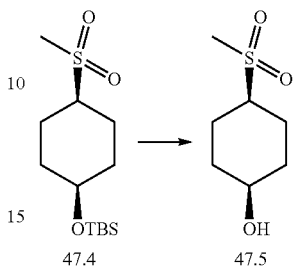

To a solution of 47.4 (3 g, 9.23 mmol) in THF (40 mL) was added a solution of TBAF in THF (1 M, 18.46 mL, 18.46 mmol). The mixture was stirred at rt for 20 hr. The mixture was concentrated in vacuum to afford a syrup residue. The residue was purified by CombiFlash, eluted with methanol in DCM (0-6%, 30 min), collected the desired fraction to afford the title compound (1.25 g, 76%) as white solid. 1H NMR (400 MHz, Methanol-$d_4$) δ 3.98 (t, J=3.0 Hz, 1H), 3.10-2.96 (m, 1H), 2.89 (s, 3H), 1.93 (dt, J=10.2, 3.4 Hz, 6H), 1.61 (dtt, J=12.6, 9.7, 4.2 Hz, 2H).

Intermediate 47.6

(1S,4S)-4-(methylsulfonyl)cyclohexyl methanesulfonate

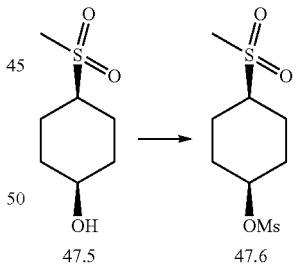

To a solution of 47.5 (350 mg, 1.964 mmol) and TEA (0.411 mL, 2.95 mmol) in DCM (20 mL) was added MsCl (0.184 mL, 2.356 mmol) under ice-bath. Then the mixture was allowed to stir at rt for another 2 hr. Then the mixture was washed with water, the organic layer was dried over magnesium sulfate, filtered and concentrated in vacuum. The residue was purified by CombiFlash, eluted with methanol in DCM (0-2%, 30 min). Collected the desired fraction and concentrated in vacuum to afford the title compound (330 mg, 65.6%) as white solid. $^1$H NMR (400 MHz, Methanol-$d_4$) δ 4.97 (t, J=3.3 Hz, 1H), 3.10 (s, 4H), 2.92 (s, 3H), 2.33-2.13 (m, 2H), 2.07 (dt, J=13.2, 3.7 Hz, 2H), 1.98-1.67 (m, 4H).

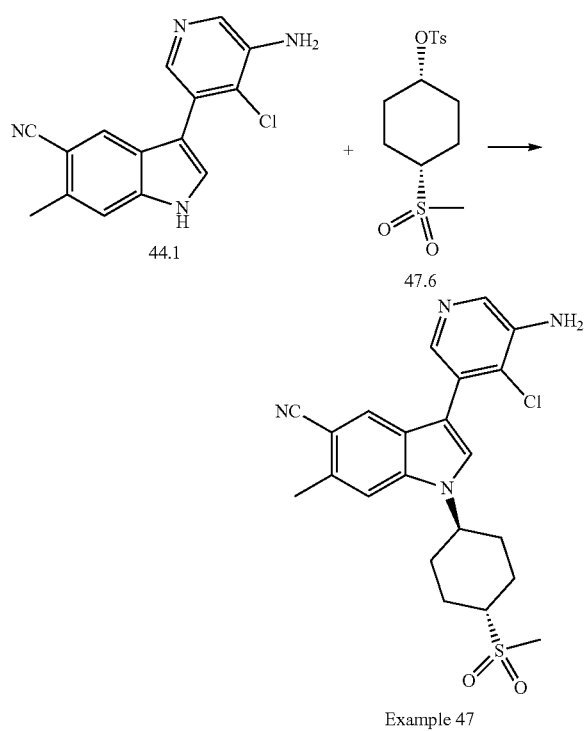

Example 47

A solution of 44.1 (150 mg, 0.531 mmol) and 47.6 (327 mg, 1.061 mmol) and Cs$_2$CO$_3$ (864 mg, 2.65 mmol) in MeCN (15 mL) was stir at 65° C. for 3 days. The mixture was filtered and the filter was further purified by basic Prep-HPLC (0.1% NH$_4$OH/ACN/H$_2$O). Collected the desired fraction and lyophilized to afford the title compound (40 mg, 17%) as white powder. 1H NMR (400 MHz, Methanol-d$_4$) δ 8.04 (s, 1H), 7.83 (s, 1H), 7.76 (s, 1H), 7.69 (s, 1H), 7.62 (s, 1H), 4.55 (tt, J=11.8, 3.8 Hz, 1H), 3.23 (tt, J=11.9, 3.6 Hz, 1H), 2.97 (s, 3H), 2.63 (s, 3H), 2.40 (dt, J=12.4, 2.7 Hz, 2H), 2.32-2.21 (m, 2H), 2.09-1.78 (m, 4H). LC-MS: [M+H]$^+$=442.8, 444.8.

Example 48

3-(5-amino-4-chloropyridin-3-yl)-6-methyl-1-((1S,4S)-4-(methylsulfonyl)cyclohexyl)-1H-indole-5-carbonitrile Intermediate 48.1

8-(methylthio)-1,4-dioxaspiro[4.5]decane

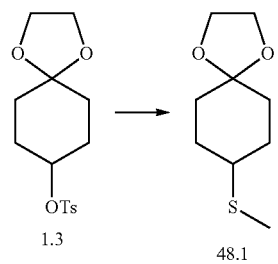 [SMILES: Cc1ccc(S(=O)(=O)OC2CCC3(CC2)OCCO3)cc1 ; CSC1CCC2(CC1)OCCO2]

A solution of 1.3 (1.5 g, 4.80 mmol), NaSMe (500 mg, 7.20 mmol) in ethanol (15 mL) was stirred at 70° C. for 20 hr. The mixture was diluted with water, extracted with DCM (20 mL*3), the organic layer was dried over magnesium sulfate, filtered and concentrated in vacuum to afford a brown syrup. The residue was purified by CombiFlash, eluted with ethyl acetate in hexane (10-30%, 30 min). Collected the desired fraction to afford the title compound (600 mg, 66.4%) as white solid. $^1$H NMR (400 MHz, Methanol-d$_4$) δ 3.91 (s, 4H), 2.74-2.53 (m, 1H), 2.06 (s, 3H), 1.99-1.90 (m, 2H), 1.79 (ddd, J=10.8, 5.5, 2.7 Hz, 2H), 1.66-1.45 (m, 4H).

Intermediate 48.2

8-(methylsulfonyl)-1,4-dioxaspiro[4.5]decane

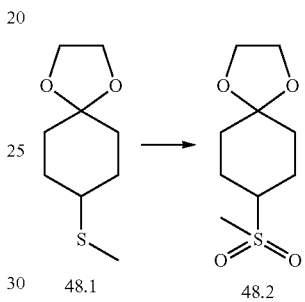

The title compound was prepared by using a procedure similar to that of intermediate 47.4 by replacing intermediate 47.3 with intermediate 48.1. $^1$HNMR (400 MHz, Methanol-d$_4$) δ 3.93 (s, 4H), 3.07 (tt, J=11.9, 3.6 Hz, 1H), 2.90 (s, 3H), 2.22-2.08 (m, 2H), 1.94-1.72 (m, 4H), 1.61 (td, J=12.9, 3.4 Hz, 2H). LC-MS: [M+H]$^+$=221.1.

Intermediate 48.3

4-(methylsulfonyl)cyclohexan-1-one

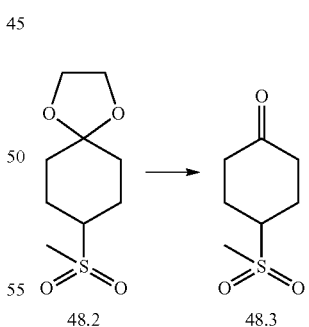

To a solution of 48.2 (570 mg, 2.59 mmol) in THF (10 mL) was added HCl (6 M, 5 mL, 30.0 mmol). The mixture was stir at 60° C. for 4 hr. Then the mixture was diluted with water (30 mL). extracted with DCM twice. The organic layer was dried over magnesium sulfate, filtered and concentrated in vacuum to afford 400 mg colorless syrup; it was used for the next directly. $^1$H NMR (400 MHz, DMSO-d$_6$) δ 3.00 (s, 3H), 2.48-2.41 (m, 1H), 2.39-2.25 (m, 4H), 1.97-1.72 (m, 4H).

Intermediate 48.4

(1R,4R)-4-(methylsulfonyl)cyclohexan-1-ol

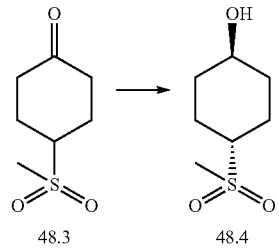

To a solution of 48.3 (400 mg, 2.270 mmol) in methanol (10 mL) was added NaBH$_4$ (103 mg, 2.72 mmol), the mixture was stirred at 0° C. for 10 min. Then the mixture was diluted with water (20 mL), extracted with DCM twice. The organic layer was dried over magnesium sulfate, filtered and concentrated in vacuum to afford the title compound (320 mg, 79%) as colorless syrup, it was used for the next step directly. LC-MS: [M+H–17]$^+$=161.0.

Intermediate 48.5

(1R,4R)-4-(methylsulfonyl)cyclohexyl 4-methylbenzenesulfonate

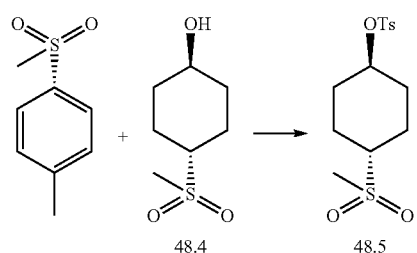

To a solution of 48.4 (270 mg, 1.515 mmol) and DMAP (296 mg, 2.424 mmol) in DCM (20 mL) was added Ts-Cl (433 mg, 2.272 mmol). The mixture was stir at rt for 20 hr. The mixture was washed with water; the organic layer was dried over magnesium sulfate, filtered and concentrated in vacuum. The residue was purified by CombiFlash, eluted with ethyl acetate in hexane (20-60%, 30 min). Collected the desired fraction to afford the title compound (160 mg white solid. $^1$H NMR (400 MHz, Methanol-d$_4$) δ 7.87-7.73 (m, 2H), 7.49-7.30 (m, 2H), 4.43 (dt, J=10.6, 5.6 Hz, 1H), 3.13-2.94 (m, 1H), 2.87 (s, 3H), 2.46 (s, 3H), 2.27-2.13 (m, 2H), 2.10-1.97 (m, 2H), 1.68-1.45 (m, 4H).

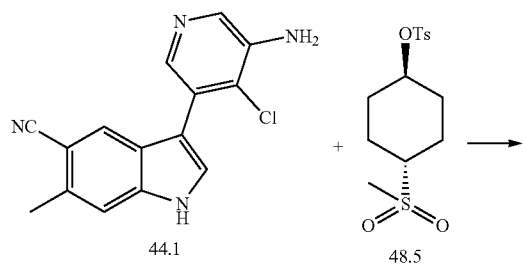

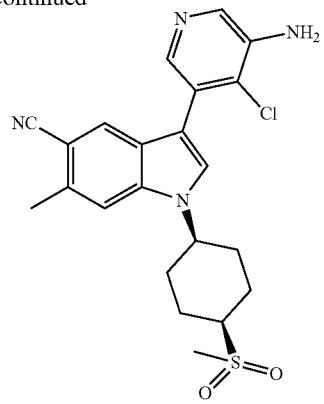

Example 48

A mixture of 44.1 (30 mg, 0.106 mmol), 48.5 (42.3 mg, 0.127 mmol) and Cs$_2$CO$_3$ (69.1 mg, 0.212 mmol) in DMF (4 mL) was stirred at 70° C. for 20 hr. The mixture was filtered and the filter was further purified by basic Prep-HPLC (0.1% NH$_4$OH/ACN/H$_2$O), collected the desired fraction and lyophilized to afford the title compound (12 mg, 25.6%) as white powder. $^1$H NMR (400 MHz, Methanol-d$_4$) δ 8.03 (s, 1H), 7.83 (s, 1H), 7.78 (s, 1H), 7.65 (s, 1H), 7.63 (s, 1H), 4.60 (m, 1H), 3.35 (s, 1H), 3.04 (s, 3H), 2.73-2.58 (s, 3H), 2.60-2.47 (m, 4H), 2.14 (ddd, J=15.7, 9.7, 6.0 Hz, 2H), 2.01 (dt, J=8.5, 4.8 Hz, 2H). LC-MS: [M+H]$^+$=442.8, 444.8.

Example 49

3-(5-amino-4-chloropyridin-3-yl)-1-(1,1-dioxidotetrahydro-2H-thiopyran-4-yl)-6-methyl-1H-indole-5-carbonitrile Intermediate 49.1 tetrahydro-2H-thiopyran-4-yl 4-methylbenzenesulfonate

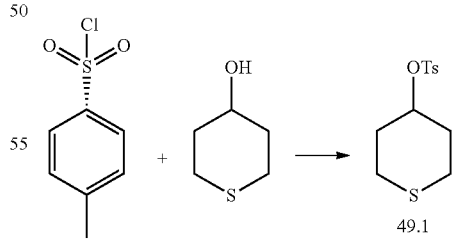

The title compound was prepared by using a procedure similar to that of intermediate 40.1 by replacing tert-butyl 3-hydroxyazetidine-1-carboxylate with tetrahydro-2H-thiopyran-4-ol. $^1$H NMR (400 MHz, DMSO-d6) δ 7.81 (d, J=8.3 Hz, 2H), 7.48 (d, J=8.1 Hz, 2H), 4.59 (td, J=8.5, 4.2 Hz, 1H), 2.70-2.61 (m, 2H), 2.56 (dt, J=8.2, 3.9 Hz, 2H), 2.42 (s, 3H), 1.94 (ddt, J=13.9, 7.1, 3.3 Hz, 2H), 1.81-1.63 (m, 2H).

Intermediate 49.2

1,1-dioxidotetrahydro-2H-thiopyran-4-yl 4-methylbenzenesulfonate

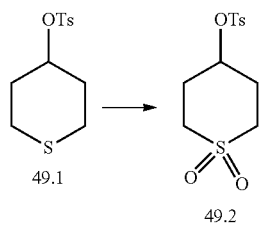 [SMILES: Cc1ccc(S(=O)(=O)OC2CCSCC2)cc1 ; Cc1ccc(S(=O)(=O)OC2CCS(=O)(=O)CC2)cc1]

The title compound was prepared by using a procedure similar to that of intermediate 47.4 by replacing intermediate 47.3 with intermediate 49.1. $^1$H NMR (400 MHz, DMSO-$d_6$) δ 7.85 (d, J=8.4 Hz, 2H), 7.50 (d, J=8.0 Hz, 2H), 4.83 (tt, J=6.8, 3.4 Hz, 1H), 3.13 (dtq, J=22.3, 8.5, 4.5 Hz, 4H), 2.43 (s, 3H), 2.18-1.90 (m, 4H). LC-MS: [M+H]$^+$=305.0.

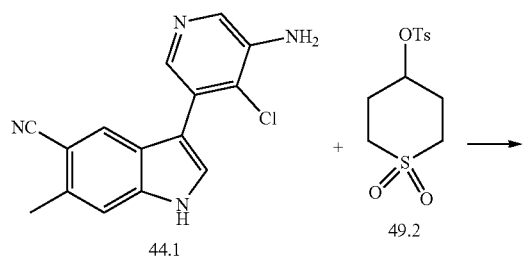

The title compound was prepared by using a procedure similar to that of Example 48 by replacing intermediate 48.2 with intermediate 49.2. $^1$H NMR (400 MHz, Methanol-$d_4$) δ 8.06 (s, 1H), 8.84 (s, 1H), 7.79 (s, 1H), 7.75 (s, 1H), 7.66 (s, 1H), 4.89 (m, 1H), 3.54 (t, J=2.64 Hz, 2H), 3.31 (s, 3H), 3.23 (d, J=2.64 Hz, 2H), 2.76-2.62 (m, 5H), 2.19 (d, J=2.64 Hz, 2H). LC-MS: [M+H]$^+$=414.9, 416.9.

Example 050 methyl 4-(3-(5-amino-4-chloropyridin-3-yl)-5-cyano-6-methyl-1H-indol-1-yl)piperidine-1-carboxylate

Intermediate 50.1 tert-butyl 4-(tosyloxy)piperidine-1-carboxylate

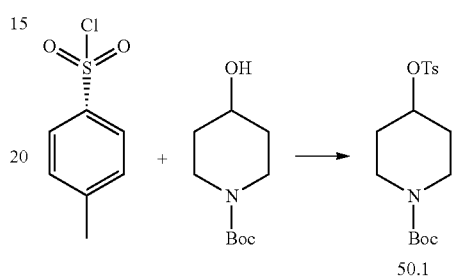

The title compound was prepared by using a procedure similar to that of intermediate 40.1 by replacing tert-butyl 3-hydroxyazetidine-1-carboxylate with tert-butyl 4-hydroxypiperidine-1-carboxylate. $^1$H NMR (400 MHz, DMSO-$d_6$) δ 7.90-7.73 (m, 2H), 7.48 (d, J=8.1 Hz, 2H), 4.67 (dq, J=8.0, 4.0 Hz, 1H), 3.48 (dt, J=10.7, 4.8 Hz, 2H), 3.14 (s, 2H), 2.43 (s, 3H), 1.69 (t, J=9.9 Hz, 2H), 1.48 (ddt, J=13.1, 8.7, 4.3 Hz, 2H), 1.37 (s, 9H).

Intermediate 50.2 piperidin-4-yl 4-methylbenzenesulfonate

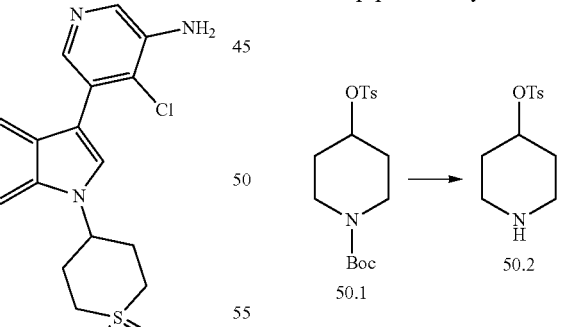

A solution of 50.1 (600 mg, 1.688 mmol) in HCl/idioxane (4M, 10 mL, 40.0 mmol) was stir at rt for 2 hr. Then the mixture was concentrated in vacuum to afford HCl salt of the title compound (480 mg, 97%) as white solid. $^1$H NMR (400 MHz, DMSO-$d_6$) b 8.91 (s, 2H), 8.00-7.75 (m, 2H), 7.50 (d, J=8.0 Hz, 2H), 4.79 (dt, J=7.8, 4.0 Hz, 1H), 3.22-2.88 (m, 4H), 2.43 (s, 3H), 1.93 (ddt, J=14.5, 7.6, 3.8 Hz, 2H), 1.88-1.64 (m, 2H). LC-MS: [M+H]$^+$=256.0.

Intermediate 50.3 methyl 4-(tosyloxy)piperidine-1-carboxylate

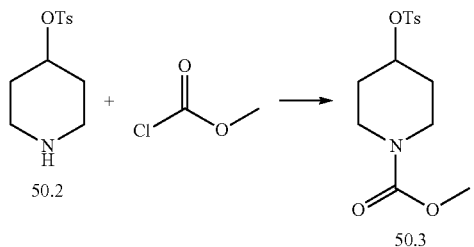

To a solution of 50.2 (300 mg, 1.028 mmol) and DIPEA (0.395 mL, 2.262 mmol) in DCM (20 mL) was added methyl carbonochloridate (0.096 mL, 1.234 mmol). The mixture was stir at rt for 30 min. The mixture was washed by water, brine. The organic layer was dried over magnesium sulfate, filtered and concentrated in vacuum. The residue was purified by CombiFlash, eluted with ethyl acetate in hexane (30-60%, 30 min). The desired fraction was collected and concentrated in vacuum to afford the title compound (280 mg, 87%) as white solid. LC-MS: [M+H]$^+$=313.9.

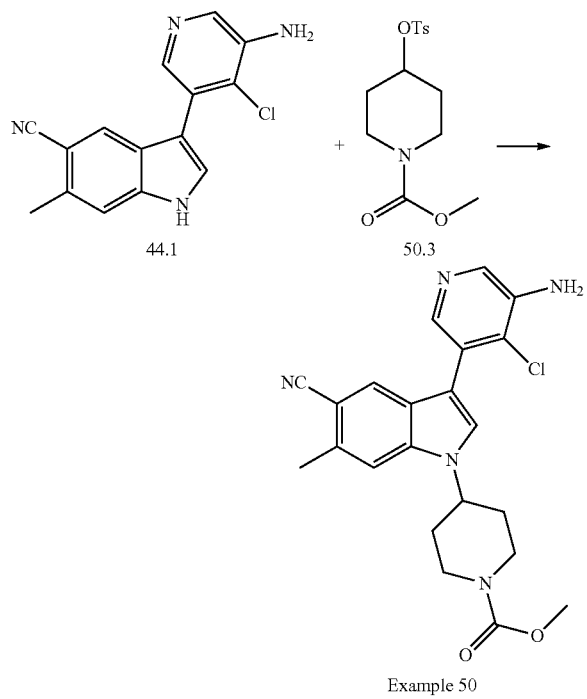

Example 50

The title compound was prepared by using a procedure similar to that of Example 48 by replacing intermediate 48.2 with intermediate 50.3. $^1$H NMR (400 MHz, Methanol-d$_4$) δ 8.05 (s, 1H), 7.83 (s, 1H), 7.78 (s, 1H), 7.72 (s, 1H), 7.65 (s, 1H), 4.71 (ddt, J=11.8, 7.7, 4.1 Hz, 1H), 4.34 (d, J=13.4 Hz, 2H), 3.72 (s, 3H), 3.21-2.98 (m, 2H), 2.65 (s, 3H), 2.16-1.91 (m, 4H). LC-MS: [M+H]$^+$=423.9, 425.9.

Example 51

3-(5-amino-4-chloropyridin-3-yl)-1-(4-hydroxy-4-methylcyclohexyl)-6-methyl-1H-indole-5-carbonitrile

Intermediate 51.1

4-oxocyclohexyl 4-methylbenzenesulfonate

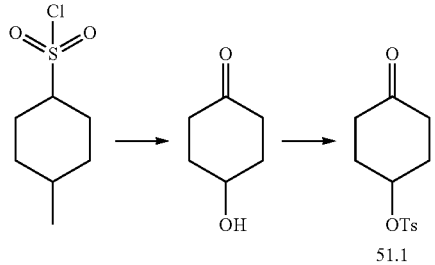 [SMILES: CC1CCC(S(=O)(=O)Cl)CC1 ; O=C1CCC(O)CC1 ; Cc1ccc(S(=O)(=O)OC2CCC(=O)CC2)cc1]

The title compound was prepared by using a procedure similar to that of intermediate 40.1 by replacing tert-butyl 3-hydroxyazetidine-1-carboxylate with 4-hydroxycyclohexanone. $^1$H NMR (400 MHz, DMSO-d$_6$) δ 8.01-7.76 (m, 2H), 7.50 (d, J=8.0 Hz, 2H), 4.89 (td, J=6.3, 3.2 Hz, 1H), 2.43 (s, 3H), 2.40-2.20 (m, 4H), 2.05-1.83 (m, 4H).

Intermediate 51.2

4-hydroxy-4-methylcyclohexyl 4-methylbenzenesulfonate

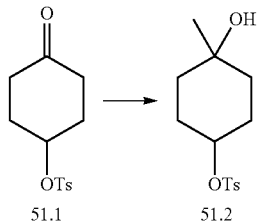 [SMILES: Cc1ccc(S(=O)(=O)OC2CCC(=O)CC2)cc1 ; Cc1ccc(S(=O)(=O)OC2CCC(C)(O)CC2)cc1]

To a solution of 50.1 (1.2 g, 4.47 mmol) in THF (20 mL) was added a solution of methyllithium in DCM (3.1M, 1.587 mL, 4.92 mmol). The mixture was stirred at −78° C. for 2 hr. The mixture was quenched by water, removed most THF in vacuum, the residue was extracted with DCM twice; the organic layer was dried over magnesium sulfate, filtered and concentrated in vacuum. The residue was purified by CombiFlash, eluted with ethyl acetate in hexane (10-40%, 30 min). Collected the desired fraction and concentrated in vacuum to afford the title compound (700 mg, 55%) as colorless syrup. $^1$H NMR (400 MHz, Methanol-d$_4$) δ 7.89-7.72 (m, 2H), 7.54-7.30 (m, 2H), 4.76-4.31 (m, 1H), 2.45 (s, 3H), 1.92-1.74 (m, 2H), 1.71-1.56 (m, 4H), 1.51-1.32 (m, 2H), 1.14 (s, 3H). LC-MS: [M+H]$^+$=286.1.

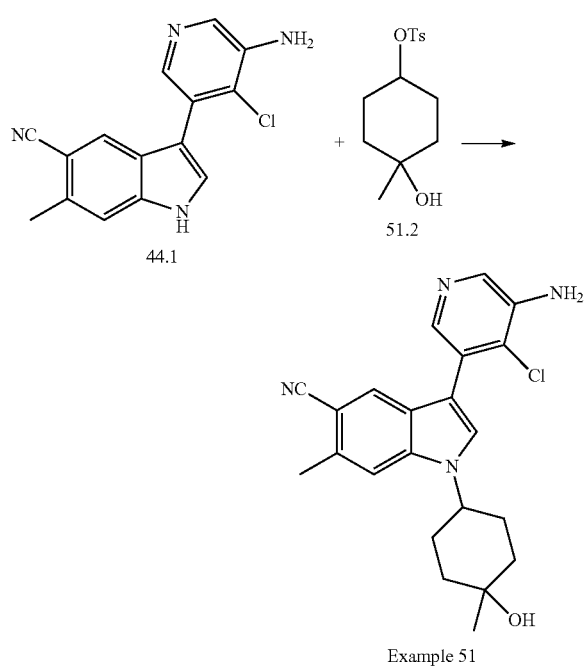

Example 51

The title compound was prepared by using a procedure similar to that of Example 48 by replacing intermediate 48.2 with intermediate 51.2. ¹H NMR (400 MHz, Methanol-d₄) δ 8.05 (s, 1H), 7.84 (s, 1H), 7.77 (s, 1H), 7.75 (s, 1H), 7.58 (s, 1H), 4.50 (td, J=11.0, 5.7 Hz, 1H), 2.65 (s, 3H), 2.02 (m, 4H), 1.91-1.77 (m, 4H), 1.40 (s, 3H). LC-MS: [M+H]⁺ =394.2, 396.2.

Example 52

N-((1S,4S)-4-(3-(5-amino-4-chloropyridin-3-yl)-5-cyano-6-methyl-1H-indol-1-yl)cyclohexyl)acetamide Example 53

N-((1R,4R)-4-(3-(5-amino-4-chloropyridin-3-yl)-5-cyano-6-methyl-1H-indol-1-yl)cyclohexyl)acetamide Intermediate 52.1

4-acetamidocyclohexyl 4-methylbenzenesulfonate

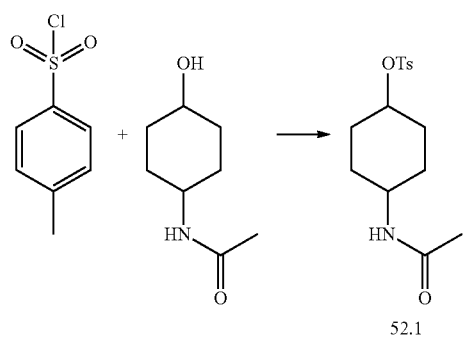

The title compound was prepared by using a procedure similar to that of intermediate 40.1 by replacing tert-butyl 3-hydroxyazetidine-1-carboxylate with N-(4-hydroxycyclohexyl)acetamide. ¹H NMR (400 MHz, DMSO-d₆) δ 7.93-7.65 (m, 3H), 7.48 (dd, J=8.3, 2.2 Hz, 2H), 4.60-4.43 (m, 1H), 3.69-3.39 (m, 1H), 2.42 (s, 3H), 1.88-1.08 (m, 11H).

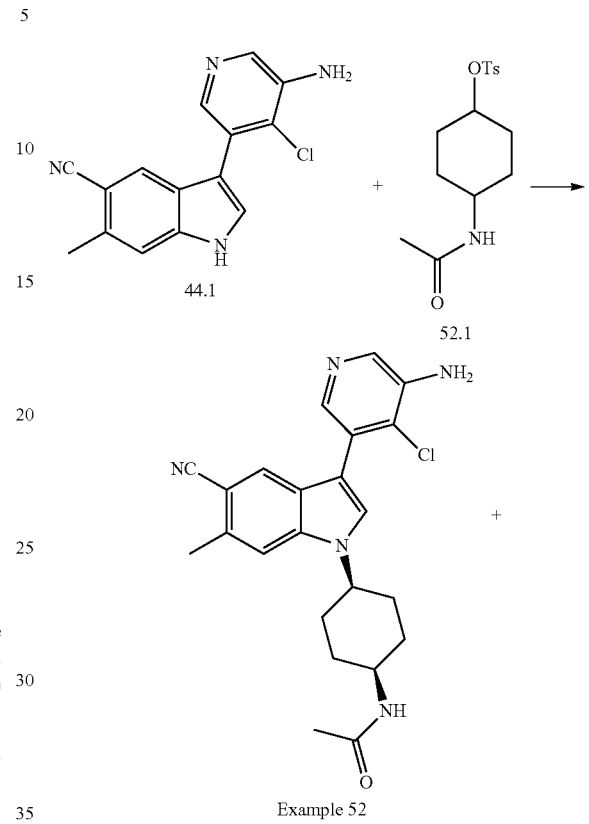

Example 52

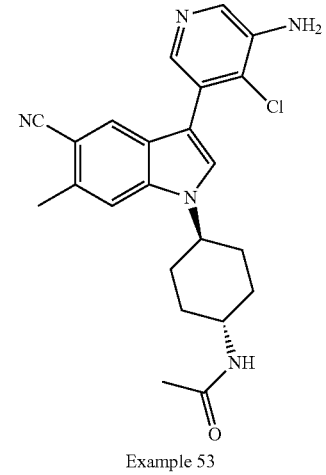

Example 53

A mixture of 44.1 (50 mg, 0.177 mmol), 52.1 (66 mg, 0.212 mmol) and Cs₂CO₃ (115 mg, 0.354 mmol) in DMF (4 mL) was stirred at 70° C. for 20 hr. The mixture was filtered, the filter was further purified by basic Prep-HPLC (0.1% NH₄OH/ACN/H₂O). Collected the desired fraction and lyophilized to afford the title compound Example 52 (6 mg, 8%) and the title compound Example 53 (1.8 mg, 2.4%) as off-white powder.

Example 52

¹H NMR (400 MHz, Methanol-d₄) δ 8.06 (s, 1H), 7.86 (s, 1H), 7.79 (s, 1H), 7.77 (s, 1H), 7.61 (s, 1H), 4.65-4.41 (m, 1H), 4.25-4.04 (m, 1H), 2.65 (s, 3H), 2.23-2.05 (m, 2H), 2.02 (s, 3H), 2.01-1.85 (m, 6H). LC-MS: [M+H]⁺=422.1, 423.1.

Example 53

¹H NMR (400 MHz, Methanol-d₄) δ 8.05 (s, 1H), 7.85 (s, 1H), 7.78 (s, 1H), 7.74 (s, 1H), 7.60 (s, 1H), 4.60-4.34 (m, 1H), 3.87-3.70 (m, 1H), 2.65 (s, 3H), 2.24-1.97 (m, 6H), 1.95 (s, 3H), 1.59 (dt, J=13.5, 10.4 Hz, 2H). LC-MS: [M+H]⁺=422.1, 423.1.

Example 54

3-(5-amino-4-chloropyridin-3-yl)-1-(4-aminocyclohexyl)-6-methyl-1H-indole-5-carbonitrile Intermediate 54.1

4-((tert-butoxycarbonyl)amino)cyclohexyl 4-methylbenzenesulfonate

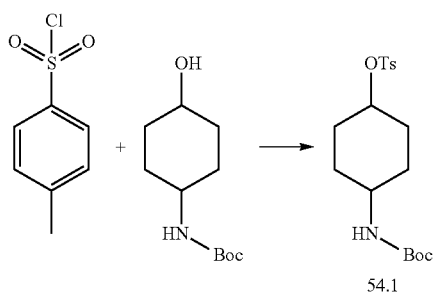

54.1

The title compound was prepared by using a procedure similar to that of intermediate 40.1 by replacing tert-butyl 3-hydroxyazetidine-1-carboxylate with tert-butyl (4-hydroxycyclohexyl)carbamate. ¹H NMR (400 MHz, DMSO-d₆) δ 7.85-7.72 (m, 2H), 7.47 (d, J=8.0 Hz, 2H), 6.74 (d, J=7.7 Hz, 1H), 4.34 (tt, J=10.3, 4.0 Hz, 1H), 3.20 (d, J=8.0 Hz, 1H), 2.42 (s, 3H), 1.80-1.65 (m, 4H), 1.54-1.39 (m, 2H), 1.35 (s, 9H), 1.16 (qd, J=13.3, 11.7, 5.0 Hz, 2H).

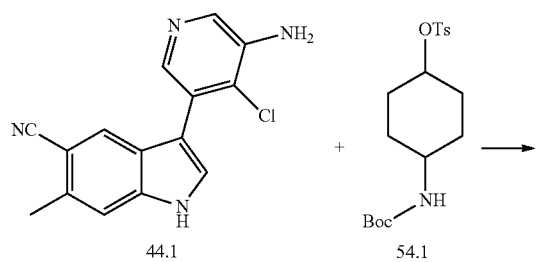

44.1 + 54.1 →

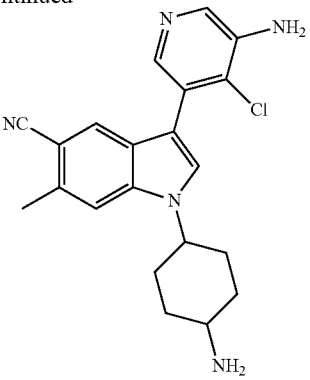

Example 54

A mixture of 44.1 (50 mg, 0.177 mmol), 54.1 (78 mg, 0.212 mmol) and Cs₂CO₃ (115 mg, 0.354 mmol) in DMF (4 mL) was stirred at 70° C. for 2 days, 27% target was found in LC-MS: [M+H]⁺=480.1, 481.1, then the mixture was filtered and aqueous HCl (3 M, 2 mL) was added to the filter, the mixture was stir at rt for 5 hr. Then the mixture was purified by basic Prep-HPLC (0.1% NH₄OH/ACN/H₂O). Collected the desired fraction and lyophilized to afford the title compound (4 mg, 6%) as off-white powder. ¹H NMR (400 MHz, Methanol-d₄) δ 8.05 (s, 1H), 7.86 (s, 1H), 7.84 (s, 1H), 7.78 (s, 1H), 7.60 (s, 1H), 4.49 (td, J=9.8, 8.0, 5.9 Hz, 1H), 3.26 (q, J=3.4 Hz, 1H), 2.69 (s, 3H), 2.32-2.16 (m, 2H), 1.91 (dd, J=14.9, 3.2 Hz, 6H). LC-MS: [M+H]⁺=380.1, 381.1.

Example 55

3-(5-amino-4-chloropyridin-3-yl)-6-methyl-1-(1-(methylsulfonyl)piperidin-4-yl)-1H-indole-5-carbonitrile Intermediate 55.1

1-(methylsulfonyl)piperidin-4-yl methanesulfonate

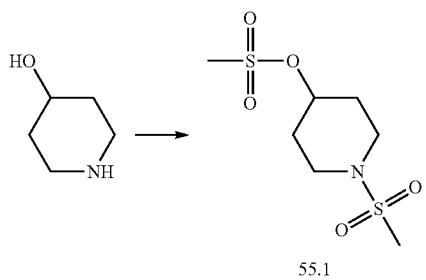

55.1

To a solution of compound piperidin-4-ol (100 mg, 0.98 mmol, 1.0 eq) and Et₃N (198.3 mg, 1.96 mmol, 2.0 eq) in CH₂Cl₂ (5.0 mL, anhydrous) was added methanesulfonyl chloride (200 mg, 1.74 mmol, 1.77 eq) at 0° C. and the mixture was stirred at 10-13° C. for 3 hours. TLC showed most of the starting material was consumed. The mixture was quenched with water (20 mL) and extracted with CH₂Cl₂ (30 mL×2). The combined organic phase was dried over anhydrous sodium sulfate, filtered and concentrated to give the crude 55.1 (0.98 mmol), which was used to next step without further purification.

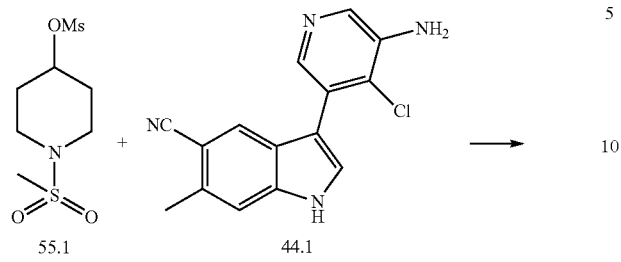

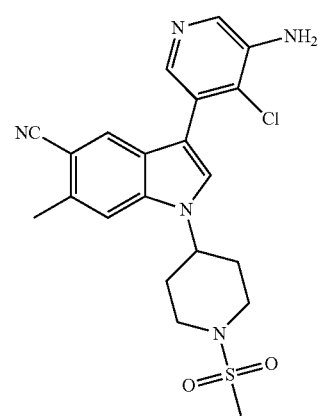

Example 55

The title compound was prepared by using a procedure similar to that of Example 48 by replacing intermediate 48.2 with intermediate 55.1. ¹HNMR (400 MHz, CDCl₃): δ ppm 8.14 (s, 1H), 8.05 (s, 1H), 7.90 (s, 1H), 7.43 (s, 1H), 7.29 (s, 1H), 4.43-4.38 (m, 1H), 4.23 (brs, 2H), 4.10-4.07 (m, 2H), 3.01-2.94 (m, 2H), 2.90 (s, 3H), 2.67 (s, 3H), 2.27-2.19 (m, 4H). LC-MS: [M+H]⁺=444.1.

Example 56

3-(5-amino-4-chloropyridin-3-yl)-6-methyl-1-(1-methyl-6-oxopiperidin-3-yl)-1H-indole-5-carbonitrile

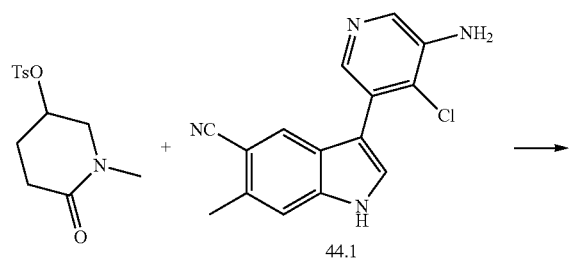

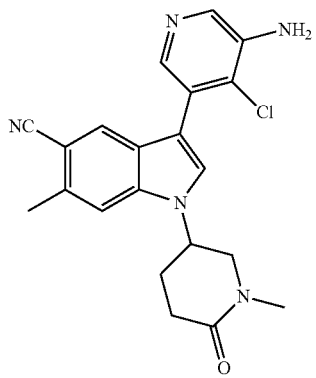

Example 56

The title compound was prepared by using a procedure similar to that of Example 48 by replacing intermediate 48.2 with 1-methyl-6-oxopiperidin-3-yl 4-methylbenzenesulfonate. ¹HNMR (400 MHz, CDCl₃) δ ppm 8.17 (s, 1H), 8.06 (s, 1H), 7.93 (s, 1H), 7.42 (s, 1H), 7.37 (s, 1H), 4.90 (m, 1H), 4.25 (s, 2H), 3.80 (m, 1H) 3.67 (m, 1H), 3.06 (s, 3H), 2.72 (s, 3H), 2.62-2.72 (m, 2H) 2.30-2.52 (m, 2H). LC-MS: [M+H]⁺=394.1.

Example 57

1-(1-acetylpiperidin-3-yl)-3-(5-amino-4-chloropyridin-3-yl)-6-methyl-1H-indole-5-carbonitrile Intermediate 57.1

1-(3-hydroxypiperidin-1-yl)ethanone

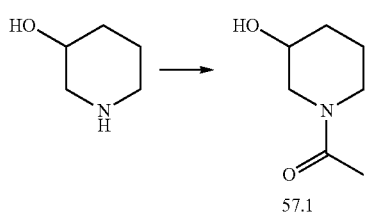

To a solution of compound piperidin-3-ol (2.5 g, 24.71 mmol, 1.0 eq) in DCM (25 ml) was added compound Ac₂O (2.92 g, 28.42 mmol, 1.15 eq) at 00° C., the mixture was stirred at 00° C. for 2.5 hours. The mixture was concentrated in vacuum and purified by column chromatography (DCM:MEOH=100:1~20:1), Compound 2 (1.9 g, 45%) was obtained as a yellow solid. ¹H NMR (400 MHz, CDCl₃) δ ppm 3.95-3.55 (m, 2H), 3.45-3.20 (m, 3H), 2.11 (s, 3H), 1.95-1.70 (m, 2H), 1.65-1.40 9m, 2H).

159

Intermediate 57.2

1-acetylpiperidin-3-yl methanesulfonate

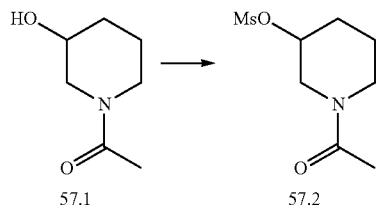

The title compound was prepared by using a procedure similar to that of intermediate 47.6 by replacing intermediate 47.5 with intermediate 57.1. $^1$HNMR (400 MHz, CDCl$_3$) δ ppm 4.73-4.65 (m, 1H), 3.35-3.20 (m, 1H), 3.75-3.95 (m, 1H), 3.40-3.65 (m, 2H), 2.99 (s, 3H), 2.06 (s, 3H), 1.92-1.84 (m, 2H), 1.63-1.45 (m, 2H).

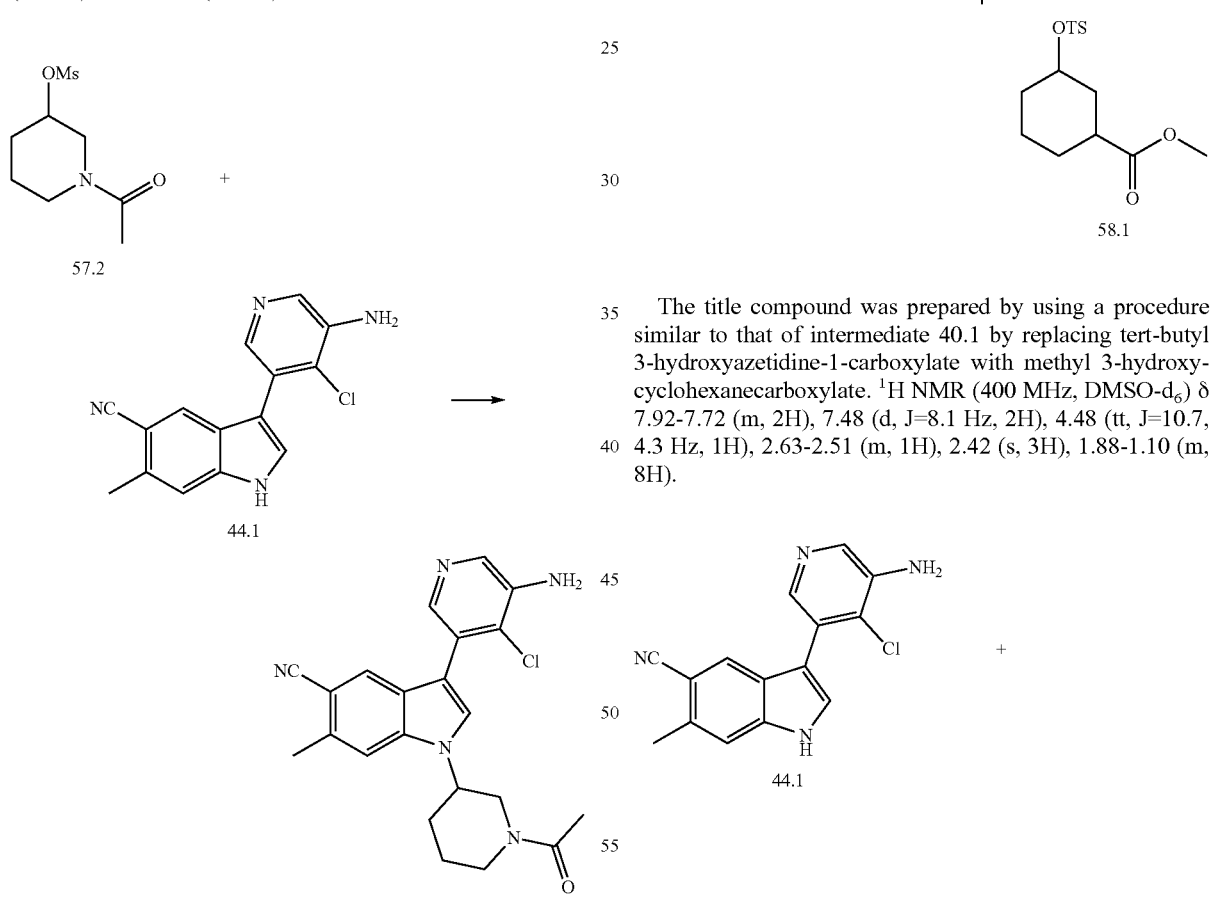

Example 57

The title compound was prepared by using a procedure similar to that of Example 48 by replacing intermediate 48.2 with intermediate 57.2. $^1$HNMR (400 MHz, CDCl3) δ ppm 8.17 (s, 1 H), 8.06 (s, 1 H), 7.93 (s, 1H) 7.41 (s, 1 H), 7.37 (s, 1 H), 4.90 (brs, 1 H), 4.25 (s, 2 H), 3.75-3.90 (m, 2 H), 3.60-3.71 (m, 2 H), 3.05 (s, 3 H), 2.55-2.80 9m, 5 H), 2.30-2.55 (m, 2H). LC-MS: [M+H]$^+$=408.1.

160

Example 58 methyl 3-(3-(5-amino-4-chloropyridin-3-yl)-5-cyano-6-methyl-1H-indol-1-yl)cyclohexane-1-carboxylate

Intermediate 58.1 methyl 3-(tosyloxy)cyclohexane-1-carboxylate

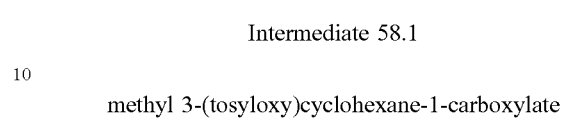

The title compound was prepared by using a procedure similar to that of intermediate 40.1 by replacing tert-butyl 3-hydroxyazetidine-1-carboxylate with methyl 3-hydroxy-cyclohexanecarboxylate. $^1$H NMR (400 MHz, DMSO-d$_6$) δ 7.92-7.72 (m, 2H), 7.48 (d, J=8.1 Hz, 2H), 4.48 (tt, J=10.7, 4.3 Hz, 1H), 2.63-2.51 (m, 1H), 2.42 (s, 3H), 1.88-1.10 (m, 8H).

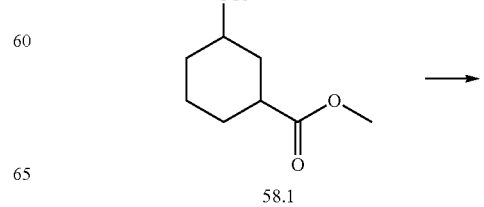

-continued

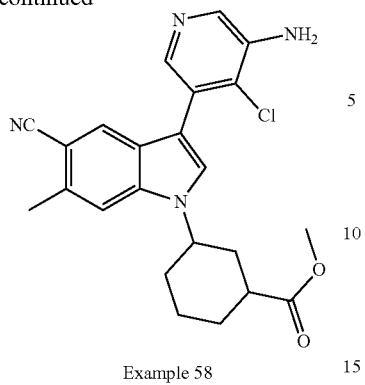

Example 58

The title compound was prepared by using a procedure similar to that of Example 48 by replacing intermediate 48.2 with intermediate 58.1. $^1$H NMR (400 MHz, Methanol-d$_4$) δ 8.05 (s, 1H), 7.93-7.76 (m, 2H), 7.71 (s, 1H), 7.60 (s, 1H), 4.79-4.31 (m, 1H), 3.91-3.56 (m, 3H), 3.25-2.98 (m, 1H), 2.65 (d, J=5.8 Hz, 3H), 2.57-2.32 (m, 1H), 2.31-2.06 (m, 2H), 2.05-1.91 (m, 2H), 1.79-1.36 (m, 3H). LC-MS: [M+H]$^+$=423.2, 425.2.

Example 59

3-(3-(5-amino-4-chloropyridin-3-yl)-5-cyano-6-methyl-1H-indol-1-yl)cyclohexane-1-carboxamide

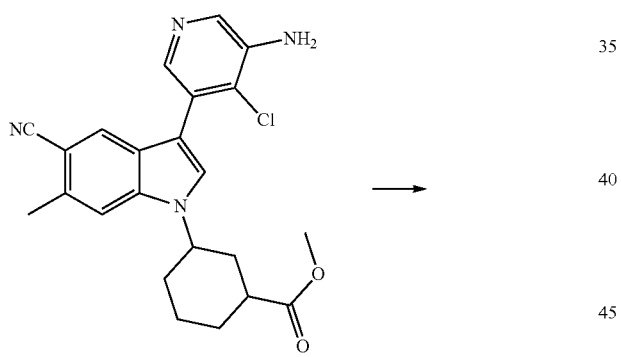

Example 59

A solution of Example 58 (35 mg, 0.083 mmol) in NH$_3$/methanol (7M, 4 mL, 8.00 mmol) was sealed and heated at 100° C. for 20 hr. The mixture was purified by acid Prep-HPLC (0.1% NH$_4$OH/ACN/H$_2$O). Collected the desired fraction and lyophilized to afford the title compound (6 mg, 17.7%) as white powder. $^1$H NMR (400 MHz, Methanol-d$_4$) δ 8.05 (s, 1H), 7.85 (s, 1H), 7.78 (s, 1H), 7.73 (s, 1H), 7.60 (s, 1H), 4.54 (tt, J=12.0, 3.8 Hz, 1H), 2.67-2.64 (m, 3H), 2.59 (dt, J=12.2, 3.5 Hz, 1H), 2.23-1.85 (m, 6H), 1.78-1.61 (m, 1H), 1.62-1.45 (m, 1H). LC-MS: [M+H]$^+$= 407.2, 409.3.

Example 60 methyl 3-(3-(5-amino-4-chloropyridin-3-yl)-5-cyano-6-methyl-1H-indol-1-yl)pyrrolidine-1-carboxylate Intermediate 60.1 tert-butyl 3-(tosyloxy)pyrrolidine-1-carboxylate

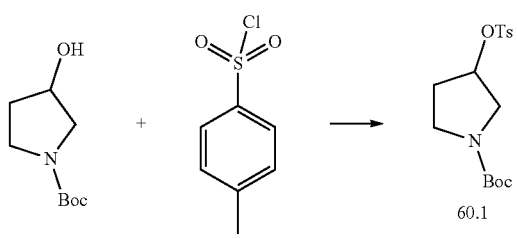 [SMILES: CC(C)(C)OC(=O)N1CCC(O)C1 ; Cc1ccc(S(=O)(=O)Cl)cc1 ; Cc1ccc(S(=O)(=O)OC2CCN(C(=O)OC(C)(C)C)C2)cc1]

The title compound was prepared by using a procedure similar to that of intermediate 40.1 by replacing tert-butyl 3-hydroxyazetidine-1-carboxylate with tert-butyl 3-hydroxypyrrolidine-1-carboxylate. $^1$H NMR (400 MHz, DMSO-d$_6$) δ 7.82 (d, J=8.3 Hz, 2H), 7.50 (d, J=8.0 Hz, 2H), 5.05 (s, 1H), 3.43-3.34 (m, 2H), 3.29-3.13 (m, 2H), 2.43 (s, 3H), 2.13-1.80 (m, 2H), 1.37 (d, J=12.3 Hz, 9H).

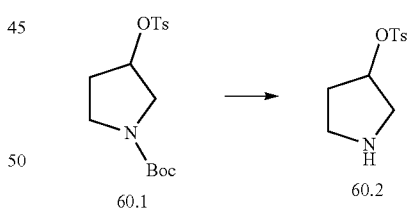

Intermediate 60.2 pyrrolidin-3-yl 4-methylbenzenesulfonate

The title compound was prepared by using a procedure similar to that of intermediate 50.2 by replacing intermediate 50.1 with intermediate 60.1. $^1$H NMR (400 MHz, DMSO-d$_6$) δ 9.28 (s, 2H), 7.97-7.78 (m, 2H), 7.65-7.39 (m, 2H), 5.30-5.02 (m, 1H), 3.34 (m, 2H), 3.30-3.09 (m, 2H), 2.44 (s, 3H), 2.08 (tq, J=16.2, 6.7, 5.5 Hz, 2H). LC-MS: [M+H]$^+$= 242.2.

Intermediate 60.3 methyl 3-(tosyloxy)pyrrolidine-1-carboxylate

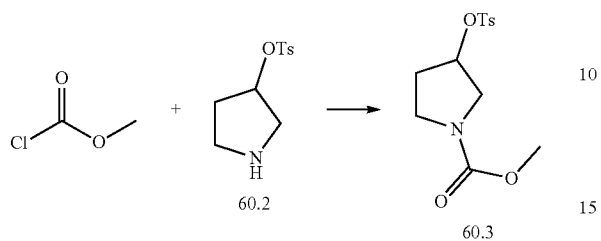

The title compound was prepared by using a procedure similar to that of intermediate 50.3 by replacing intermediate 50.2 with intermediate 60.2. LC-MS: [M+H]⁺=300.2.

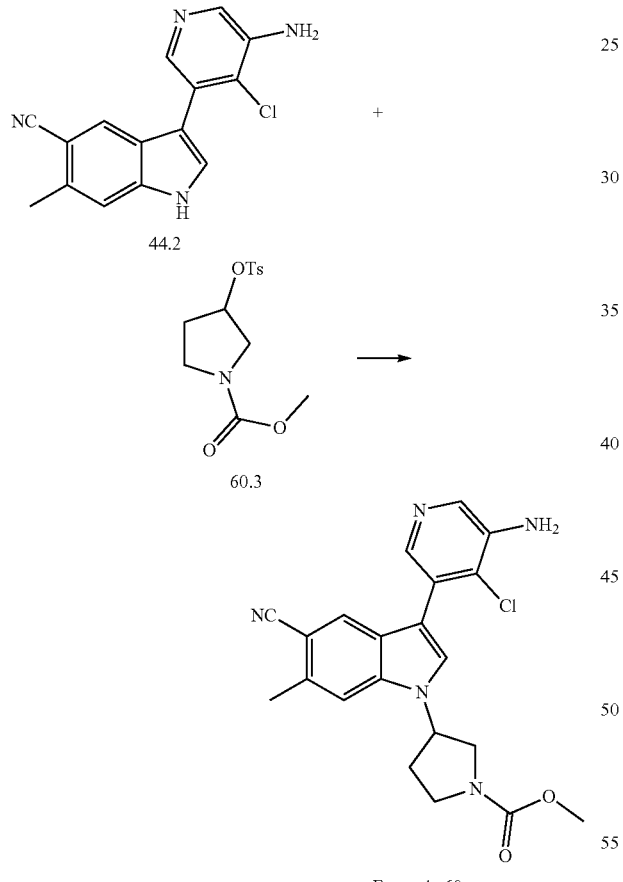

Example 60

The title compound was prepared by using a procedure similar to that of Example 48 by replacing intermediate 48.2 with intermediate 60.3. ¹H NMR (400 MHz, Methanol-d₄) δ 8.05 (s, 1H), 7.85 (s, 1H), 7.80 (s, 1H), 7.63 (d, J=7.3 Hz, 2H), 5.30 (q, J=6.0 Hz, 1H), 3.99 (dt, J=11.5, 5.7 Hz, 1H), 3.72 (d, J=7.1 Hz, 4H), 3.69-3.56 (m, 2H), 2.73-2.60 (m, 3H), 2.52 (dp, J=13.8, 6.9 Hz, 1H), 2.41 (dt, J=12.8, 6.5 Hz, 1H). LC-MS: [M+H]⁺=409.2, 411.2.

Example 61

3-(5-amino-4-chloropyridin-3-yl)-6-methyl-1-(1-(methylsulfonyl)pyrrolidin-3-yl)-1H-indole-5-carbonitrile

Intermediate 61.1

1-(methylsulfonyl)pyrrolidin-3-yl 4-methylbenzenesulfonate

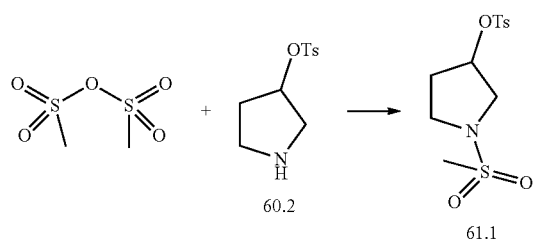

To a solution of 60.2 (300 mg, 1.080 mmol) and DIPEA (0.566 mL, 3.24 mmol) in DCM (15 mL) was added methanesulfonic anhydride (376 mg, 2.160 mmol). The mixture was stirred at rt for 20 hr. Then the mixture was purified by CombiFlash, eluted with ethyl acetate in hexane (10-40%, 30 min). Collected the desired fraction to afford the title compound (320 mg, 93%) as white solid. ¹H NMR (400 MHz, DMSO-d₆) δ 7.92-7.77 (m, 2H), 7.51 (d, J=8.0 Hz, 2H), 5.09 (dq, J=4.3, 2.2, 1.7 Hz, 1H), 3.45 (dd, J=12.3, 4.4 Hz, 1H), 3.40-3.33 (m, 2H), 3.33-3.20 (m, 2H), 2.89 (s, 3H), 2.44 (s, 3H), 2.11 (dtd, J=14.0, 9.3, 4.7 Hz, 1H), 2.03-1.92 (m, 1H). LC-MS: [M+H]⁺=320.0.

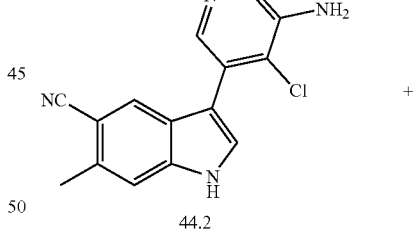

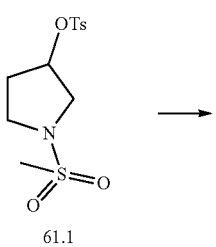

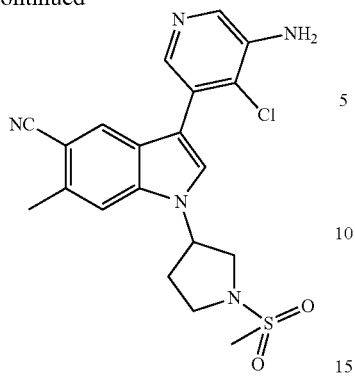

Example 61

The title compound was prepared by using a procedure similar to that of Example 48 by replacing intermediate 48.2 with intermediate 61.1. $^1$H NMR (400 MHz, Methanol-d$_4$) δ 8.06 (s, 1H), 7.86 (s, 1H), 7.81 (s, 1H), 7.78 (s, 1H), 7.65 (s, 1H), 5.43-5.26 (m, 1H), 3.91 (dd, J=10.6, 6.7 Hz, 1H), 3.74-3.62 (m, 2H), 3.57 (ddd, J=10.1, 8.2, 6.4 Hz, 1H), 2.97 (s, 3H), 2.66 (s, 3H), 2.65-2.56 (m, 1H), 2.46 (tt, J=13.5, 6.5 Hz, 1H). LC-MS: [M+H]$^+$=429.8, 431.8.

Example 62

N-((1R,3R)-3-(3-(5-amino-4-chloropyridin-3-yl)-5-cyano-6-methyl-1H-indol-1-yl)cyclopentyl)acetamide (trans relative)

Intermediate 62.1

3-((tert-butoxycarbonyl)amino)cyclopentyl 4-methylbenzenesulfonate

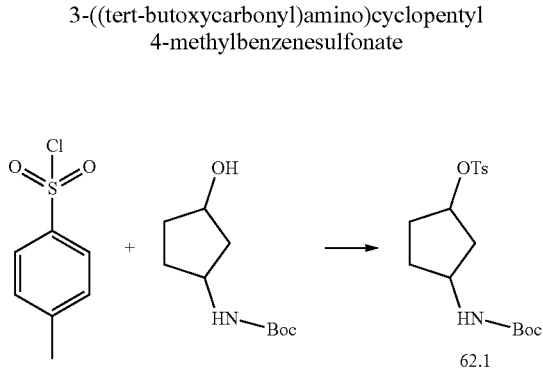

The title compound was prepared by using a procedure similar to that of intermediate 40.1 by replacing tert-butyl 3-hydroxyazetidine-1-carboxylate with tert-butyl (3-hydroxycyclopentyl)carbamate. $^1$H NMR (400 MHz, DMSO-d$_6$) δ 7.78 (d, J=8.4 Hz, 2H), 7.47 (d, J=8.2 Hz, 2H), 7.23-6.82 (m, 1H), 5.05-4.64 (m, 1H), 3.97-3.53 (m, 1H), 2.42 (s, 3H), 2.12 (dt, J=14.5, 7.4 Hz, 1H), 1.49 (dt, J=13.3, 4.2 Hz, 5H), 1.35 (d, J=1.6 Hz, 9H).

Intermediate 62.2

3-aminocyclopentyl 4-methylbenzenesulfonate

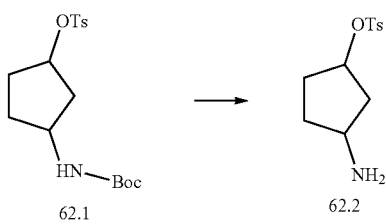 [SMILES: Cc1ccc(S(=O)(=O)OC2CCC(NC(=O)OC(C)(C)C)C2)cc1 ; Cc1ccc(S(=O)(=O)OC2CCC(N)C2)cc1]

The title compound was prepared by using a procedure similar to that of intermediate 50.2 by replacing intermediate 50.1 with intermediate 62.1. LC-MS: [M+H]$^+$=256.0.

Intermediate 62.3

3-acetamidocyclopentyl 4-methylbenzenesulfonate

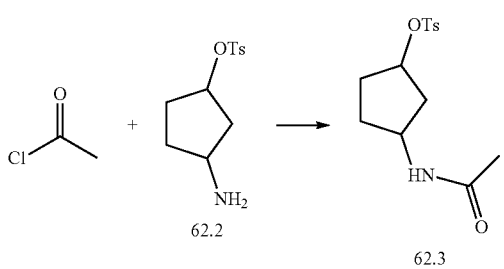

The title compound was prepared by using a procedure similar to that of intermediate 50.3 by replacing intermediate 50.2 with intermediate 62.2. LC-MS: [M+H]$^+$=298.0.

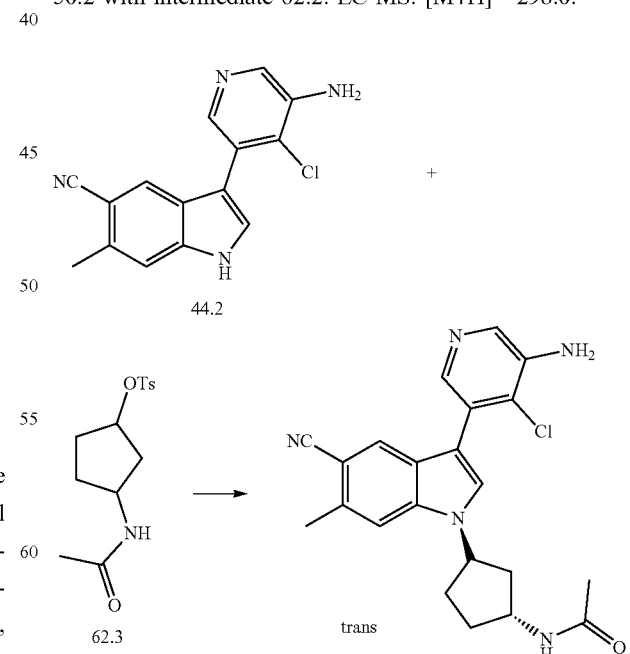

Example 62

The title compound was prepared by using a procedure similar to that of Example 48 by replacing intermediate 48.2 with intermediate 62.3. ¹H NMR (400 MHz, Methanol-d₄) δ 8.05 (s, 1H), 7.85 (s, 1H), 7.77 (s, 1H), 7.72 (s, 1H), 7.56 (s, 1H), 5.23-5.00 (m, 1H), 4.58-4.30 (m, 1H), 2.65 (s, 3H), 2.44 (tdd, J=13.4, 9.0, 4.9 Hz, 1H), 2.38-2.27 (m, 2H), 2.18 (ddd, J=13.8, 8.1, 5.5 Hz, 1H), 2.11-1.99 (m, 1H), 1.97 (s, 3H), 1.72 (dtd, J=13.1, 8.4, 6.7 Hz, 1H). LC-MS: [M+H]⁺= 407.9, 408.9.

Example 63

N-((1R,3R)-3-(3-(5-amino-4-chloropyridin-3-yl)-5-cyano-6-methyl-1H-indol-1-yl)cyclopentyl)methanesulfonamide Example 64

N-((1S,3R)-3-(3-(5-amino-4-chloropyridin-3-yl)-5-cyano-6-methyl-1H-indol-1-yl)cyclopentyl)methanesulfonamide Example 65

N-((1R,3S)-3-(3-(5-amino-4-chloropyridin-3-yl)-5-cyano-6-methyl-1H-indol-1-yl)cyclopentyl)methanesulfonamide Example 66

N-((1S,3S)-3-(3-(5-amino-4-chloropyridin-3-yl)-5-cyano-6-methyl-1H-indol-1-yl)cyclopentyl)methanesulfonamide Intermediate 63.1

(1R,3R)-3-((tert-butoxycarbonyl)amino)cyclopentyl methanesulfonate (trans relative)

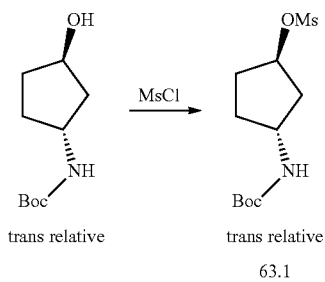 [SMILES: "MsCl" ; CC(C)(C)OC(=O)N[C@@H]1CC[C@@H](O)C1 ; CC(C)(C)OC(=O)N[C@@H]1CC[C@@H](OS(C)(=O)=O)C1]

To a solution of tert-butyl ((1R,3R)-3-hydroxycyclopentyl)carbamate(trans relative) (200 mg, 0.994 mmol) and TEA (0.208 mL, 1.491 mmol) in DCM (15 mL) was added MsCl (0.093 mL, 1.192 mmol), the mixture was stir at 0° C. for 3 hr. Then the mixture was washed with water. The organic layer was dried over magnesium sulfate, filtered and concentrated in vacuum. The residue was purified by CombiFlash, eluting with ethyl acetate in hexane (10-30%, 30 min). The desired fraction was collected to afford the title compound (260 mg, 94%) as white solid. ¹H NMR (400 MHz, DMSO-d₆) δ 7.92 (d, J=7.7 Hz, 1H), 5.56 (d, J=3.7 Hz, 1H), 5.24 (dq, J=6.0, 3.0 Hz, 1H), 5.05 (q, J=7.4 Hz, 1H), 3.16-2.90 (m, 2H), 2.83 (ddd, J=10.7, 7.3, 2.9 Hz, 1H), 2.62 (ddd, J=13.3, 7.7, 6.0 Hz, 1H), 2.51 (s, 3H), 2.41 (ddt, J=12.6, 8.4, 6.4 Hz, 2H).

Intermediate 63.2

(1R,3R)-3-aminocyclopentyl methanesulfonate (trans relative)

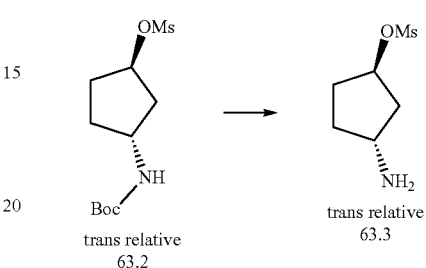

The title compound was prepared by using a procedure similar to that of intermediate 50.2 by replacing intermediate 50.1 with intermediate 63.1. ¹H NMR (400 MHz, DMSO-d₆) δ 8.06 (s, 3H), 5.20 (dt, J=5.7, 2.8 Hz, 1H), 3.67 (q, J=6.3 Hz, 1H), 3.37 (t, J=6.1 Hz, 1H), 2.29-2.14 (m, 2H), 2.14-1.92 (m, 2H), 1.86 (m, 1H), 1.65 (ddt, J=14.3, 8.9, 5.5 Hz, 1H).

Intermediate 63.4

(1R,3R)-3-(methylsulfonamido)cyclopentyl methanesulfonate (trans relative)

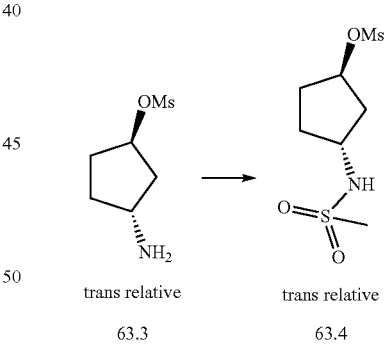

To a solution of 63.3 (210 mg, 0.974 mmol) and TEA (0.543 mL, 3.89 mmol) in DCM (10 mL) was added MsCl (0.083 mL, 1.071 mmol). The mixture was stir at 0° C. for 30 min, and then it was quenched with water. The organic layer was dried over magnesium sulfate, filtered and concentrated in vacuum. The residue was purified by CombiFlash, eluted with ethyl acetate in hexane (10-30%, 30 min). Collected the desired fraction and concentrated in vacuum to afford the title compound (200 mg, 80%) as white solid. ¹H NMR (400 MHz, DMSO-d₆) δ 7.20 (d, J=7.4 Hz, 1H), 5.13 (dt, J=6.1, 3.1 Hz, 1H), 3.82 (p, J=7.4 Hz, 1H), 3.16 (s, 3H), 2.92 (s, 3H), 2.24-2.00 (m, 3H), 1.92-1.68 (m, 2H), 1.51 (ddt, J=12.9, 9.3, 6.5 Hz, 1H).

169

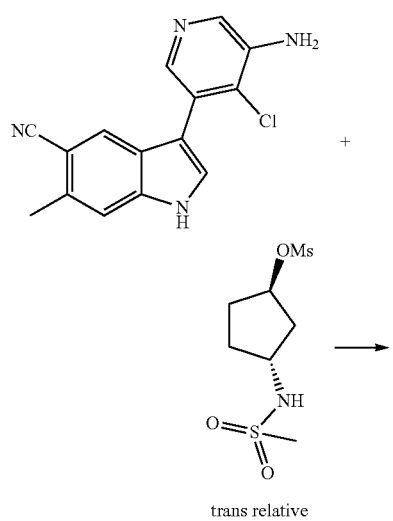

+

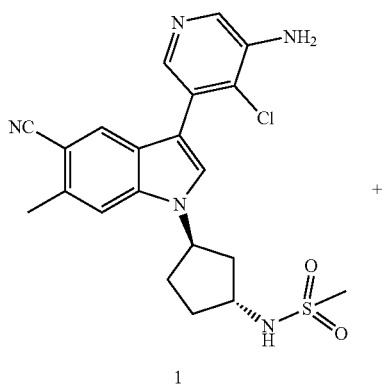

trans relative

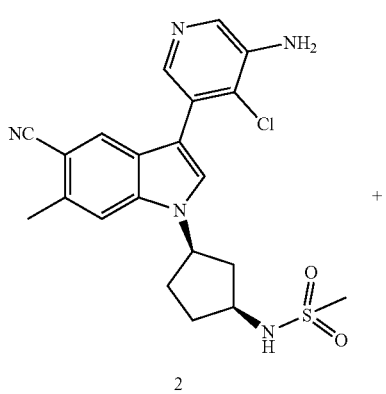

1

Example 63

2

Example 64

170

-continued

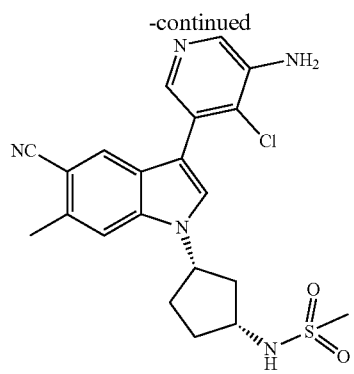

3

Example 65

+

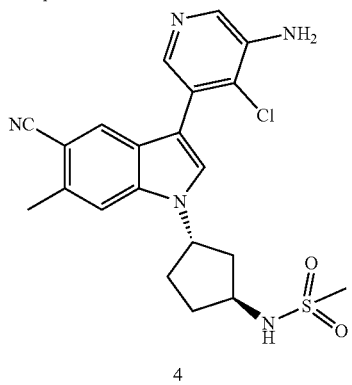

4

Example 66

A suspension of 44.2 (98 mg, 0.382 mmol), 63.4 (90 mg, 0.318 mmol) and Cs$_2$CO$_3$ (259 mg, 0.796 mmol) in DMF (5 mL) was stirred at 80° C. for 20 h. The mixture was diluted with DCM (20 mL), washed with water, the organic layer was dried over magnesium sulfate, filtered and concentrated in vacuum. The residue was purified by CombiFlash, eluted with methanol in DCM (0-5%, 30 min). Collected the desired fraction and concentrated in vacuum to afford 70 mg colorless syrup, which was further purified by SFC to get the four isomers. Title compound Example 63 (16.7 mg, 10%), title compound Example 64 (5.4 mg, 3.2%), title compound Example 64 (8.7 mg, 5.2%) and title compound Example 66 (23.5 mg, 14%) as white powder.

Example 63

$^1$H NMR (400 MHz, Methanol-d$_4$) δ 8.05 (s, 1H), 7.85 (s, 1H), 7.78 (s, 1H), 7.72 (s, 1H), 7.57 (s, 1H), 5.16 (p, J=7.7 Hz, 1H), 4.22-4.00 (m, 1H), 2.98 (s, 3H), 2.70-2.60 (m, 3H), 2.53-2.25 (m, 4H), 2.12-1.99 (m, 1H), 1.91-1.75 (m, 1H). LC-MS: [M+H]$^+$=443.8, 445.8.

Example 64

$^1$H NMR (400 MHz, Methanol-d$_4$) δ 8.05 (s, 1H), 7.86 (s, 1H), 7.78 (d, J=2.9 Hz, 2H), 7.60 (s, 1H), 5.04 (p, J=8.1 Hz, 1H), 4.10-3.86 (m, 1H), 2.98 (s, 3H), 2.74 (dt, J=13.9, 7.3 Hz, 1H), 2.68-2.58 (m, 3H), 2.35-1.96 (m, 5H). LC-MS: [M+H]$^+$=443.8, 445.8.

Example 65

$^1$H NMR (400 MHz, Methanol-d$_4$) δ 8.05 (s, 1H), 7.86 (s, 1H), 7.78 (d, J=2.7 Hz, 2H), 7.60 (s, 1H), 5.04 (p, J=8.1 Hz, 1H), 4.07-3.86 (m, 1H), 2.98 (s, 3H), 2.74 (dt, J=14.0, 7.3 Hz, 1H), 2.69-2.59 (m, 3H), 2.42-1.89 (m, 5H). LC-MS: [M+H]⁺=443.8, 445.8.

Example 66

¹H NMR (400 MHz, Methanol-d₄) δ 8.06 (s, 1H), 7.86 (s, 1H), 7.78 (s, 1H), 7.72 (s, 1H), 7.57 (s, 1H), 5.16 (p, J=7.7 Hz, 1H), 4.25-3.97 (m, 1H), 2.98 (s, 3H), 2.65 (s, 3H), 2.55-2.25 (m, 4H), 2.12-1.99 (m, 1H), 1.89-1.73 (m, 1H). LC-MS: [M+H]⁺=443.8, 445.8.

Example 67 methyl 3-(3-(5-amino-4-chloropyridin-3-yl)-5-cyano-6-methyl-1H-indol-1-yl)cyclopentane-1-carboxylate Intermediate 67.1 methyl 3-(tosyloxy)cyclopentane-1-carboxylate

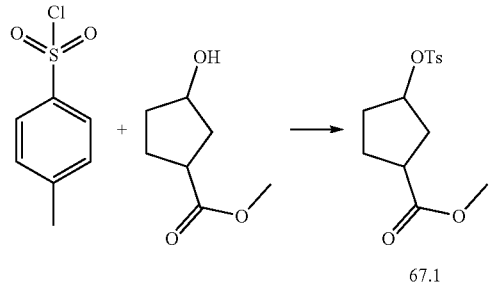

67.1

The title compound was prepared by using a procedure similar to that of intermediate 40.1 by replacing tert-butyl 3-hydroxyazetidine-1-carboxylate with methyl 3-hydroxycyclopentane-1-carboxylate. LC-MS: [M+H]⁺=299.3

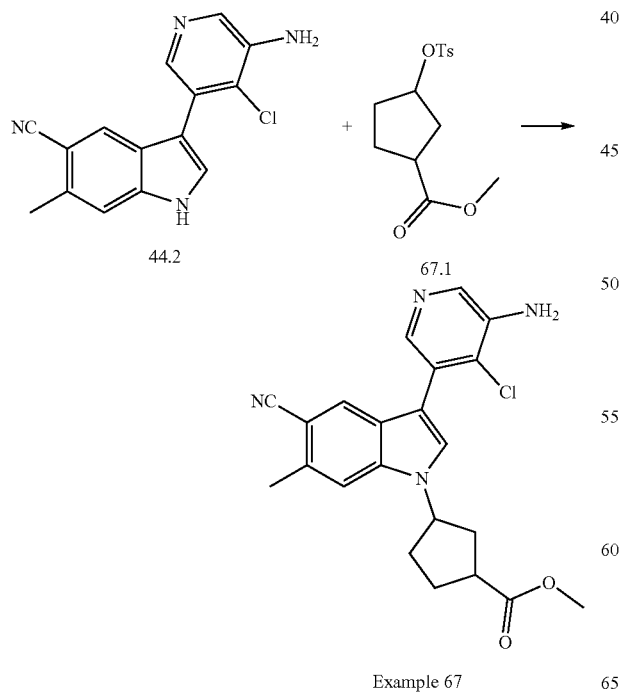

Example 67

The title compound was prepared by using a procedure similar to that of Example 48 by replacing intermediate 48.2 with intermediate 67.1. ¹H NMR (400 MHz, Methanol-d₄) δ 8.05 (s, 1H), 7.85 (s, 1H), 7.78 (s, 1H), 7.70 (s, 1H), 7.59 (s, 1H), 5.09 (dt, J=21.8, 7.0 Hz, 1H), 3.71 (dd, J=6.4, 1.8 Hz, 3H), 3.17-3.01 (m, 1H), 2.63-1.92 (m, 6H). LC-MS: [M+H]⁺=408.1, 410.0.

Example 68

3(3-(5-amino-4-chloropyridin-3-yl)-5-cyano-6-methyl-1H-indol-1-yl)cyclopentane-1-carboxamide

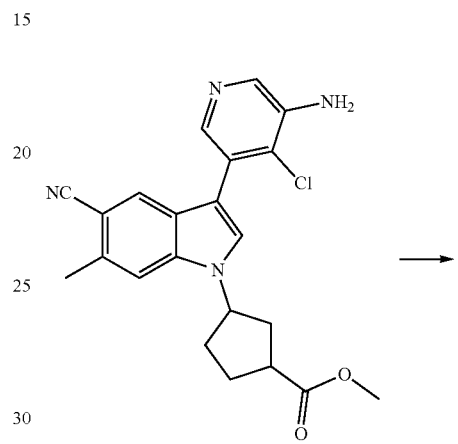

Example 67

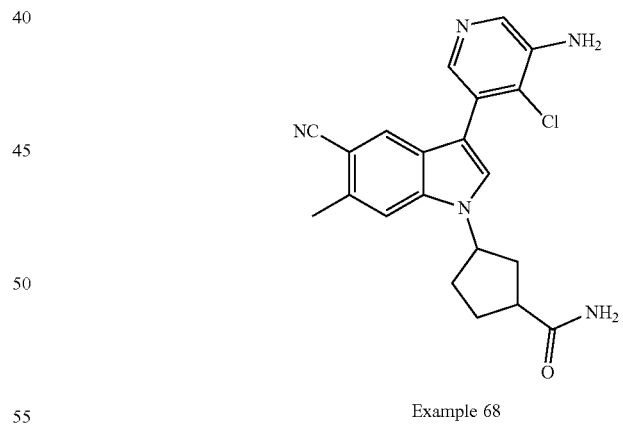

Example 68

A solution of Example 67 (35 mg, 0.098 mmol) in an ammonia methanol solution (7M, 5 mL, 35.0 mmol) in a sealed tube was heated at 100° C. for 20 hr. The mixture was purified by basic Prep-HPLC (0.1% NH₄OH/ACN/H₂O), collected the desired fraction and lyophilized to afford the title compound (32 mg, 82.8%) as white powder. ¹H NMR (400 MHz, Methanol-d₄) δ 8.05 (d, J=2.1 Hz, 1H), 7.91-7.66 (m, 3H), 7.60 (d, J=5.8 Hz, 1H), 5.10 (dp, J=36.8, 7.5 Hz, 1H), 3.21-2.91 (m, 1H), 2.64 (s, 3H), 2.61-1.89 (m, 6H). LC-MS: [M+H]⁺=393.1, 395.0.

Example 69

1-(1-acetylpyrrolidin-3-yl)-3-(5-amino-4-chloropyridin-3-yl)-6-methyl-1H-indole-5-carbonitrile

Intermediate 69.1

1-acetylpyrrolidin-3-yl 4-methylbenzenesulfonate

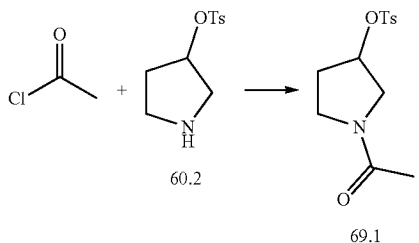

The title compound was prepared by using a procedure similar to that of intermediate 50.3 by replacing intermediate 50.2 with intermediate 60.2. ¹H NMR (400 MHz, DMSO-d₆) δ 7.83 (t, J=8.1 Hz, 2H), 7.59-7.39 (m, 2H), 5.23-4.98 (m, 1H), 3.70-3.34 (m, 4H), 2.43 (s, 3H), 2.21-1.81 (m, 5H). LC-MS: [M+H]⁺=284.0.

The title compound was prepared by using a procedure similar to that of Example 48 by replacing intermediate 48.2 with intermediate 69.1. ¹H NMR (400 MHz, Methanol-d₄) δ 8.17-8.00 (m, 1H), 7.82 (d, J=22.6 Hz, 2H), 7.68 (d, J=15.6 Hz, 1H), 7.62 (s, 1H), 5.51-5.18 (m, 1H), 4.10 (ddd, J=56.0, 11.9, 6.9 Hz, 1H), 3.95-3.56 (m, 3H), 2.77-2.33 (m, 5H), 2.12 (d, J=11.1 Hz, 3H). LC-MS: [M+H]⁺=393.9, 395.9.

Example 70

3-(3-(5-amino-4-chloropyridin-3-yl)-5-cyano-6-methyl-1H-indol-1-yl)-N-methylpyrrolidine-1-carboxamide

Intermediate 70.1

1-(methylcarbamoyl) pyrrolidin-3-yl 4-methylbenzenesulfonate

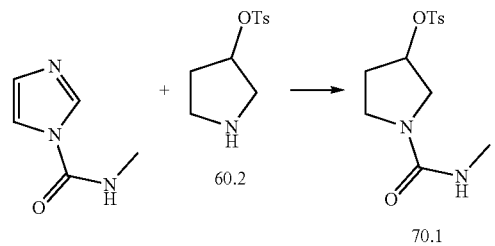

To a solution of 60.2 (500 mg, 1.800 mmol) and TEA (0.552 mL, 3.96 mmol) in DCM (15 mL) was added N-methyl-1H-imidazole-1-carboxamide (270 mg, 2.160 mmol). The mixture was stirred at rt for 20 hr. Then the mixture was washed with water, the organic layer was dried over magnesium sulfate, filtered and concentrated in vacuum. The residue was purified by CombiFlash, eluted with ethyl acetate in hexane (20-60%, 30 min). The desired fraction was collected to afford the title compound (480 mg, 89%) as white solid. LC-MS: [M+H]⁺=299.2.

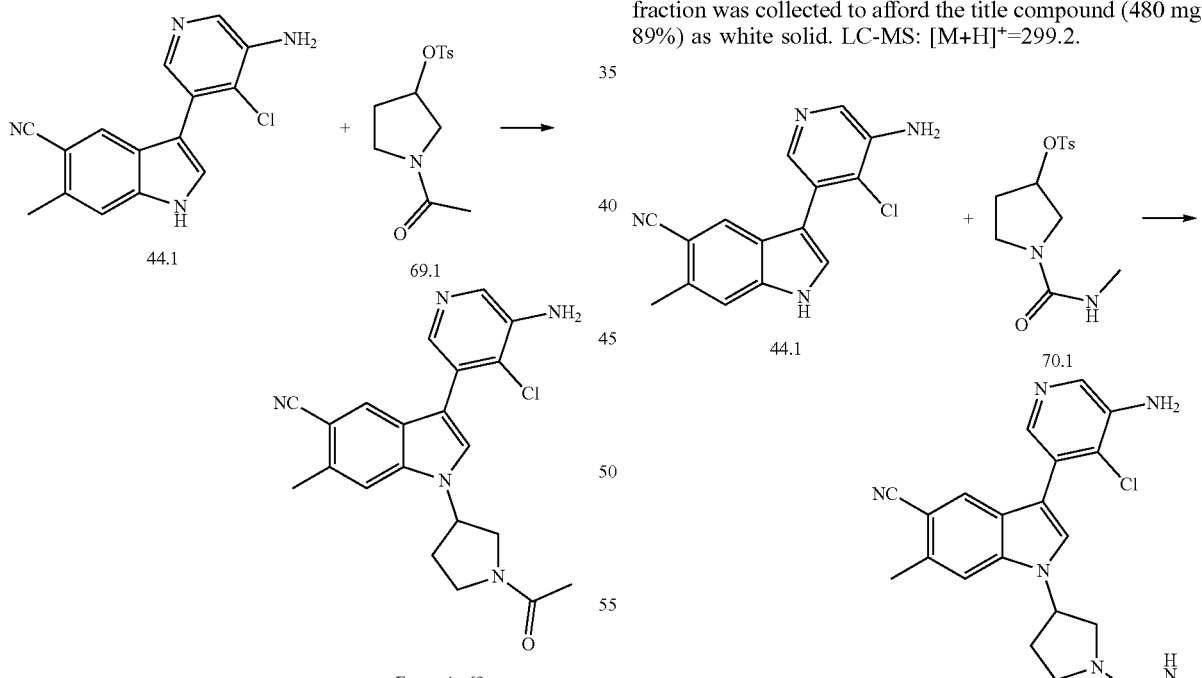

The title compound was prepared by using a procedure similar to that of Example 48 by replacing intermediate 48.2 with intermediate 70.1. ¹H NMR (400 MHz, Methanol-d₄) δ 8.05 (s, 1H), 7.85 (s, 1H), 7.81 (s, 1H), 7.63 (s, 1H), 7.60

(s, 1H), 5.45-5.21 (m, 1H), 3.93 (dd, J=11.1, 6.5 Hz, 1H), 3.75 (dd, J=11.1, 4.6 Hz, 1H), 3.66-3.50 (m, 2H), 2.76 (s, 3H), 2.65 (s, 3H), 2.61-2.48 (m, 1H), 2.42 (dt, J=12.9, 6.4 Hz, 1H). LC-MS: [M+H]⁺=408.3, 410.2.

Example 71

3-(3-(5-amino-4-chloropyridin-3-yl)-5-cyano-6-methyl-1H-indol-1-yl)cyclobutane-1-carboxamide Intermediate 71.1 methyl 3-(tosyloxy)cyclobutane-1-carboxylate

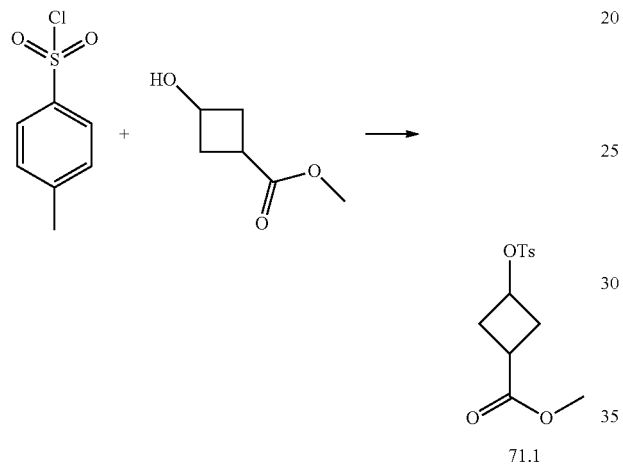

The title compound was prepared by using a procedure similar to that of intermediate 40.1 by replacing tert-butyl 3-hydroxyazetidine-1-carboxylate with methyl 3-hydroxycyclobutanecarboxylate. ¹H NMR (400 MHz, Chloroform-d) δ 7.88-7.67 (m, 2H), 7.46-7.31 (m, 2H), 4.74 (tt, J=8.0, 7.1 Hz, 1H), 3.67 (s, 3H), 2.75-2.54 (m, 1H), 2.54-2.31 (m, 7H).

Intermediate 71.2 methyl 3-(3-(5-amino-4-chloropyridin-3-yl)-5-cyano-6-methyl-1H-indol-1-yl)cyclobutane-1-carboxylate

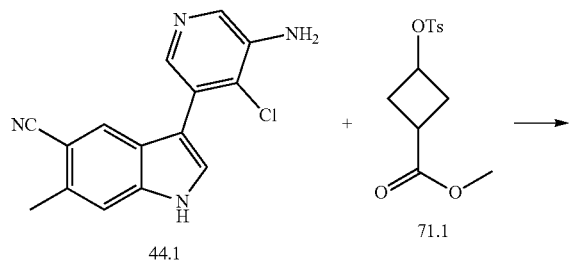

The title compound was prepared by using a procedure similar to that of Example 48 by replacing intermediate 48.2 with intermediate 71.1. LC-MS: [M+H]⁺=394.1, 396.1.

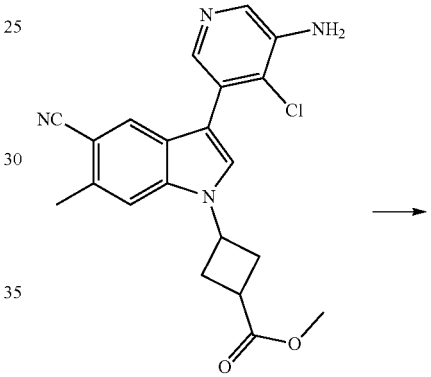

Example 71

A solution of 71.2 (40 mg, 0.101 mmol) in NH₃/MeOH (7M, 5 mL, 35.0 mmol) in a sealed tube was sealed and heated at 100° C. for 20 hr. The mixture was purified by basic Prep-HPLC (0.1% NH₄OH/ACN/H₂O), collected the desired fraction and lyophilized to afford the title compound (15.4 mg, 40.1%) as white powder. ¹H NMR (400 MHz, Methanol-d₄) δ 8.06 (d, J=1.2 Hz, 1H), 7.89-7.82 (m, 2H), 7.78 (s, 1H), 7.58 (d, J=41.0 Hz, 1H), 5.05 (tt, J=9.3, 7.7 Hz, 1H), 3.26-3.00 (m, 1H), 2.96-2.68 (m, 4H), 2.64 (d, J=2.9 Hz, 3H). LC-MS: [M+H]⁺=379.1, 381.1.

Example 72

N-(3-(3-(5-amino-4-chloropyridin-3-yl)-5-cyano-6-methyl-1H-indol-1-yl)cyclobutyl)-N-methylacetamide

Intermediate 72.1

3-((tert-butoxycarbonyl)amino)cyclobutyl 4-methylbenzenesulfonate

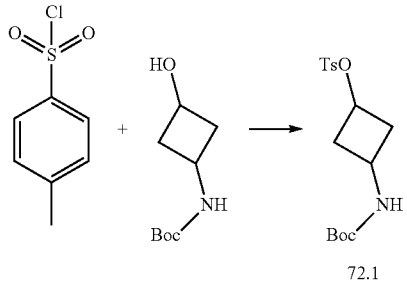 [SMILES: Cc1ccc(S(=O)(=O)Cl)cc1 ; CC(C)(C)OC(=O)NC1CC(O)C1 ; Cc1ccc(S(=O)(=O)OC2CC(NC(=O)OC(C)(C)C)C2)cc1]

72.1

The title compound was prepared by using a procedure similar to that of intermediate 40.1 by replacing tert-butyl 3-hydroxyazetidine-1-carboxylate with tert-butyl (3-hydroxycyclobutyl)carbamate. $^1$H NMR (400 MHz, DMSO-$d_6$) δ 7.77 (d, J=8.2 Hz, 2H), 7.48 (d, J=8.0 Hz, 2H), 7.21 (dd, J=38.1, 7.8 Hz, 1H), 4.50 (p, J=7.3 Hz, 1H), 3.55 (q, J=8.1 Hz, 1H), 2.43 (m, 5H), 2.21 (m, 1H), 1.94 (dd, J=8.7, 2.9 Hz, 1H), 1.34 (d, J=3.2 Hz, 9H).

Intermediate 72.2

3-((tert-butoxycarbonyl)(methyl)amino)cyclobutyl 4-methylbenzenesulfonate

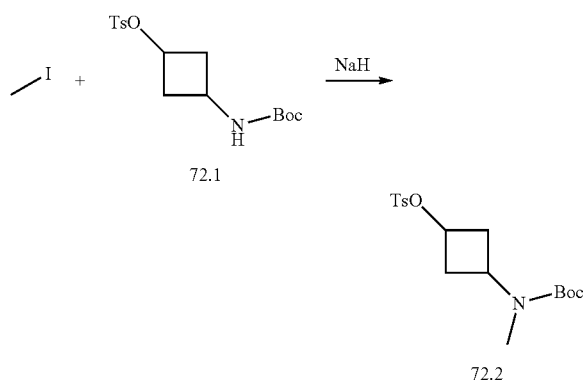

To a suspension of sodium hydride (127 mg, 60%, 3.16 mmol) in DMF (3 mL) was added a solution of 72.1 (900 mg, 2.64 mmol) in DMF (3 mL) under ice-bath. The mixture was stirred at 0° C. for 30 min, and then MeI (0.494 mL, 7.91 mmol) was added. The mixture was stirred at rt for another 2 h. The mixture was quenched by water, extracted with DCM twice. The organic layer was dried over magnesium sulfate, filtered and concentrated in vacuum. The residue was purified by CombiFlash, eluted with ethyl acetate in hexane (20-40, 30 min). Collected the desired fraction to afford title compound (820 mg, 88%) as colorless syrup. It was used for the next directly. LC-MS: [M+H–100]$^+$=256.2.

Intermediate 72.3

3-(methylamino)cyclobutyl 4-methylbenzenesulfonate

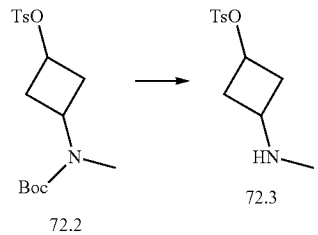 [SMILES: Cc1ccc(S(=O)(=O)OC2CC(N(C)C(=O)OC(C)(C)C)C2)cc1 ; CNC1CC(OS(=O)(=O)c2ccc(C)cc2)C1]

A solution of 72.2 (750 mg, 2.110 mmol) in HCl/dioxane (4 M, 15 mL, 2.110 mmol) was stirred at rt for 2 hr. The mixture was concentrated in vacuum to afford the title compound (620 mg, 100%) as HCl salt. It was used for the next step directly. LC-MS: [M+H]$^+$=256.2.

Intermediate 72.4

3-(N-methylacetamido)cyclobutyl 4-methylbenzenesulfonate

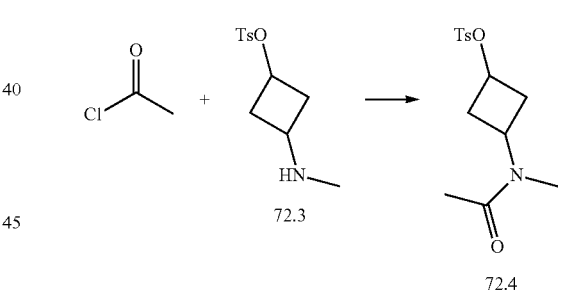

To a solution of 72.3 (300 mg, 1.028 mmol) and DIPEA (0.539 mL, 3.08 mmol) in DCM (20 mL) was added AcCl (0.088 mL, 1.234 mmol). The mixture was stirred at 0° C. for 30 min. The mixture was washed with water, brine. The organic layer was dried over magnesium sulfate, filtered and concentrated in vacuum. The residue was purified by CombiFlash, eluted with ethyl acetate in hexane (10-40%, 30 min). Collected the desired fraction to afford title compound (240 mg, 78%) as colorless syrup. $^1$HNMR (400 MHz, Methanol-$d_4$) δ 7.92-7.60 (m, 2H), 7.51-7.13 (m, 2H), 4.68-4.47 (m, 1H), 4.36 (tt, J=9.7, 7.4 Hz, 1H), 2.89 (d, J=35.0 Hz, 3H), 2.63-2.44 (m, 5H), 2.40-2.16 (m, 2H), 2.04 (d, J=5.1 Hz, 3H). LC-MS: [M+H]$^+$=298.2.

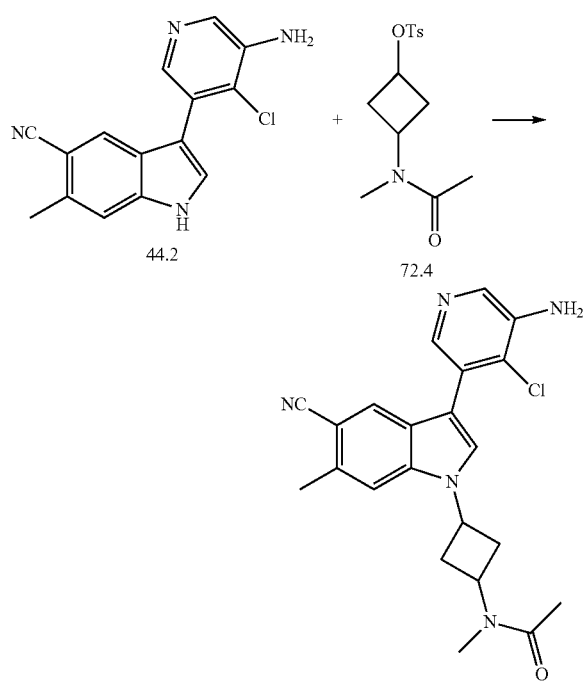

44.2 + 72.4 →

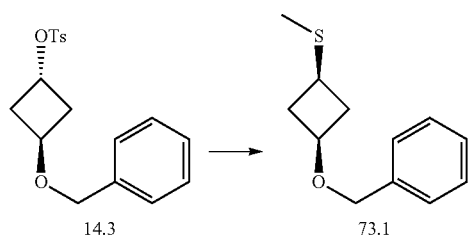

Example 72

The title compound was prepared by using a procedure similar to that of Example 48 by replacing intermediate 48.2 with intermediate 72.4. $^1$HNMR (400 MHz, Methanol-$d_4$) δ 8.10-7.85 (m, 3H), 7.78 (s, 1H), 7.45 (d, J=9.4 Hz, 1H), 5.28-4.92 (m, 2H), 3.13 (d, J=28.5 Hz, 3H), 3.07-2.67 (m, 4H), 2.62 (s, 3H), 2.13 (d, J=3.4 Hz, 3H). LC-MS: [M+H]$^+$= 407.2, 409.3.

Example 73

3-(5-amino-4-chloropyridin-3-yl)-6-methyl-1-((1R, 3R)-3-(methylsulfonyl)cyclobutyl)-1H-indole-5-carbonitrile Example 74

3-(5-amino-4-chloropyridin-3-yl)-6-methyl-1-((1S, 3S)-3-(methylsulfonyl)cyclobutyl)-1H-indole-5-carbonitrile Intermediate 73.1

((1S,3S)-3-(benzyloxy)cyclobutyl)(methyl)sulfane

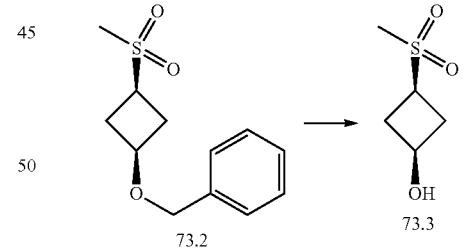

14.3 → 73.1

The title compound was prepared by using a procedure similar to that of intermediate 37.2 by replacing intermediate 37.1 with intermediate 14.3. $^1$H NMR (400 MHz, Methanol-d4) δ 7.43-7.10 (m, 5H), 4.41 (s, 2H), 3.93 (tt, J=7.7, 6.7 Hz, 1H), 2.92 (tt, J=9.5, 7.4 Hz, 1H), 2.69-2.51 (m, 2H), 2.03 (s, 3H), 1.97-1.76 (m, 2H).

Intermediate 73.2

(((1S,3S)-3-(methylsulfonyl)cyclobutoxy)methyl)benzene

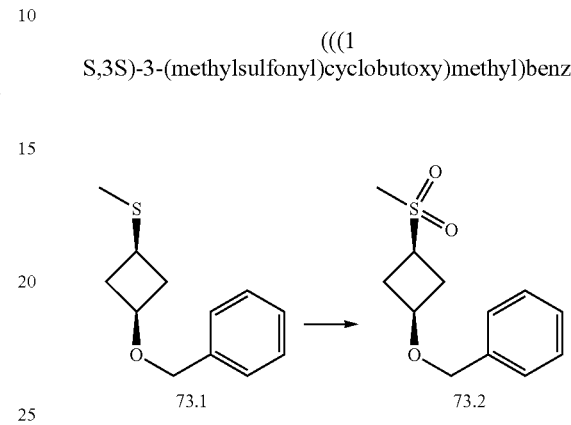

73.1    73.2

The title compound was prepared by using a procedure similar to that of Example 37.3 by replacing intermediate 37.2 with intermediate 73.1. $^1$H NMR (400 MHz, Methanol-$d_4$) δ 7.44-7.16 (m, 5H), 4.46 (s, 2H), 4.07 (tt, J=7.7, 6.8 Hz, 1H), 3.65-3.36 (m, 1H), 2.84 (s, 3H), 2.67-2.47 (m, 2H), 2.33 (tdd, J=9.6, 7.7, 2.8 Hz, 2H). LC-MS: [M+H]$^+$=241.0.

Intermediate 73.3

(1s,3s)-3-(methylsulfonyl)cyclobutan-1-ol

To a solution of 73.2 (250 mg, 1.040 mmol) in DCM (20 mL) was added a solution of $BBr_3$ in DCM (1M, 1.144 mL, 1.144 mmol) under an ice-bath. The mixture was stir at 0° C. for 1 hr. The mixture was quenched by water (10 mL), the organic layer was dried over magnesium sulfate, LCMS indicated all the product was in aqueous phase, the aqueous phase was lyophilized to afford the title compound 220 mg as brown powder, it was used for the next step directly. LC-MS: [M+H]$^+$=151.1.

Intermediate 73.4

(1s,3s)-3-(methylsulfonyl)cyclobutyl 4-methylbenzenesulfonate

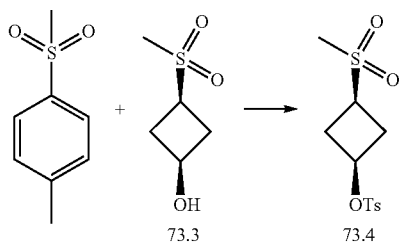

The title compound was prepared by using a procedure similar to that of intermediate 40.1 by replacing tert-butyl 3-hydroxyazetidine-1-carboxylate with intermediate 73.3. $^1$H NMR (400 MHz, DMSO-d$_6$) δ 7.89-7.74 (m, 2H), 7.50 (d, J=8.0 Hz, 2H), 4.82 (p, J=7.4 Hz, 1H), 3.59 (ddd, J=9.3, 7.7, 1.7 Hz, 1H), 2.88 (s, 3H), 2.50 (m, 2H), 2.43 (s, 3H), 2.29 (m, 2H). LC-MS: [M+H]$^+$=304.9.

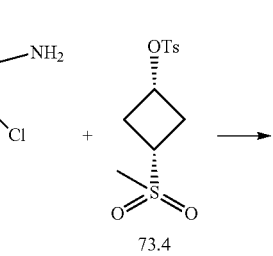

Example 73

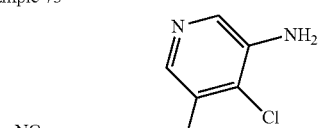

Example 74

A mixture of 44.1 (40 mg, 0.141 mmol), 73.4 (48 mg, 0.156 mmol) and Cs$_2$CO$_3$ (92 mg, 0.283 mmol) in DMF (3 mL) was stirred at 70° C. for 20 hr. The mixture was filtered and the filter was further purified by basic Prep-HPLC (0.1% NH$_4$OH/ACN/H$_2$O). Collected the two desired fractions and lyophilized to afford the title compound Example 73 (7.5 mg, 12.8%) and the title compound example 74 (3 mg, 3.1%) as white powder.

Example 73

$^1$HNMR (400 MHz, Methanol-d$_4$) δ 8.07 (s, 1H), 7.86 (s, 1H), 7.80 (s, 1H), 7.78 (s, 1H), 7.67 (s, 1H), 5.21 (p, J=8.6 Hz, 1H), 4.10-3.81 (m, 1H), 3.02 (tt, J=8.7, 2.0 Hz, 4H), 2.64 (s, 3H). LC-MS: [M+H]$^+$=414.8, 416.8.

Example 74

$^1$HNMR (400 MHz, Methanol-d$_4$) δ 8.07 (s, 1H), 7.90 (s, 1H), 7.87 (s, 1H), 7.77 (s, 1H), 7.51 (s, 1H), 5.38 (p, J=8.4 Hz, 1H), 4.15-3.96 (m, 1H), 3.22-3.12 (m, 2H), 3.12-3.05 (m, 2H), 3.03 (s, 3H). LC-MS: [M+H]$^+$=414.8, 416.8.

Example 75

1-(1-acetylpiperidin-4-yl)-3-(5-amino-4-chloropyridin-3-yl)-6-methyl-1H-indole-5-carbonitrile Intermediate 75.1

1-acetylpiperidin-4-yl methanesulfonate

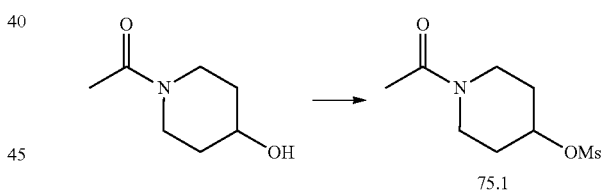

The title compound was prepared by using a procedure similar to that of intermediate 47.6 by replacing intermediate 47.5 with 1-(4-hydroxypiperidin-1-yl)ethan-1-one. $^1$H NMR: (400 MHz, CDCl$_3$): δ 4.97-4.91 (m, 1H), 3.86-3.80 (m, 1H), 3.70-3.64 (m, 1H), 3.58-3.53 (m, 1H), 3.43-3.37 (m, 1H), 3.05 (s, 3H), 2.11 (s, 3H), 2.05-1.80 (m, 4H).

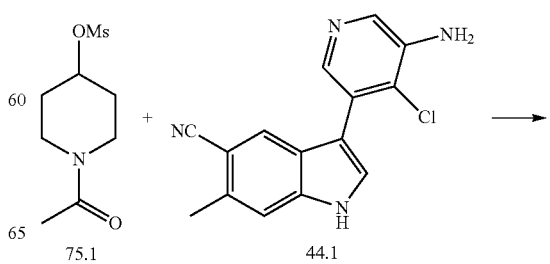

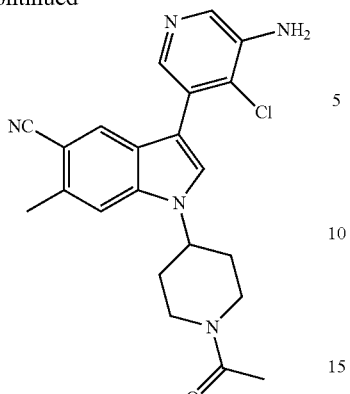

Example 75

The title compound was prepared by using a procedure similar to that of Example 48 by replacing intermediate 48.2 with intermediate 75.1. ¹HNMR (400 MHz, CDCl₃): δ 8.13 (s, 1H), 8.04 (s, 1H), 7.90 (s, 1H), 7.40 (s, 1H), 7.32 (s, 1H), 4.93 (d, J=14.0 Hz, 1H), 4.53-4.47 (m, 1H), 4.23 (brs, 2H), 4.07 (d, J=13.6 Hz, 1H), 3.34 (t, J=12.8 Hz, 1H), 2.78 (t, J=11.6 Hz, 1H), 2.68 (s, 3H), 2.23-2.15 (m, 2H), 2.19 (s, 3H), 2.02-1.93 (m, 2H). LC-MS: [M+H]⁺=408.1.

Example 76

3-(5-amino-4-chloropyridin-3-yl)-6-methyl-1-(2-oxaspiro[3.3]heptan-6-yl)-1H-indole-5-carbonitrile Intermediate 76.1

2-oxaspiro[3.3]heptan-6-yl methanesulfonate

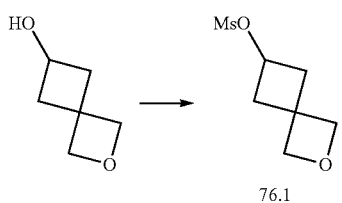 [SMILES: OC1CC2(COC2)C1 ; CS(=O)(=O)OC1CC2(COC2)C1]

The title compound was prepared by using a procedure similar to that of intermediate 47.6 by replacing intermediate 47.5 with 2-oxaspiro[3.3]heptan-6-ol.

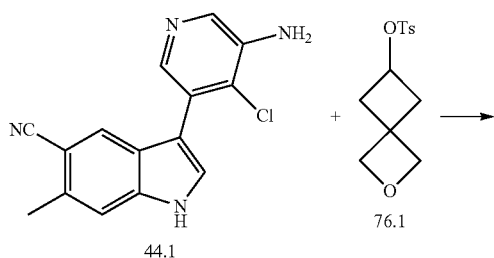

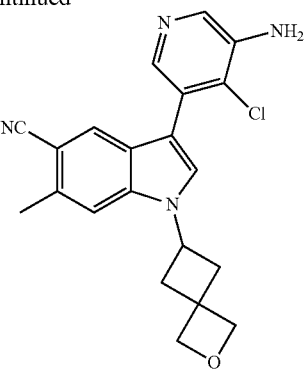

Example 76

The title compound was prepared by using a procedure similar to that of Example 48 by replacing intermediate 48.2 with intermediate 76.1. ¹H NMR (400 MHz, CDCl₃): δ ppm 8.17 (s, 1H), 8.08 (s, 1H), 7.91 (s, 1H), 7.42 (s, 1H), 7.30 (s, 1H), 4.95 (s, 2H), 4.81-4.73 (m, 1H), 4.78 (s, 2H), 4.26 (brs, 2H), 3.10-3.05 (m, 2H), 2.74-2.68 (m, 2H), 2.73 (s, 3H). LC-MS: [M+H]⁺=379.1.

Example 77

3-(5-amino-4-chloropyridin-3-yl)-6-methyl-1-(4-(methylsulfonyl)phenyl)-1H-indole-5-carbonitrile Intermediate 77.1

6-methyl-1-(4-(methylsulfonyl)phenyl)-1H-indole-5-carbonitrile

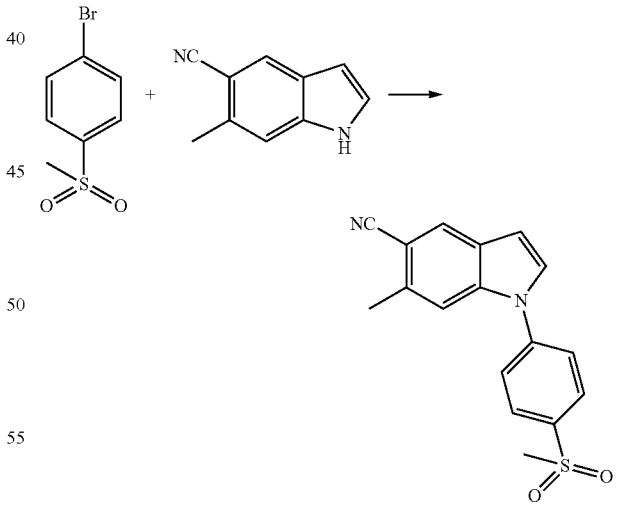

A suspension of 1-bromo-4-(methylsulfonyl)benzene (542 mg, 2.305 mmol), 6-methyl-1H-indole-5-carbonitrile (300 mg, 1.921 mmol) 1,10-phenanthroline (69.2 mg, 0.384 mmol) and Cu₂O (27.5 mg, 0.192 mmol) in a solution of TBAF in THF (1M, 6 mL, 6.00 mmol) was get rid off the organic solvent in high vacuum. The residue was heated at 150° C. for 2 hr under nitrogen protection. The mixture was re-dissolved in DCM, filtered and the filter was purified by CombiFlash, eluted with ethyl acetate in hexane (30-70%, 30 min). The desired fraction was collected to afford the title compound (260 mg, 43.6%) as white solid. $^1$H NMR (400 MHz, DMSO-d$_6$) δ 8.23-8.10 (m, 3H), 7.98-7.85 (m, 3H), 7.79-7.61 (m, 1H), 6.87 (dd, J=3.4, 0.8 Hz, 1H), 3.32 (s, 3H), 2.57 (s, 3H). LC-MS: [M+H]$^+$=311.2.

Intermediate 77.2

3-bromo-6-methyl-1-(4-(methylsulfonyl)phenyl)-1H-indole-5-carbonitrile

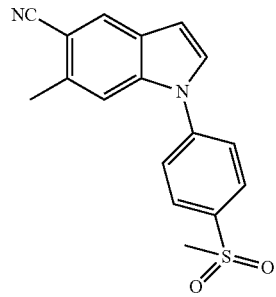

77.1

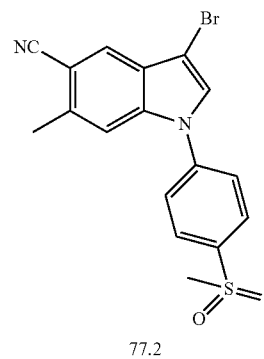

77.2

To a solution of 77.1 (500 mg, 1.611 mmol) in DMF (3 mL) was added NBS (315 mg, 1.772 mmol). The mixture was stir at 0° C. for 1 hr. Then water was added, filtered and dried in vacuum to afford the title compound (480 mg, 77%) as brown solid. $^1$H NMR (400 MHz, DMSO-d$_6$) δ 8.22 (s, 1H), 8.14 (d, J=8.6 Hz, 2H), 8.02 (s, 1H), 7.94 (d, J=8.7 Hz, 2H), 7.77 (s, 1H), 3.33 (s, 3H), 2.59 (s, 3H).

Intermediate 77.3

6-methyl-1-(4-(methylsulfonyl)phenyl)-3-(4,4,5,5-tetramethyl-1,3,2-dioxaborolan-2-yl)-1H-indole-5-carbonitrile

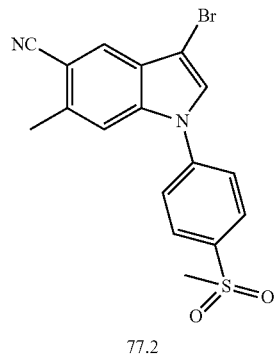

77.2

+

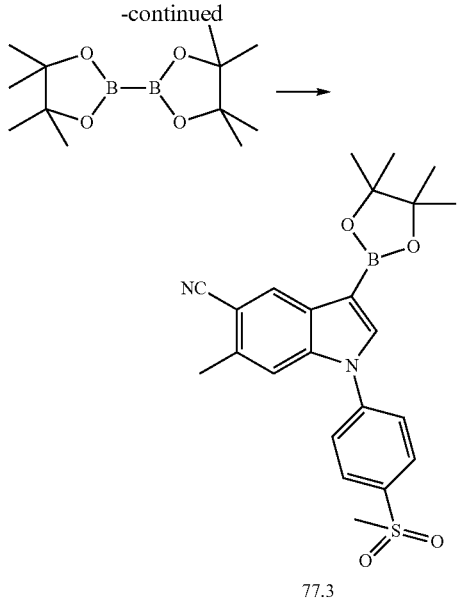

77.3

The title compound was prepared by using a procedure similar to that of intermediate 1.7 by replacing intermediate 1.6 with intermediate 77.2. LC-MS: [M+H]$^+$=437.3.

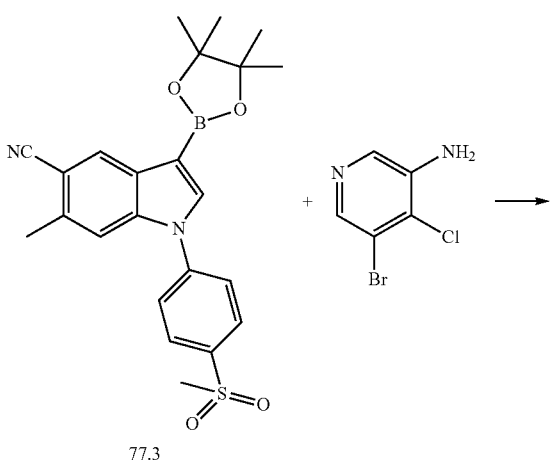

77.3

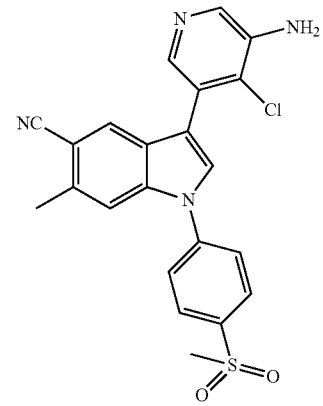

Example 77

The title compound was prepared by using a procedure similar to that of example 1 by replacing intermediate 1.7 and 5-bromo-4-chloropyridin-3-amine with 77.3 and 5-bromo-4-chloropyridin-3-amine. ¹H NMR (400 MHz, Methanol-d₄) δ 8.24-8.17 (m, 2H), 8.11 (s, 1H), 7.96-7.91 (m, 4H), 7.88 (s, 1H), 7.71 (t, J=0.8 Hz, 1H), 3.22 (s, 3H), 2.64 (d, J=0.8 Hz, 3H). LC-MS: [M+H]⁺=437.2, 439.2.

Example 78

3-(5-amino-4-chloropyridin-3-yl)-6-methyl-1-(6-(methylsulfonyl)pyridin-3-yl)-1H-indole-5-carbonitrile Intermediate 78.2

3-(5-(bis(4-methoxybenzyl)amino)-4-chloropyridin-3-yl)-6-methyl-1-(6-(methylsulfonyl)pyridin-3-yl)-1H-indole-5-carbonitrile

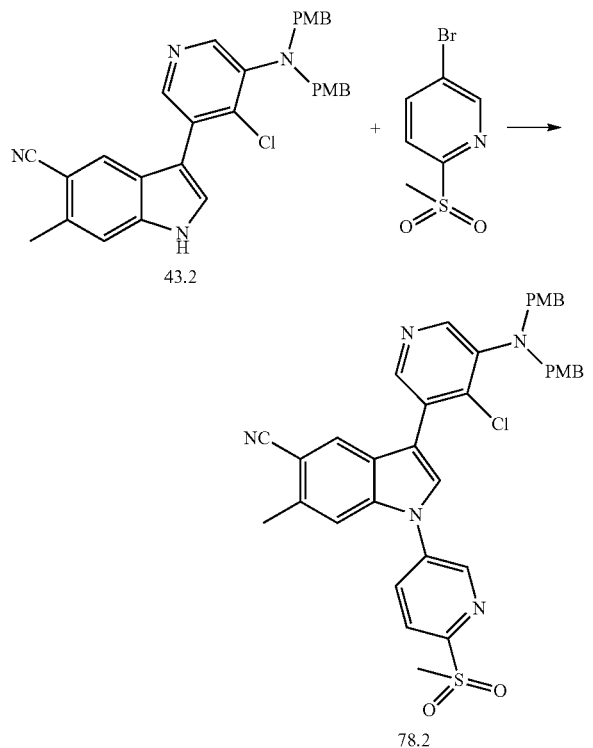

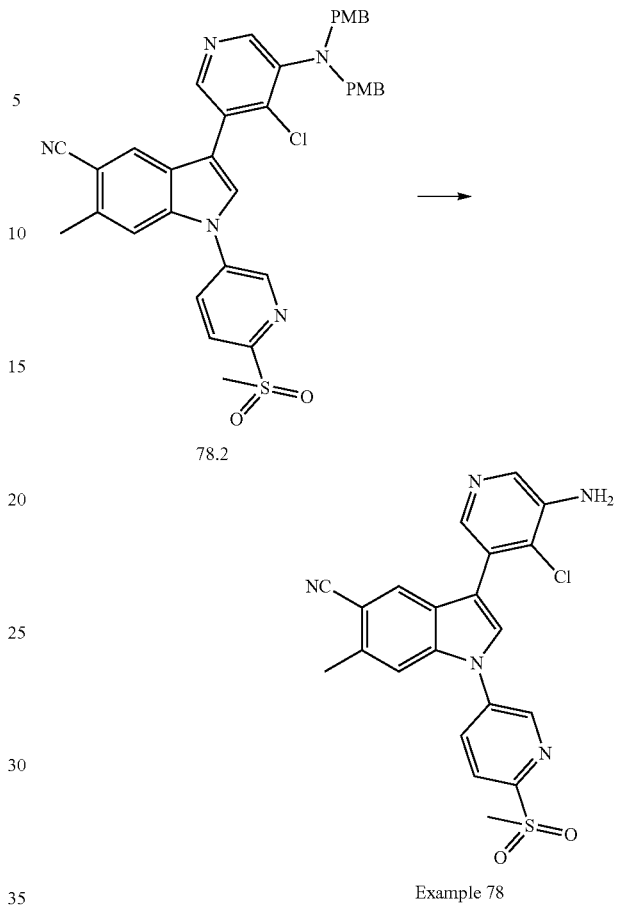

A solution of 78.1 (100 mg, 0.191 mmol), K₃PO₄ (101 mg, 0.478 mmol), CuI (8 mg, 0.038 mmol) and (1S,2S)-N1,N2-dimethylcyclohexane-1,2-diamine (5.44 mg, 0.038 mmol) in DMF (3 mL) was stirred at 110° C. for 20 hr under nitrogen protection. The mixture was diluted with water, extracted with DCM twice. The organic layer was dried over magnesium sulfate, filtered and concentrated in vacuum to afford a brown residue. The residue was purified by CombiFlash, eluted with methanol in DCM (0-10%, 30 min). The desired fraction was collected to afford the title compound (60 mg, 37%) as colorless syrup. LC-MS: [M+H]⁺=677.6, 678.7.

The title compound was prepared by using a procedure similar to that of example 43 by replacing intermediate 43.3 with intermediate 78.2. ¹HNMR (400 MHz, Methanol-d₄) δ 9.12 (d, J=2.4 Hz, 1H), 8.44 (dd, J=8.4, 2.6 Hz, 1H), 8.33 (d, J=8.4 Hz, 1H), 8.13 (s, 1H), 7.99 (s, 1H), 7.94 (s, 1H), 7.90 (s, 1H), 7.75 (s, 1H), 2.66 (s, 3H), 2.21 (s, 3H). LC-MS: [M+H]⁺=437.8, 439.7.

Example 79

4-(3-(5-amino-4-chloropyridin-3-yl)-5-cyano-6-methyl-1H-indol-1-yl)benzenesulfonamide Intermediate 79.1

4-iodo-N,N-bis(4-methoxybenzyl)benzenesulfonamide (6)

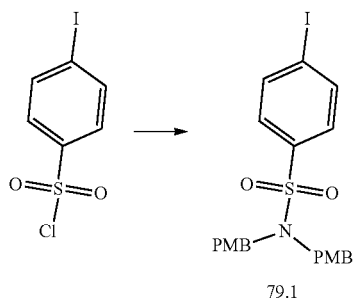

To a stirred solution of 4-iodobenzene-1-sulfonyl chloride (400 mg, 1.322 mmol) and triethylamine (0.276 mL, 1.983 mmol) in CH₂Cl₂ (5 mL) was added dropwise bis(4-methoxybenzyl)amine (374 mg, 1.454 mmol) at 0° C., and the mixture was stirred at rt overnight. LCMS showed the reaction was complete, water was added, and the mixture was extracted with CH₂Cl₂, washed with brine, dried, concentrated, and purified by flash chromatography (3% MeOH in CH₂Cl₂ as eluent) to afford 688 mg of title compound as white solid. ¹H-NMR (400 MHz, DMSO-d₆) δ ppm 7.96 (d, 2H), 7.58 (d, 2H), 6.99 (d, 4H), 6.79 (d, 4H), 4.19 (s, 4H), 3.71 (s, 6H).

Intermediate 79.2

4-(3-(5-(bis(4-methoxybenzyl)amino)-4-chloropyridin-3-yl)-5-cyano-6-methyl-1H-indol-1-yl)-N,N-bis(4-methoxybenzyl)benzenesulfonamide (7)

The title compound was prepared by using a procedure similar to that of intermediate 78.2 by replacing 5-bromo-2-(methylsulfonyl)pyridine with intermediate 79.1. ¹HNMR (400 MHz, DMSO-d₆) δ ppm 8.37 (s, 1H), 8.32 (s, 1H), 8.19 (s, 1H), 8.05 (s, 1H), 8.03 (d, 2H), 8.03 (s, 1H), 7.92 (d, 2H), 7.75 (s, 1H), 7.32 (d, 4H), 7.05 (d, 4H), 6.90 (d, 4H), 6.82 (d, 4H), 4.26-4.33 (m, 8H), 3.72 (s, 6H), 3.69 (s, 6H), 2.62 (s, 3H). LC-MS: [M+H]⁺=917.8.

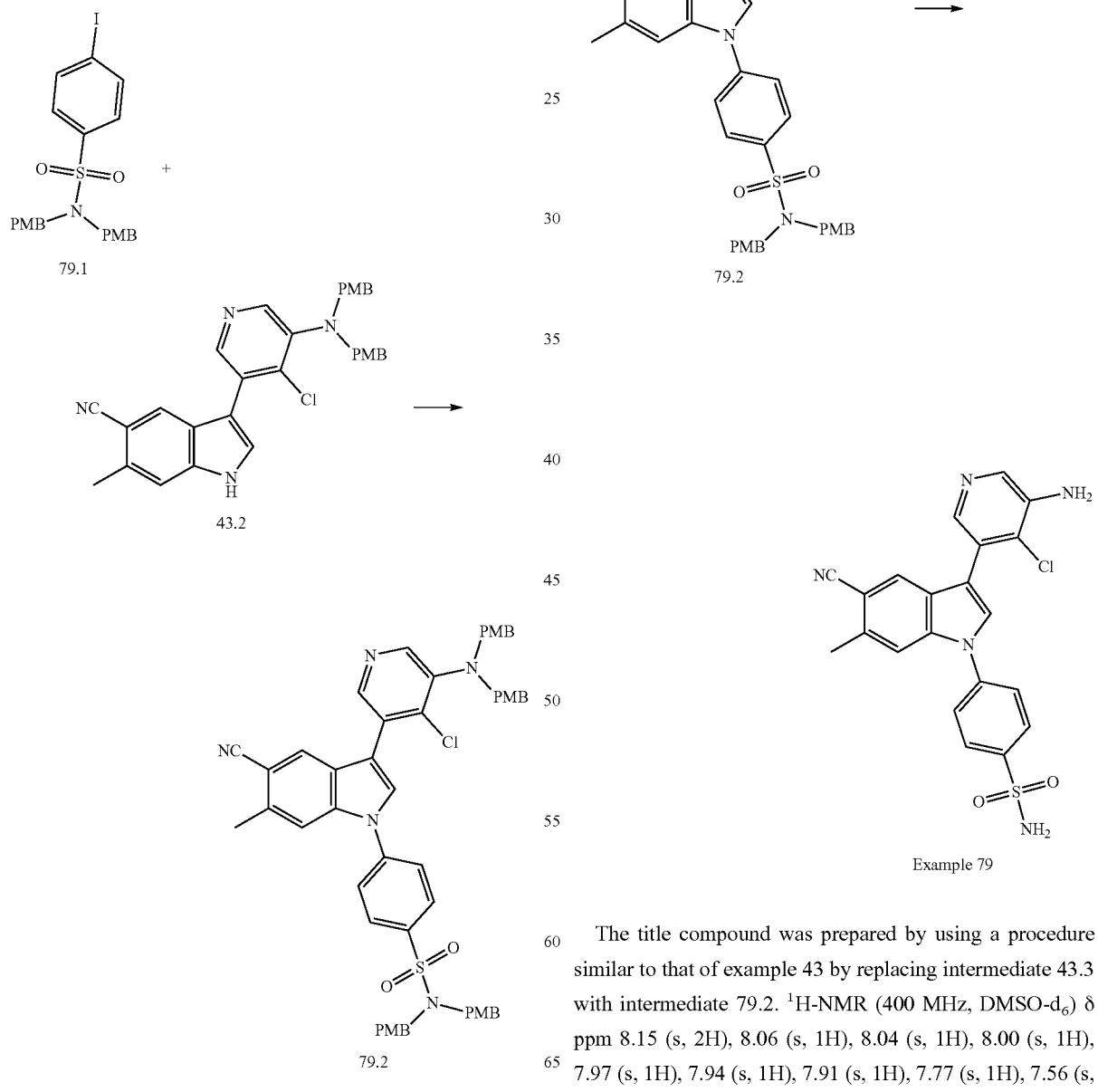

Example 79

The title compound was prepared by using a procedure similar to that of example 43 by replacing intermediate 43.3 with intermediate 79.2. ¹H-NMR (400 MHz, DMSO-d₆) δ ppm 8.15 (s, 2H), 8.06 (s, 1H), 8.04 (s, 1H), 8.00 (s, 1H), 7.97 (s, 1H), 7.94 (s, 1H), 7.91 (s, 1H), 7.77 (s, 1H), 7.56 (s, 2H), 6.01 (br s, 2H), 2.59 (s, 3H). LC-MS: [M+H]⁺=437.9.

Example 80

3-(5-amino-4-chloropyridin-3-yl)-6-methyl-1-(5-(methylsulfonyl)pyridin-2-yl)-1H-indole-5-carbonitrile

Intermediate 80.1

3-(5-(bis(4-methoxybenzyl)amino)-4-chloropyridin-3-yl)-6-methyl-1-(5-(methylsulfonyl)pyridin-2-yl)-1H-indole-5-carbonitrile

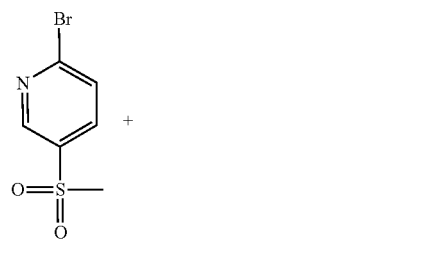

+

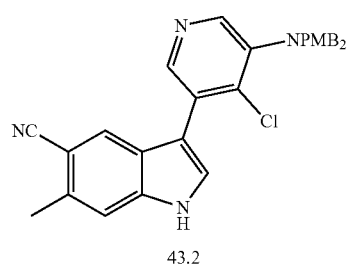

43.2

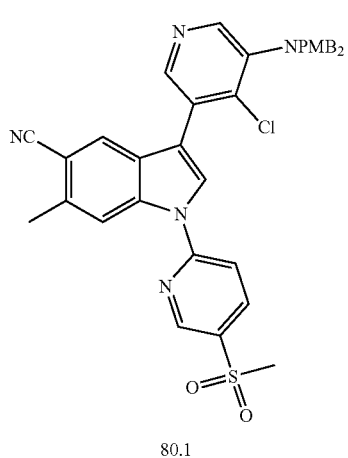

80.1

To a solution of 43.2 (200 mg, 382.39 umol, 1.0 eq) in DMF (2 mL) was added 2-bromo-5-(methylsulfonyl)pyridine (135.42 mg, 573.59 umol, 1.5 eq), Cu(acac)$_2$ (20 mg, 0.08 mmol, 0.2 eq) and Cs$_2$CO$_3$ (249.18 mg, 764.78 umol, 2.0 eq). The mixture was stirred at 90° C. for 16 hours. Water (20 mL) and EA (20 mL) was added to the mixture. The organic layer was dried over sodium sulfate, filtered and concentrated to afford the title compound (320 mg, crude) as a yellow solid. It was used for the next step directly. LC-MS: [M+H]$^+$=678.2.

Example 80

3-(5-amino-4-chloropyridin-3-yl)-6-methyl-1-(5-(methylsulfonyl)pyridin-2-yl)-1H-indole-5-carbonitrile

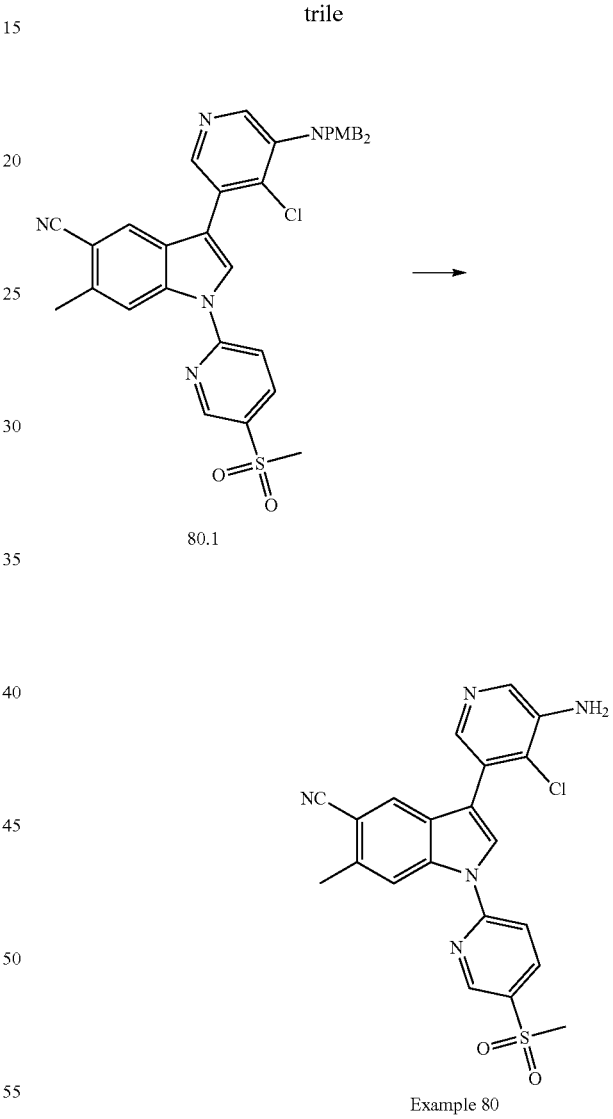

Example 80

The title compound was prepared by using a procedure similar to that of example 43 by replacing intermediate 43.3 with intermediate 80.1. $^1$HNMR: (400 MHz, DMSO-d$_6$) δ ppm 9.12 (d, J=2.26 Hz, 1 H) 8.70 (s, 1 H) 8.42-8.60 (m, 2 H) 8.12-8.27 (m, 2 H) 7.91 (d, J=14.31 Hz, 2 H) 5.75-5.93 (m, 2 H) 3.40 (s, 3 H) 3.33 (s, 6 H) 2.64 (s, 3 H). LC-MS: [M+H]$^+$=438.1.

Example 81

3-(5-amino-4-chloropyridin-3-yl)-1-(imidazo[1,5-a]pyridin-6-yl)-6-methyl-1H-indole-5-carbonitrile

Intermediate 81.1 methoxybenzyl)amino)-4-chloropyridin-3-yl)-1-(imidazo[1,5-a]pyridin-6-yl)-6-methyl-1H-indole-5-carbonitrile

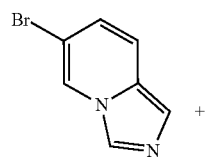
+
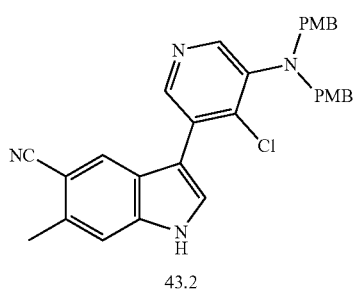

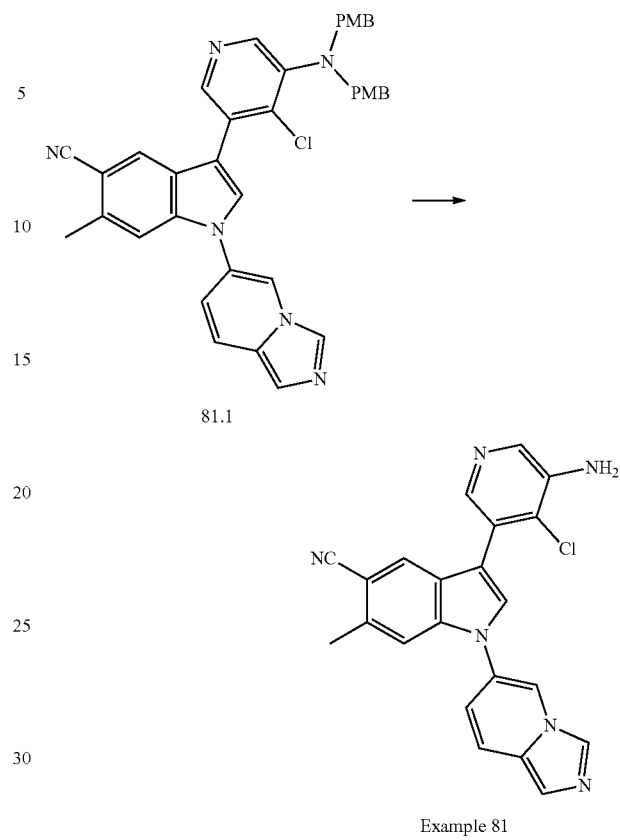

The title compound was prepared by using a procedure similar to that of intermediate 78.2 by replacing 5-bromo-2-(methylsulfonyl)pyridine with intermediate 6-bromoimidazo[1,5-a]pyridine.
LC-MS: [M+H]⁺=638.9.

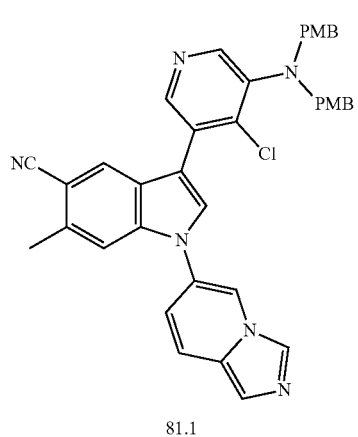

The title compound was prepared by using a procedure similar to that of example 43 by replacing intermediate 43.3 with intermediate 81.1. ¹HNMR (400 MHz, DMSO-d₆) δ ppm 8.87 (s, 1H), 8.49 (s, 1H), 8.13 (s, 1H), 8.05 (s, 1H), 7.93 (s, 1H), 7.92 (s, 1H), 7.81 (d, 1H), 7.71 (s, 1H), 7.54 (s, 1H), 7.10 (dd, 1H), 5.81 (brs, 2H), 2.58 (s, 3H). LC-MS: [M+H]⁺=398.9.

Example 82

1-([1,2,4]triazolo[4,3-a]pyridin-7-yl)-3-(5-amino-4-chloropyridin-3-yl)-6-methyl-1H-indole-5-carbonitrile

Intermediate 82.1

1-([1,2,4]triazolo[4,3-a]pyridin-7-yl)-6-methyl-1H-indole-5-carbonitrile

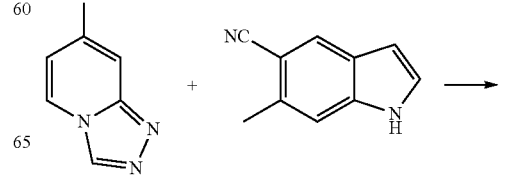

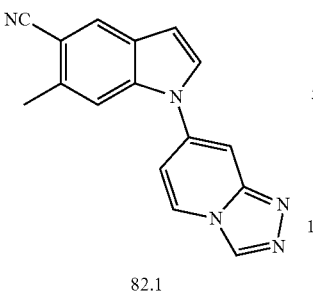

82.1

The title compound was prepared by using a procedure similar to that of intermediate 77.1 by replacing 1-bromo-4-(methylsulfonyl)benzene with 6-methyl-1H-indole-5-carbonitrile. $^1$HNMR (400 MHz, DMSO-d$_6$) δ 9.27-9.13 (m, 1H), 8.62 (s, 1H), 8.19 (s, 1H), 8.15 (d, J=2.3 Hz, 1H), 7.96 (d, J=3.4 Hz, 1H), 7.81 (s, 1H), 7.57 (dd, J=7.3, 2.4 Hz, 1H), 6.88 (dd, J=3.4, 0.8 Hz, 1H), 2.58 (s, 3H). LC-MS: [M+H]$^+$=274.0.

Intermediate 82.2

1-([1,2,4]triazolo[4,3-a]pyridin-7-yl)-3-bromo-6-methyl-1H-indole-5-carbonitrile

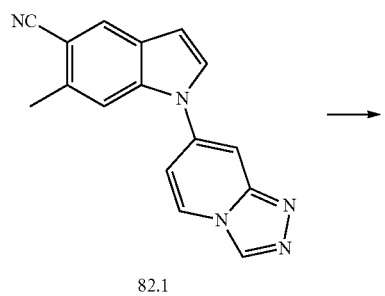

82.1

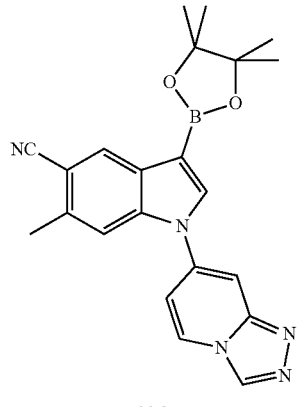

82.2

The title compound was prepared by using a procedure similar to that of intermediate 77.2 by replacing intermediate 77.1 with intermediate 82.1. $^1$H NMR (400 MHz, DMSO-d$_6$) δ 9.20 (d, J=7.4 Hz, 1H), 8.64 (s, 1H), 8.26 (s, 1H), 8.19 (d, J=2.1 Hz, 1H), 8.05 (s, 1H), 7.85 (s, 1H), 7.57 (dd, J=7.3, 2.4 Hz, 1H), 2.60 (s, 3H). LC-MS: [M+H]$^+$=351.0, 353.0.

Intermediate 82.3

1-([1,2,4]triazolo[4,3-a]pyridin-7-yl)-6-methyl-3-(4,4,5,5-tetramethyl-1,3,2-dioxaborolan-2-yl)-1H-indole-5-carbonitrile

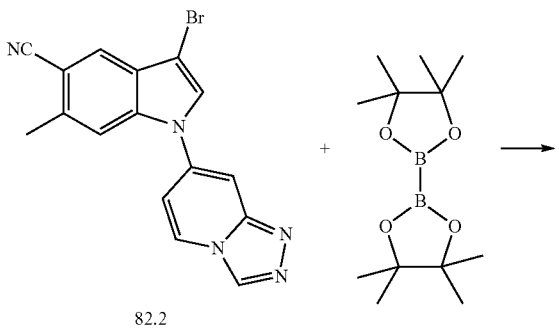

82.2

The title compound was prepared by using a procedure similar to that of intermediate 77.3 by replacing intermediate 77.2 with intermediate 82.2. LC-MS: [M+H]$^+$=399.9.

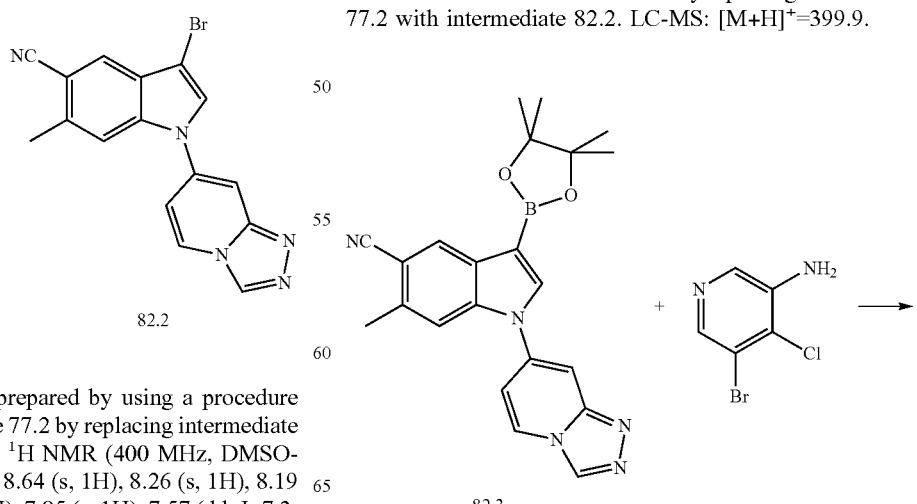

82.3

-continued

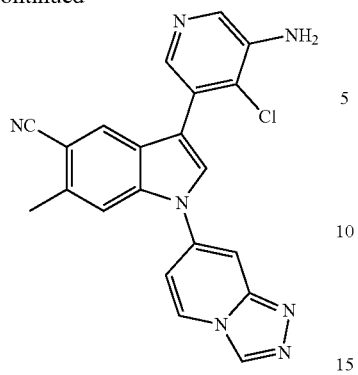

Example 82

The title compound was prepared by using a procedure similar to that of example 77 by replacing intermediate 77.3 with intermediate 82.3. $^1$H NMR (400 MHz, DMSO-d$_6$) δ 9.22 (d, J=7.3 Hz, 1H), 8.64 (s, 1H), 8.26 (d, J=2.3 Hz, 1H), 8.21 (s, 1H), 8.15 (s, 1H), 7.95 (d, J=1.7 Hz, 2H), 7.89 (s, 1H), 7.65 (dd, J=7.3, 2.4 Hz, 1H), 5.83 (s, 2H), 2.61 (s, 3H). LC-MS: [M+H]$^+$=399.8, 401.8.

Example 83

3-(5-amino-4-chloropyridin-3-yl)-1-(imidazo[1,5-a]pyridin-7-yl)-6-methyl-1H-indole-5-carbonitrile Intermediate 83.1

3-(5-(bis(4-methoxybenzyl)amino)-4-chloropyridin-3-yl)-1-(imidazo[1,5-a]pyridin-7-yl)-6-methyl-1H-indole-5-carbonitrile

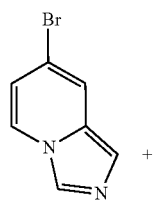

+

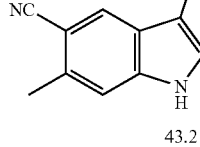

43.2

→

-continued

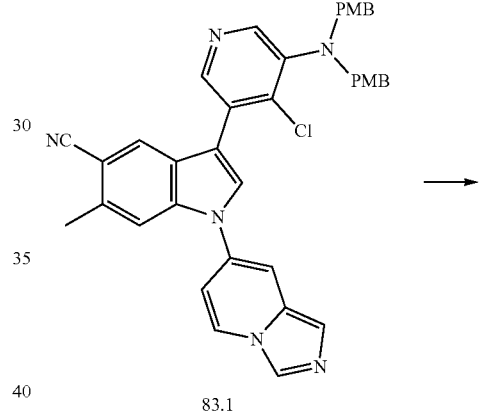

83.1

The title compound was prepared by using a procedure similar to that of intermediate 78.2 by replacing intermediate 6-bromoimidazo[1,5-a]pyridine with 7-bromoimidazo[1,5-a]pyridine. LC-MS: [M+H]$^+$=639.8.

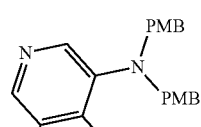

83.1

→

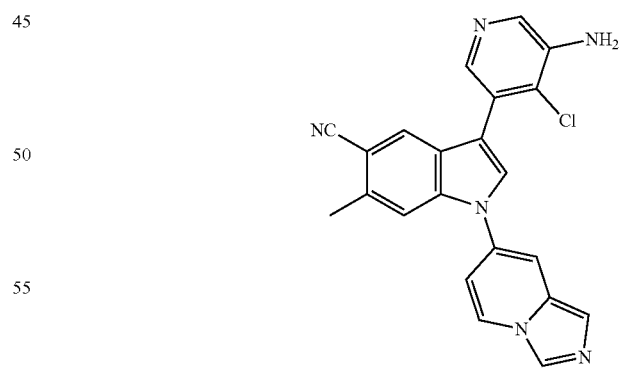

Example 83

The title compound was prepared by using a procedure similar to that of example 43 by replacing intermediate 43.3 with intermediate 83.1. $^1$H-NMR (400 MHz, DMSO-d$_6$) δ ppm 8.58 (d, 1H), 8.51 (s, 1H), 8.13 (s, 1H), 8.06 (s, 1H), 7.91-7.94 (m, 3H), 7.72 (s, 1H), 7.50 (s, 1H), 7.05 (dd, 1H), 5.81 (br s, 2H), 2.59 (s, 3H). LC-MS: [M+H]$^+$=398.9.

Example 84

3-(5-amino-4-chloropyridin-3-yl)-6-methyl-1-(1-methyl-6-oxo-1,6-dihydropyridin-3-yl)-1H-indole-5-carbonitrile

Intermediate 84.1

6-methyl-1-(1-methyl-6-oxo-1,6-dihydropyridin-3-yl)-1H-indole-5-carbonitrile

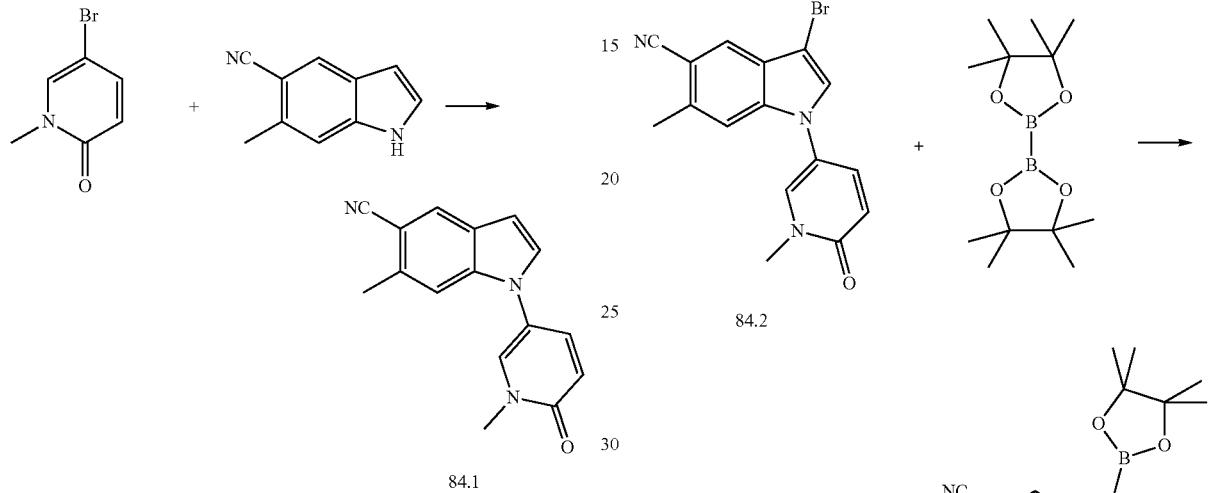

The title compound was prepared by using a procedure similar to that of intermediate 77.1 by replacing 1-bromo-4-(methylsulfonyl)benzene with 5-bromo-1-methylpyridin-2(1H)-one. $^1$HNMR (400 MHz, DMSO-$d_6$) δ 8.16 (d, J=2.9 Hz, 1H), 8.12 (s, 1H), 7.64 (dd, J=9.6, 3.0 Hz, 1H), 7.61 (d, J=3.3 Hz, 1H), 7.44 (d, J=1.1 Hz, 1H), 6.73 (dd, J=3.3, 0.8 Hz, 1H), 6.55 (d, J=9.6 Hz, 1H), 3.50 (s, 3H), 2.54 (s, 3H). LC-MS: [M+H]$^+$=264.3.

Intermediate 84.2

3-bromo-6-methyl-1-(1-methyl-6-oxo-1,6-dihydropyridin-3-yl)-1H-indole-5-carbonitrile The title compound was prepared by using a procedure similar to that of intermediate 77.2 by replacing intermediate 77.1 with intermediate 84.1. $^1$HNMR (400 MHz, DMF-$d_7$) δ 8.63 (d, J=2.9 Hz, 1H), 8.39 (s, 1H), 8.34 (s, 1H), 8.08 (dd, J=9.6, 3.0 Hz, 1H), 7.94 (s, 1H), 6.97 (d, J=9.6 Hz, 1H), 3.91 (s, 3H), 2.98 (s, 3H). LC-MS: [M+H]$^+$=342.1, 344.1.

Intermediate 84.3

6-methyl-1-(1-methyl-6-oxo-1,6-dihydropyridin-3-yl)-3-(4,4,5,5-tetramethyl-1,3,2-dioxaborolan-2-yl)-1H-indole-5-carbonitrile

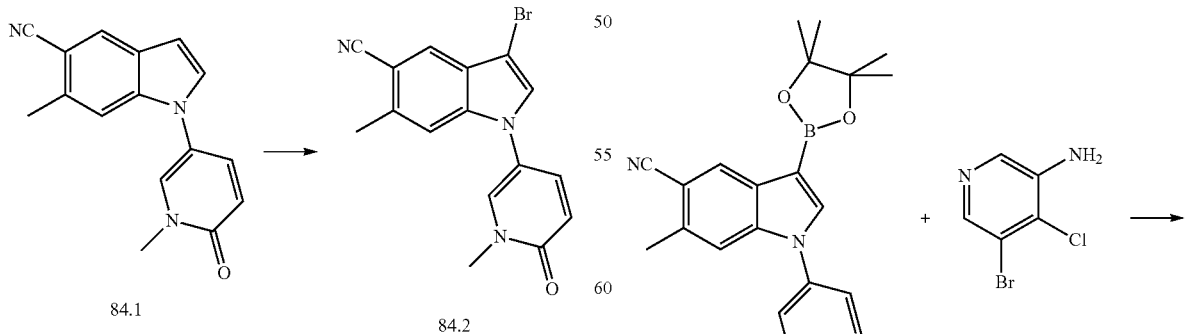

The title compound was prepared by using a procedure similar to that of intermediate 77.3 by replacing intermediate 77.2 with intermediate 84.2. LC-MS: [M+H]$^+$=390.4.

-continued

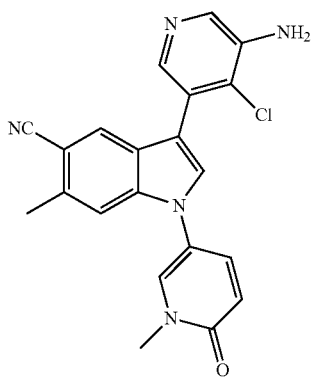

Example 84

The title compound was prepared by using a procedure similar to that of example 77 by replacing intermediate 77.3 with intermediate 84.3. $^1$H NMR (400 MHz, Methanol-$d_4$) δ 8.12 (d, J=2.9 Hz, 1H), 8.09 (s, 1H), 7.90 (s, 1H), 7.85 (s, 1H), 7.78 (dd, J=9.6, 2.9 Hz, 1H), 7.70 (s, 1H), 7.45 (s, 1H), 6.73 (d, J=9.6 Hz, 1H), 3.67 (s, 3H), 2.62 (s, 3H). LC-MS: [M+H]$^+$=389.2, 391.1.

Example 85

3-(5-amino-4-chloropyridin-3-yl)-6-methyl-1-(1-methyl-2-oxo-1,2-dihydropyridin-4-yl)-1H-indole-5-carbonitrile Intermediate 85.1

3-(5-(bis(4-methoxybenzyl)amino)-4-chloropyridin-3-yl)-6-methyl-1-(1-methyl-2-oxo-1,2-dihydropyridin-4-yl)-1H-indole-5-carbonitrile

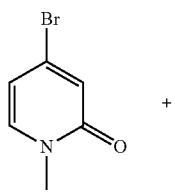

+

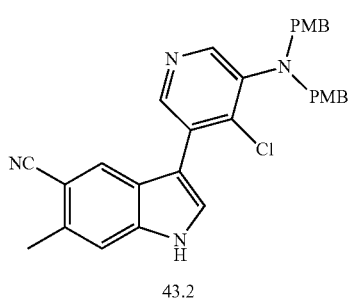

43.2

-continued

To a mixture of compound 43.2 (100 mg, 0.19 mmol, 1.0 eq), compound 4-bromo-1-methylpyridin-2(1H)-one (135 mg, 0.29 mmol, 1.5 eq) and Cs$_2$CO$_3$ (125 mg, 0.38 mmol, 2 eq) in DMA (10 mL) was added Cu(acac)$_2$ (10 mg, 0.04 mmol, 0.2 eq) under N$_2$ atmosphere. The mixture was heated to 140° C. for 1 hour. The mixture was diluted with H$_2$O and extracted with EA. The combined organic phase was washed with H$_2$O dried over anhydrous sodium sulfate, filtered and concentrated to give the crude product. The crude was purified by preparative TLC (DCM:MeOH=10:1) to afford title compound 2 (60 mg, 40.28%) as a yellow solid. LC-MS: [M+H]$^+$=630.2.

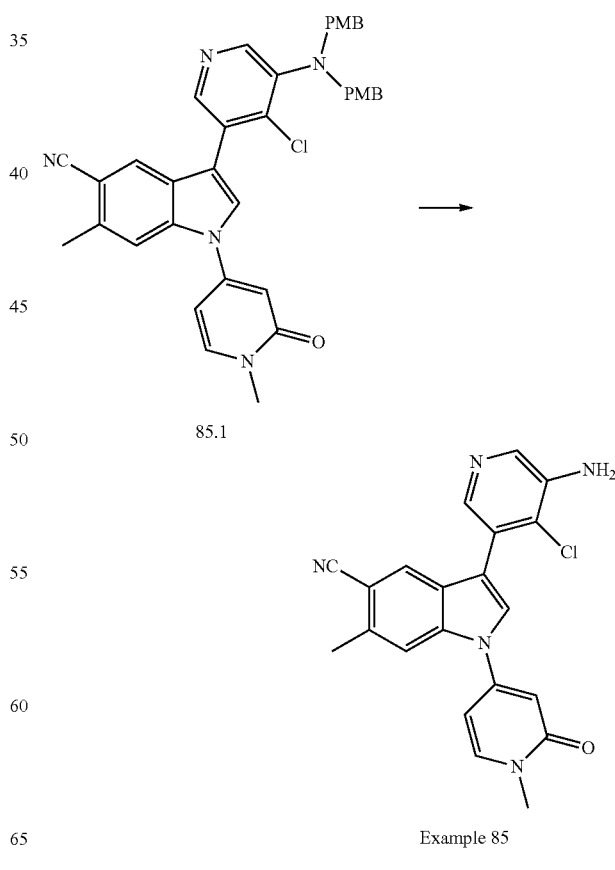

Example 85

The title compound was prepared by using a procedure similar to that of example 43 by replacing intermediate 43.3 with intermediate 85.1. ¹HNMR (400 MHz, DMSO-d₆) δ ppm 8.14 (s, 1H), 8.06 (s, 1H), 7.97 (d, J=7.6 Hz, 1H), 7.90-7.89 (m, 2H), 7.83 (s, 1H), 6.73-6.72 (m, 1H), 6.70 (s, 1H), 5.80 (s, 2H), 3.51 (s, 3H), 2.60 (s, 3H). LC-MS: [M+H]⁺=389.9.

Example 86

1-([1,2,4]triazolo[4,3-a]pyridin-6-yl)-3-(5-amino-4-chloropyridin-3-yl)-6-methyl-1H-indole-5-carbonitrile Intermediate 86.1

1-([1,2,4]triazolo[4,3-a]pyridin-6-yl)-3-(5-(bis(4-methoxybenzyl)amino)-4-chloropyridin-3-yl)-6-methyl-1H-indole-5-carbonitrile

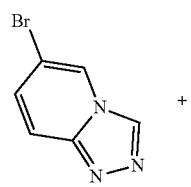

+

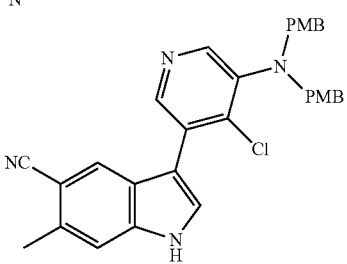

43.2

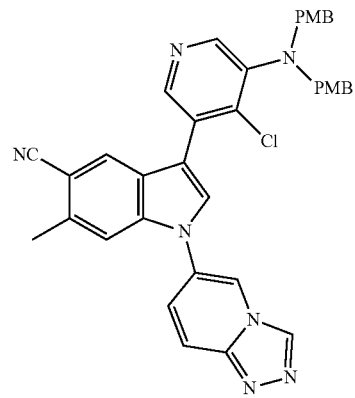

86.1

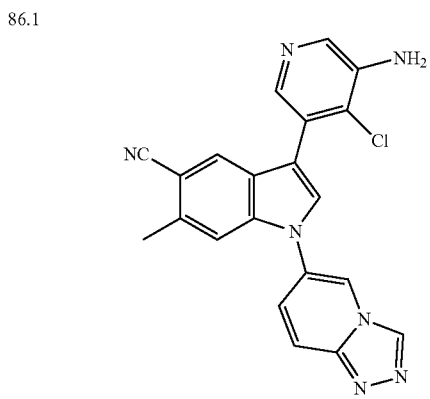

Example 86

The title compound was prepared by using a procedure similar to that of example 43 by replacing intermediate 43.3 with 86.1. ¹HNMR (400 MHz, DMSO-d₆) δ ppm 9.36 (d, 1H), 9.11 (dd, 1H), 8.14 (s, 1H), 8.09 (s, 1H), 8.04 (dd, 1H), 7.95 (s, 1H), 7.93 (s, 1H), 7.77 (s, 1H), 7.73 (dd, 1H), 5.82 (br s, 2H), 2.58 (s, 3H). LC-MS: [M+H]⁺=400.9.

Example 87

3-(3-amino-4-bromo-2-methylphenyl)-1-((1R,4R)-4-hydroxycyclohexyl)-6-methyl-1H-indole-5-carbonitrile Intermediate 87.1

3-(3-amino-2-methylphenyl)-1-((1R,4R)-4-hydroxycyclohexyl)-6-methyl-1H-indole-5-carbonitrile

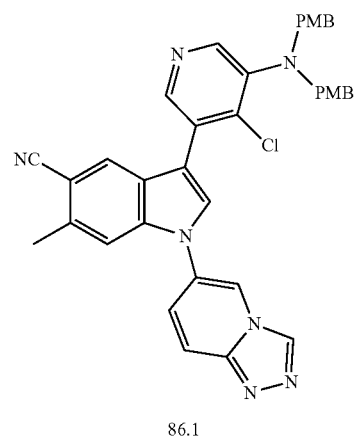

1.6

+

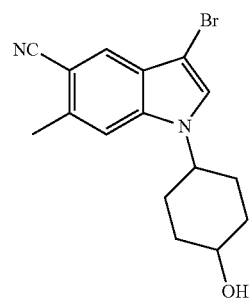

The title compound was prepared by using a procedure similar to that of intermediate 81.1 by replacing intermediate 6bromoimidazo[1,5-a]pyridine with 6-bromo-[1,2,4]triazolo[4,3-a]pyridine. LC-MS: [M+H]⁺=639.9.

-continued

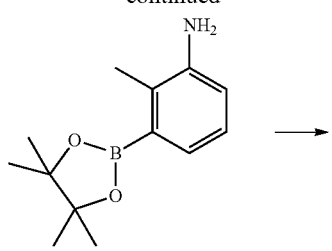

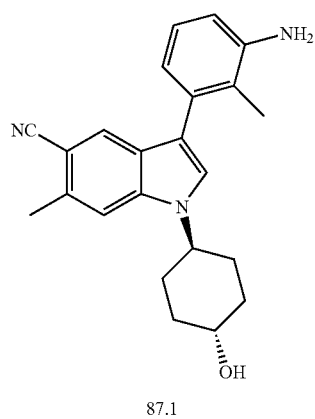

87.1

The title compound was prepared by using a procedure similar to that of example 1 by replacing intermediate 1.7 and 5-bromo-4-chloropyridin-3-amine with 2-methyl-3-(4,4,5,5-tetramethyl-1,3,2-dioxaborolan-2-yl)aniline and 1.6. H NMR (400 MHz, DMSO-d$_6$) δ ppm 7.76 (s, 1H), 7.69 (d, 1H), 7.64 (s, 1H), 7.21 (t, 1H), 7.07 (d, 2H), 4.47 (d, 2H), 3.84 (s, 1H), 3.58 (t, 2H), 2.59 (s, 3H), 2.13 (d, 3H), 1.94 (t, 6H), 1.53-1.44 (m, 2H). LC-MS: [M+H]$^+$=360.3.

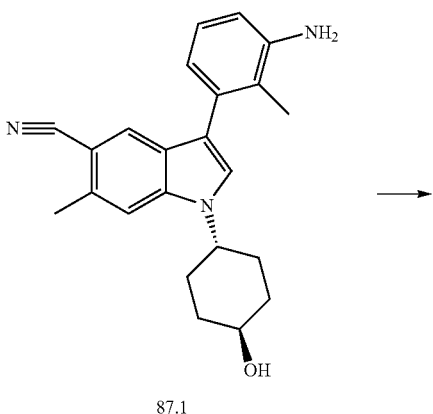

87.1

-continued

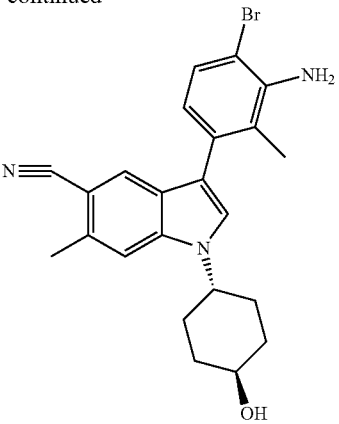

Example 87

In a 10 mL round-bottomed flask was Reactant 2 (50 mg, 0.139 mmol) in DMF (2 mL) to give a colorless solution. The reaction was cooled to 0° C., NBS (29.7 mg, 0.167 mmol) in DMF (0.5 mL) was added dropwise. The reaction was quenched with NH$_4$Cl(aq). The reaction was extracted with EA. The combined organic phase was washed with brine and dried over Na$_2$SO$_4$, concentrated and purified by prep-HPLC (0.1% NH$_3$H$_2$O/ACN/H$_2$O) to give the title compound (25 mg, 40%) as white powder. $^1$HNMR (METHANOL-d$_4$) δ 7.54 (s, 1H), 7.39 (s, 1H), 7.34 (s, 1H), 7.27 (d, J=8.4 Hz, 1H), 6.71 (d, J=8.6 Hz, 1H), 4.40-4.50 (m, 1H), 3.66-3.79 (m, 1H), 2.63 (s, 3H), 2.11 (br s, 4H), 1.91-2.02 (m, 2H), 1.89 (s, 3H), 1.55-1.69 (m, 2H). LC-MS: [M+H]$^+$=439.9.

Example 88

3-(2,2-dimethyl-1,2-dihydro-1,7-naphthyridin-5-yl)-1-((1R,4R)-4-hydroxycyclohexyl)-6-methyl-1H-indole-5-carbonitrile Intermediate 88.1

3-bromo-4-iodo-5-nitropyridine

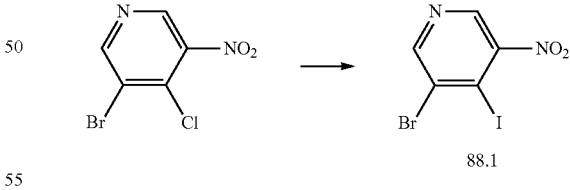

88.1

A mixture of compound 3-bromo-4-chloro-5-nitropyridine (1.5 g, 6.32 mmol), NaI (2.842 g, 2.87 mmol), and HI (371 uL, 5.69 mmol) in 2-butanone (30 mL) was stirred at 85° C. overnight. After removal of the solvent, the residue was diluted with water (30 mL) and extracted with EA (3×30 mL). The combined organic layers were washed with brine, dried over sodium sulfate and concentrated in vacuum. The residue was purified by flashed chromatography (PE/EA, EA=0~30%) to give the desired compound B (1.3 g, 63%) as a light yellow solid. $^1$H NMR (400 MHz, DMSO) δ 8.98 (s, 1H), 8.92 (s, 1H). LC-MS: [M+H]$^+$=328.84.

Intermediate 88.2

5-bromo-4-iodopyridin-3-amine

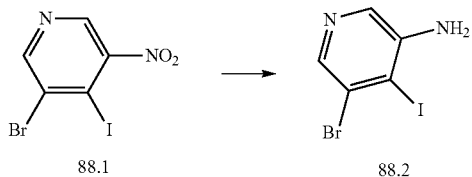 [SMILES: O=[N+]([O-])c1cncc(Br)c1I ; Nc1cncc(Br)c1I]

A mixture of compound 88.1 (325 mg, 0.988 mmol), Fe (221 mg, 3.95 mmol) and NH$_4$Cl (264 mg, 4.94 mmol) in EtOH/H$_2$O (10:1, 4 mL/400 uL) was stirred at 80° C. for 5 hrs. After cooled to r.t., the mixture was filtered. Water (20 mL) was added and the mixture was extracted with EA (3×10 mL). The combined organic layers were washed with brine (3×10 mL), dried over sodium sulfate and concentrated in vacuum. The residue was purified by flash chromatography (PE/EA, EA=0~30%) to give the target compound C (190 mg, 64%). $^1$H NMR (400 MHz, DMSO) δ 7.85 (d, 2H), 5.84 (s, 2H). LC-MS: [M+H]$^+$=298.9.

Intermediate 88.3

(E)-4-(3-amino-5-bromopyridin-4-yl)-2-methylbut-3-en-2-ol

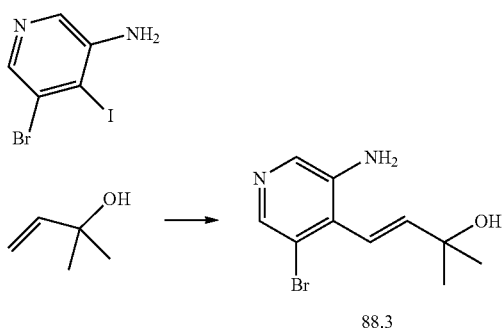

To a mixture of compound 88.2 (300 mg, 1.0 mmol), 2-methylbut-3-en-2-ol (86 mg, 1.0 mmol), dicylohexylmethylamine (390.7 mg, 2.0 mmol) and TBACl (278 mg, 1.0 mmol) in DMA (3.0 mL) was added Pd(OAc)$_2$ (22.5 mg, 0.10 mmol) under nitrogen atmosphere. The mixture was stirred at 90° C. overnight. After cooled to r.t., EA was added and the mixture washed with water and brine, dried over sodium sulfate, concentrated and purified by column chromatography on silica gel (PE/EA=10:1-2:1) to give the desired compound E (70 mg, 27%) as a white solid. $^1$H NMR (400 MHz, CDCl$_3$) δ 8.14 (s, 1H), 8.00 (s, 1H), 6.50 (d, 1H), 6.35 (d, 1H), 1.49 (s, 6H). LC-MS: [M+H]$^+$=257.2.

Intermediate 88.4

5-bromo-2,2-dimethyl-1,2-dihydro-1,7-naphthyridine

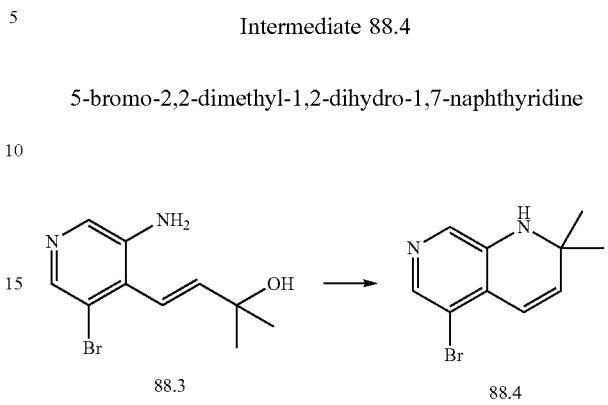

The solution of compound 88.3 (10 mg, 0.03889 mmol) in con. HCl (8 mL) was stirred at 95° C. for 1.5 h. Another 3 batches of reactions were carried out in the same reaction scale by above method. The 4 batches of reaction mixture were concentrated and purified by pre-HPLC (0.1% TFA/CH$_3$CN/H$_2$O) to give a residue, which was dissolved in DCM, washed with sat. NaHCO$_3$, water and brine, dried over Na$_2$SO$_4$ and concentrated to give title compound (16 mg 43%). $^1$HNMR (400 MHz, CDCl$_3$) δ 8.11 (s, 1H), 7.74 (s, 1H), 6.57 (d, 1H), 5.98 (d, 1H), 1.45 (s, 6H). LC-MS: [M+H]$^+$=239.06, 241.04.

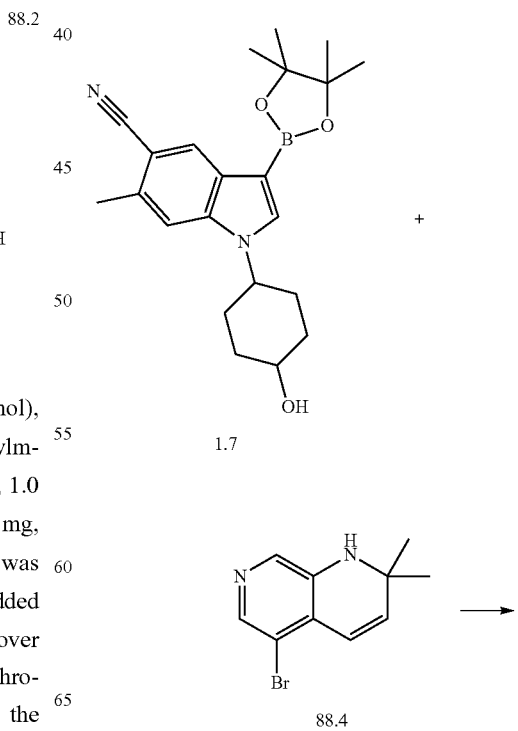

209
-continued

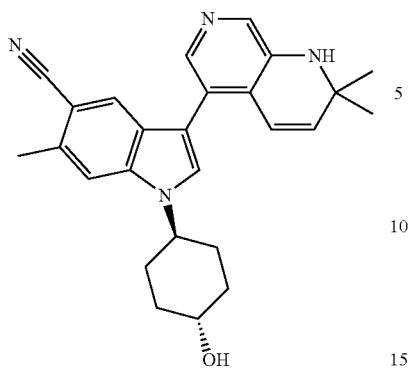

Example 88

To a solution of compound 1.7 (51 mg, 0.13 mmol) in DMF (3 mL) was added compound 88.4 (16 mg, 0.066 mmol) and 2N $Na_2CO_3$ (200 uL, 0.40 mmol). The mixture was degassed with $N_2$ for 0.5 min. $Pd(dppf)Cl_2$ (7 mg, 0.01 mmol) was added and the mixture was degassed with $N_2$ for 0.5 min. The mixture was stirred at 100° C. under $N_2$ atmosphere overnight. After cooled to r.t., EA was added and the mixture was filtered. The filtrate was washed with water and brine, dried over $Na_2SO_4$, concentrated to give a dark residue, which was purified by pre-HPLC ((0.1% $NH_3.H_2O$/ $CH_3CN/H_2O$) to give title compound (7 mg, 13%). $^1$H-NMR (400 MHz, DMSO-$d_6$) δ ppm 7.77 (d, 2H), 7.69 (d, 3H), 6.25 (s, 1H), 6.14 (d, 1H), 5.68 (dd, 1H), 4.73 (s, 1H), 4.47 (s, 1H), 3.58 (s, 1H), 2.59 (s, 3H), 1.96 (d, 6H), 1.49 (d, 2H), 1.31 (s, 6H). LC-MS: $[M+H]^+$=413.30.

Example 89

3-(2,2-dimethyl-1,2,3,4-tetrahydro-1,7-naphthyridin-5-yl)-1-((1R,4R)-4-hydroxycyclohexyl)-6-methyl-1H-indole-5-carbonitrile

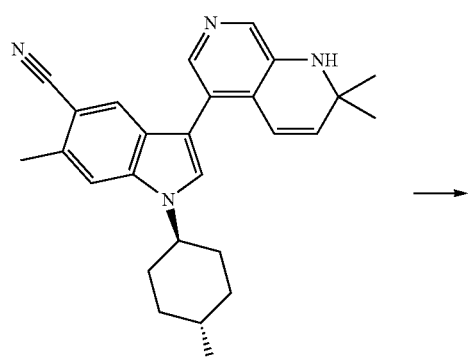

Example 88

210
-continued

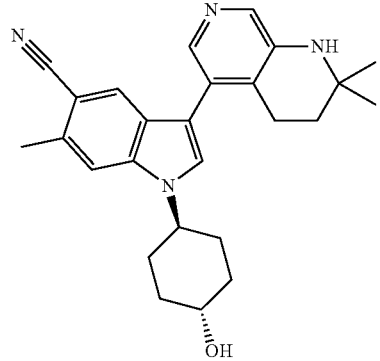

Example 89

To a solution of compound 88 (26 mg, 0.06302 mmol) in MeOH (10 mL) was added Pd/C (6 mg). The mixture was stirred at r.t. under a $H_2$ balloon for 2.5 h. The mixture was filtered and the filtrate was concentrated and purified by Prep-HPLC (0.1% $NH_4OH/CH_3CN/H_2O$) to give title compound (8 mg, 32%). $^1$H-NMR (400 MHz, DMSO-$d_6$) δ ppm 7.82-7.76 (m, 3H), 7.75 (s, 1H), 7.69 (s, 1H), 5.97 (s, 1H), 4.75 (s, 1H), 4.47 (s, 1H), 3.58 (s, 1H), 2.65-2.56 (m, 5H), 1.94 (t, 6H), 1.59-1.41 (m, 4H), 1.19 (s, 6H). LC-MS: $[M+H]^+$=415.4.

Example 90

3-(3,4-dihydro-2H-pyrido[4,3-b][1,4]oxazin-8-yl)-1-((1R,4R)-4-hydroxycyclohexyl)-6-methyl-1H-indole-5-carbonitrile Intermediate 90.1

3-amino-5-bromopyridin-4-ol

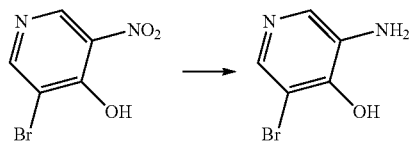

To a mixture of compounds 3-bromo-5-nitropyridin-4-ol (1.5 g, 6.85 mmol), $NH_4Cl$ (1.8 g, 33.65 mmol) and iron powder (1.5 g, 26.86 mmol) in ethanol (40 mL) was $H_2O$ (4 mL) and the mixture was heated to reflux for 5 hours. The mixture was cooled to room temperature and the solid was filtered off through celite. The filtrate was evaporated to give 2.5 g crude product which was used to next step directly. LC-MS: $[M+H]^+$=191.0.

Intermediate 90.2

8-bromo-3,4-dihydro-2H-pyrido[4,3-b][1,4]oxazine

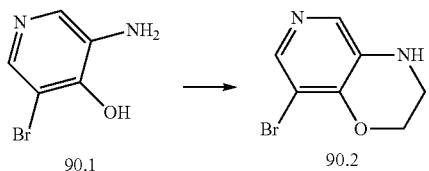 [SMILES: Nc1cncc(Br)c1O ; Brc1cncc2c1OCCN2]

A mixture of compound 90.1 (1.0 g, 5.29 mmol), 1,2-dibromoethane (0.6 g, 3.19 mmol) and K$_3$CO$_3$ (2.2 g, 15.92 mmol) in DMF (15 mL) was stirred at room temperature for 3 hours. The mixture was diluted with EA (150 mL) and washed with brine (50 mL*3). The organic phase was dried over anhydrous Na$_2$SO$_4$, filtered and evaporated under vacuum to give 230 mg of crude product, which was purified by Pre-TLC to give 130 mg of pure compound. $^1$HNMR (300 MHz, CDCl$_3$) δ 7.95 (d, 2H), 4.43 (t, 2H), 3.47 (t, 2H).

$^1$HNMR (400 MHz, DMSO-d$_6$) δ ppm 7.92 (s, 1H), 7.85 (s, 1H), 7.80 (s, 1H), 7.78 (s, 1H), 7.73 (s, 1H), 6.05 (s, 1H), 4.73 (d, 1H), 4.48-4.40 (m, 1H), 4.25 (t, 2H), 3.75-3.48 (m, 1H), 3.47-3.34 (m, 2H), 2.58 (s, 3H), 2.08-1.75 (m, 6H), 1.66-1.27 (m, 2H). LC-MS: [M+H]$^+$=389.3.

Example 95

3-(2,2-dimethyl-1,2-dihydroquinolin-5-yl)-1-((1R,4R)-4-hydroxycyclohexyl)-6-methyl-1H-indole-5-carbonitrile Example 96

3-(2,2-dimethyl-1,2-dihydroquinolin-5-yl)-1-((1s,4s)-4-hydroxycyclohexyl)-6-methyl-1H-indole-5-carbonitrile

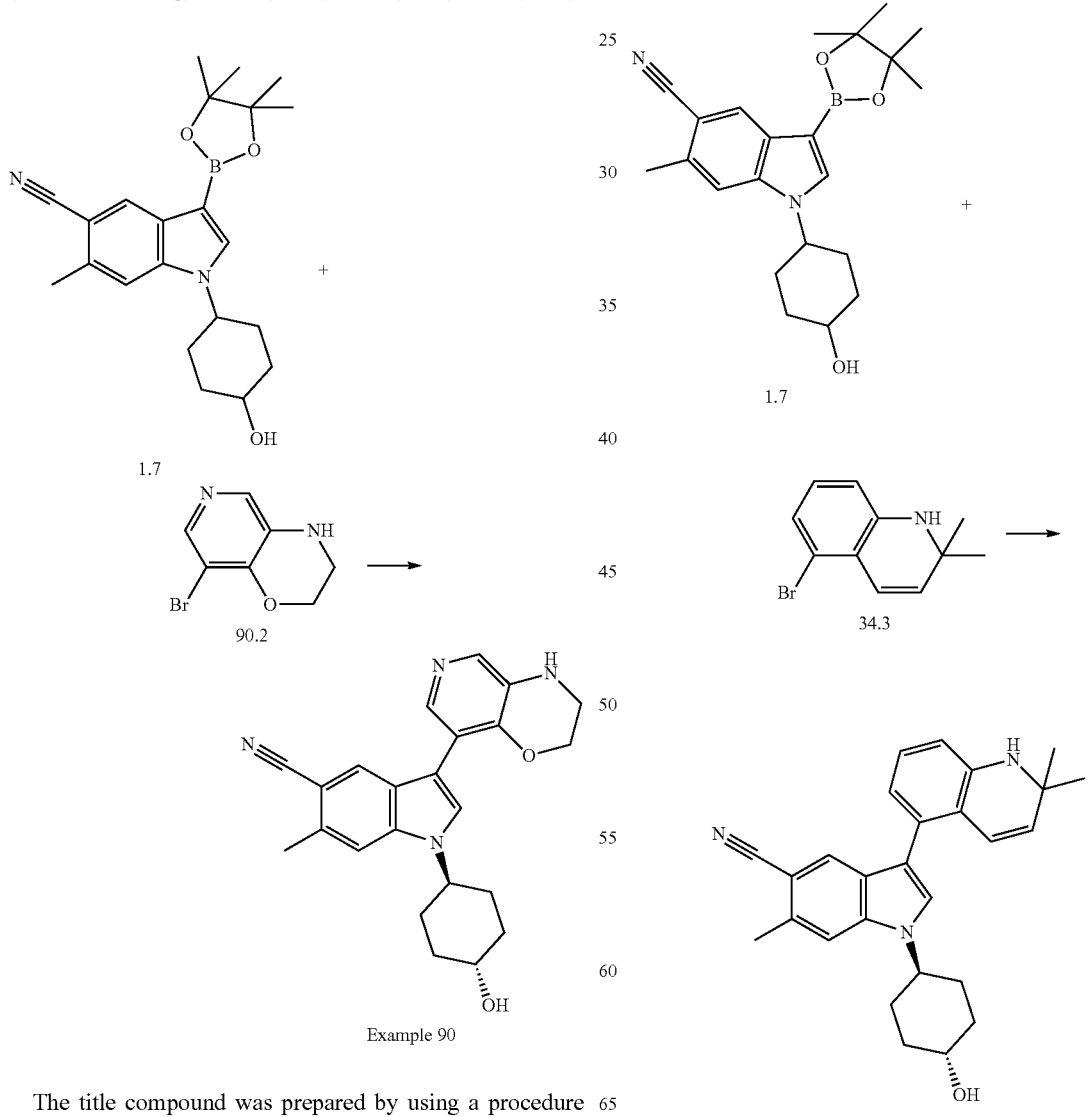

The title compound was prepared by using a procedure similar to that of example 1 by replacing intermediate 1.7 and 5-bromo-4-chloropyridin-3-amine with 1.7 and 90.2.

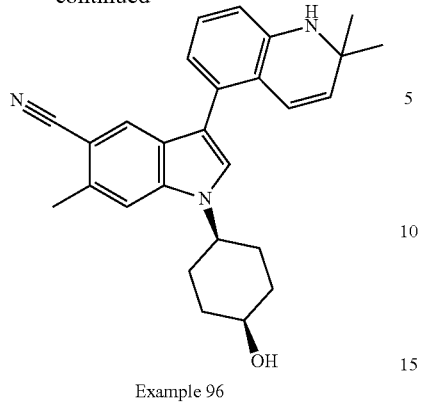

Example 96

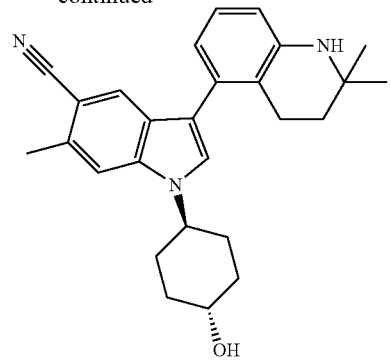

Example 97

The title compound was prepared by using a procedure similar to that of example 1 by replacing intermediate 5-bromo-4-chloropyridin-3-amine with intermediate 34.3.

Example 95

¹HNMR (300 MHz, DMSO-d₆) δ: 7.73 (s, 1H), 7.64 (s, 1H), 7.58 (s, 1H), 6.91-6.92 (m, 1H), 6.48 (t, J=7.2 Hz, 2H), 6.14 (d, J=9.8 Hz, 1H), 5.41 (d, J=10.0 Hz, 1H), 4.45 (br d, J=5.5 Hz, 2H), 3.58 (brt, J=10.9 Hz, 1H), 2.58 (s, 3H), 1.88-2.01 (m, 6H), 1.40-1.55 (m, 2H), 1.27 (s, 6H). LC-MS: [M+H]⁺=412.0.

Example 96

¹HNMR (300 MHz, DMSO-d₆)¹H NMR (DMSO-d₆) δ: 7.70 (s, 1H), 7.68 (s, 1H), 7.52 (s, 1H), 6.96 (t, J=7.7 Hz, 1H), 6.49 (dd, J=7.8, 2.0 Hz, 2H), 6.16 (d, J=9.8 Hz, 1H), 5.98 (s, 1H), 5.42 (d, J=10.0 Hz, 1H), 4.47 (br t, J=11.7 Hz, 1H), 3.94 (br s, 1H), 2.58 (s, 3H), 2.19 (q, J=11.7 Hz, 2H), 1.80-1.88 (m, 3H), 1.66-1.80 (m, 4H), 1.27 (s, 6H). LC-MS: [M+H]⁺=411.9.

Example 97

3-(2,2-dimethyl-1,2,3,4-tetrahydroquinolin-5-yl)-1-((1r,4r)-4-hydroxycyclohexyl)-6-methyl-1H-indole-5-carbonitrile

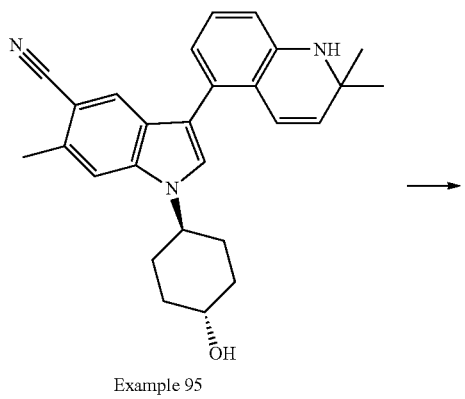

Example 95

The mixture of 95 (17 mg, 0.041 mmol) in MeOH (3 mL) was added Pd—C (8.79 mg, 8.26 μmol). Then the reaction mixture was stirred at 25° C. for 19 hr. Pre-HPLC deliver title compound (11 mg, 64%). ¹H NMR (300 MHz, Methanol-d₄) δ: 7.65 (s, 1H), 7.53 (s, 1H), 7.41 (s, 1H), 6.97-7.02 (m, 1H), 6.55-6.62 (m, 2H), 4.39-4.50 (m, 1H), 3.69-3.80 (m, 1H), 2.64 (s, 3H), 2.56-2.62 (m, 2H), 2.09-2.18 (m, 4H), 1.92-2.03 (m, 2H), 1.56-1.68 (m, 4H), 1.24 (s, 6H). LC-MS: [M+H]⁺=413.9.

Example 98

1-((1R,4R)-4-hydroxycyclohexyl)-6-methyl-3-(1,2,3,4-tetrahydroquinolin-5-yl)-1H-indole-5-carbonitrile Intermediate 98.1

5-bromo-1,2,3,4-tetrahydroquinoline

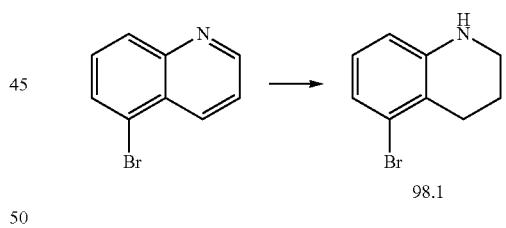

At r.t, the mixture of compound 5-bromoquinoline (600 mg, 2.884 mmol) and PtO₂.3H₂O (8 mg, 0.029 mmol) in AcOH (15 mL) was stirred under a H₂ balloon for 5 h. And additional PtO₂.3H₂O (16 mg, 0.058 mmol) was added and it was stirred under a H₂ balloon overnight. LC-MS showed 40% of compound B was found. So additional PtO₂.3H₂O (16 mg, 0.058 mmol) was added and it was stirred under a H₂ balloon for 10 h. Then it was diluted with MTBE, filtered and washed with MTBE. The filtrate was concentrated to give title compound (360 mg, 58.8%) as a brown oil ¹H NMR (300 MHz, CDCl₃) δ 6.83 (m, 2H), 6.40 (d, 1H), 3.87 (s, 1H), 3.25 (t, 2H), 2.76 (t, 2H), 1.99-1.93 (m, 2H). LC-MS: [M+H]⁺=212.17, 214.12.

Intermediate 98.2

5-(4,4,5,5-tetramethyl-1,3,2-dioxaborolan-2-yl)-1,2,3,4-tetrahydroquinoline

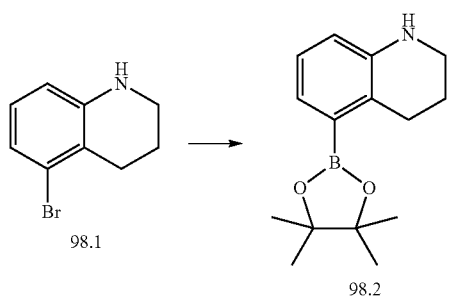 [SMILES: Brc1cccc2c1CCCN2 ; CC1(C)OB(c2cccc3c2CCCN3)OC1(C)C]

The title compound was prepared by using a procedure similar to that of intermediate 1.7 by replacing intermediate 1.6 with 98.1. $^1$HNMR (300 MHz, CDCl$_3$) δ 7.12 (d, 1H), 6.96 (t, 1H), 6.58 (d, 1H), 3.27 (t, 2H), 3.03 (t, 2H), 1.94 (m, 2H), 1.32 (s, 12H). LC-MS: [M+H]$^+$=260.3.

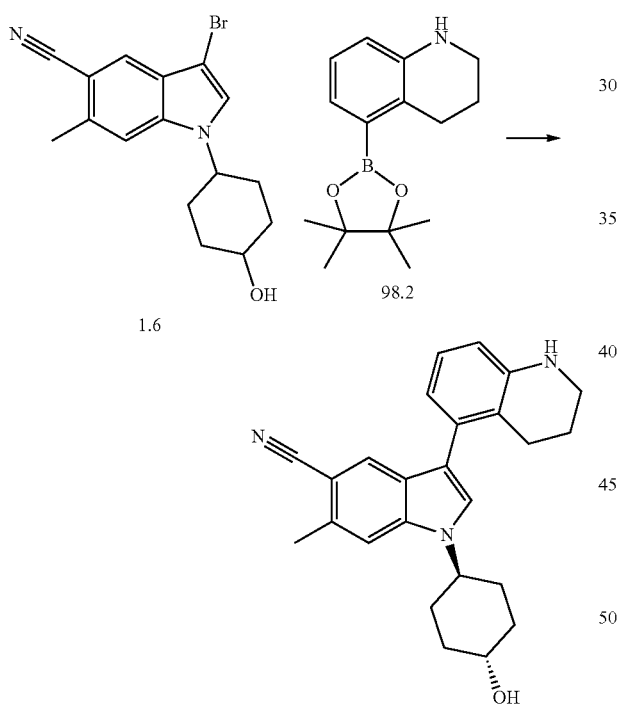

Example 98

To a mixture of compound 1.6 (150 mg, 0.450 mmol) and compound 98.2 (175 mg, 0.675 mmol) in the co-solvent of i-PrOH/H$_2$O (6 mL, 10:1) was added 2N Na$_2$CO$_3$ aq. (1.35 mL, 2.7 mmol) and Pd(PPh$_3$)$_2$Cl$_2$ (25 mg, 0.036 mmol). The mixture was stirred at 100° C. for 3 h under N$_2$ atmosphere. Then it was diluted with brine and extracted with EA for three times. The combined organic phase was dried over anhydrous Na$_2$SO$_4$, filtered and concentrated to give a crude product which was purified by prep-TLC (eluent: PE/EA=1:1) to give a crude product. It was purified by prep-HPLC (0.1% NH$_3$.H$_2$O/ACN/H$_2$O) and lyophilized to give title compound (31 mg, 18%) as a white solid. $^1$H-NMR (400 MHz, DMSO-d$_6$) δ ppm 7.72 (d, 2H), 7.60 (s, 1H), 6.93 (t, 1H), 6.46 (m, 2H), 5.74 (s, 1H), 4.71 (d, 1H), 4.44 (m, 1H), 3.57 (m, 1H), 3.20 (m, 2H), 2.58 (s, 3H), 2.56 (d, 2H), 2.06-1.82 (m, 6H), 1.69 (m, 2H), 1.48 (m, 2H). LC-MS: [M+H]$^+$=386.3.

Example 99

1-(3-hydroxycyclopentyl)-6-methyl-3-(1,2,3,4-tetrahydroquinolin-5-yl)-1H-indole-5-carbonitrile

Intermediate 99.1

3-bromo-1-(3-((tert-butyldimethylsilyl)oxy)cyclopentyl)-6-methyl-1H-indole-5-carbonitrile

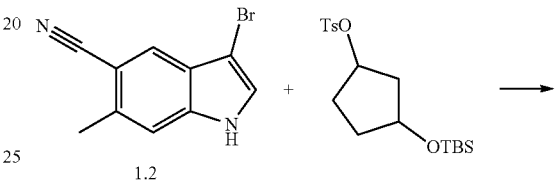

The title compound was prepared by using a procedure similar to that of intermediate 1.4 by replacing intermediate 1.3 with 11.2. $^1$H NMR (300 MHz, CDCl$_3$) δ 7.84 (s, 1H), 7.26 (s, 1H), 7.20 (s, 1H), 5.00 (m, 1H), 4.50 (m, 1H), 2.66 (s, 3H), 2.45 (s, 1H), 2.23-2.08 (m, 2H), 1.99 (m, 2H), 1.89-1.75 (m, 3H), 0.92 (s, 9H), 0.09 (s, 6H). LC-MS: [M+H]$^+$=433.4.

Intermediate 99.2

1-(3-((tert-butyldimethylsilyl)oxy)cyclopentyl)-6-methyl-3-(1,2,3,4-tetrahydroquinolin-5-yl)-1H-indole-5-carbonitrile

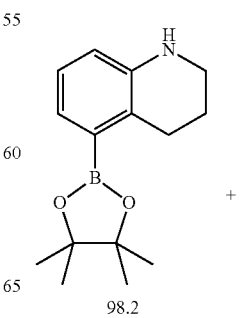

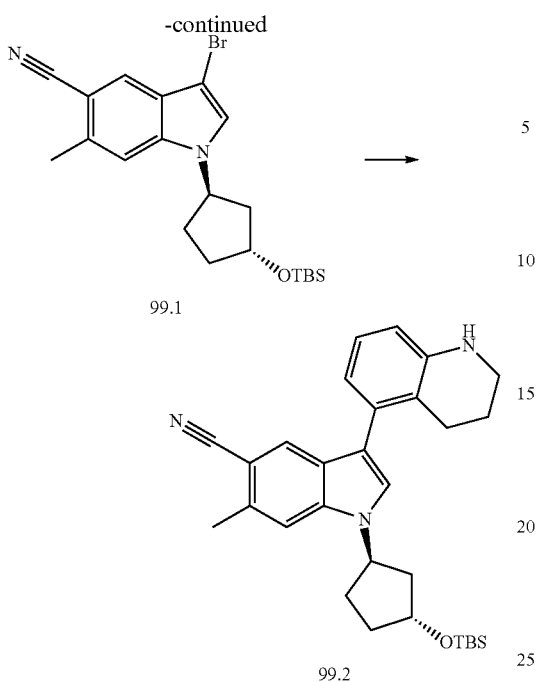

99.1

99.2

The title compound was prepared by using a procedure similar to that of example 1 by replacing intermediate 1.7 and 5-bromo-4-chloropyridin-3-amine with 99.1 and 98.2. $^1$H NMR (300 MHz, CDCl$_3$) δ ppm 7.82 (s, 1H), 7.29 (s, 1H), 7.13 (s, 1H), 7.05 (t, 1H), 6.67 (d, 1H), 6.55 (d, 1H), 5.17-4.96 (m, 1H), 4.52 (dd, 1H), 3.71 (s, 2H), 3.39-3.27 (m, 2H), 2.66 (s, 3H), 2.62 (t, 1H), 2.48 (dd, 1H), 2.32-2.00 (m, 3H), 1.94-1.70 (m, 3H), 0.92 (s, 9H), 0.09 (s, 6H). LC-MS: [M+H]$^+$=486.4.

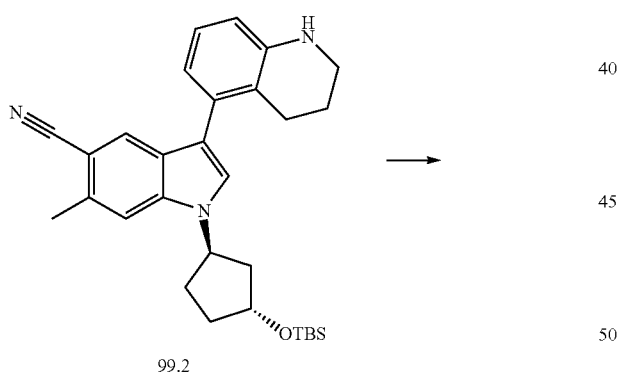

99.2

Example 99

The title compound was prepared by using a procedure similar to that of intermediate 9.5 by replacing intermediate 9.4 with 99.2. $^1$H-NMR (400 MHz, DMSO-d$_6$) δ ppm 7.72 (s, 1H), 7.61 (d, 2H), 6.93 (t, 1H), 6.47 (dd, 2H), 5.74 (s, 1H), 5.15 (p, 1H), 4.80 (s, 1H), 4.39 (s, 1H), 3.20 (s, 2H), 2.67-2.54 (m, 5H), 2.35 (dt, 1H), 2.13 (tt, 3H), 1.84 (dt, 1H), 1.74-1.54 (m, 3H). LC-MS: [M+H]$^+$=372.2.

Example 100

1-((1R,3R)-3-hydroxycyclopentyl)-3-(indolin-4-yl)-6-methyl-1H-indole-5-carbonitrile Intermediate 100.1 tert-butyl 4-(4,4,5,5-tetramethyl-1,3,2-dioxaborolan-2-yl)indoline-1-carboxylate

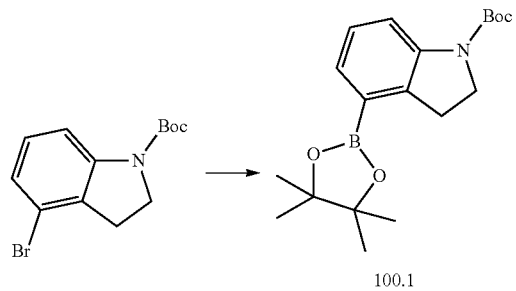 [SMILES: CC(C)(C)OC(=O)N1CCc2c(Br)cccc21 ; CC(C)(C)OC(=O)N1CCc2c(B3OC(C)(C)C(C)(C)O3)cccc21]

100.1

The title compound was prepared by using a procedure similar to that of intermediate 1.7 by replacing intermediate 1.6 with intermediate tert-butyl 4-bromoindoline-1-carboxylate. $^1$H NMR (300 MHz, CDCl$_3$) δ 7.36 (d, 1H), 7.26 (s, 1H), 7.15 (t, 1H), 3.94 (t, 2H), 3.27 (t, 2H), 1.32 (s, 12H), 1.26 (s, 9H). LC-MS: [M−99]$^+$=246.2.

Intermediate 100.2 tert-butyl 4-(1-(3-((tert-butyldimethylsilyl)oxy)cyclopentyl)-5-cyano-6-methyl-1H-indol-3-yl)indoline-1-carboxylate

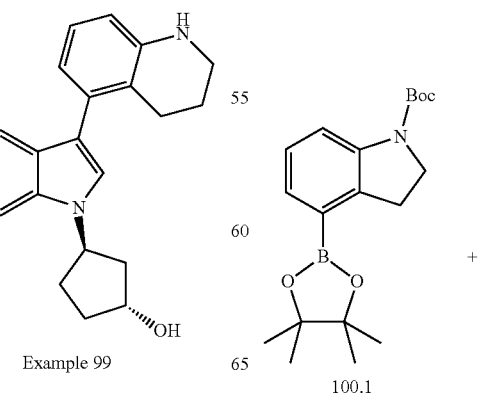

100.1

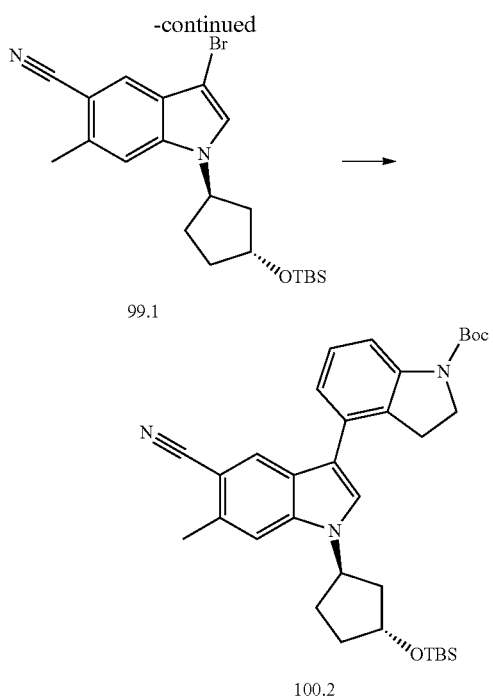

99.1

100.2

The title compound was prepared by using a procedure similar to that of example 1 by replacing intermediate 1.7 and 5-bromo-4-chloropyridin-3-amine with 100.1 and 99.1. LC-MS: [M+H]⁺=572.8.

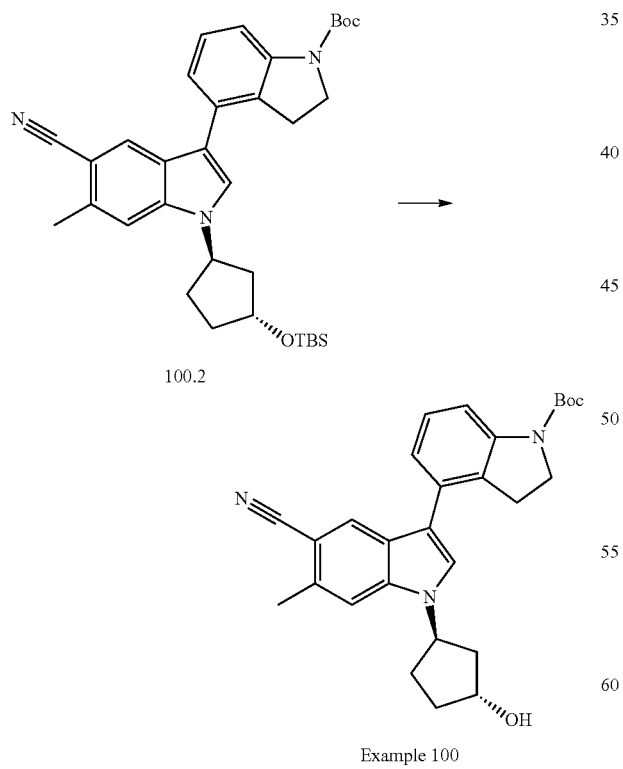

100.2

Example 100

A mixture of compound 100.2 (90 mg, 0.157 mmol) and TFA (2 mL) in DCM (4 mL) was stirred at room temperature for 2 hours. The mixture was concentrated and then purified by pre-HPLC (0.1% NH₃.H₂O/ACN/H₂O) to give title compound (16.6 mg, 30%). ¹H-NMR (400 MHz, DMSO-d₆) δ ppm 7.99 (s, 1H), 7.68 (d, 2H), 7.03 (t, 1H), 6.77 (d, 1H), 6.48 (d, 1H), 5.56 (s, 1H), 5.16 (p, 1H), 4.81 (d, 1H), 4.40 (d, 1H), 3.54-3.37 (m, 2H), 3.00 (t, 2H), 2.59 (s, 3H), 2.35 (dt, 1H), 2.24-1.98 (m, 3H), 1.85 (dt, 1H), 1.74-1.54 (m, 1H). LC-MS: [M+H]⁺=358.3.

Example 101

3-(3,3-dimethyl-1,2,3,4-tetrahydroquinolin-5-yl)-1-((1R,4R)-4-hydroxycyclohexyl)-6-methyl-1H-indole-5-carbonitrile Example 102

3-(3,3-dimethyl-1,2,3,4-tetrahydroquinolin-5-yl)-1-((1S,4S)-4-hydroxycyclohexyl)-6-methyl-1H-indole-5-carbonitrile

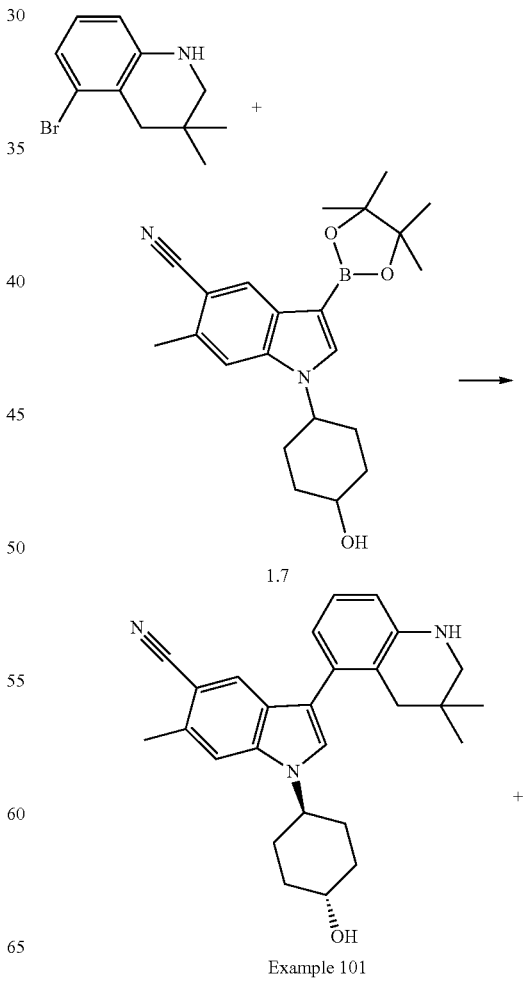

1.7

Example 101

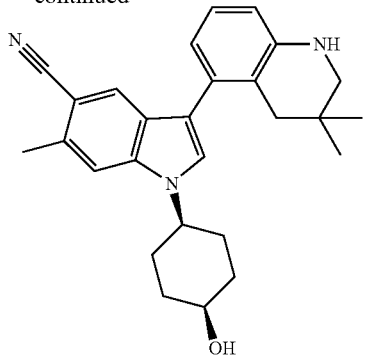

Example 102

The title compound was prepared by using a procedure similar to that of example 1 by replacing intermediate 5-bromo-4-chloropyridin-3-amine with 5-bromo-3,3-dimethyl-1,2,3,4-tetrahydroquinoline.

Example 101

$^1$HNMR (DMSO-d$_6$) δ: 7.69 (s, 1H), 7.66 (s, 1H), 7.53-7.57 (m, 1H), 6.91 (t, J=7.8 Hz, 1H), 6.46 (t, J=8.0 Hz, 2H), 5.88 (br s, 1H), 4.69 (br s, 1H), 4.42 (br s, 1H), 3.56 (br s, 1H), 2.82 (br s, 2H), 2.56 (s, 3H), 2.29 (s, 2H), 1.87-1.99 (m, 6H), 1.39-1.53 (m, 2H), 0.83 (s, 6H). LC-MS: [M+H]$^+$=414.0.

Example 102

$^1$HNMR (DMSO-d$_6$) δ: 7.69 (s, 1H), 7.65-7.68 (m, 1H), 7.47-7.51 (m, 1H), 6.90-6.96 (m, 1H), 6.48-6.50 (m, 1H), 6.45-6.48 (m, 1H), 5.85-5.89 (m, 1H), 4.49-4.54 (m, 1H), 4.38-4.49 (m, 1H), 3.89-3.95 (m, 1H), 2.80-2.86 (m, 2H), 2.30 (s, 3H), 2.09-2.24 (m, 2H), 1.64-1.86 (m, 6H), 0.84 (s, 6H). LC-MS: [M+H]$^+$=413.9.

Example 103

1-((1R,4R)-4-hydroxycyclohexyl)-6-methyl-3-(2-oxo-1,2,3,4-tetrahydroquinolin-5-yl)-1H-indole-5-carbonitrile

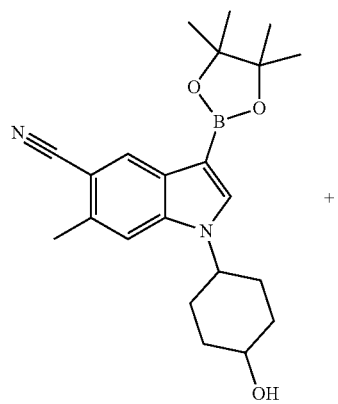

1.7

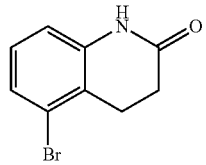

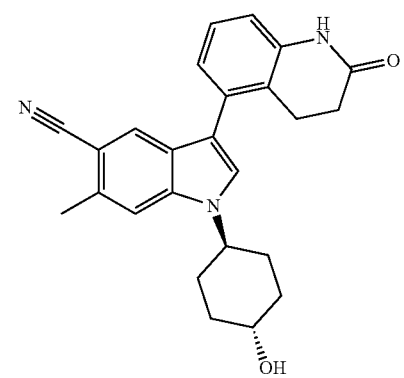

Example 103

The title compound was prepared by using a procedure similar to that of example 1 by replacing intermediate 5-bromo-4-chloropyridin-3-amine with with 5-bromo-3,4-dihydroquinolin-2(1H)-one. $^1$H-NMR (400 MHz, DMSO-d$_6$) δ ppm 10.15 (s, 1H), 7.81 (s, 1H), 7.76 (s, 1H), 7.69 (s, 1H), 7.23 (t, 1H), 7.04 (dd, 1H), 6.89 (d, 1H), 4.56-4.36 (m, 1H), 3.70-3.48 (m, 1H), 2.92-2.79 (m, 2H), 2.59 (s, 3H), 2.43-2.31 (m, 2H), 2.04-1.84 (m, 6H), 1.64-1.33 (m, 2H). LC-MS: [M+H]$^+$=400.2.

Example 104

1-((1R,4R)-4-hydroxycyclohexyl)-3-(indolin-4-yl)-6-methyl-1H-indole-5-carbonitrile Intermediate 104.1 tert-butyl 4-(5-cyano-1-(4-hydroxycyclohexyl)-6-methyl-1H-indol-3-yl)indoline-1-carboxylate

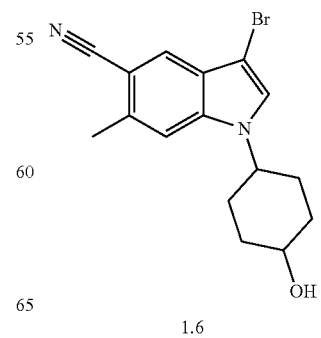

1.6

223

-continued

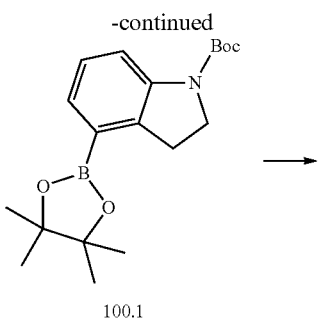

100.1

The title compound was prepared by using a procedure similar to that of example 1 by replacing intermediate 1.7 and 5-bromo-4-chloropyridin-3-amine with intermediate 1.6 and intermediate 100.1. ¹HNMR (300 MHz, CDCl₃) δ ppm 7.94 (s, 1H), 7.35-7.22 (m, 4H), 7.07 (d, 1H), 4.24 (m, 1H), 3.98 (t, 2H), 3.81 (m, 1H), 3.05 (t, 2H), 2.67 (s, 3H), 2.20 (d, 4H), 1.85 (m, 3H), 1.59 (s, 9H), 1.25 (t, 2H). LC-MS: [M+H]⁺=472.0.

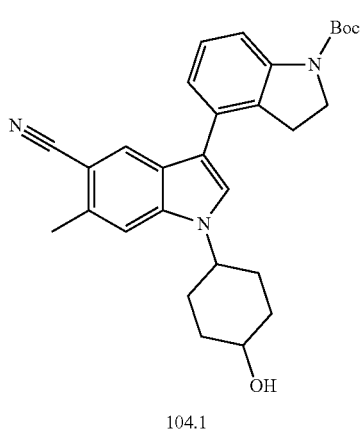

104.1

224

-continued

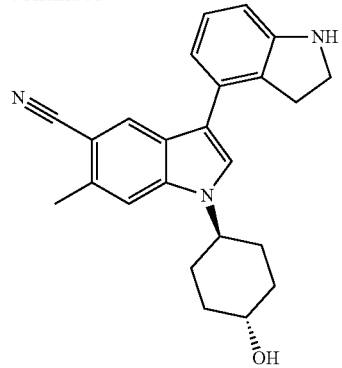

Example 104

The mixture of compound 104.1 (85 mg, 0.180 mmol) in 4N HCl/EA (3 mL) was stirred at r.t for 1 h. Much solid precipitated. Then it was filtered and washed with EA. The solid was treated with 4 mL sat. NaHCO₃ and extracted with EA for 3 times. The organic phase was combined and dried over anhydrous Na₂SO₄, filtered and concentrated to give a residue which was purified by prep-HPLC (0.1% NH₄OH/ACN/H₂O) and lyophilized to give title compound (27 mg, 40%) as a white solid. ¹HNMR (400 MHz, DMSO-d₆) δ ppm 7.99 (s, 1H), 7.73 (d, 2H), 7.02 (t, 1H), 6.77 (d, 1H), 6.47 (d, 1H), 5.55 (s, 1H), 4.73 (d, 1H), 4.54-4.37 (m, 1H), 3.67-3.52 (m, 1H), 3.42 (t, 2H), 3.00 (t, 2H), 2.59 (s, 3H), 2.07-1.75 (m, 6H), 1.60-1.39 (m, 2H). LC-MS: [M+H]⁺=372.2.

Example 105

1-((1R,4R)-4-hydroxycyclohexyl)-6-methyl-3-(7-methylindolin-6-yl)-1H-indole-5-carbonitrile ¹HNMR (300 MHz, DMSO-d₆) δ ppm 7.71 (s, 1H), 7.67 (s, 1H), 7.56 (s, 1H), 6.95 (d, J=6 Hz, 1H), 6.56 (d, J=6 Hz, 1H), 5.26 (s, 1H), 4.72 (d, J=3 Hz, 1H), 4.43-4.45 (m, 1H), 3.50-3.60 (m, 1H), 3.48 (t, 2H), 2.96 (t, J=6 Hz, 2H), 2.51 (s, 3H), 1.90-1.95 (m, 6H), 1.45-1.50 (m, 2H). LC-MS: [M+H]⁺=386.3.

Example 106

3-(5-amino-4-chloropyridin-3-yl)-2,6-dimethyl-1-(3-(methylsulfonyl)propyl)-1H-indole-5-carbonitrile

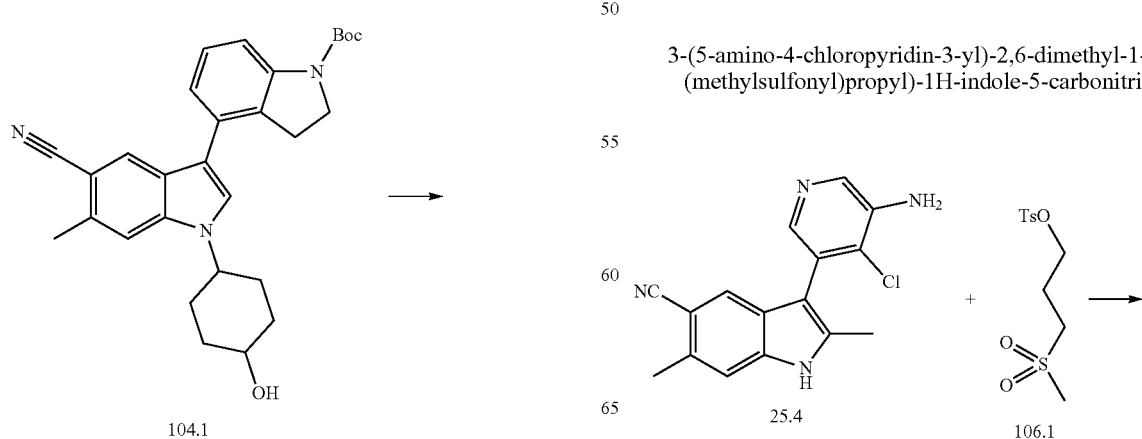

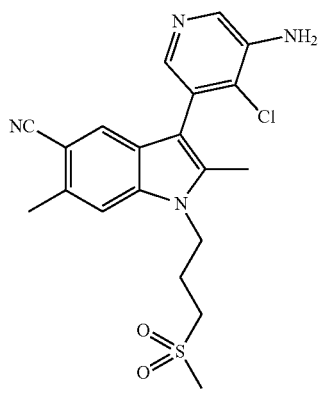

Example 106

The title compound can be prepared by using a procedure similar to that of Example 25 by replacing 3-bromopropan-1-ol with intermediate 106.1.

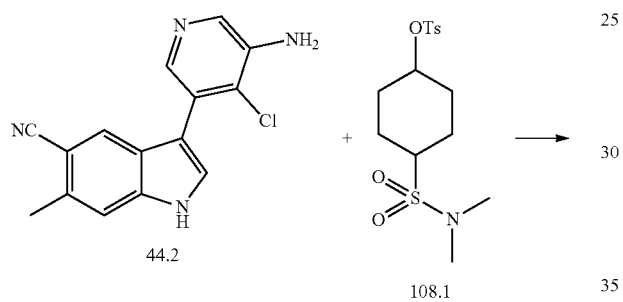

Example 108

The title compound can be prepared by using a procedure similar to that of Example 44 by replacing intermediate 44.3 with intermediate 108.1.

Example 109

1-((1R,4R)-1-aminosulfonylcyclohexyl)-6-methyl-3-(5-amino-4-chloropyridin-3-yl)-1H-indole-5-carbonitrile

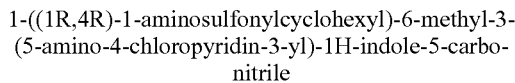

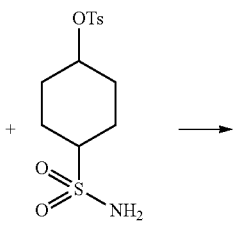

Example 109

The title compound can be prepared by using a procedure similar to that of Example 44 by replacing intermediate 44.3 with intermediate 109.1.

Example 110

1-((1R,4R)-4-acetylcyclohexyl)-6-methyl-3-(5-amino-4-chloropyridin-3-yl)-1H-indole-5-carbonitrile

Example 111

1-((1S,4S)-4-acetylcyclohexyl)-6-methyl-3-(5-amino-4-chloropyridin-3-yl)-1H-indole-5-carbonitrile

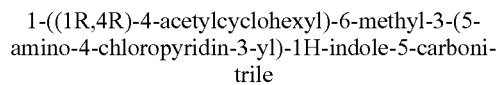

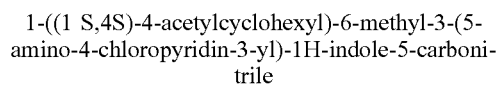

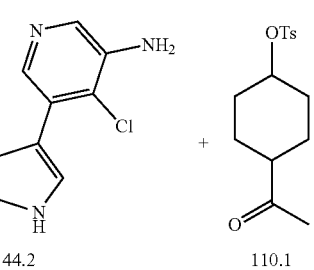

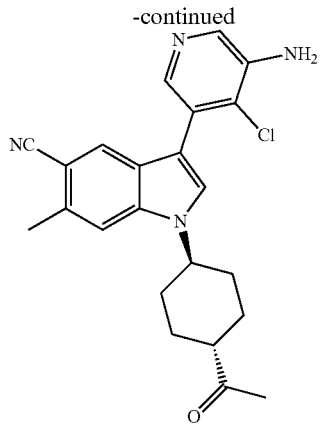

Example 110

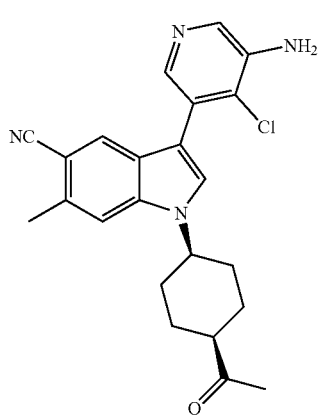

Example 111

The title compounds can be prepared by using a procedure similar to that of Example 44 by replacing intermediate 44.3 with intermediate 111.1.

Example 112

1-((1R,4R)-4-cyanocyclohexyl)-6-methyl-3-(5-amino-4-chloropyridin-3-yl)-1H-indole-5-carbonitrile

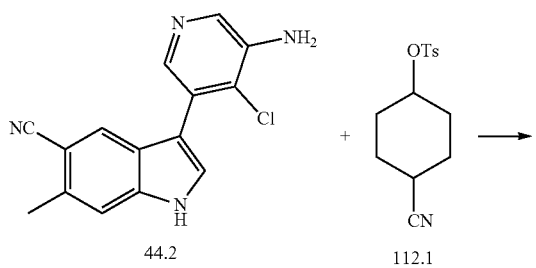

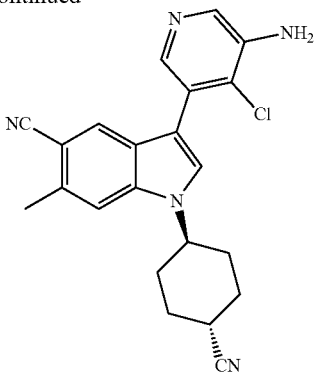

Example 112

The title compound can be prepared by using a procedure similar to that of Example 44 by replacing intermediate 44.3 with intermediate 112.1.

Example 113

1-((1R,4R)-4-cyanocyclohexyl)-6-methyl-3-(5-amino-4-chloropyridin-3-yl)-1H-indole-5-carbonitrile

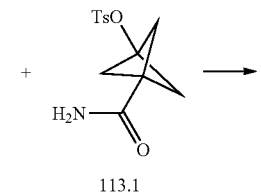

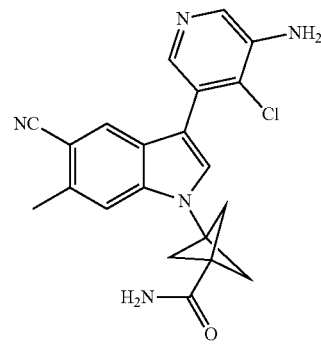

Example 113

The title compound can be prepared by using a procedure similar to that of Example 44 by replacing intermediate 44.3 with intermediate 112.1.

TABLE 1

| Ex # | Struture | ¹H NMR and LC-MS Data |
|---|---|---|
| 1 | | ¹H NMR (400 MHz, Methanol-d₄) δ 8.14 (s, 1H), 8.08 (s, 1H), 7.94-7.86 (m, 2H), 7.66 (s, 1H), 4.51 (td, J = 10.5, 9.4, 6.3 Hz, 1H), 3.83-3.61 (m, 1H), 2.66 (s, 3H), 2.21-2.06 (m, 4H), 2.04-1.87 (m, 2H), 1.63 (q, J = 12.4, 11.9 Hz, 2H). LC-MS: [M + H]⁺ = 380.9, 382.0. |
| 2 | | ¹H NMR (400 MHz, Methanol-d₄) δ 8.11 (d, J = 12.5 Hz, 2H), 7.91 (s, 2H), 7.67 (s, 1H), 4.53 (t, J = 12.3 Hz, 1H), 4.11 (d, J = 3.1 Hz, 1H), 2.66 (s, 3H), 2.38-2.19 (m, 2H), 2.00 (d, J = 13.6 Hz, 2H), 1.94-1.81 (m, 4H). LC-MS: [M + H]⁺ = 380.9, 382.0. |
| 3 | | ¹H NMR (400 MHz, Methanol-d₄) δ 8.21 (s, 1H), 7.97 (s, 1H), 7.83 (s, 1H), 7.68 (d, J = 9.9 Hz, 2H), 6.77 (t, J = 52.8 Hz, 1H), 4.50 (dq, J = 12.0, 6.0, 3.8 Hz, 1H), 3.75 (td, J = 11.2, 5.5 Hz, 1H), 2.65 (s, 3H), 2.15 (d, J = 10.0 Hz, 4H), 2.06-1.86 (m, 2H), 1.72-1.52 (m, 2H). LC-MS: [M + H]⁺ = 397.0, 398.0 |
| 4 | | ¹H NMR (400 MHz, Methanol-d₄) δ 8.17 (s, 1H), 7.91 (s, 1H), 7.81 (s, 1H), 7.66 (d, J = 4.6 Hz, 2H), 6.73 (t, J = 53.1 Hz, 1H), 4.52 (t, J = 12.0 Hz, 1H), 4.10 (s, 1H), 2.66 (s, 3H), 2.26 (q, J = 11.8 Hz, 2H), 2.02-1.83 (m, 6H). LC-MS: [M + H]⁺ = 397.0, 398.0. |

TABLE 1-continued
| Ex # | Struture | ¹H NMR and LC-MS Data |
|---|---|---|
| 5 | 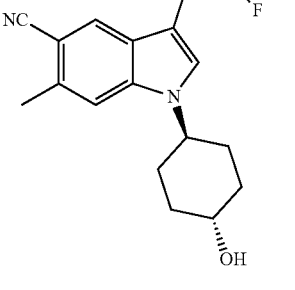 | ¹H NMR (400 MHz, Methanol-$d_4$) δ 8.08-7.90 (m, 3H), 7.77 (s, 1H), 7.60 (s, 1H), 4.48 (s, 1H), 3.74 (s, 1H), 2.65 (s, 3H), 2.25-2.07 (m, 4H), 2.06-1.90 (m, 2H), 1.62 (d, J =12.6 Hz, 2H). LC-MS: [M + H]⁺ = 364.9, 365.9 |
| 6 | 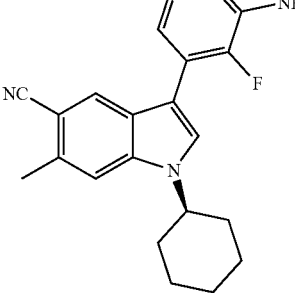 | ¹H NMR (400 MHz, Methanol-$d_4$,) δ 8.05 (d, J = 2.5 Hz, 1H), 8.03 (d, J = 0.8 Hz, 1H), 7.98 (d, J = 1H), 7.79 (d, J = 1.1 Hz, 1H), 7.61 (s, 1H), 4.48 (d, J = 11.9 Hz, 1H), 4.09 (s, 1H), 2.65 (s, 3H), 2.27 (q, J = 13.0, 12.4 Hz, 2H), 2.00 (d, J = 14.2 Hz, 2H), 1.87 (t, J = 11.7 Hz, 4H). LC-MS: [M + H]⁺ = 364.9, 365.9. |
| 7 | 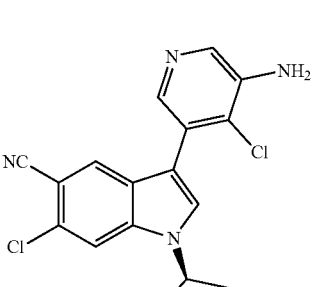 | ¹H NMR (500 MHz, DMSO-$d_6$) δ 8.19 (s, 1H), 8.09 (s, 1H), 7.99 (s, 1H), 7.97 (s, 1H), 7.82 (s, 1H), 5.75 (s, 2H), 4.58 (s, 1H), 3.56 (s, 1H), 1.93 (q, J = 13.3, 11.5 Hz, 6H), 1.49 (d, J = 11.6 Hz, 2H). LC-MS: [M + H]⁺ = 400.8, 402.8. |
| 8 | 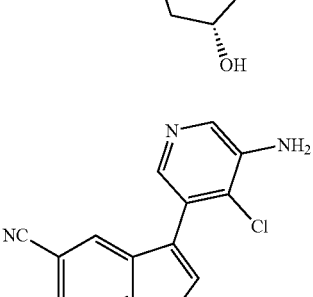 | ¹H NMR (500 MHz, DMSO-$d_6$) δ 8.15 (s, 1H), 8.09 (s, 1H), 7.99 (s, 1H), 7.96 (s, 1H), 7.85 (s, 1H), 5.75 (s, 2H), 4.59 (s , 1H), 4.55 (d, J = 3.8 Hz, 1H), 3.93 (s, 1H), 2.24-2.12 (m, 2H), 1.82 (d, J = 13.0 Hz, 2H), 1.74 (t, J = 12.0 Hz, 4H). LC-MS: [M + H]⁺ = 400.8, 402.8. |

TABLE 1-continued

| Ex # | Structure | ¹H NMR and LC-MS Data |
|---|---|---|
| 9 | 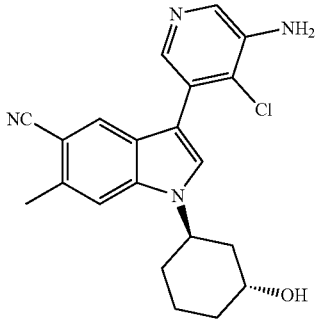 [SMILES: Cc1cc2c(cc1C#N)c(-c1cncc(N)c1Cl)cn2[C@@H]1CCC[C@@H](O)C1] | ¹H NMR (400 MHz, Methanol-d₄) δ 8.04 (s, 1H), 7.84 (s, 1H), 7.77 (s, 1H), 7.71 (s, 1H), 7.60 (s, 1H), 4.84 (ddd, J = 12.1, 8.2, 3.7 Hz, 1H), 4.30 (p, J = 3.0 Hz, 1H), 2.64 (s, 3H), 2.20-1.97 (m, 4H), 1.96-1.81 (m, 2H), 1.81-1.72 (m, 1H), 1.62 (tdd, J = 13.5, 4.3, 2.6 Hz, 1H). LC-MS: [M + H]⁺ = 381.2, 382.2. |
| 10 | 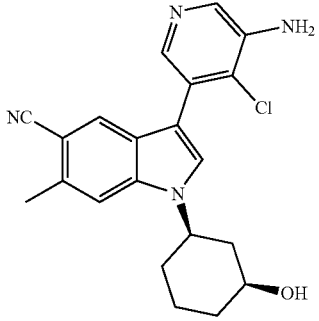 [SMILES: Cc1cc2c(cc1C#N)c(-c1cncc(N)c1Cl)cn2[C@@H]1CCC[C@H](O)C1] | ¹H NMR (400 MHz, Methanol-d₄) δ 8.05 (s, 1H), 7.84 (s, 1H), 7.77 (s, 1H), 7.72 (s, 1H), 7.59 (s, 1H), 4.64-4.39 (m, 1H), 3.83 (tt, J = 11.0, 4.2 Hz, 1H), 2.64 (s, 3H), 2.36 (ddq, J = 11.6, 4.1, 1.9 Hz, 1H), 2.14-2.00 (m, 2H), 1.96 (dt, J = 13.2, 3.2 Hz, 1H), 1.91-1.68 (m, 2H), 1.61 (ddt, J = 16.6, 13.2, 6.5 Hz, 1H), 1.47-1.21 (m, 1H). LC-MS: [M + H]⁺ = 380.2, 382.2. |
| 11 | 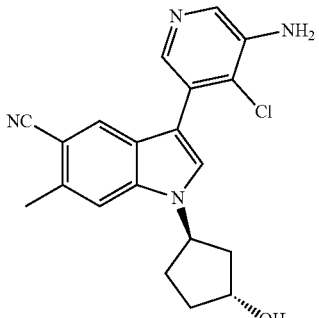 | ¹H NMR (400 MHz, Methanol-d₄) δ 8.05 (s, 1H), 7.84 (s, 1H), 7.77 (s, 1H), 7.68 (s, 1H), 7.57 (s, 1H), 5.21 (p, J = 8.0 Hz, 1H), 4.54 (dt, J = 5.7, 2.8 Hz, 1H), 2.64 (s, 3H), 2.49 (dtd, J = 14.1, 8.2, 6.0 Hz, 1H), 2.36-2.20 (m, 3H), 2.07-1.88 (m, 1H), 1.81 (m, 1H). LC-MS: [M + H]⁺ = 366.9, 368.9. |
| 12 | 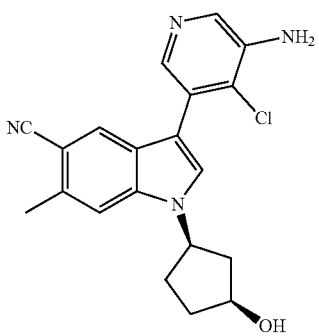 [SMILES: Cc1cc2c(cc1C#N)c(-c1cncc(N)c1Cl)cn2[C@@H]1CC[C@H](O)C1] | ¹H NMR (400 MHz, Methanol-d₄) δ 8.04 (s, 1H), 7.87 (s, 1H), 7.86 (s, 1H), 7.78 (s, 1H), 7.63 (s, 1H), 5.18-5.00 (m, 1H), 4.44 (dq, J = 8.1, 3.8 Hz, 1H), 2.64 (m, 4H), 2.33 (dtd, J = 14.6, 7.1, 4.7 Hz, 1H), 2.19 (m, 1H), 1.95 (ddd, J = 8.9, 7.0, 4.2 Hz, 3H). LC-MS: [M + H]⁺ = 366.9, 368.9. |

TABLE 1-continued
| Ex # | Structure | ¹H NMR and LC-MS Data |
|---|---|---|
| 13 | 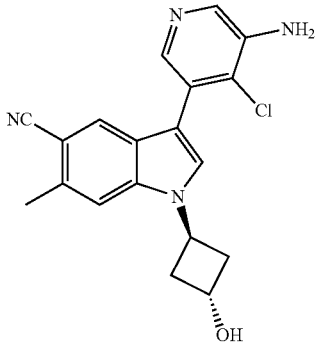 [SMILES: Cc1cc2c(cc1C#N)c(-c1cncc(N)c1Cl)cn2[C@H]1C[C@H](O)C1] | ¹H NMR (400 MHz, Methanol-d₄) δ 8.06 (s, 1H), 7.86 (s, 1H), 7.79 (s, 1H), 7.78 (s, 1H), 7.47 (s, 1H), 5.27 (p, J = 7.2 Hz, 1H), 4.59 (dt, J = 6.8, 3.3 Hz, 1H), 2.85-2.72 (m, 2H), 2.71-2.53 (m, 5H). LC-MS: [M + H]⁺ = 352.9, 354.9. |
| 14 | 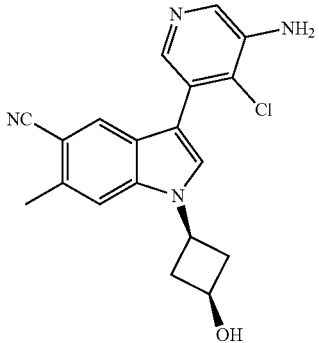 [SMILES: Cc1cc2c(cc1C#N)c(-c1cncc(N)c1Cl)cn2[C@H]1C[C@@H](O)C1] | ¹H NMR (400 MHz, Methanol-d₄) δ 8.06 (s, 1H), 7.86 (s, 1H), 7.78 (s, 1H), 7.75 (s, 1H), 7.52 (s, 1H), 4.66-4.55 (m, 1H), 4.27-4.16 (m, 1H), 3.06 (d, J = 8.4 Hz, 2H), 2.64 (s, 3H), 2.39 (d, J = 9.8 Hz, 2H). LC-MS: [M + H]⁺ = 352.9, 353.9. |
| 15 | 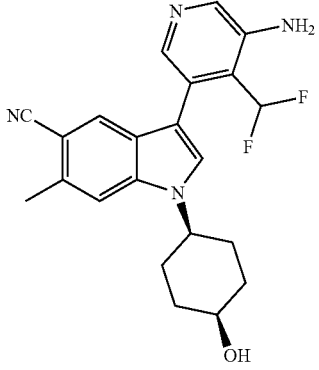 | ¹H NMR (400 MHz, Methanol-d₄) δ 8.13 (s, 1H), 7.79 (s, 1H), 7.72 (s, 1H), 7.61 (s, 1H), 7.54 (s, 1H), 6.65 (t, J = 53.5 Hz, 1H), 4.61 (p, J = 8.2 Hz, 1H), 4.22 (p, J = 7.3 Hz, 1H), 3.13-2.95 (m, 2H), 2.64 (s, 3H), 2.39 (q, J = 9.6 Hz, 2H). LC-MS: [M + H]⁺ = 369.0. |
| 16 | 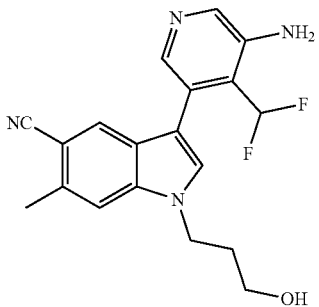 [SMILES: Cc1cc2c(cc1C#N)c(-c1cncc(N)c1C(F)F)cn2CCCO] | ¹H NMR (400 MHz. Methanol-d₄) δ 8.17 (s, 1H), 7.94 (s, 1H), 7.84 (s, 1H), 7.63 (s, 1H), 7.57 (s, 1H), 6.79 (t, J = 52.9 Hz, 1H), 4.41 (t, J = 6.9 Hz, 2H), 3.57 (t, J = 5.9 Hz, 2H), 2.66 (s, 3H), 2.20-1.93 (m, 2H). LC-MS: [M + H]⁺ = 357.3. |

TABLE 1-continued
| Ex # | Structure | ¹H NMR and LC-MS Data |
|---|---|---|
| 17 | 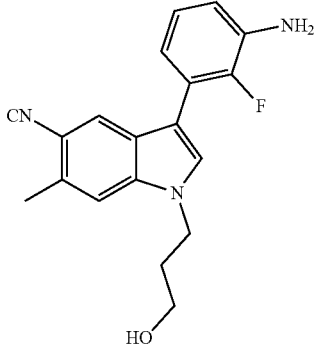 | ¹H NMR (400 MHz, Methanol-d₄) δ: 8.01 (s, 1H), 7.57 (s, 1H), 7.2 (s, 1H), 6.97-7.01 (m, 1H), 6.87-6.93 (m, 1H), 6.77-6.83 (m, 1H), 4.33-4.39 (t, 2H), 3.53-3.59 (t, 2H), 2.63 (s, 3H), 2.01-2.10 (m, 2H), LC-MS: [M + H]⁺ = 324.2. |
| 18 | 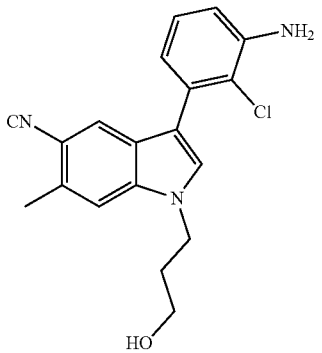 | ¹H NMR (400 MHz, Methanol-d₄) δ: 7.77 (s, 1H), 7.45-7.53 (m, 2H), 7.07-7.14 (m, 1H), 6.75-6.88 (m, 2H), 4.31-4.40 (m, 2H), 3.53-3.59 (m, 2H), 2.60 (s, 3H), 1.99-2.10 (m, 2H). LC-MS: [M + H]⁺ = 340.2. |
| 19 | 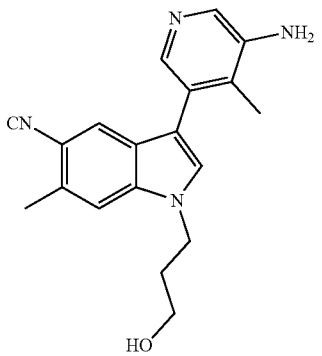 | ¹H NMR (400 MHz, Methanol-d₄) δ: 7.98 (s, 2H), 7.80 (s, 1H), 7.63 (s, 2H), 4.42 (t, J = 4.7 Hz, 2H), 3.57 (m, J = 5.9 Hz, 2H), 2.66 (s, 3H), 2.31 (s, 3H), 2.01-2.15 (m, 2H). LC-MS: [M + H]⁺ = 321.3 |
| 20 | 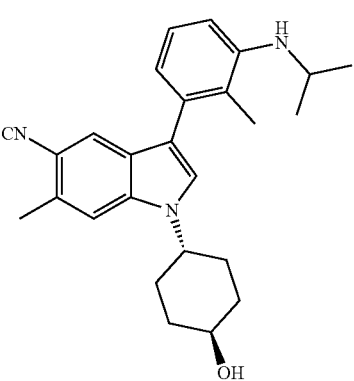 | ¹H NMR (METHANOL-d₄) δ: 7.64 (s, 1H), 7.61 (s, 1H), 7.56 (s, 1H), 7.43-7.47 (m, 2H), 7.29-7.34 (m, 1H), 4.43-4.54 (m, 1H), 3.80-3.89 (m, 1H), 3.68-3.79 (m, 1H), 2.65 (s, 3H), 2.31 (s, 3H). 2.09-2.17 (m, 4H), 1.92-2.06 (m, 2H), 1.56-1.68 (m, 2H), 1.43 (d, J = 6.5 Hz, 6H). LC-MS: [M + H]⁺ = 402.4. |

TABLE 1-continued

| Ex # | Struture | ¹H NMR and LC-MS Data |
|---|---|---|
| 21 | | ¹H NMR (400 MHz, Methanol-d₄) δ 8.22-8.05 (m, 3H), 7.96 (d, J = 15.9 Hz, 1H), 7.87 (s, 2H), 7.79-7.71 (m, 2H), 7.65 (d, J = 0.9 Hz, 1H), 2.63 (d, J = 0.8 Hz, 3H). LC-MS: [M + H]⁺ = 401.8, 402.8. |
| 22 | | ¹H NMR (400 MHz, DMSO-d₆) δ ppm 7.90 (d, 1H), 7.71 (d, 1H), 7.68 (s, 1H), 6.96 (t, 1H), 6.66 (d, 1H), 6.54 (d, 1H), 4.92 (s, 2H), 4.72 (d, 1H), 4.62-4.30 (m, 1H), 3.72-3.42 (m, 1H), 2.04-1.76 (m, 9H), 1.64-1.38 (m, 2H). LC-MS: [M + H]⁺ = 364.1. |
| 23 | | ¹H NMR (METHANOL-d₄) δ: 7.93 (d, J = 2.6 Hz, 1H), 7.85 (d, J = 1.8 Hz, 1H), 7.81 (s, 1H), 7.49 (s, 1H), 7.17-7.20 (m, 1H), 4.31-4.38 (m, 2H), 3.60 (t, J = 5.9 Hz, 2H), 2.62 (s, 3H), 2.52 (s, 3H), 1.98 (quin, J = 6.5 Hz, 2H). LC-MS: [M + H]⁺ = 321.0. |
| 24 | | ¹H NMR (METHANOL-d₄) δ: 7.44 (s, 1H), 7.40 (s, 1H), 7.02-7.07 (m, 1H), 6.80 (d, J = 7.8 Hz, 1H), 6.61 (d, J = 6.7 Hz, 1H), 4.33 (t, J = 7.2 Hz, 2H), 3.60 (t, J = 5.9 Hz, 2H), 2.61 (s, 3H), 2.29 (s, 3H), 1.99 (quin, J = 6.6 Hz, 2H), 1.91 (s, 3H). LC-MS: [M + H]⁺ = 334.0. |

TABLE 1-continued

| Ex # | Structure | ¹H NMR and LC-MS Data |
|---|---|---|
| 25 | | ¹H NMR (400 MHz, Methanol-d₄) δ: 8.08 (s, 1H), 7.72 (s, 1H), 7.48-7.51 (m, 2H), 4.33-4.39 (m, 2H), 3.58-3.62 (m, 2H), 2.62 (s, 3H), 2.36 (s, 3H), 2.18-2.22 (m, 2H). LC-MS: [M + H]⁺ = 355.0. |
| 26 | | ¹H NMR (400 MHz, Methanol-d₄) δ 7.61 (s, 1H), 7.55 (s, 1H), 7.50 (s, 1H), 7.36 (dd, J = 8.9, 4.8 Hz, 1H), 7.19 (t, J = 8.7 Hz, 1H), 4.49 (dd, J = 13.7, 10.1 Hz, 1H), 3.73 (td, J = 10.8, 5.5 Hz, 1H), 2.65 (s, 3H), 2.16 (d, J = 24.8 Hz, 7H), 1.96 (q, J = 12.2 Hz, 2H), 1.75-1.50 (m, 2H). LC-MS: [M + H]⁺ = 378.0. |
| 27 | | ¹H NMR (400 MHz, Methanol-d₄) δ 7.62 (s, 1H), 7.54 (s, 1H), 7.51 (s, 1H), 7.34 (dd, J = 9.0, 4.8 Hz, 1H), 7.18 (t, J = 8.7 Hz, 1H), 4.51 (t, J = 12.1 Hz, 1H), 4.10 (s, 1H), 2.65 (s, 3H), 2.36-2.15 (m, 5H), 1.99 (d, J = 13.7 Hz, 2H), 1.87 (q, J = 13.8 Hz, 4H). LC-MS: [M + H]⁺ = 378.0. |
| 28 | | ¹H NMR (400 MHz. Methanol-d₄) δ 7.74 (t, J = 2.0 Hz, 1H), 7.59 (d, J = 4.8 Hz, 1H), 7.53 (d, J = 4.0 Hz, 1H), 6.96-6.69 (m, 2H), 4.43 (ddt, J = 12.0, 8.3, 3.7 Hz, 1H), 3.71 (ddt, J = 11.0, 6.8, 4.0 Hz, 1H), 2.62 (s, 3H), 2.10 (tt, J = 8.4, 3.8 Hz, 4H), 1.90 (qd, J = 13.3, 12.6, 3.9 Hz, 2H), 1.71-1.50 (m, 2H). LC-MS: [M + H]⁺ = 381.2. |

TABLE 1-continued

| Ex # | Struture | ¹H NMR and LC-MS Data |
|---|---|---|
| 29 | 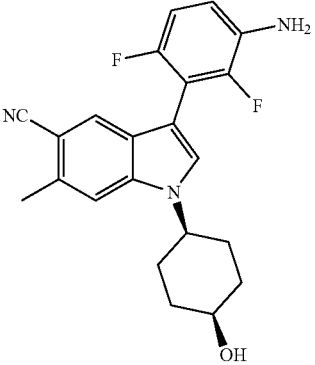 [SMILES: Cc1cc2c(cc1C#N)c(-c1c(F)ccc(N)c1F)cn2[C@H]1CC[C@@H](O)CC1] | ¹H NMR (400 MHz, Methanol-d₄) δ 7.77 (d, J = 2.4 Hz, 1H), 7.69 (s, 1H), 7.59 (s, 1H), 7.11-6.87 (m, 2H), 4.50 (t, J = 12.1 Hz, 1H), 4.09 (s, 1H), 2.65 (d, J = 4.2 Hz, 3H), 2.26 (q, J = 12.6, 11.4 Hz, 2H), 1.91 (dq, J = 39.8. 14.0 Hz, 6H). LC-MS: [M + H]⁺ = 381.2. |
| 30 | 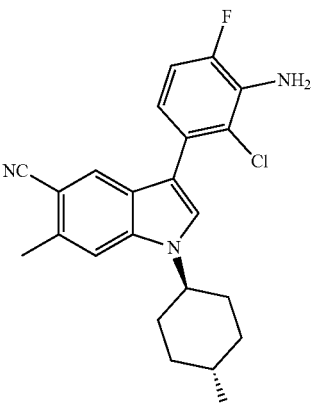 | ¹H NMR (400 MHz, Methanol-d₄) δ 7.72 (s, 1H), 7.54 (d, J = 2.6 Hz, 2H), 7.02 (dd, J = 10.6, 8.4 Hz, 1H), 6.73 (dd, J = 8.4, 5.6 Hz, 1H), 4.44 (tt, J = 12.1. 3.6 Hz, 1H), 3.73 (tt, J = 11.0, 4.0 Hz, 1H), 2.68-2.55 (m, 3H), 2.18-2.05 (m, 4H), 2.02-1.83 (m, 2H), 1.72-1.46 (m, 2H). LC-MS: [M + H]⁺ = 398.1, 399.1 |
| 31 | 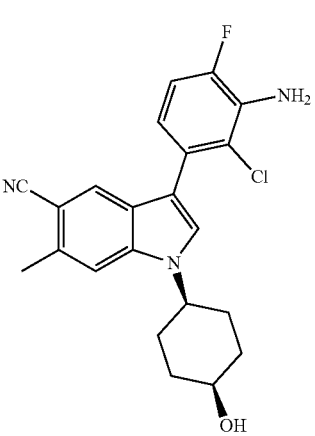 [SMILES: Cc1cc2c(cc1C#N)c(-c1ccc(F)c(N)c1Cl)cn2[C@H]1CC[C@@H](O)CC1] | ¹H NMR (400 MHz, Methanol-d₄) δ 7.74 (s, 1H), 7.56 (d, J = 8.4 Hz, 2H), 7.04 (dd, J = 10.6, 8.5 Hz, 1H), 6.81-6.69 (m, 1H), 4.46 (ddt, J = 12.1, 7.6, 3.7 Hz, 1H), 4.09 (t, J = 2.9 Hz, 1H), 2.72-2.57 (m, 3H), 2.42-1.73 (m, 8H). LC-MS: [M + H]⁺ = 398.1, 399.1 |
| 32 | 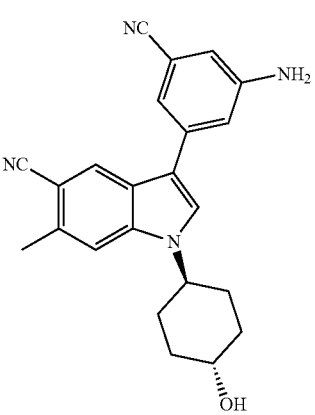 [SMILES: Cc1cc2c(cc1C#N)c(-c1cc(N)cc(C#N)c1)cn2[C@H]1CC[C@H](O)CC1] | ¹H NMR (400 MHz, Methanol-d₄) δ 8.18 (s, 1H), 7.76 (s, 1H), 7.57 (s, 1H), 7.29-7.22 (m, 1H), 7.17 (t, J = 1.5 Hz, 1H), 6.84 (dd, J = 2.2, 1.4 Hz, 1H), 4.44 (ddd, J = 11.8, 8.0, 3.8 Hz, 1H), 3.74 (ddd, J = 15.2, 10.9, 4.2 Hz, 1H), 2.70-2.57 (m, 3H), 2.17-2.0 (m, 4H), 1.97 (qd, J = 13.2, 12.7, 3.5 Hz, 2H), 1.73-1.55 (m, 2H). LC-MS: [M + H]⁺ = 371.0, 372.0. |

TABLE 1-continued

| Ex # | Structure | ¹H NMR and LC-MS Data |
|---|---|---|
| 33 | 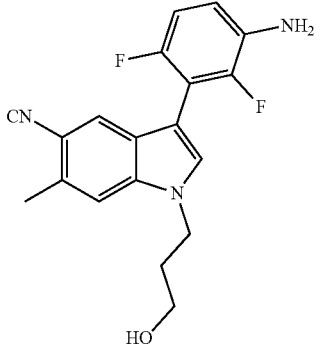 | ¹H NMR (DMSO-d6) δ: 7.69-7.79 (m, 2H), 7.66 (s, 1H), 6.87-6.99 (m, 1H), 6.69-6.82 (m, 1H), 4.62-4.74 (m, 1H), 4.28-4.37 (m, 2H), 3.38-3.43 (m, 2H), 2.59 (s, 3H), 1.92-1.98 (m, 2H). LC-MS: [M + H]⁺ = 342.2. |
| 34 | 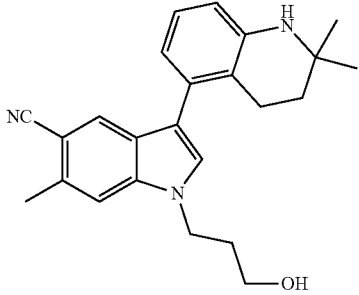 | ¹H NMR (400 MHz, Methanol-d₄) δ 7.67 (s, 1H), 7.48 (s, 1H), 7.31 (s, 1H), 6.99 (t, J = 7.7 Hz, 1H), 6.58 (dd, J = 25.2, 7.7 Hz, 2H), 4.33 (t, J = 6.9 Hz, 2H), 3.55 (t, J = 6.0 Hz, 2H), 2.62 (d, J = 4.0 Hz, 5H), 2.10-1.98 (m, 2H), 1.58 (t, J = 6.7 Hz, 2H), 1.21 (s, 6H). LC-MS: [M + H]⁺ = 374.3. 375.3. |
| 35 | 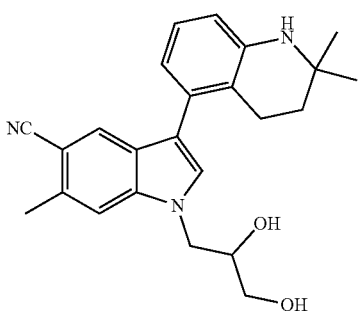 | ¹H NMR (400 MHz, Methanol-d₄) δ 7.67 (s, 1H), 7.51 (s, 1H), 7.33 (s, 1H), 6.99 (t, J = 7.7 Hz, 1H), 6.62 (d, J = 7.4 Hz, 1H), 6.56 (d, J = 8.0 Hz, 1H), 4.40 (dd, J = 14.5, 4.2 Hz, 1H), 4.19 (dd, J = 14.5, 7.2 Hz, 1H), 3.99 (dq, J = 9.8, 5.3 Hz, 1H), 3.54 (d, J = 5.4 Hz, 2H), 2.63 (d, J = 2.2 Hz, 5H), 1.59 (t, J = 6.7 Hz, 2H), 1.22 (s, 6H). LC-MS: [M + H]⁺ = 390.3. |
| 36 | 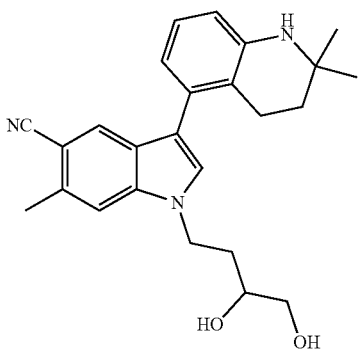 | ¹H NMR (400 MHz, Methanol-d₄) δ 7.67 (s, 1H), 7.51 (s, 1H), 7.33 (s, 1H), 6.98 (t, J = 7.7 Hz, 1H), 6.62 (d, J = 7.4 Hz, 1H), 6.55 (d, J = 8.0 Hz, 1H), 4.40 (dd, J = 14.5, 4.2 Hz, 2H), 3.44-3.55 (m, 3H), 2.62 (s, 5H), 2.12 (m, 1H), 2.08 (m, 1H), 1.59 (t, J = 6.8 Hz, 2H), 1.21 (s, 6H). LC-MS: [M + H]⁺ = 404.3 |

TABLE 1-continued

| Ex # | Structure | ¹H NMR and LC-MS Data |
|---|---|---|
| 37 | 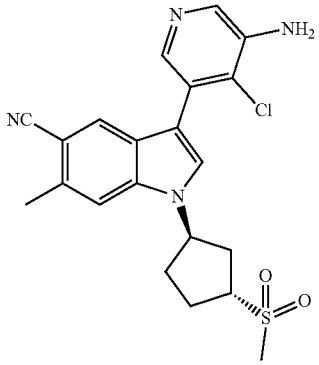 [SMILES: Cc1cc2c(cc1C#N)c(-c1cncc(N)c1Cl)cn2[C@@H]1CC[C@@H](S(C)(=O)=O)C1] | ¹H NMR (400 MHz, Methanol-d₄) δ 8.06 (s, 1H), 7.86 (s, 1H), 7.78 (s, 1H), 7.73 (s, 1H), 7.59 (s, 1H), 5.17 (p, J = 7.4 Hz, 1H), 4.08 - 3.87 (m, 1H), 3.01 (s, 3H), 2.76 (ddd, J = 13.8, 7.8. 5.4 Hz, 1H), 2.65 (s, 3H), 2.53-2.12 (m, 5H). LC-MS: [M + H]⁺ = 428.9, 430.9. |
| 38 | 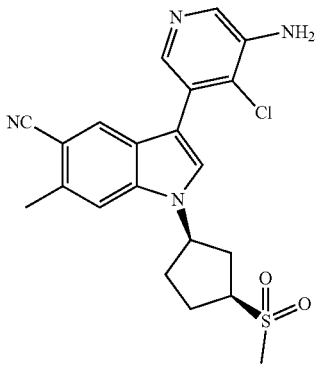 [SMILES: Cc1cc2c(cc1C#N)c(-c1cncc(N)c1Cl)cn2[C@@H]1CC[C@H](S(C)(=O)=O)C1] | ¹H NMR (400 MHz, Methanol-d₄) δ 8.05 (s, 1H), 7.85 (s, 1H), 7.80 (s, 1H), 7.78 (s, 1H), 7.65 (s, 1H), 5.15 (p, J = 8.2 Hz, 1H), 3.98-3.73 (m, 1H), 3.01 (s, 3H), 2.80 (dt, J = 13.6, 8.2 Hz, 1H), 2.65-2.62 (m, 3H), 2.50-2.12 (m, 5H). LC-MS: [M + H]⁺ = 428.9, 430.9. |
| 39 | 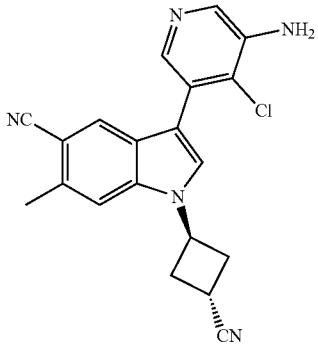 [SMILES: Cc1cc2c(cc1C#N)c(-c1cncc(N)c1Cl)cn2[C@H]1C[C@H](C#N)C1] | ¹H NMR (400 MHz, Methanol-d₄) δ 8.13-7.99 (m, 1H), 7.96-7.80 (m, 2H), 7.78 (q, J = 2.8 Hz, 1H), 7.54 (d, J = 5.1 Hz, 1H), 5.12 (s, 1H), 3.25 (s, 1H), 3.16-3.01 (m, 2H), 2.91 (t, J = 8.0 Hz, 2H), 2.64 (q, J = 3.0 Hz, 3H). LC-MS: [M + H]⁺ = 361.2, 363.1. |
| 40 | 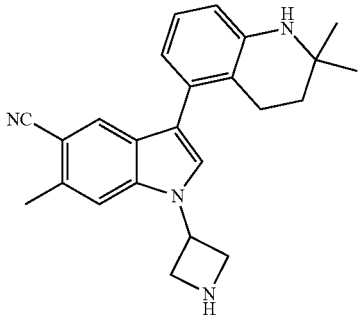 | ¹H NMR (400 MHz, Methanol-d₄) δ 7.92 (s, 1H), 7.70 (s, 1H), 7.60 (s, 1H), 7.41 (t, J = 7.8 Hz, 1H), 7.32 (d, J = 7.1 Hz, 1H), 7.16 (d, J = 7.9 Hz, 1H), 5.81 (p, J = 8.1 Hz, 1H), 4.65 (d, J = 8.1 Hz, 4H), 2.84 (t, J = 6.7 Hz, 2H), 2.65 (s, 3H), 1.89 (t, J = 6.7 Hz, 2H), 1.43 (s, 6H). LC-MS: [M + H]⁺ = 370.2. |

TABLE 1-continued
| Ex # | Struture | $^1$H NMR and LC-MS Data |
|---|---|---|
| 41 | 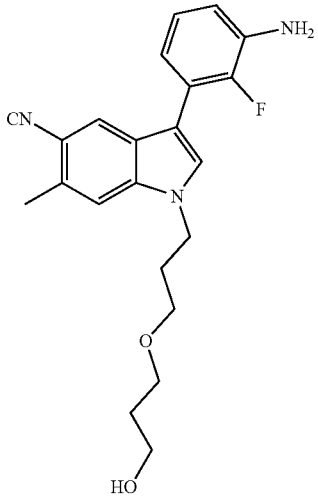 | $^1$H NMR (400 MHz, Methanol-d4) δ: 8.01 (s, 1H), 7.55 (s, 1H), 7.50 (s, 1H), 6.96-7.04 (m, 1H), 6.87-6.94 (m, 1H), 6.80 (t, J = 8.0 Hz, 1H), 4.36 (s, 2H), 3.66 (t, J = 6.4 Hz, 2H), 3.49 (t, J = 6.3 Hz, 2H), 3.33-3.39 (m, 2H), 2.64 (s, 3H), 2.04-2.15 (m, 2H), 1.76-1.87 (m, 2H). LC-MS: [M + H]$^+$ = 382.2. |
| 42 | 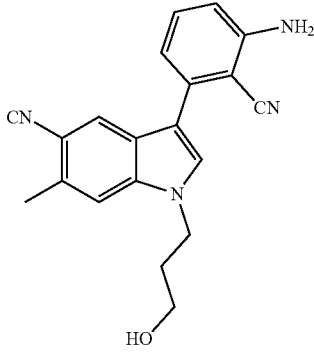 | $^1$H NMR (400 MHz, Methanol-d$_4$) δ: 7.95 (s, 1H), 7.68 (s, 1H), 7.55 (s, 1H), 7.43-7.44 (m, 1H), 6.73-6.88 (m, 2H), 4.37 (m, 2H), 3.57 (m, 2H), 2.64 (s, 3H), 2.06 (m, 2H). LC-MS: [M + H]$^+$ = 331.2. |
| 43 | 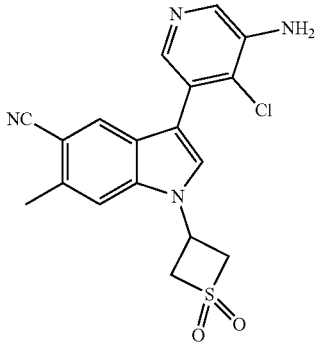 [SMILES: Cc1cc2c(cc1C#N)c(-c1cncc(N)c1Cl)cn2C1CS(=O)(=O)C1] | $^1$H NMR (400 MHz, CDCl$_3$) δ: 8.17 (s, 1H), 8.04 (s, 1H), 7.90 (s, 1H), 7.70 (s, 1H), 7.35 (s, 1H), 5.41-5.38 (m, 1H), 4.92-4.86 (m, 2H), 4.63-4.58 (m, 2H), 4.25 (brs, 2H), 2.69 (s, 3H). LC-MS: [M + H]$^+$ = 387.0. |
| 44 | 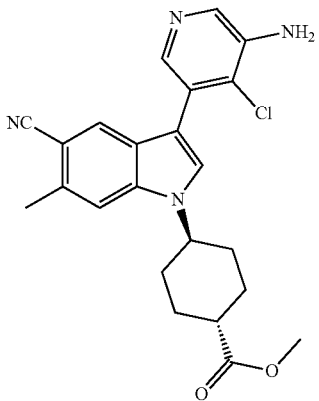 | $^1$H NMR (400 MHz, Methanol-d$_4$) δ 8.05 (s, 1H), 7.84 (s, 1H), 7.77 (s, 1H), 7.71 (s, 1H), 7.60 (s, 1H), 4.49 (t, J = 12.0 Hz, 1H), 3.70 (s, 3H), 2.65 (s, 3H), 2.56-2.42 (m, 1H), 2.19 (d, J = 11.8 Hz, 4H), 2.04-1.86 (m, 2H), 1.86-1.65 (m, 2H). LC-MS: [M + H]$^+$ = 422.2, 424.2. |

TABLE 1-continued
| Ex # | Structure | ¹H NMR and LC-MS Data |
|---|---|---|
| 45 | 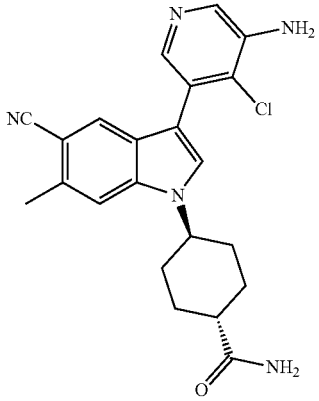 [SMILES: Cc1cc2c(cc1C#N)c(-c1cncc(N)c1Cl)cn2[C@H]1CC[C@H](C(N)=O)CC1] | ¹H NMR (400 MHz, Methanol-$d_4$) δ 8.05 (s, 1H), 7.84 (s, 1H), 7.77 (s, 1H), 7.70 (s, 1H), 7.61 (s, 1H), 4.50 (ddd, J = 11.7, 7.9, 3.8 Hz, 1H), 2.65 (s, 3H), 2.41 (tt, J = 11.9, 3.6 Hz, 1H), 2.28-2.15 (m, 2H), 2.15-2.05 (m, 2H), 2.05-1.71 (m, 4H). LC-MS: [M + H]⁺ = 407.1, 409.1 |
| 46 | 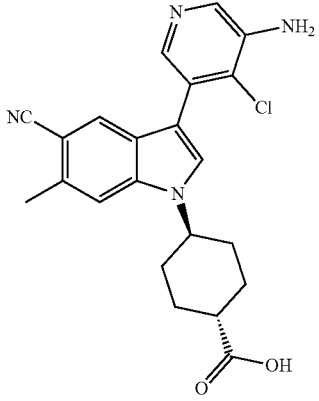 [SMILES: Cc1cc2c(cc1C#N)c(-c1cncc(N)c1Cl)cn2[C@H]1CC[C@H](C(=O)O)CC1] | ¹H NMR (400 MHz, Methanol-$d_4$) δ 8.04 (s, 1H), 7.85 (s, 1H), 7.77 (s, 1H), 7.72 (s, 1H), 7.62 (s, 1H), 4.57-4.36 (m, 1H), 2.74-2.55 (m, 3H), 2.31 (dd, J = 14.0, 10.7 Hz, 1H), 2.21-2.09 (m, 4H), 1.99-1.86 (m, 2H), 1.86-1.67 (m, 2H). LC-MS: [M + H]⁺ = 408.9, 410.9. |
| 47 | 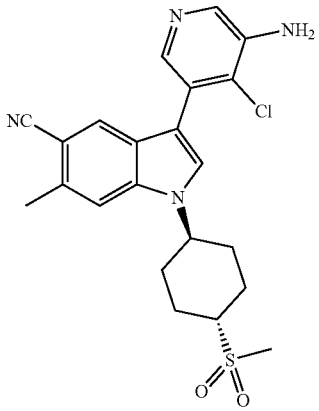 [SMILES: Cc1cc2c(cc1C#N)c(-c1cncc(N)c1Cl)cn2[C@H]1CC[C@H](S(C)(=O)=O)CC1] | 1H NMR (400 MHz, Methanol-$d_4$) δ 8.04 (s, 1H), 7.83 (s, 1H), 7.76 (s, 1H), 7.69 (s, 1H), 7.62 (s, 1H), 4.55 (tt, J = 11.8, 3.8 Hz, 1H), 3.23 (tt, J = 11.9, 3.6 Hz, 1H), 2.97 (s, 3H), 2.63 (s, 3H), 2.40 (dt, J = 12.4, 2.7 Hz, 2H), 2.32-2.21 (m, 2H), 2.09-1.78 (m, 4H). LC-MS: [M + H]⁺ = 442.8, 444.8. |

TABLE 1-continued

| Ex # | Struture | ¹H NMR and LC-MS Data |
|---|---|---|
| 48 | | ¹H NMR (400 MHz, Methanol-d₄) δ 8.03 (s, 1H), 7.83 (s, 1H), 7.78 (s, 1H), 7.65 (s, 1H), 7.63 (s, 1H), 4.60 (m, 1H), 3.35 (s, 1H), 3.04 (s, 3H), 2.73-2.58 (s, 3H), 2.60-2.47 (m, 4H), 2.14 (ddd, J = 15.7, 9.7, 6.0 Hz, 2H), 2.01 (dt, J = 8.5, 4.8 Hz, 2H). LC-MS: [M + H]⁺ = 442.8, 444.8. |
| 49 | | ¹H NMR (400 MHz, Methanol-d₄) δ 8.06 (s, 1H), 8.84 (s, 1H), 7.79 (s, 1H), 7.75 (s, 1H), 7.66 (s, 1H), 4.89 (m, 1H), 3.54 (t, J = 2.64 Hz, 2H), 3.31 (s, 3H), 3.23 (d, J = 2.64 Hz, 2H), 2.76-2.62 (m, 5H), 2.19 (d, J = 2.64 Hz, 2H). LC-MS: [M + H]⁺ = 414.9, 416.9. |
| 50 | | ¹H NMR (400 MHz, Methanol-d₄) δ 8.05 (s, 1H), 7.83 (s, 1H), 7.78 (s, 1H), 7.72 (s, 1H), 7.65 (s, 1H), 4.71 (ddt, J = 11.8, 7.7, 4.1 Hz, 1H), 4.34 (d, J = 13.4 Hz, 2H), 3.72 (s, 3H), 3.21-2.98 (m, 2H), 2.65 (s, 3H), 2.16-1.91 (m, 4H). LC-MS: [M + H]⁺ = 423.9, 425.9. |
| 51 | | ¹H NMR (400 MHz, Methanol-d₄) δ 8.05 (s, 1H), 7.84 (s, 1H), 7.77 (s, 1H), 7.75 (s, 1H), 7.58 (s, 1H), 4.50 (td, J = 11.0, 5.7 Hz, 1H), 2.65 (s, 3H), 2.02 (m, 4H), 1.91-1.77 (m, 4H), 1.40 (s, 3H). LC-MS: [M + H]⁺ = 394.2, 396.2. |

TABLE 1-continued
| Ex # | Structure | ¹H NMR and LC-MS Data |
|---|---|---|
| 52 | 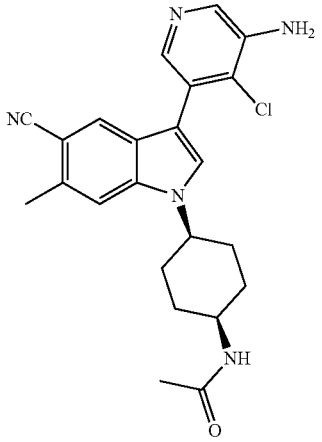 [SMILES: CC(=O)N[C@H]1CC[C@@H](n2cc(-c3cncc(N)c3Cl)c3cc(C#N)c(C)cc32)CC1] | ¹H NMR (400 MHz, Methanol-d$_4$) δ 8.06 (s, 1H), 7.86 (s, 1H), 7.79 (s, 1H), 7.77 (s, 1H), 7.61 (s, 1H), 4.65-4.41 (m, 1H), 4.25-4.04 (m, 1H), 2.65 (s, 3H), 2.23-2.05 (m, 2H), 2.02 (s, 3H), 2.01-1.85 (m, 6H). LC-MS: [M + H]$^+$ = 422.1, 423.1. |
| 53 | 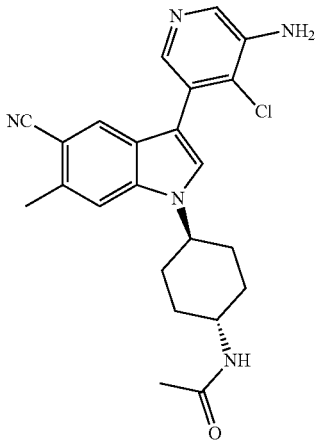 [SMILES: CC(=O)N[C@H]1CC[C@H](n2cc(-c3cncc(N)c3Cl)c3cc(C#N)c(C)cc32)CC1] | ¹H NMR (400 MHz, Methanol-d$_4$) δ 8.05 (s, 1H), 7.85 (s, 1H), 7.78 (s, 1H), 7.74 (s, 1H), 7.60 (s, 1H), 4.60-4.34 (m, 1H), 3.87-3.70 (m, 1H), 2.65 (s, 3H), 2.24-1.97 (m, 6H), 1.95 (s, 3H), 1.59 (dt, J = 13.5, 10.4 Hz, 2H). LC-MS: [M + H]$^+$ = 422.1, 423.1 |
| 54 | 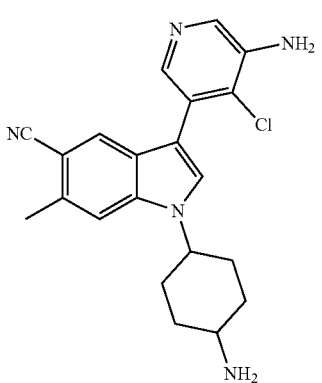 [SMILES: Cc1cc2c(cc1C#N)c(-c1cncc(N)c1Cl)cn2C1CCC(N)CC1] | ¹H NMR (400 MHz, Methanol-d$_4$) δ 8.05 (s, 1H), 7.86 (s, 1H), 7.84 (s, 1H), 7.78 (s, 1H), 7.60 (s, 1H), 4.49 (td, J = 9.8, 8.0, 5.9 Hz, 1H), 3.26 (q, J = 3.4 Hz, 1H), 2.69 (s, 3H), 2.32-2.16 (m, 2H), 1.91 (dd, J = 14.9, 3.2 Hz, 6H). LC-MS: [M + H]$^+$ = 380.1, 381.1. |

TABLE 1-continued
| Ex # | Struture | ¹H NMR and LC-MS Data |
|---|---|---|
| 55 | 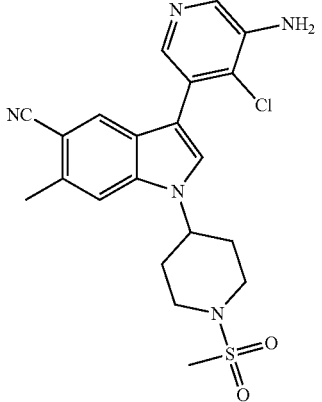 [SMILES: Cc1cc2c(cc1C#N)c(-c1cncc(N)c1Cl)cn2C1CCN(S(C)(=O)=O)CC1] | ¹HNMR (400 MHz, CDCl₃): δ ppm 8.14 (s, 1H), 8.05 (s, 1H), 7.90 (s, 1H), 7.43 (s, 1H), 7.29 (s, 1H), 4.43-4.38 (m, 1H), 4.23 (brs, 2H), 4.10-4.07 (m, 2H), 3.01-2.94 (m, 2H), 2.90 (s, 3H), 2.67 (s, 3H), 2.27-2.19 (m, 4H). LC-MS: [M + H]⁺ = 444.1. |
| 56 | 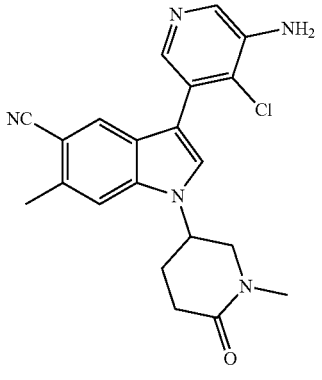 | ¹HNMR (400 MHz, CDCl₃) δ ppm 8.17 (s, 1H), 8.06 (s, 1H), 7.93 (s, 1H), 7.42 (s, 1H), 7.37 (s, 1H), 4.90 (m, 1H), 4.25 (s, 2H), 3.80 (m, 1H) 3.67 (m, 1H), 3.06 (s, 3H), 2.72 (s, 3H), 2.62-2.72 (m, 2H) 2.30-2.52 (m, 2H). LC-MS: [M + H]⁺ = 394.1. |
| 57 | 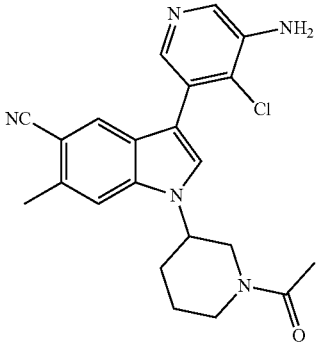 [SMILES: CC(=O)N1CCCC(n2cc(-c3cncc(N)c3Cl)c3cc(C#N)c(C)cc32)C1] | ¹HNMR (400 MHz. CDCl₃) δ ppm 8.17 (s, 1H), 8.06 (s, 1H), 7.93 (s, 1H) 7.41 (s, 1H), 7.37 (s, 1H), 4.90 (brs, 1H), 4.25 (s, 2H), 3.75-3.90 (m, 2H), 3.60-3.71 (m, 2H), 3.05 (s, 3H), 2.55-2.80 9m, 5H), 2.30-2.55 (m, 2H). LC-MS: [M + H]⁺ = 408.1. |
| 58 | 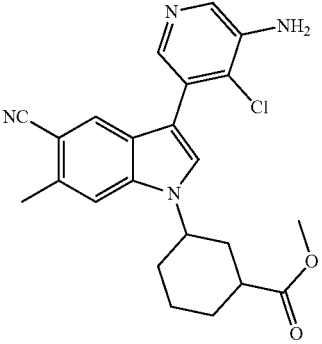 [SMILES: COC(=O)C1CCCC(n2cc(-c3cncc(N)c3Cl)c3cc(C#N)c(C)cc32)C1] | ¹H NMR (400 MHz, Methanol-d₄) δ 8.05 (s, 1H), 7.93-7.76 (m, 2H), 7.71 (s, 1H), 7.60 (s, 1H), 4.79-4.31 (m, 1H), 3.91-3.56 (m, 3H), 3.25-2.98 (m, 1H), 2.65 (d, J = 5.8 Hz, 3H), 2.57-2.32 (m, 1H), 2.31-2.06 (m, 2H), 2.05-1.91 (m, 2H), 1.79-1.36 (m, 3H). LC-MS: [M + H]⁺ = 423.2, 425.2. |

TABLE 1-continued

| Ex # | Struture | ¹H NMR and LC-MS Data |
|---|---|---|
| 59 | | ¹H NMR (400 MHz, Methanol-d₄) δ 8.05 (s, 1H), 7.85 (s, 1H), 7.78 (s, 1H), 7.73 (s, 1H), 7.60 (s, 1H), 4.54 (tt, J = 12.0, 3.8 Hz, 1H), 2.67-2.64 (m, 3H), 2.59 (dt, J = 12.2, 3.5 Hz, 1H), 2.23-1.85 (m, 6H), 1.78-1.61 (m, 1H), 1.62-1.45 (m, 1H). LC-MS: [M + H]⁺ = 407.2, 409.3. |
| 60 | | ¹H NMR (400 MHz, Methanol-d₄) δ 8.05 (s, 1H), 7.85 (s, 1H), 7.80 (s, 1H), 7.63 (d, J = 7.3 Hz, 2H), 5.30 (q, J = 6.0 Hz, 1H), 3.99 (dt, J = 11.5, 5.7 Hz, 1H), 3.72 (d, J = 7.1 Hz, 4H), 3.69-3.56 (m, 2H), 2.73-2.60 (m, 3H), 2.52 (dp, J = 13.8, 6.9 Hz, 1H), 2.41 (dt, J = 12.8, 6.5 Hz, 1H). LC-MS: [M + H]⁺ = 409.2, 411.2. |
| 61 | | ¹H NMR (400 MHz, Methanol-d₄) δ 8.06 (s, 1H), 7.86 (s, 1H), 7.81 (s, 1H), 7.78 (s, 1H), 7.65 (s, 1H), 5.43-5.26 (m, 1H), 3.91 (dd, J = 10.6, 6.7 Hz, 1H), 3.74-3.62 (m, 2H), 3.57 (ddd, J = 10.1, 8.2, 6.4 Hz, 1H), 2.97 (s, 3H), 2.66 (s, 3H), 2.65-2.56 (m, 1H), 2.46 (tt, J = 13.5, 6.5 Hz, 1H). ). LC-MS: [M + H]⁺ = 429.8, 431.8. |
| 62 | | ¹H NMR (400 MHz, Methanol-d₄) δ 8.05 (s, 1H), 7.85 (s, 1H), 7.77 (s, 1H), 7.72 (s, 1H), 7.56 (s, 1H), 5.23-5.00 (m, 1H), 4.58-4.30 (m, 1H), 2.65 (s, 3H), 2.44 (tdd, J = 13.4, 9.0, 4.9 Hz, 1H), 2.38-2.27 (m, 2H), 2.18 (ddd, J = 13.8, 8.1, 5.5 Hz, 1H), 2.11-1.99 (m, 1H), 1.97 (s, 3H), 1.72 (dtd, J = 13.1, 8.4, 6.7 Hz, 1H). LC-MS: [M + H]⁺ = 407.9, 408.9. |

TABLE 1-continued

| Ex # | Struture | ¹H NMR and LC-MS Data |
|---|---|---|
| 63 | | ¹H NMR (400 MHz, Methanol-d$_4$) δ 8.05 (s, 1H), 7.85 (s, 1H), 7.78 (s, 1H), 7.72 (s, 1H), 7.57 (s, 1H), 5.16 (p, J = 7.7 Hz, 1H), 4.22-4.00 (m, 1H), 2.98 (s, 3H), 2.70-2.60 (m, 3H), 2.53-2.25 (m, 4H), 2.12-1.99 (m, 1H), 1.91-1.75 (m, 1H). LC-MS: [M + H]⁺ = 443.8, 445.8. |
| 64 | | ¹H NMR (400 MHz, Methanol-d$_4$) δ 8.05 (s, 1H), 7.86 (s, 1H), 7.78 (d, J = 2.9 Hz, 2H), 7.60 (s, 1H), 5.04 (p, J = 8.1 Hz, 1H), 4.10-3.86 (m, 1H), 2.98 (s, 3H), 2.74 (dt, J = 13.9, 7.3 Hz, 1H), 2.68-2.58 (m, 3H), 2.35-1.96 (m, 5H). LC-MS: [M + H]⁺ = 443.8, 445.8. |
| 65 | | ¹H NMR (400 MHz, Methanol-d$_4$) δ 8.05 (s, 1H), 7.86 (s, 1H), 7.78 (d, J = 2.7 Hz, 2H), 7.60 (s, 1H), 5.04 (p, J = 8.1 Hz, 1H), 4.07-3.86 (m, 1H), 2.98 (s, 3H), 2.74 (dt, J = 14.0, 7.3 Hz, 1H), 2.69-2.59 (m, 3H), 2.42-1.89 (m, 5H). LC-MS: [M + H]⁺ = 443.8, 445.8. |
| 66 | | ¹H NMR (400 MHz, Methanol-d$_4$) δ 8.06 (s, 1H), 7.86 (s, 1H), 7.78 (s, 1H), 7.72 (s, 1H), 7.57 (s, 1H), 5.16 (p, J = 7.7 Hz, 1H), 4.25-3.97 (m, 1H), 2.98 (s, 3H), 2.65 (s, 3H), 2.55-2.25 (m, 4H), 2.12-1.99 (m, 1H), 1.89-1.73 (m, 1H). LC-MS: [M + H]⁺ = 443.8, 445.8. |

TABLE 1-continued

| Ex # | Struture | ¹H NMR and LC-MS Data |
|---|---|---|
| 67 | | ¹H NMR (400 MHz, Methanol-d₄) δ 8.05 (s, 1H), 7.85 (s, 1H), 7.78 (s, 1H), 7.70 (s, 1H), 7.59 (s, 1H), 5.09 (dt, J = 21.8, 7.0 Hz, 1H), 3.71 (dd, J = 6.4, 1.8 Hz, 3H), 3.17-3.01 (m, 1H), 2.63-1.92 (m, 6H). LC-MS: [M + H]⁺ = 408.1, 410.0. |
| 68 | | ¹H NMR (400 MHz, Methanol-d₄) δ 8.05 (d, J = 2.1 Hz, 1H), 7.91-7.66 (m, 3H), 7.60 (d, J = 5.8 Hz, 1H), 5.10 (dp, J = 36.8, 7.5 Hz, 1H), 3.21-2.91 (m, 1H), 2.64 (s, 3H), 2.61-1.89 (m, 6H). LC-MS: [M + H]⁺ = 393.1, 395.0. |
| 69 | | ¹H NMR (400 MHz, Methanol-d₄) δ 8.17-8.00 (m, 1H), 7.82 (d, J = 22.6 Hz, 2H), 7.68 (d, J = 15.6 Hz, 1H), 7.62 (s, 1H), 5.51-5.18 (m, 1H), 4.10 (ddd, J = 56.0, 11.9, 6.9 Hz, 1H), 3.95-3.56 (m, 3H), 2.77-2.33 (m, 5H), 2.12 (d, J = 11.1 Hz, 3H). LC-MS: [M + H]⁺ = 393.9, 395.9. |
| 70 | | ¹H NMR (400 MHz, Methanol-d₄) δ 8.05 (s, 1H), 7.85 (s, 1H), 7.81 (s, 1H), 7.63 (s, 1H), 7.60 (s, 1H), 5.45-5.21 (m, 1H), 3.93 (dd, J = 11.1, 6.5 Hz, 1H), 3.75 (dd, J = 11.1, 4.6 Hz, 1H), 3.66-3.50 (m, 2H), 2.76 (s, 3H), 2.65 (s, 3H), 2.61-2.48 (m, 1H), 2.42 (dt, J = 12.9, 6.4 Hz, 1H). LC-MS: [M + H]⁺ = 408.3, 410.2. |

TABLE 1-continued

| Ex # | Struture | ¹H NMR and LC-MS Data |
|---|---|---|
| 71 | | ¹H NMR (400 MHz, Methanol-d₄) δ 8.06 (d, J = 1.2 Hz, 1H), 7.89-7.82 (m, 2H), 7.78 (s, 1H), 7.58 (d, J = 41.0 Hz, 1H), 5.05 (tt, J = 9.3, 7.7 Hz, 1H), 3.26-3.00 (m, 1H), 2.96-2.68 (m, 4H), 2.64 (d, J = 2.9 Hz, 3H). LC-MS: [M + H]⁺ = 379.1, 381.1. |
| 72 | | ¹HNMR (400 MHz, Methanol-d₄) δ 8.10-7.85 (m, 3H), 7.78 (s, 1H), 7.45 (d, J = 9.4 Hz, 1H), 5.28-4.92 (m, 2H), 3.13 (d, J = 28.5 Hz, 3H), 3.07-2.67 (m, 4H), 2.62 (s, 3H), 2.13 (d, J = 3.4 Hz, 3H). LC-MS: [M + H]⁺ = 407.2, 409.3. |
| 73 | | ¹H NMR (400 MHz, Methanol-d₄) δ 8.07 (s, 1H), 7.86 (s, 1H), 7.80 (s, 1H), 7.78 (s, 1H), 7.67 (s, 1H), 5.21 (p, J = 8.6 Hz, 1H), 4.10-3.81 (m, 1H), 3.02 (tt, J = 8.7, 2.0 Hz, 4H), 2.64 (s, 3H). LC-MS: [M + H]⁺ = 414.8, 416.8. |
| 74 | | ¹H NMR (400 MHz, Methanol-d₄) δ 8.07 (s, 1H), 7.90 (s, 1H), 7.87 (s, 1H), 7.77 (s, 1H), 7.51 (s, 1H), 5.38 (p, J = 8.4 Hz, 1H), 4.15-3.96 (m, 1H), 3.22-3.12 (m, 2H), 3.12-3.05 (m, 2H), 3.03 (s, 3H). LC-MS: [M + H]⁺ = 414.8, 416.8. |

TABLE 1-continued

| Ex # | Struture | ¹H NMR and LC-MS Data |
|---|---|---|
| 75 | | ¹H NMR (400 MHz, CDCl$_3$) δ: 8.13 (s, 1H), 8.04 (s, 1H), 7.90 (s, 1H), 7.40 (s, 1H), 7.32 (s, 1H), 4.93 (d, J = 14.0 Hz, 1H), 4.53-4.47 (m, 1H), 4.23 (brs, 2H), 4.07 (d, J = 13.6 Hz, 1H), 3.34 (t, J = 12.8 Hz, 1H), 2.78 (t, J = 11.6 Hz, 1H), 2.68 (s, 3H), 2.23-2.15 (m, 2H), 2.19 (s, 3H), 2.02-1.93 (m, 2H). LC-MS: [M + H]$^+$ = 408.1. |
| 76 | | ¹H NMR (400 MHz, CDCl$_3$): δ ppm 8.17 (s, 1H), 8.08 (s, 1H), 7.91 (s, 1H), 7.42 (s, 1H), 7.30 (s, 1H), 4.95 (s, 2H), 4.81-4.73 (m, 1H), 4.78 (s, 2H), 4.26 (brs, 2H), 3.10-3.05 (m, 2H), 2.74-2.68 (m, 2H), 2.73 (s, 3H). LC-MS: [M + H]$^+$ = 379.1. |
| 77 | | ¹H NMR (400 MHz, Methanol-d$_4$) δ 8.24-8.17 (m, 2H), 8.11 (s, 1H), 7.96-7.91 (m, 4H), 7.88 (s, 1H), 7.71 (t, J = 0.8 Hz, 1H), 3.22 (s, 3H), 2.64 (d, J = 0.8 Hz, 3H). LC-MS: [M + H]$^+$ = 437.2, 439.2 |
| 78 | | ¹HNMR (400 MHz, Methanol-d$_4$) δ 9.12 (d, J = 2.4 Hz, 1H), 8.44 (dd, J = 8.4, 2.6 Hz, 1H), 8.33 (d, J = 8.4 Hz, 1H), 8.13 (s, 1H), 7.99 (s, 1H), 7.94 (s, 1H), 7.90 (s, 1H), 7.75 (s, 1H), 2.66 (s, 3H), 2.21 (s, 3H). LC-MS: [M + H]$^+$ = 437.8, 439.7. |

TABLE 1-continued
| Ex # | Struture | ¹H NMR and LC-MS Data |
|---|---|---|
| 79 | 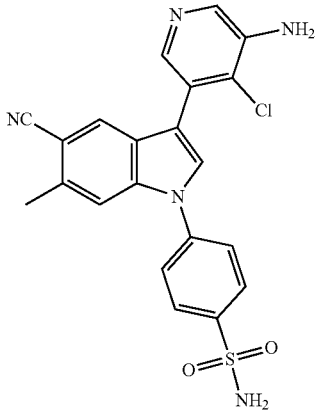 [SMILES: Cc1cc2c(cc1C#N)c(-c1cncc(N)c1Cl)cn2-c1ccc(S(N)(=O)=O)cc1] | ¹H-NMR (400 MHz, DMSO-d$_6$) δ ppm 8.15 (s, 2H), 8.06 (s, 1H), 8.04 (s, 1H), 8.00 (s, 1H), 7.97 (s, 1H), 7.94 (s, 1H), 7.91 (s, 1H), 7.77 (s, 1H), 7.56 (s, 2H), 6.01 (br s, 2H), 2.59 (s, 3H). LC-MS: [M + H]⁺ = 437.9. |
| 80 | 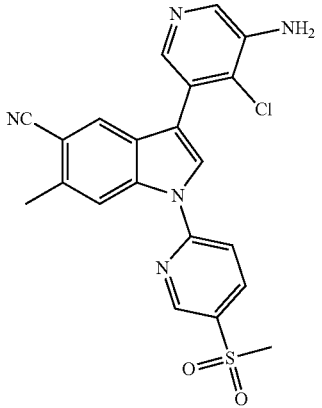 [SMILES: Cc1cc2c(cc1C#N)c(-c1cncc(N)c1Cl)cn2-c1ccc(S(C)(=O)=O)cn1] | ¹HNMR: (400 MHz, DMSO-d$_6$) δ ppm 9.12 (d, J = 2.26 Hz, 1H) 8.70 (s, 1H) 8.42-8.60 (m, 2H) 8.12-8.27 (m, 2H) 7.91 (d, J = 14.31 Hz, 2H) 5.75-5.93 (m, 2H) 3.40 (s, 3H) 3.33 (s, 6H) 2.64 (s, 3H). LC-MS: [M + H]⁺ = 438.1. |
| 81 | 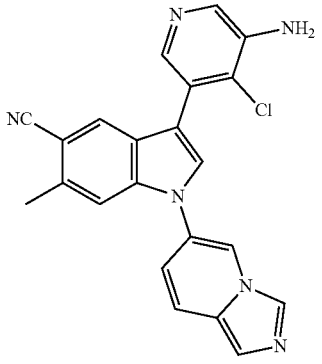 [SMILES: Cc1cc2c(cc1C#N)c(-c1cncc(N)c1Cl)cn2-c1ccc2cncn2c1] | ¹HNMR (400 MHz, DMSO-d$_6$) δ ppm 8.87 (s, 1H), 8.49 (s, 1H), 8.13 (s, 1H), 8.05 (s, 1H), 7.93 (s, 1H), 7.92 (s, 1H), 7.81 (d, 1H), 7.71 (s, 1H), 7.54 (s, 1H), 7.10 (dd, 1H), 5.81 (brs, 2H), 2.58 (s, 3H). LC-MS: [M + H]⁺ = 398.9. |
| 82 | 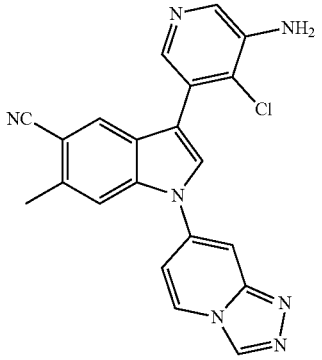 [SMILES: Cc1cc2c(cc1C#N)c(-c1cncc(N)c1Cl)cn2-c1ccn2cnnc2c1] | ¹H NMR (400 MHz, DMSO-d$_6$) δ 9.22 (d, J = 7.3 Hz, 1H), 8.64 (s, 1H), 8.26 (d, J = 2.3 Hz, 1H), 8.21 (s, 1H), 8.15 (s, 1H), 7.95 (d, J = 1.7 Hz, 2H), 7.89 (s, 1H), 7.65 (dd, J = 7.3, 2.4 Hz, 1H), 5.83 (s, 2H), 2.61 (s, 3H). LC-MS: [M + H]⁺ = 399.8, 401.8. |

TABLE 1-continued

| Ex # | Struture | ¹H NMR and LC-MS Data |
|---|---|---|
| 83 | | ¹H-NMR (400 MHz, DMSO-d$_6$) δ ppm 8.58 (d, 1H), 8.51 (s, 1H), 8.13 (s, 1H), 8.06 (s, 1H), 7.91-7.94 (m, 3H), 7.72 (s, 1H), 7.50 (s, 1H), 7.05 (dd, 1H), 5.81 (br s, 2H), 2.59 (s, 3H). LC-MS: [M + H]$^+$ = 398.9. |
| 84 | | ¹H NMR (400 MHz, Methanol-d$_4$) δ 8.12 (d, J = 2.9 Hz, 1H), 8.09 (s, 1H), 7.90 (s, 1H), 7.85 (s, 1H), 7.78 (dd, J = 9.6, 2.9 Hz, 1H), 7.70 (s, 1H), 7.45 (s, 1H), 6.73 (d, J = 9.6 Hz, 1H), 3.67 (s, 3H), 2.62 (s, 3H). LC-MS: [M + H]$^+$ = 389.2, 391.1. |
| 85 | | ¹H NMR (400 MHz, DMSO-d$_6$) δ ppm 8.14 (s, 1H), 8.06 (s, 1H), 7.97 (d, J = 7.6 Hz, 1H), 7.90-7.89 (m, 2H), 7.83 (s, 1H), 6.73-6.72 (m, 1H), 6.70 (s, 1H), 5.80 (s, 2H), 3.51 (s, 3H), 2.60 (s, 3H). LC-MS: [M + H]$^+$ = 389.9. |
| 86 | | ¹HNMR (400 MHz, DMSO-d$_6$) δ ppm 9.36 (d, 1H), 9.11 (dd, 1H), 8.14 (s, 1H), 8.09 (s, 1H), 8.04 (dd, 1H), 7.95 (s, 1H), 7.93 (s, 1H), 7.77 (s, 1H), 7.73 (dd, 1H), 5.82 (br s, 2H), 2.58 (s, 3H). LC-MS: [M + H]$^+$ = 400.9. |

TABLE 1-continued
| Ex # | Structure | ¹H NMR and LC-MS Data |
|---|---|---|
| 87 | 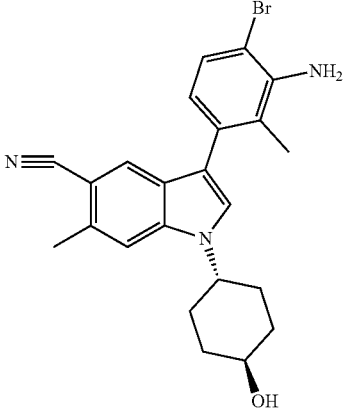 [SMILES: Cc1cc2c(cc1C#N)c(-c1ccc(Br)c(N)c1C)cn2[C@H]1CC[C@H](O)CC1] | ¹HNMR (METHANOL-d₄) δ: 7.54 (s, 1H), 7.39 (s, 1H), 7.34 (s, 1H), 7.27 (d, J = 8.4 Hz, 1H), 6.71 (d, J = 8.6 Hz, 1H), 4.40-4.50 (m, 1H), 3.66-3.79 (m, 1H), 2.63 (s, 3H), 2.11 (br s, 4H), 1.91-2.02 (m, 2H), 1.89 (s, 3H), 1.55-1.69 (m, 2H). LC-MS: [M + H]⁺ = 439.9. |
| 88 | 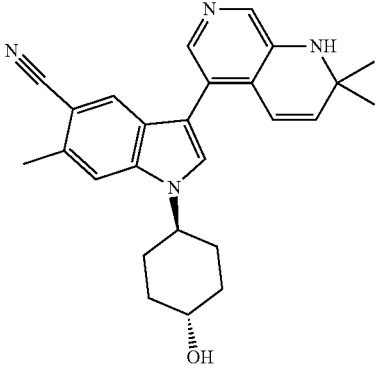 | ¹H-NMR (400 MHz, DMSO-d₆) δ ppm 7.77 (d, 2H), 7.69 (d, 3H), 6.25 (s, 1H), 6.14 (d, 1H), 5.68 (dd, 1H), 4.73 (s, 1H), 4.47 (s, 1H), 3.58 (s, 1H), 2.59 (s, 3H), 1.96 (d, 6H), 1.49 (d, 2H), 1.31 (s, 6H). LC-MS: [M + H]⁺ = 413.30. |
| 89 | 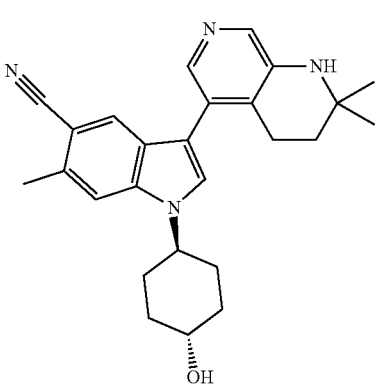 [SMILES: Cc1cc2c(cc1C#N)c(-c1cncc3c1CCC(C)(C)N3)cn2[C@H]1CC[C@H](O)CC1] | ¹H-NMR (400 MHz, DMSO-d₆) δ ppm 7.82-7.76 (m, 3H), 7.75 (s, 1H), 7.69 (s, 1H), 5.97 (s, 1H), 4.75 (s, 1H), 4.47 (s, 1H), 3.58 (s, 1H), 2.65-2.56 (m, 5H), 1.94 (t, 6H), 1.59-1.41 (m, 4H), 1.19 (s, 6H). LC-MS: [M + H]⁺ = 415.4. |
| 90 | 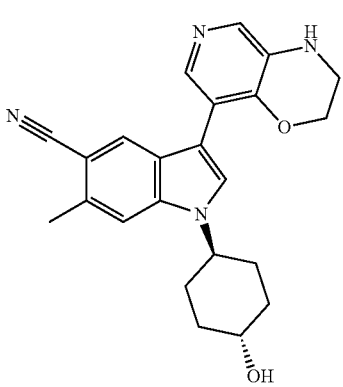 [SMILES: Cc1cc2c(cc1C#N)c(-c1cncc3c1OCCN3)cn2[C@H]1CC[C@H](O)CC1] | ¹HNMR (400 MHz, DMSO-d₆) δ ppm 7.92 (s, 1H), 7.85 (s, 1H), 7.80 (s, 1H), 7.78 (s, 1H), 7.73 (s, 1H), 6.05 (s, 1H), 4.73 (d, 1H), 4.48-4.40 (m, 1H), 4.25 (t, 2H), 3.75-3.48 (m, 1H), 3.47-3.34 (m, 2H), 2.58 (s, 3H), 2.08-1.75 (m, 6H), 1.66-1.27 (m, 2H). LC-MS: [M + H]⁺ = 389.3. |

TABLE 1-continued
| Ex # | Struture | ¹H NMR and LC-MS Data |
|---|---|---|
| 91 | 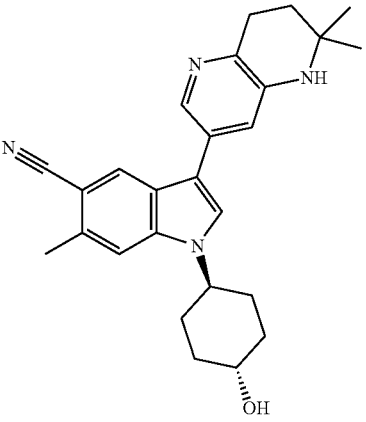 [SMILES: Cc1cc2c(cc1C#N)c(-c1cnc3c(c1)NC(C)(C)CC3)cn2[C@H]1CC[C@H](O)CC1] | ¹H NMR (400 MHz, DMSO-d₆) δ 8.19 (s, 1H), 7.99 (d, 1H), 7.96 (s, 1H), 7.75 (s, 1H), 7.16 (s, 1H), 5.79 (s, 1H), 4.75 (s, 1H), 4.45 (m, 1H), 3.58 (t, 1H), 2.80 (t, 2H), 2.59 (s, 3H), 2.03-1.81 (m, 6H), 1.71 (t, 2H), 1.54-1.40 (m, 2H), 1.19 (s, 6H). LC-MS: [M + H]⁺ = 415.3. |
| 92 | 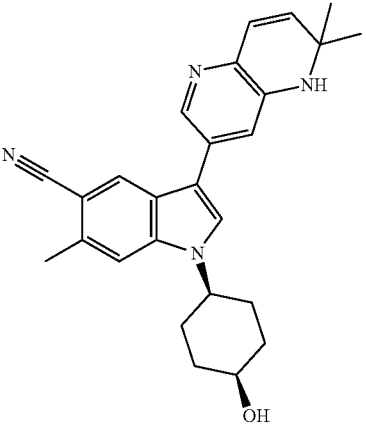 [SMILES: Cc1cc2c(cc1C#N)c(-c1cnc3c(c1)NC(C)(C)C=C3)cn2[C@H]1CC[C@@H](O)CC1] | 1H NMR (400 MHz, DMSO) δ 8.20 (s, 1H), 8.01-7.92 (m, 2H), 7.72 (s, 1H), 7.12 (d, 1H), 6.30 (d, 1H), 6.04 (d, 1H), 5.71 (dd, 1H), 4.56 (s, 1H), 4.46 (t, 1H), 3.93 (s, 1H), 2.58 (s, 3H), 2.26-2.12 (m, 2H), 1.83 (d, 2H), 1.70 (t, 4H), 1.29 (s, 6H). LC-MS: [M + H]⁺ = 413.2. |
| 93 | 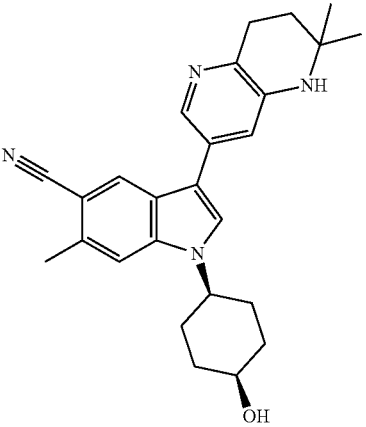 [SMILES: Cc1cc2c(cc1C#N)c(-c1cnc3c(c1)NC(C)(C)CC3)cn2[C@H]1CC[C@@H](O)CC1] | 1H NMR (400 MHz, DMSO-d₆) δ 8.20 (s, 1H), 8.02 (d, 1H), 7.90 (s, 1H), 7.71 (s, 1H), 7.17 (d, 1H), 5.76 (s, 1H), 4.56 (s, 1H), 4.46 (t, 1H), 3.94 (s, 1H), 2.80 (t, 2H), 2.58 (s, 3H), 2.27-2.12 (m, 2H), 1.83 (d, 2H), 1.70 (dd, 6H), 1.19 (s, 6H). LC-MS: [M + H]⁺ = 415.3. |

TABLE 1-continued

| Ex # | Struture | ¹H NMR and LC-MS Data |
|---|---|---|
| 94 | | ¹H NMR (400 MHz, DMSO-$d_6$) δ 8.20 (s, 1H), 8.01 (s, 1H), 7.95 (d, 1H), 7.76 (s, 1H), 7.12 (d, 1H), 6.31 (d, 1H), 6.06 (d, 1H), 5.72 (dd, 1H), 4.74 (d, 1H), 4.51-4.41 (m, 1H), 3.63-3.53 (m, 1H), 2.59 (s, 3H), 1.94 (dd, 6H), 1.54-1.44 (m, 2H), 1.30 (s, 6H). LC-MS: [M + H]⁺ = 413.2. |
| 95 | | ¹HNMR (300 MHz, DMSO-$d_6$) δ: 7.73 (s, 1H), 7.64 (s, 1H), 7.58 (s, 1H), 6.91-6.92 (m, 1H), 6.48 (t, J = 7.2 Hz, 2H), 6.14 (d, J = 9.8 Hz, 1H), 5.41 (d, J = 10.0 Hz, 1H), 4.45 (br d, J = 5.5 Hz, 2H), 3.58 (br t, J = 10.9 Hz, 1H), 2.58 (s, 3H), 1.88-2.01 (m, 6H), 1.40-1.55 (m, 2H), 1.27 (s, 6H). LC-MS: [M + H]⁺ = 412.0. |
| 96 | | ¹HNMR (300 MHz, DMSO-$d_6$) ¹HNMR (DMSO-$d_6$) δ: 7.70 (s, 1H), 7.68 (s, 1H), 7.52 (s, 1H), 6.96 (t, J = 7.7 Hz, 1H), 6.49 (dd, J = 7.8, 2.0 Hz, 2H), 6.16 (d, J = 9.8 Hz, 1H), 5.98 (s, 1H), 5.42 (d, J = 10.0 Hz, 1H), 4.47 (br t, J = 11.7 Hz, 1H), 3.94 (br s, 1H), 2.58 (s, 3H), 2.19 (q, J = 11.7 Hz, 2H), 1.80-1.88 (m, 3H), 1.66-1.80 (m, 4H), 1.27 (s, 6H). LC-MS: [M + H]⁺ = 411.9. |
| 97 | | ¹H NMR (300 MHz, Methanol-$d_4$) δ: 7.65 (s, 1H), 7.53 (s, 1H), 7.41 (s, 1H), 6.97-7.02 (m, 1H), 6.55-6.62 (m, 2H), 4.39-4.50 (m, 1H), 3.69-3.80 (m, 1H), 2.64 (s, 3H), 2.56-2.62 (m, 2H), 2.09-2.18 (m, 4H), 1.92-2.03 (m, 2H), 1.56-1.68 (m, 4H), 1.24 (s, 6H). LC-MS: [M + H]⁺ = 413.9. |

TABLE 1-continued

| Ex # | Structure | ¹H NMR and LC-MS Data |
|---|---|---|
| 98 | | ¹H-NMR (400 MHz, DMSO-d₆) δ ppm 7.72 (d, 2H), 7.60 (s, 1H), 6.93 (t, 1H), 6.46 (m, 2H), 5.74 (s, 1H), 4.71 (d, 1H), 4.44 (m, 1H), 3.57 (m, 1H), 3.20 (m, 2H), 2.58 (s, 3H), 2.56 (d, 2H), 2.06-1.82 (m, 6H), 1.69 (m, 2H), 1.48 (m, 2H). LC-MS: [M + H]⁺ = 386.3. |
| 99 | | . ¹H-NMR (400 MHz, DMSO-d₆) δ ppm 7.72 (s, 1H), 7.61 (d, 2H), 6.93 (t, 1H), 6.47 (dd, 2H), 5.74 (s, 1H), 5.15 (p, 1H), 4.80 (s, 1H), 4.39 (s, 1H), 3.20 (s, 2H), 2.67-2.54 (m, 5H), 2.35 (dt, , 1H), 2.13 (tt, 3H), 1.84 (dt, 1H), 1.74-1.54 (m, 3H). LC-MS: [M + H]⁺ = 372.2. |
| 100 | | ¹H-NMR (400 MHz, DMSO-d₆) δ ppm 7.99 (s, 1H), 7.68 (d, 2H), 7.03 (t, 1H), 6.77 (d, 1H), 6.48 (d, 1H), 5.56 (s, 1H), 5.16 (p, 1H), 4.81 (d, 1H), 4.40 (d, 1H), 3.54-3.37 (m, 2H), 3.00 (t, 2H), 2.59 (s, 3H), 2.35 (dt, 1H), 2.24-1.98 (m, 3H), 1.85 (dt, 1H), 1.74-1.54 (m, 1H). LC-MS: [M + H]⁺ = 358.3. |
| 101 | | ¹HNMR (DMSO-d₆) δ: 7.69 (s, 1H), 7.66 (s, 1H), 7.53-7.57 (m, 1H), 6.91 (t, J = 7.8 Hz, 1H), 6.46 (t, J = 8.0 Hz, 2H), 5.88 (br s, 1H), 4.69 (br s, 1H), 4.42 (br s, 1H), 3.56 (br s, 1H), 2.82 (br s, 2H), 2.56 (s, 3H), 2.29 (s, 2H), 1.87-1.99 (m, 6H), 1.39-1.53 (m, 2H), 0.83 (s, 6H). LC-MS: [M + H]⁺ = 414.0. |

TABLE 1-continued

| Ex # | Structure | ¹H NMR and LC-MS Data |
|---|---|---|
| 102 | | ¹HNMR (DMSO-d$_6$) δ: 7.69 (s, 1H), 7.65-7.68 (m, 1H), 7.47-7.51 (m, 1H), 6.90-6.96 (m, 1H), 6.48-6.50 (m, 1H), 6.45-6.48 (m, 1H), 5.85-5.89 (m, 1H), 4.49-4.54 (m, 1H), 4.38-4.49 (m, 1H), 3.89-3.95 (m, 1H), 2.80-2.86 (m, 2H), 2.30 (s, 3H), 2.09-2.24 (m, 2H), 1.64-1.86 (m, 6H), 0.84 (s, 6H). LC-MS: [M + H]$^+$ = 413.9. |
| 103 | | ¹H-NMR (400 MHz, DMSO-d$_6$) δ ppm 10.15 (s, 1H), 7.81 (s, 1H), 7.76 (s, 1H), 7.69 (s, 1H), 7.23 (t, 1H), 7.04 (dd, , 1H), 6.89 (d, 1H), 4.56-4.36 (m, 1H), 3.70-3.48 (m, 1H), 2.92-2.79 (m, 2H), 2.59 (s, 3H), 2.43-2.31 (m, 2H), 2.04-1.84 (m, 6H), 1.64-1.33 (m, 2H). LC-MS: [M + H]$^+$ = 400.2. |
| 104 | | ¹H NMR (400 MHz, DMSO-d$_6$) δ ppm 7.99 (s, 1H), 7.73 (d, 2H), 7.02 (t, 1H), 6.77 (d, 1H), 6.47 (d, 1H), 5.55 (s, 1H), 4.73 (d, 1H), 4.54-4.37 (m, 1H), 3.67-3.52 (m, 1H), 3.42 (t, 2H), 3.00 (t, 2H), 2.59 (s, 3H), 2.07-1.75 (m, 6H), 1.60-1.39 (m, 2H). LC-MS: [M + H]$^+$ = 372.2. |
| 105 | | ¹HNMR (300 MHz, DMSO-d$_6$) δ ppm 7.71 (s, 1H), 7.67 (s, 1H), 7.56 (s, 1H), 6.95 (d, J = 6 Hz, 1H), 6.56 (d, J = 6 Hz, 1H), 5.26 (s, 1H), 4.72 (d, J = 3 Hz, 1H), 4.43-4.45 (m, 1H), 3.50-3.60 (m, 1H), 3.48 (t, 2H), 2.96 (t, J = 6 Hz, 2H), 2.51 (s, 3H), 1.90-1.95 (m, 6H), 1.45-1.50 (m, 2H). LC-MS: [M + H]$^+$ = 386.3. |

TABLE 1-continued
| Ex # | Structure | $^1$H NMR and LC-MS Data |
|---|---|---|
| 106 | 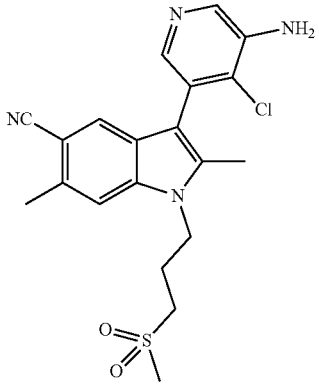 [SMILES: Cc1cc2c(cc1C#N)c(-c1cncc(N)c1Cl)c(C)n2CCCS(C)(=O)=O] | $^1$HNMR (400 MHz, Methanol-d$_4$) δ: 8.09 (s, 1H), 7.74 (s, 1H), 7.55 (s, 1H), 7.51 (s, 1H), 4.41-4.47 (m, 2H), 3.23-3.28 (m, 2H), 3.00 (s, 3H), 2.63 (s, 3H), 2.38 (s, 3H), 2.29 (quin, J = 7.5 Hz, 2H). LC-MS: [M + H]$^+$ = 416.9. |
| 107 | 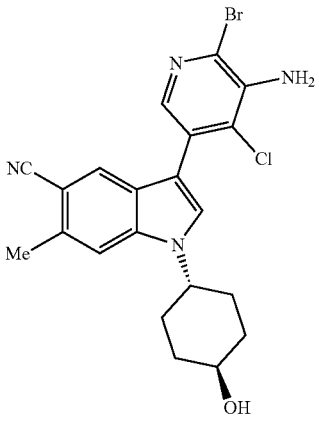 [SMILES: Cc1cc2c(cc1C#N)c(-c1cnc(Br)c(N)c1Cl)cn2[C@H]1CC[C@H](O)CC1] | $^1$H NMR (METHANOL-d$_4$) δ: 7.78 (s, 1H), 7.71 (d, J = 4.6 Hz, 2H), 7.60 (s, 1H), 4.48 (br t, J = 12.3 Hz, 1H), 3.74 (br t, J = 11.3 Hz, 1H), 2.65 (s, 3H), 2.13 (br d, J = 8.3 Hz, 4H), 1.56-1.67 (m, 4H). LC-MS: [M + H]$^+$ = 459.0. |
| 108 | 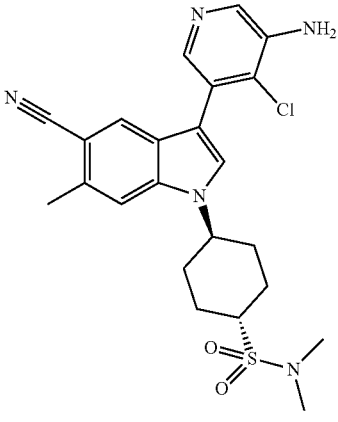 [SMILES: Cc1cc2c(cc1C#N)c(-c1cncc(N)c1Cl)cn2[C@H]1CC[C@H](S(=O)(=O)N(C)C)CC1] | $^1$H NMR (400 MHz, Methanol-d$_4$) δ 8.06 (s, 1H), 7.84 (s, 1H), 7.77 (s, 1H), 7.69 (s, 1H), 7.63 (s, 1H), 4.53 (t, J = 11.5 Hz, 1H), 3.41-3.34 (m, 1H), 2.96 (s, 6H), 2.65 (s, 3H), 2.40-2.19 (m, 4H), 2.09-1.83 (m, 4H). LC-MS: [M + H]$^+$ = 472.1. |

TABLE 1-continued

| Ex # | Struture | ¹H NMR and LC-MS Data |
| --- | --- | --- |
| 109 | | ¹H NMR (400MHz, DMSO-d₄) δ 8.08 (s, 1H), 7.87 (s, 1H), 7.85 (s, 1H), 7.83 (s, 1H), 7.80 (s, 1H), 6.85 (s, 2H), 5.74 (s, 2H), 4.65-4.52 (m, 1H), 3.01-2.95 (m, 1H), 2.59 (s, 3H), 2.27-2.24 (m, 2H), 2.15-1.91 (m, 4H), 1.85-1.69 (m, 2H). LCMS: [M + H]⁺ = 444.0. |
| 110 | | 1H NMR (400 MHz, DMSO) δ ppm 8.08 (s, 1H), 7.87 (s, 1H), 7.84 (s, 1H), 7.80-7.78 (d, J = 6.0 Hz, 2H), 5.74 (s, 2H), 4.54 m 4.48 (m, 1H), 2.58 (s, 3H), 2.57 (m, 1H), 2.17 (s, 3H), 2.05-2.03 (m, 4H), 1.97-1.88 (m, 2H), 1.60-1.51 (m, 2H). LCMS: [M + H]⁺ = 407.3. |
| 111 | | ¹H NMR (400 MHz, DMSO) δ ppm 8.08 (s, 1H), 7.87 (s, 1H), 7.84 (s, 1H), 7.80 (s, 1H), 7.78 (s, 1H), 5.74 (s, 2H), 4.54-4.48 (m, 1H), 2.58 (s, 3H), 2.57 (m, 1H), 2.17 (s, 3H), 2.05-2.03 (m, 4H), 1.97-1.88 (m, 2H), 1.60-1.51 (m, 2H). LCMS: [M + H]⁺ = 407.3. |
| 112 | | ¹H NMR: (400MHz, CHLOROFORM-d, δ 8.15 (s, 1H), 8.05 (s, 1H), 7.91 (s, 1H), 7.39 (s, 1H), 7.31 (s, 1H), 4.40-4.30 (m, 1H), 4.26 (s, 2H), 2.70 (s, 3H), 2.67-2.58 (m, 1H), 2.43 (m, 2H), 2.34 (m, 2H), 2.01-1.79 (m, 4H). LCMS: [M + H]⁺ = 390.3. |

TABLE 1-continued

| Ex # | Struture | 1H NMR and LC-MS Data |
|---|---|---|
| 113 | 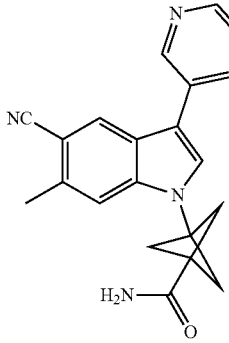 | 1H NMR (400 MHz, Methanol-d4) δ 8.07 (s, 1H), 7.84 (s, 1H), 7.77 (d, J = 0.6 Hz, 1H), 7.67 (t, J = 0.8 Hz, 1H), 7.51 (s, 1H), 2.74 (s, 6H), 2.65 (d, J = 0.8 Hz, 3H). LC-MS: $[M + H]^+$ = 392.2. |

VI. Pharmacology and Utility

As a histone demethylase, LSD1 can directly binds to its substrates (e.g. methylated histones H3K4) and repress/promote corresponding gene transcription. Therefore, targeting LSD1 represents a highly attractive strategy for the development of a novel therapy for the treatment of many forms of cancers. In particular, the need exists for small molecules that inhibit the activity of LSD1. It has now been found that LSD1 inhibitors as presently disclosed are useful to target LSD1 for the treatment of LSD1-mediated diseases or disorders, especially cancers.

The utility of the compounds of the present invention may be demonstrated using any one of the following test procedures. Compounds of the present invention were assessed for their ability to inhibit LSD1 activity to demethylate mono-methylated histone H3 lysine4in presence of FAD in biochemical assays. The ability of compounds of the present invention to inhibit cellular activity of LSD1 was assessed by analyzing the expression level of genes that regulated by LSD1's demethylase activity (e.g. CD11b), or region specific histone H3 lysine 4 methylation in human cell lines. The ability of compounds of the present invention to inhibit cancers was derived from their ability to modulate activity in human cancer cell lines bearing specific dependence to LSD1 activity to maintain cancerous growth or maintain stem cell like phenotype (e.g. less differentiated).

FL-LSD1 LC-MS Assay

Representative compounds of the present invention were serially and separately diluted 3-fold in DMSO to obtain a total of twelve concentrations. Then the test compounds at each concentration (100 nL of each) were transferred into a 384-well Perkin Elmer ProxiPlate 384 plus plates by Mosquito™ Solutions (5 μL) of 0.8 nM, the full-length LSD1 and 0.5 μM FAD in reaction buffer (40 mM Tris-HCl, 0.01% Triton-x100.10 mM KCl, 1 mM DTT) were added into the wells and then incubated with the test compound for 30 min. A 5 μL solution of 1 μM of the peptide substrate H3K4me1 (histone H3[1-21]-biotin) in reaction buffer was added to each initiate reaction. The final components in the reaction solution include 0.4 nM FL-LSD1, 0.25 μM FAD, and 0.5 μM H3K4me1 peptide with varying concentration of the compounds. A positive control consisted of the enzyme, 0.25 μM FAD and 0.5 μM substrate in the absence of the test compound, and a negative control consisted of 0.5 μM substrate only. Each reaction was incubated at room temperature for 60 min, and then stopped by the addition of 3 μL quench solution (2.5% TFA with 320 nM d4-SAH). The reaction mixture was centrifuged (Eppendorf centrifuge 5810, Rotor A-4-62) for 1 min at 2000 rpm and read on an API 4000 triple quadrupole mass spec with Turbulon Spray (Applied Biosystem) coupled with Prominence UFLC (Shimadzu). The conversion ratio of H3K4me1 substrate to the H3K4me0 product was calculated by dividing the peak area of the H3K4me0 peptide by the total peak area of all those two peptides on the assumption that the ionization efficiency of those peptides is the same. The data were then fit to a dose response equation using the program Helios to get the $IC_{50}$ values of the test compound.

A range of $IC_{50}$ values of ≤1 μM (1000 nM) was observed. Table 2 lists $IC_{50}$ values in the FL-LSD1 LC-MS Qualified assay.

TABLE 2

Compound biochemical activity in FL-LSD1 LC-MS assay

| Ex# | FL-LSD1 $IC_{50}$ (μM) |
|---|---|
| 1 | 0.010 |
| 2 | 0.002 |
| 3 | 0.005 |
| 4 | 0.026 |
| 5 | 0.135 |
| 6 | 0.206 |
| 7 | 0.028 |
| 8 | 0.063 |
| 9 | 0.006 |
| 10 | 0.017 |
| 11 | 0.028 |
| 12 | 0.006 |
| 13 | 0.030 |
| 14 | 0.024 |
| 15 | 0.027 |
| 16 | 0.094 |
| 17 | 0.073 |
| 18 | 0.034 |
| 19 | 0.071 |
| 20 | 0.153 |
| 21 | 0.012 |
| 22 | 0.181 |
| 23 | 1.587 |
| 24 | 0.005 |
| 25 | 0.031 |
| 26 | 0.014 |
| 27 | 0.002 |
| 28 | 0.029 |
| 29 | 0.012 |
| 30 | 0.243 |
| 31 | 0.204 |
| 32 | 0.016 |
| 33 | 0.162 |
| 34 | 0.004 |
| 35 | 0.025 |

TABLE 2-continued

Compound biochemical activity in FL-LSD1 LC-MS assay

| Ex# | FL-LSD1 IC$_{50}$ (μM) |
|---|---|
| 36 | 0.157 |
| 37 | 0.052 |
| 38 | 0.206 |
| 39 | 0.266 |
| 40 | 0.259 |
| 41 | 0.215 |
| 42 | 0.365 |
| 43 | 0.588 |
| 44 | 0.004 |
| 45 | 0.026 |
| 46 | 0.476 |
| 47 | 0.006 |
| 48 | 0.930 |
| 49 | 0.158 |
| 50 | 0.014 |
| 51 | 0.037 |
| 52 | 0.018 |
| 53 | 0.040 |
| 54 | 0.023 |
| 55 | 0.033 |
| 56 | 0.037 |
| 57 | 0.018 |
| 58 | 0.105 |
| 59 | 0.034 |
| 60 | 0.040 |
| 61 | 0.127 |
| 62 | 0.016 |
| 63 | 0.023 |
| 64 | 0.077 |
| 65 | 0.013 |
| 66 | 0.032 |
| 67 | 0.009 |
| 68 | 0.016 |
| 69 | 0.414 |
| 70 | 0.191 |
| 71 | 0.077 |
| 72 | 0.089 |
| 73 | 0.379 |
| 74 | 0.020 |
| 75 | 0.067 |
| 76 | 0.070 |
| 77 | 0.002 |
| 78 | 0.005 |
| 79 | 0.006 |
| 80 | 0.010 |
| 81 | 0.012 |
| 82 | 0.015 |
| 83 | 0.028 |
| 84 | 0.049 |
| 85 | 0.069 |
| 86 | 0.188 |
| 87 | 0.067 |
| 88 | 0.001 |
| 89 | 0.004 |
| 90 | 0.955 |
| 91 | 9.167 |
| 92 | 22.09 |
| 93 | 28.25 |
| 94 | 63.68 |
| 95 | 0.005 |
| 96 | 0.009 |
| 97 | 0.003 |
| 98 | 0.025 |
| 99 | 0.044 |
| 100 | 0.154 |
| 101 | 0.185 |
| 102 | 0.154 |
| 103 | 0.512 |
| 104 | 0.776 |
| 105 | 1.940 |
| 106 | 0.359 |
| 107 | 9.624 |
| 108 | 0.001 |
| 109 | 0.005 |
| 110 | 0.006 |
| 111 | 0.008 |
| 112 | 0.008 |
| 113 | |

CD86 mRNA Expression Assay (qPCR Assay)

MV4-11 cells were treated with representative compound of the present invention and RNA was extracted, followed by reverse transcription and Real-Time PCR. Compound was dissolved in DMSO and added to 0.2×10^6 MV4-11 cells cultured in 1 mL RPMI 1640+10% FBS at 1, 10, 100 and 1000 nM for 24 hours, with DMSO final concentration of 0.1%. RNA was extracted using the RNeasy Mini Kit (Qiagen, cat #74106) and the quality was confirmed with NanoDrop (Thermo Fisher Scientific). Reverse transcription and cDNA synthesis was conducted using kit (Thermo Fisher Scientific, cat #18080051). Real-Time PCR analysis was performed on ViiA 7 Real-Time PCR System (Thermo Fisher Scientific) using the SYBR Green PCR Master Mix (Thermo Fisher Scientific, cat #4367659). The relative mRNA expression of CD86 was detected using sequence specific primer pair (forward primer TCCAACAGTTAT-TATATGTGTGATGGT, reverse primer CCCTCTCCATT-GTGTTGGTT) and normalized against ACTB (forward primer CATTCCAAATATGAGATGCGTTGT, reverse primer TGTGGACTTGGGAGAGGACT), then DMSO treated group result was set up as 1 to normalize and get the activation fold of CD86 in compound treatment groups. The data were used for dose response curve fitting in GraphPad Prism to calculate the AC$_{50}$ of each compound. AC$_{50}$ of CD86 mRNA expression activation after treatment of representative compounds of present invention will reflect the inhibition of LSD1 activity.

TABLE 3

Compound activity in CD86 induction qPCR assay in MV4-11 cell

| Ex# | CD86 induction qPCR in MV4-11 AC$_{50}$ (μM) |
|---|---|
| 1 | 0.098 |
| 5 | 3.622 |
| 7 | 0.569 |
| 47 | 0.202 |
| 68 | 0.464 |
| 77 | 0.007 |
| 84 | 1.486 |

MV4-11 6-Day Cell Growth CTG (CellTiter-Glo) Assay

Acute myeloid leukemia cell MV4-11 (ATCC® CRL-9591™) was cultured with RPMI 1640 medium (Thermo Fisher Scientific, cat #11875) supplemented with 10% FBS (Thermo Fisher Scientific, cat #10099141) in humidified incubator at 37° C., 5% CO$_2$. To assess the effect of LSD1 inhibition on cell growth, the compound of the present invention was dissolved in DMSO and serially diluted at 1:3 for 12 points starting from 10 mM then 200 nL for the replicate of each dose per well was dispensed to Viewplate-384 Black (Perkin Elmer). Exponentially growing MV4-11 cells were seeded at the density of 300 cells per well in 40 μL to the plate, so the final compound working concentration starts from 50 μM. After 6 days, 40 μL CellTiter-Glo (Promega, cat #G7573) was added into the cell culture well and luminescence was read with Envision (Perkin Elmer) to determine the viable cells. The percentage inhibition was calculated against the samples treated with DMSO only and the data were used for dose response curve fitting in GraphPad Prism to get the $IC_{50}$ of representative compound of present invention, which reflects the inhibition of LSD1 activity.

TABLE 4

Compound activity in 6 d CTG antiproliferation assay in MV4-11 cell

| Ex# | 6 d CTG anti-proliferation in MV4-11 $EC_{50}$ (μM) |
|---|---|
| 1 | 0.099 |
| 47 | 0.056 |
| 77 | 0.019 |
| 79 | 0.018 |

Analysis of Pharmacokinetic Properties

Pharmacokinetic properties of the compounds as presently disclosed can be determined by using the below described protocol.

A representative compound of the present invention was dissolved in 10% PEG300, 10% Solutol HS 15 and 80% pH 4.65 Acetate buffer to yield a final concentration of 0.2 mg/mL for intravenous (IV) and oral administration (PO).

For rat PK studies, a total of three male Sprague Dawley rats each were used for rat IV and PO PK study, respectively. The formulation solution was administered via a single bolus IV at 1 mg/kg and a single oral gavage (PO) at 2 mg/kg, respectively. Blood samples (approximately 150 μL) were collected via jugular cannula at appropriate time points.

For mouse PK study, a total of twelve male ICR mice were used for IV and PO study, respectively. The formulation solution was administered via a single bolus IV at 1 mg/kg and a single oral gavage (PO) at 2 mg/kg, respectively. Blood samples (approximately 150 μL) were collected via retro-orbital puncture (~150 μL/mouse) after anesthetized by isoflurane or via cardiac puncture (terminal collection) at appropriate time points (n=3).

Samples were collected in tubes containing K3-EDTA and stored on ice until centrifuged. The blood samples were centrifuged at approximately 8000 rpm for 6 min at 2-8° C. and the resulting plasma was separated and stored frozen at approximately −80° C. After adding the internal standard, the plasma samples were quantified by LC-MS/MS using the calibration curve. PK parameters including area under concentration curve (AUC), mean residence time (MRT), plasma clearance (Cl), steady state volume of distribution (Vdss), elimination half-life ($t_{1/2}$), maximum concentration (Cmax), time of maximum concentration (Tmax) and oral bioavailability (F %) were calculated using the following equations:

$$AUC = \int_0^\infty C\, dt$$

$$MRT = \frac{\int_0^\infty tC\, dt}{\int_0^\infty C\, dt} = \frac{AUMC}{AUC}$$

t is time and C is plasma concentration at the time (t);
$Dose_{iv}$ is the dose for intravenous administration; and $Dose_{oral}$ is the dose for oral administration.

$Cl = Dose_{iv}/AUC$
$t_{1/2} = 0.693 \times MRT$
$Vdss = Cl \times MRT$ $$F\% = (Dose_{iv} \times AUC_{oral})/(Dose_{oral} \times AUC_{iv}) \times 100\%$$

Protocol for High-Throughput Equilibrium Solubility Assay

Compounds of the present invention were first solubilized at 10 mM in pure DMSO. 20 μL each of the DMSO stock solution was then transferred into 6 wells on 96-well plate. The DMSO solvent was dried with GeneVac solvent evaporator at 30° C., 1 mbar vacuum for 1 h. After the addition of 200 μL of buffer solutions (pH 6.8, or FaSSIF), the plate was sealed and shaken at 160 rpm for 24 h at rt. The plate was centrifuged at 3750 rpm for 20 min, 5 μL of supernatant is mixed with 495 μL of MeOH/$H_2O$ (1:1). 0.01 μM, 0.1 μM, 1 μM, 10 μM stock solutions were prepared by series of dilution for the calibration curves. The supernatant was quantified by HPLC or LC/MS using the calibration curve. High-Throughput equilibrium solubility was determined based on the concentration of the supernatant.

Efficacy Studies in Mouse Xenograft Model

All experiments conducted were performed in female athymic Nude-nu mice in an AAALAC certificated facility. The animals were kept under SPF conditions in individual ventilation cages at constant temperature and humidity (i.e., 20-26° C.; 40-70%) with 5 or less animals in each cage. Animals had free access to irradiation sterilized dry granule food and sterile drinking water. All procedures and protocols were approved by the Institutional Animal Care and Use and internal committee.

The cells MV4:11 or HL60 leukemia were cultured in RPMI-1640 medium (Gibco; 11875-093) supplemented with 10% FBS (Gibco; 10099-141) and 1% Pen Strep (Gibco; 15140-122) at 37° C. in an atmosphere of 5% $CO_2$ in air. Cells were maintained in suspension cultures at concentrations between $0.5\text{-}2\times10^6$ cells/ml. Cells were split at 1:5 every 2-4 days. To establish xenograft tumor models the cells were collected, suspended in PBS, mixed with Matrigel (BD Bioscience) at a volume ratio of 1:1 at a concentration of $1\times10^8$ cells/mL and then injected subcutaneously into the right flank of balb/c nude mice (Vital River) at a concentration of $5\times10^6$ cells per animal.

The compound was formulated as a suspension in 0.5% methyl cellulose (MC) and 0.5% Tween 80 in 50 mM pH6.8 buffer (prepared in house according to the USP) and administered orally by gavage at specific doses.

Treatment was initiated when the average tumor volume reached 100-300 $mm^3$. Tumor growth and body weights were monitored at regular intervals. The two largest diameters, width (W) and length (L), of the xenograft tumors were measured manually with calipers and the tumor volume was estimated using the formula: $0.5 \times L \times W^2$.

When applicable, results are presented as mean±SEM. Graphing and statistical analysis was performed using GraphPad Prism 6.00 (GraphPad Software). Tumor and body weight change data were analyzed statistically. If the variances in the data were normally distributed (Bartlett's test for equal variances), the data were analyzed using one-way ANOVA with post hoc Dunnet's test for comparison of treatment versus control group. The post hoc Tukey test was used for intragroup comparison. Otherwise, the Kruskal-Wallis ranked test post hoc Dunn's was used.

As a measure of efficacy the % T/C value is calculated at the end of the experiment according to:

$$(\Delta\text{tumor volume}^{treated}/\Delta\text{tumor volume}^{control}) \times 100$$

Tumor regression was calculated according to:

$$-(\Delta\text{tumor volume}^{treated}/\text{tumor volume}^{treated\ at\ start}) \times 100$$

Where Δtumor volumes represent the mean tumor volume on the evaluation day minus the mean tumor volume at the start of the experiment.

The exemplified Examples disclosed were tested in the LC-MS assays described above and found having LSD1 inhibitory activity. A range of $IC_{50}$ values of ≤1 μM (1000 nM) was observed.

Accordingly, the compounds of the present invention have been found to inhibit LSD1 and therefore useful in the treatment of diseases or disorders associated with LSD1, which include, but are not limited to, B cell lymphoma, acute myeloid leukemia, gastric cancer, hepatocellular carcinoma, prostate cancer, breast carcinoma, neuroblastoma, glioblastoma, nasopharyngeal carcinoma colon cancer, gallbladder cancer, esophageal cancer, head and neck cancer, lung cancer, ovarian cancer, pancreatic cancer, endometrial carcinoma and soft tissue sarcomas such as rhabdomyosarcoma (RMS), chondrosarcoma, osteosarcoma, Ewing's sarcoma, liver fibrosis, and sickle cell disease.

VII. Pharmaceutical Compositions and Combinations

The compounds of the present invention are typically used as a pharmaceutical composition (e.g., a compound of the present invention and at least one pharmaceutically acceptable carrier). A "pharmaceutically acceptable carrier (diluent or excipient)" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like and combinations thereof, as would be known to those skilled in the art (see, for example, Allen, L. V., Jr. et al., *Remington: The Science and Practice of Pharmacy* (2 Volumes), 22nd Edition, Pharmaceutical Press (2012). For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The compound of the present invention is typically formulated into pharmaceutical dosage forms to provide an easily controllable dosage of the drug and to give the patient an elegant and easily handleable product. The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. Compounds of this invention may be administered in a single daily dose, or the total daily dosage may be administered in divided doses of two, three, or four times daily.

In certain instances, it may be advantageous to administer the compound of the present invention in combination with at least one additional pharmaceutical (or therapeutic) agent, such as other anti-cancer agents, immunomodulators, anti-allergic agents, anti-nausea agents (or anti-emetics), pain relievers, cytoprotective agents, and combinations thereof.

The term "combination therapy" refers to the administration of two or more therapeutic agents to treat a therapeutic disease, disorder or condition described in the present invention. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. The compound of the present invention and additional therapeutic agents can be administered via the same administration route or via different administration routes. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamtin®), vinblastine (Velban®), vincristine (Oncovin®), and vinorelbine (Navelbine®).

Anti-cancer agents of particular interest for combinations with the compounds of the present invention include:

Cyclin-Dependent Kinase (CDK) inhibitors: (Chen, S. et al., *Nat Cell BioL*, 12(11):1108-14 (2010); Zeng, X. et al., *Cell Cycle*, 10(4):579-83 (2011)) Aloisine A; Alvocidib (also known as flavopiridol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002); Crizotinib (PF-02341066, CAS 877399-52-5); 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-Methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); Indisulam (E7070); Roscovitine (CYC202); 6-Acetyl-8-cyclopentyl-5-methyl-2-(5-piperazin-1-yl-pyridin-2-ylamino)-8H-pyrido[2,3-d]pyrimidin-7-one, hydrochloride (PD0332991); Dinaciclib (SCH727965); N-[5-[[(5-tert-Butyloxazol-2-yl)methyl]thio]thiazol-2-yl]piperidine-4-carboxamide (BMS 387032, CAS 345627-80-7); 4-[[9-Chloro-7-(2,6-difluorophenyl)-5H-pyrimido[5,4-d][2]benzazepin-2-yl]amino]-benzoic acid (MLN8054, CAS 869363-13-3); 5-[3-(4,6-Difluoro-1H-benzimidazol-2-yl)-1H-indazol-5-yl]-N-ethyl-4-methyl-3-pyridinemethanamine (AG-024322, CAS 837364-57-5); 4-(2,6-Dichlorobenzoylamino)-1H-pyrazole-3-carboxylic acid N-(piperidin-4-yl)amide (AT7519, CAS 844442-38-2); 4-[2-Methyl-1-(1-methylethyl)-1H-imidazol-5-yl]-N-[4-(methylsulfonyl)phenyl]-2-pyrimidinamine (AZD5438, CAS 602306-29-6); Palbociclib (PD-0332991); and (2R,3R)-3-[[2-[[3-[[S(R)]—S-cyclopropylsulfonimidoyl]-phenyl]amino]-5-(trifluoromethyl)-4-pyrimidinyl]oxy]-2-butanol (BAY 10000394).

Checkpoint Kinase (CHK) inhibitors: (Wu, Z. et al., *Cell Death Differ.*, 18(11):1771-9 (2011)) 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl) urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL), and CBP501 ((d-Bpa)sws(d-Phe-F5)(d-Cha)rrrqrr); and (αR)-α-amino-N-[5,6-dihydro-2-(1-methyl-1H-pyrazol-4-yl)-6-oxo-1H-pyrrolo[4,3,2-ef][2,3]benzodiazepin-8-yl]-Cyclohexaneacetamide (PF-0477736).

Histone deacetylase (HDAC) inhibitors: (Yamaguchi, J. et al., *Cancer Sci.*, 101(2):355-62 (2010)) Voninostat (Zolinza®); Romidepsin (Istodax®); Treichostatin A (TSA); Oxamflatin; Vorinostat (Zolinza®, Suberoylanilide hydroxamic acid); Pyroxamide (syberoyl-3-aminopyridineamide hydroxamic acid); Trapoxin A (RF-1023A); Trapoxin B (RF-10238); Cyclo[(αS,2S)-α-amino-η-oxo-2-oxiraneoctanoyl-O-methyl-D-tyrosyl-L-isoleucyl-L-prolyl] (Cyl-1); Cyclo[(αS,2S)-α-amino-η-oxo-2-oxiraneoctanoyl-O-methyl-D-tyrosyl-L-isoleucyl-(2S)-2-piperidinecarbonyl] (Cyl-2); Cyclic[L-alanyl-D-alanyl-(2S)-η-oxo-L-η-aminooxiraneoctanoyl-D-prolyl] (HC-toxin); Cyclo[(αS,2S)-α-amino-η-oxo-2-oxiraneoctanoyl-D-phenylalanyl-L-leucyl-(2S)-2-piperidinecarbonyl] (WF-3161); Chlamydocin ((S)-Cyclic(2-methylalanyl-L-phenylalanyl-D-prolyl-η-oxo-L-α-aminooxiraneoctanoyl); Apicidin (Cyclo(8-oxo-L-2-aminodecanoyl-1-methoxy-L-tryptophyl-L-isoleucyl-D-2-piperidinecarbonyl); Romidepsin (Istodax®, FR-901228); 4-Phenylbutyrate; Spiruchostatin A; Mylproin (Valproic acid); Entinostat (MS-275, N-(2-Aminophenyl)-4-[N-(pyridine-3-yl-methoxycarbonyl)-amino-methyl]-benzamide);
and Depudecin (4,5:8,9-dianhydro-1,2,6,7,11-pentadeoxy-D-threo-D-ido-Undeca-1,6-dienitol).

Anti-tumor antibiotics: (Bai, J. et al., *Cell Prolif.*, 47(3): 211-8 (2014)) Doxorubicin (Adriamycin® and Rubex®); Bleomycin (Lenoxane®); Daunorubicin (dauorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence™); Idarubicin (Idamycin®, Idamycin PFS®); Mitomycin C (Mutamycin®); Geldanamycin; Herbimycin; Ravidomycin; and Desacetylravidomycin.

Demethylating agents: (Musch, T. et al., *PLoS One*, (5):e10726 (2010)) 5-Azacitidine (Vidaza®); and Decitabine (Dacogen®).

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids (Knutson, S., et al., *PLoS One*, DOI:10.1371/journal.pone.0111840 (2014)), such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate@ and Lanacort®), prednisolone (sold under the tradenames Delta-Cortel®, Orapred®, Pediapred® and Prelone®), prednisone (sold under the tradenames Deltasone®, Liquid Red@, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Immunomodulators of particular interest for combinations with the compounds of the present invention include one or more of: an activator of a costimulatory molecule or an inhibitor of an immune checkpoint molecule (e.g., one or more inhibitors of PD-1, PD-L1, LAG-3, TIM-3 or CTLA4) or any combination thereof.

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40% or more is included by this term. Thus, inhibition need not be 100%.

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy for treatment of a malignancy, the compound of the present invention and other anti-cancer agent(s) may be administered simultaneously, concurrently or sequentially with no specific time limits, wherein such administration provides therapeutically effective levels of the two compounds in the body of the subject.

In a preferred embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The compounds of the present invention are also useful as standard or reference compounds, for example as a quality standard or control, in tests or assays involving LSD1. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving LSD1.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

What is claimed is:

1. A compound of formula (I):

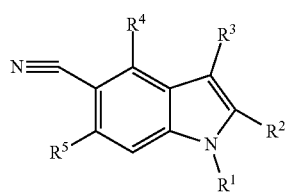

or a pharmaceutically acceptable salt thereof, wherein:
$R^1$ is selected from:
  $C_1$-$C_6$ alkyl substituted with one to two $R^a$,
  $C_3$-$C_6$ cycloalkyl substituted with at least one group selected from —$C_1$-$C_4$ alkyl, $C_1$-$C_4$ haloalkyl, halo, OH, CN, —C(O)R, —C(O)OR, —CONR$_2$, —NR—C(O)R, —NH$_2$, —NR'$_2$, —NR—C(O)OR', —NR—C(O)NR$_2$, —OC(O)NR$_2$, —NRSO$_2$R', —SO$_2$R', and —SO$_2$NR$_2$, and optionally further substituted with one to two $R^d$;
  7-11 membered spiro cyclyl optionally substituted with one or two $R^b$;
  7-11 membered spiro heterocyclyl comprising 1-2 heteroatoms selected from nitrogen, oxygen and sulfur, wherein the 7-11 membered spiroheterocyclyl is optionally substituted with one or two $R^b$;
  phenyl substituted with at least one group selected from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$, wherein the phenyl is further optionally substituted with one or two $R^b$;
  bicyclic heteroaryl comprising one to three heteroatoms selected from nitrogen, oxygen and sulfur, wherein the bicyclic heteroaryl is optionally substituted with one or two $R^b$;
  2-pyridone optionally substituted with one or two $R^b$;
  6-membered heteroaryl comprising one to two nitrogen atoms, wherein the 6-membered heteroaryl is substituted with at least one group selected from —NR—C(O)OR', —NR—C(O)NR$_2$, —NR—SO$_2$R', —NR—SO$_2$OR', —NR—SO$_2$NR$_2$, —C(O)OH, —SO$_2$R', and —SO$_2$NR$_2$, and optionally further substituted with up to three $R^b$;

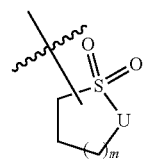

optionally substituted with one or two $R^d$; and

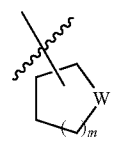

optionally substituted with one or two $R^d$;
$R^2$ is selected from: H, halogen, $C_1$-$C_4$ alkyl, $C_1$-$C_4$ haloalkyl, —C(O)OR, and —C(O)NR$_2$;
$R^3$ is selected from:

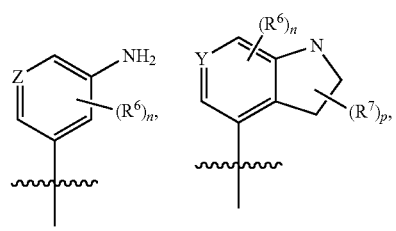

$R^4$ is selected from: H, halogen and $C_1$-$C_4$ alkyl;
$R^5$ is selected from: H, halogen, $C_1$-$C_4$ alkyl, $C_1$-$C_4$ haloalkyl, and $C_3$-$C_6$ cycloalkyl;
$R^6$ is independently at each occurrence selected from: halogen, CN, OH, $C_1$-$C_4$ alkyl, $C_1$-$C_4$ alkoxyl, and $C_1$-$C_4$ haloalkyl;

R⁷ is independently at each occurrence selected from: oxo, halogen, CN, OH, $C_1$-$C_4$ alkyl, $C_1$-$C_4$ alkoxyl, and $C_1$-$C_4$ haloalkyl;

U is selected from: CR₂, NH, N—($C_{1-4}$ alkyl), N—C(O)—($C_{1-4}$ alkyl), N—C(O)—NR₂, and N—C(O)—O—($C_{1-4}$ alkyl);

W is selected from: O, NH, N—($C_{1-4}$ alkyl), N—SO₂—($C_{1-4}$ alkyl), N—C(O)—($C_{1-4}$ alkyl), N—C(O)—NR₂, N—SO₂—O—($C_{1-4}$ alkyl), N—SO₂—NR₂, and N—C(O)—O—($C_{1-4}$ alkyl);

X is independently at each occurrence selected from: CR$^e$R$^f$, NR$^f$ and O;

Y is independently at each occurrence selected from: CR$^e$ and N;

Z is selected from: CH, CR$^h$ and N;

R is independently at each occurrence selected from H and $C_1$-$C_4$ alkyl;

R' is independently at each occurrence $C_1$-$C_4$ alkyl;

R$^a$ is independently selected from: halogen, —OH, CN, —SO₂R', —SO₂NR₂, —NRSO₂R', —NR—SO₂OR', —NR—SO₂NR₂, —NR₂, —NRC(O)R', —NR—C(O)NR₂, —NR—C(O)OR', and —$C_1$-$C_4$ alkoxy, wherein the —$C_1$-$C_4$ alkoxy is substituted with at least one group selected from —OH, halogen, and CN;

R$^b$ is independently selected from: halogen, $C_1$-$C_4$ haloalkoxy, OH, CN, —CO₂R, —C(O)NR₂, —CONRC(O)R', —CONRSO₂R', —NR₂, —NRC(O)R, —NR—C(O)OR', —NR—C(O)NR₂, —SO₂R', —SO₂NR₂, —NRSO₂R', —NR—SO₂OR', —NR—SO₂NR₂, $C_1$-$C_4$ alkyl substituted with zero to one R$^c$, and $C_1$-$C_4$ alkoxy substituted with zero to one R$^c$;

R$^c$ is independently selected from: OH, $C_1$-$C_4$ alkoxy, —CO₂R, —C(O)NR₂, —NR₂, and —NRC(O)R;

R$^d$ is independently selected from: OH, =O, —C(O)R, and —NH($C_1$-$C_4$ alkyl);

R$^e$ is independently at each occurrence selected from: H, halogen, CN, OH, $C_1$-$C_4$ alkyl, and $C_1$-$C_4$ haloalkyl;

R$^f$ is independently at each occurrence selected from: H, halogen, $C_1$-$C_4$ alkyl, and $C_1$-$C_4$ haloalkyl;

R$^h$ is independently at each occurrence selected from: halogen, CN, OH, $C_1$-$C_4$ alkyl, and $C_1$-$C_4$ haloalkyl;

m is independently selected from: 0, 1, and 2;

n, at each occurrence, is independently selected from: 0, 1, and 2; and p, at each occurrence, is independently selected from: 0, 1, and 2;

provided that:
when R¹ is $C_1$-$C_6$ alkyl substituted with OH, R² is $C_1$-$C_4$ alkyl substituted with one or two halogen; and when R¹ is $C_3$-$C_6$ cycloalkyl substituted with OH, R³ is selected from:

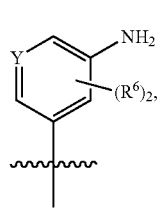 , 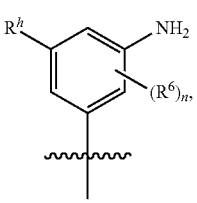

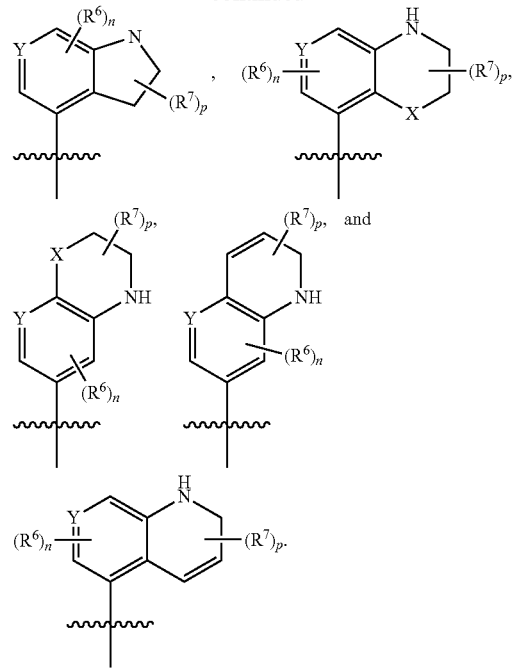

2. The compound of claim 1, or a pharmaceutically acceptable salt, wherein R¹ is selected from cyclobutyl, cyclopentyl, and cyclohexyl, wherein each of the cyclobutyl, cyclopentyl, and cyclohexyl is independently substituted with one group selected from —OH, —C(O)OR, —SO₂R', —SO₂NR₂, —NRSO₂R', and —CONR₂.

3. The compound of claim 1, or a pharmaceutically acceptable salt, wherein R¹ is selected from cyclobutyl, cyclopentyl, and cyclohexyl, wherein each of cyclobutyl, cyclopentyl, and cyclohexyl is substituted with one group selected from —OH, —SO₂CH₃, —SO₂NH₂, —NHSO₂CH₃, —COOCH₃, and —CONH₂.

4. The compound of claim 1, or a pharmaceutically acceptable salt, wherein R¹ is 6-membered heteroaryl comprising one to two nitrogen atoms as ring members, substituted with at least one group selected from —NR—C(O)OR', —NR—C(O)NR₂, —NR—SO₂R', —NR—SO₂OR', —NR—SO₂NR₂, —C(O)OH, —SO₂R', and —SO₂NR₂.

5. The compound of claim 1, or a pharmaceutically acceptable salt, wherein R¹ is phenyl substituted with at least one group selected from —NR—C(O)OR', —NR—C(O)NR₂, —NR—SO₂R', —NR—SO₂OR', —NR—SO₂NR₂, —C(O)OH, —SO₂R', and —SO₂NR₂.

6. The compound of claim 1, or a pharmaceutically acceptable salt, wherein R³ is

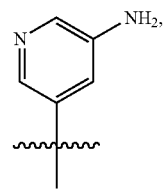 [SMILES: *c1cncc(N)c1]

further substituted with one or two R⁶.

7. The compound of claim 6, or a pharmaceutically acceptable salt, wherein R⁶ is halogen.

8. The compound of claim 1, or a pharmaceutically acceptable salt, wherein $R^4$ is H and wherein $R^5$ is —CH$_3$.
9. The compound of claim 1, or a pharmaceutically acceptable salt, wherein the compound is selected from
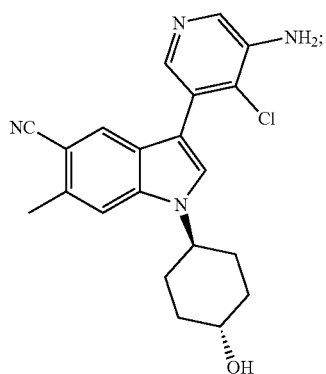
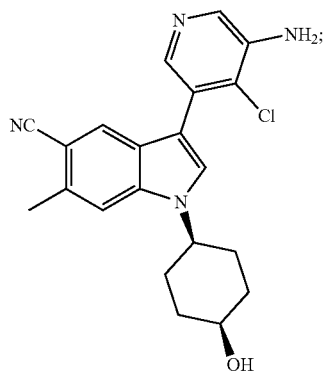
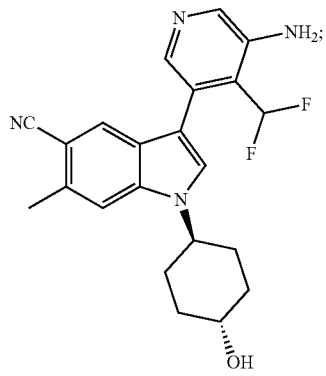
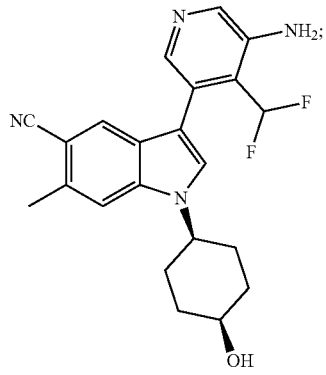
-continued
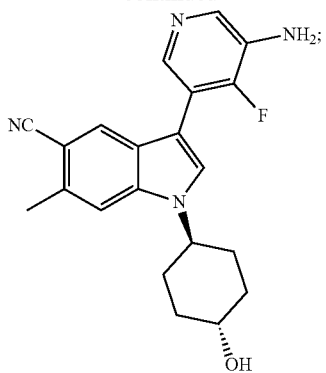
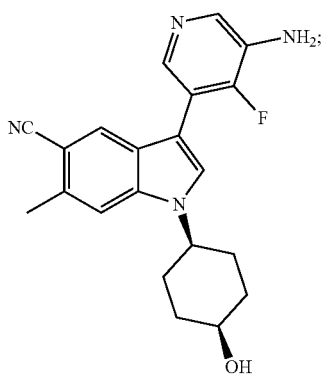
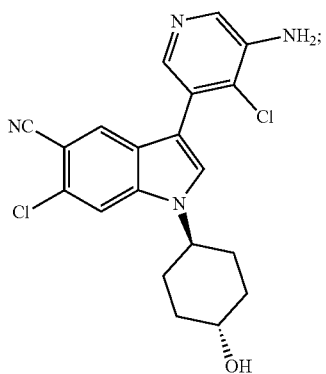
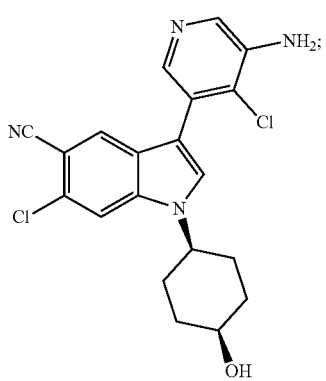

-continued
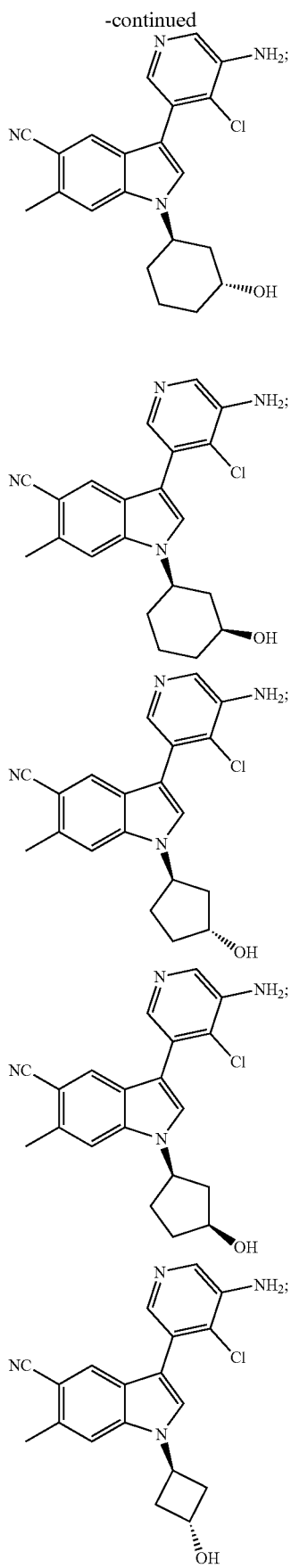
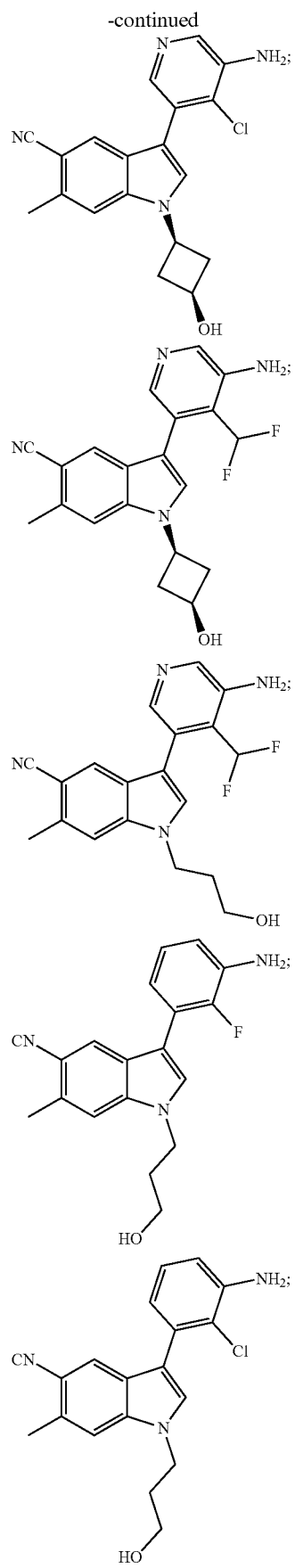

307
-continued
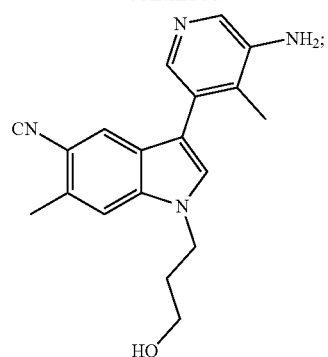
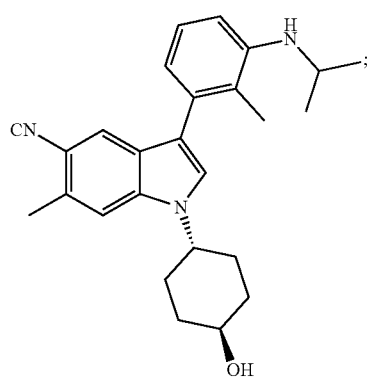
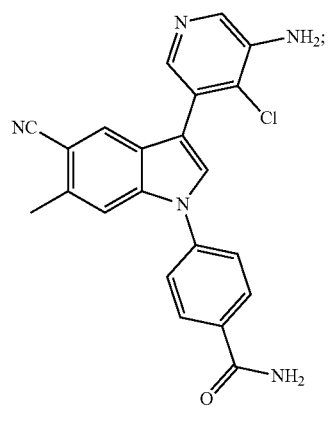
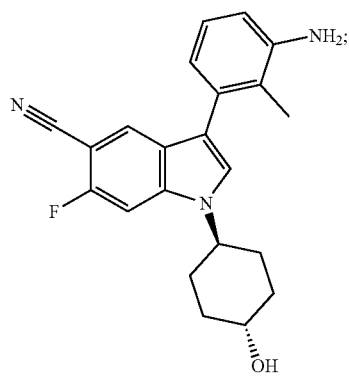
308
-continued
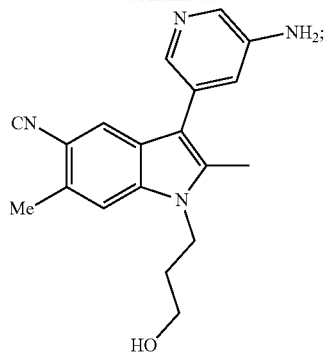
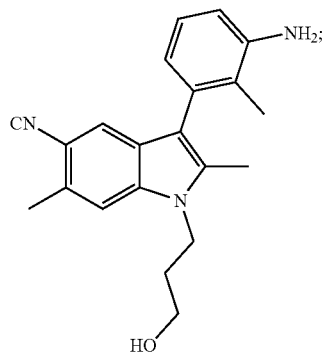
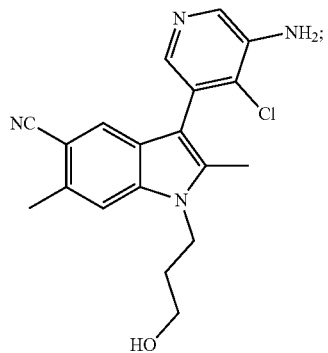
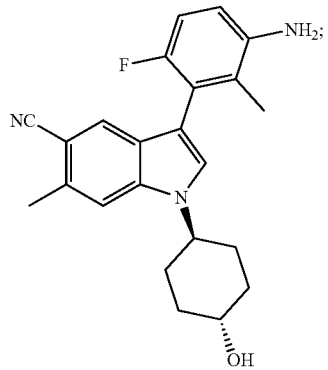

309
-continued
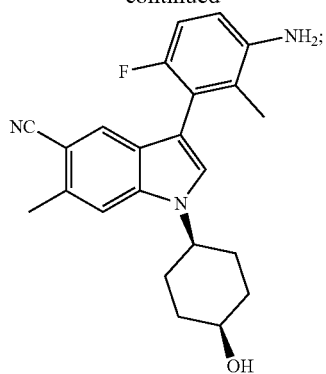
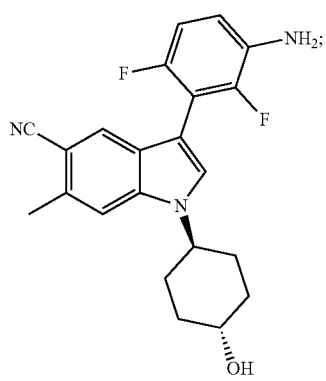
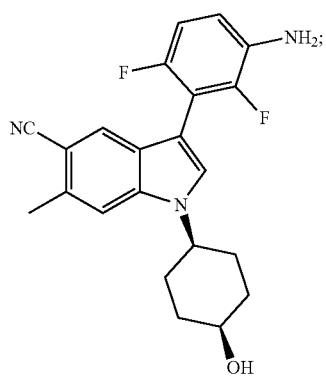
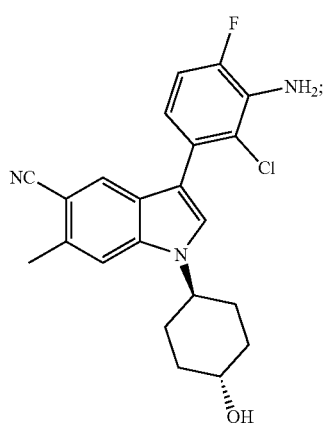
310
-continued
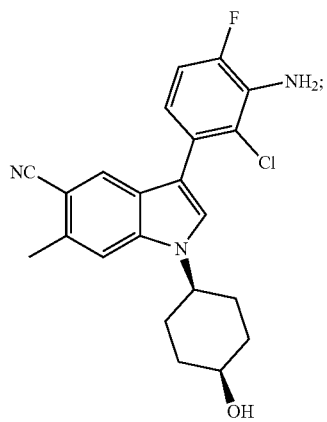
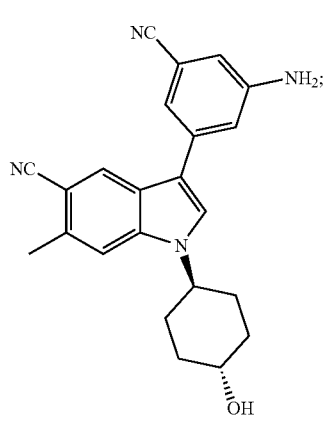
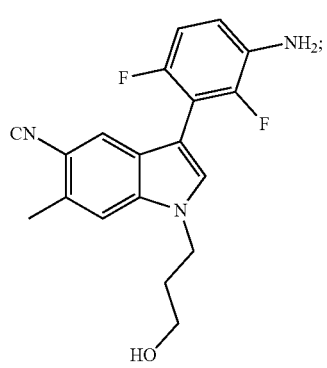
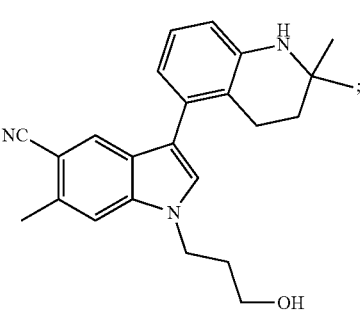

311
-continued
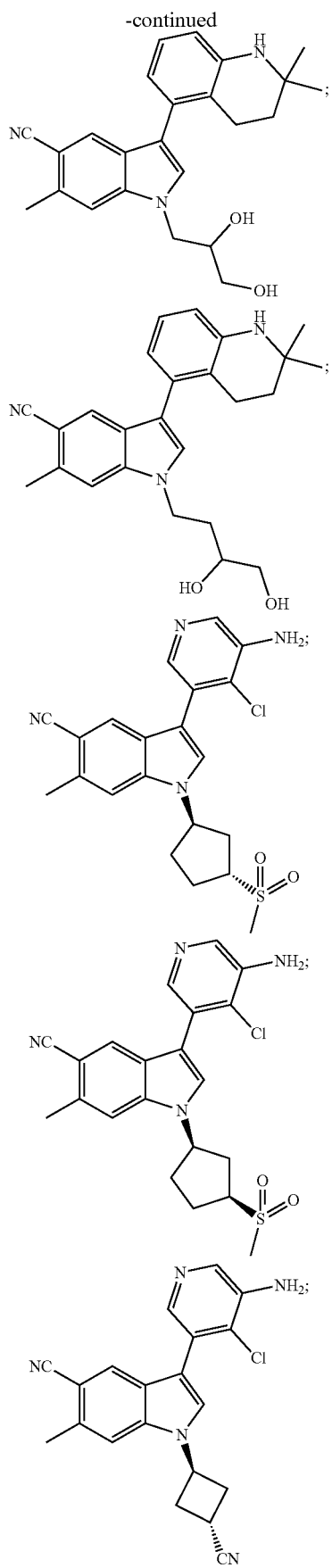
312
-continued
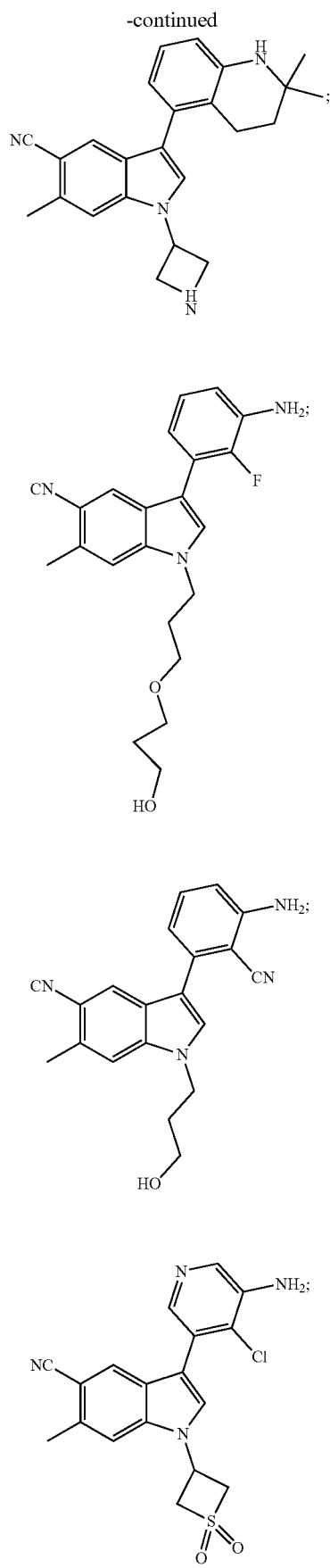

313 314
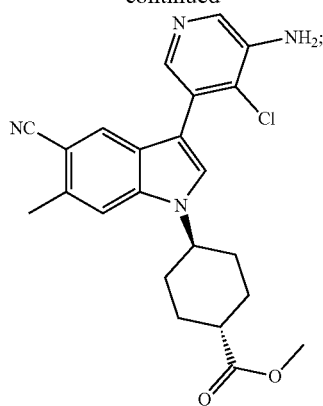
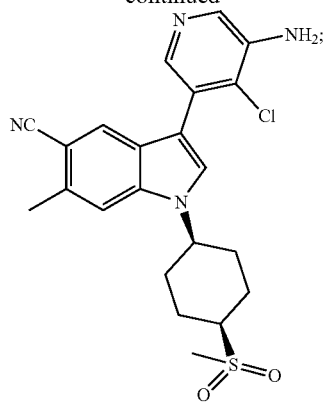

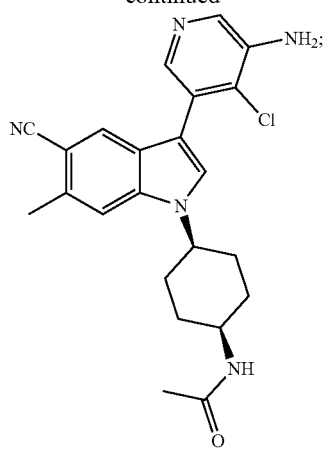
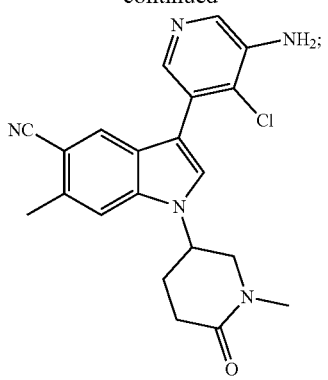

317
-continued
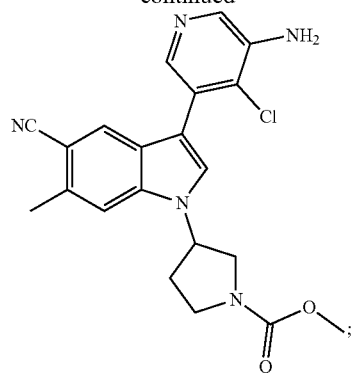
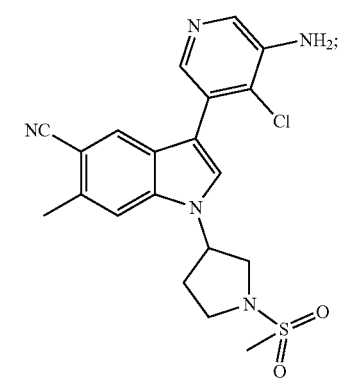
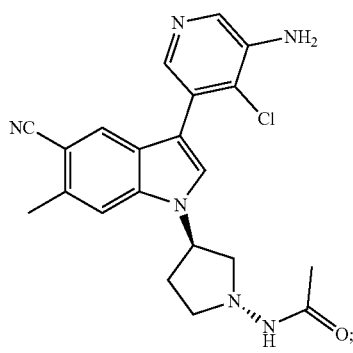
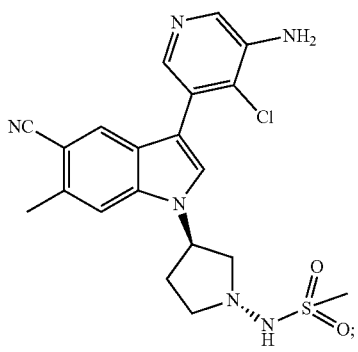
318
-continued
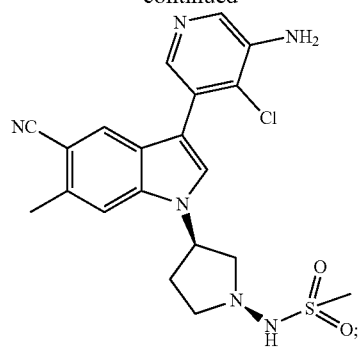
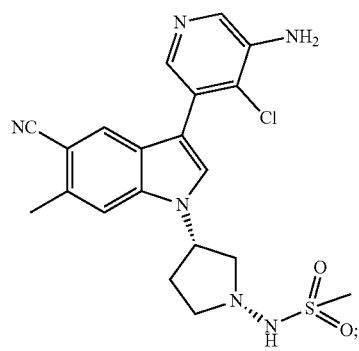
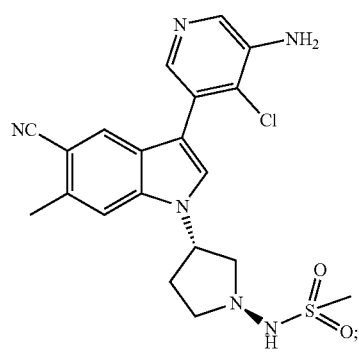
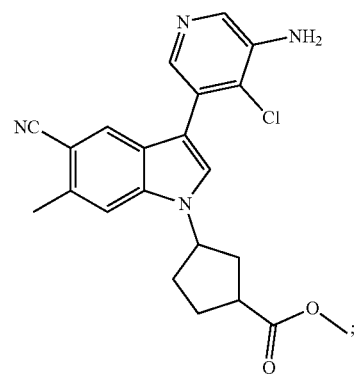

319
-continued
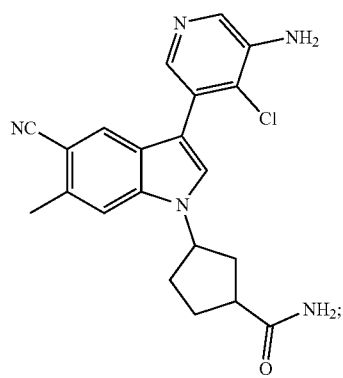
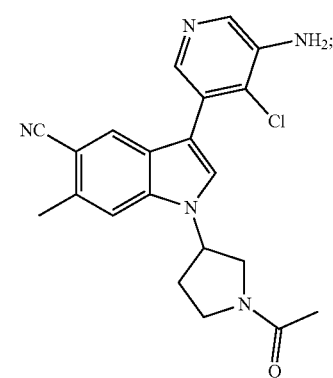
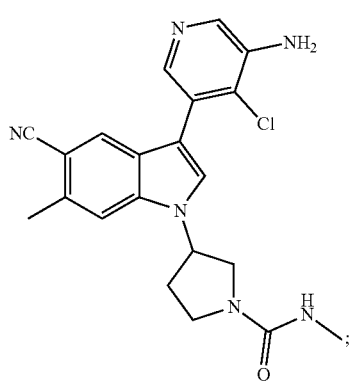
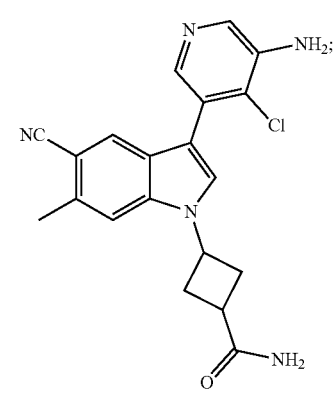
320
-continued
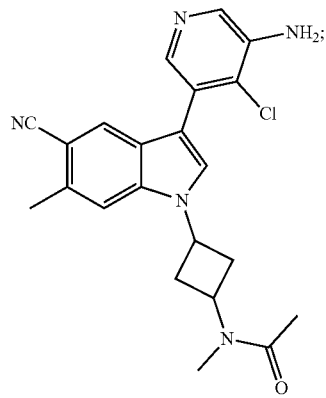
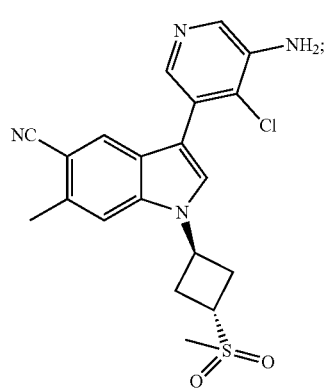
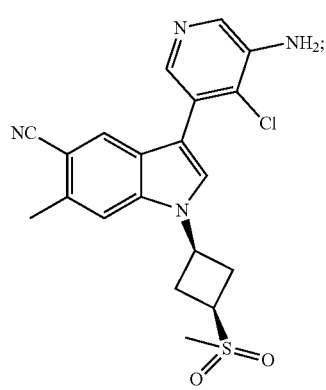
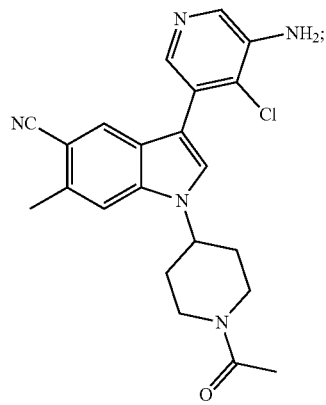

321
-continued
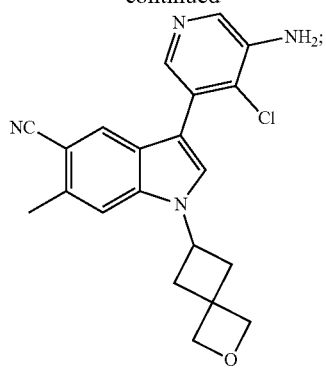
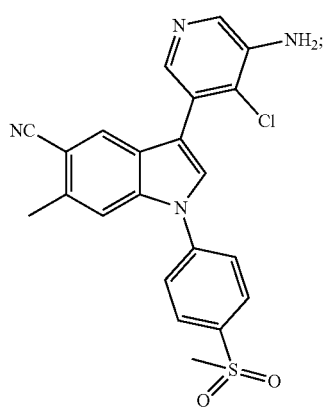
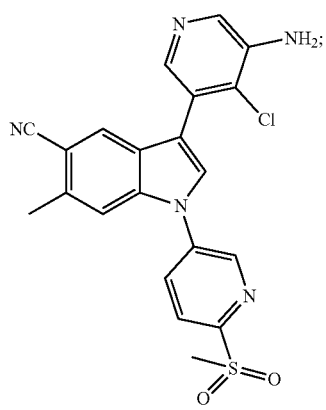
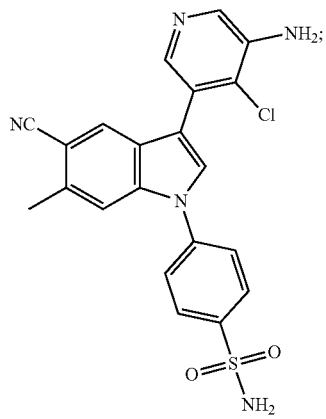
322
-continued
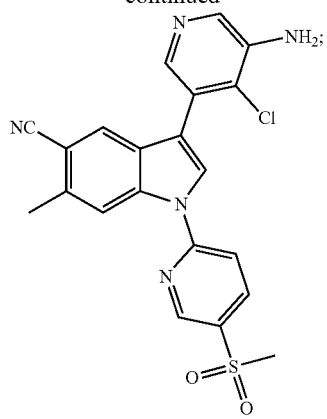
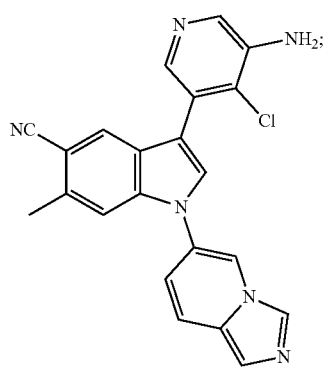
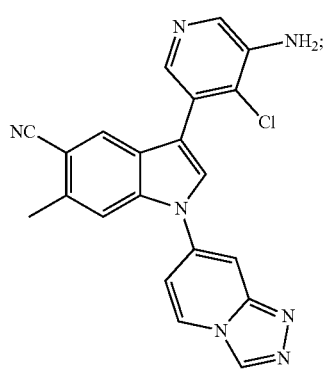
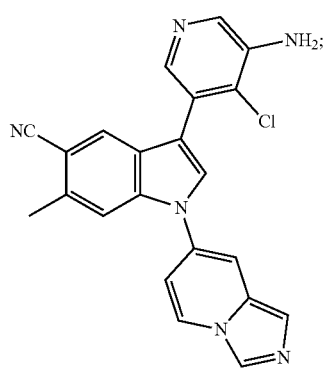

323
-continued
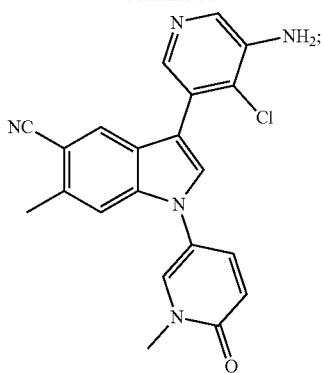
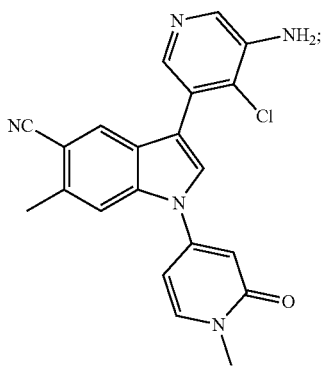
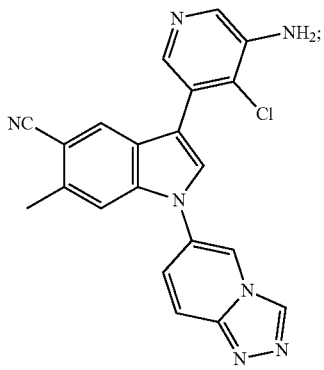
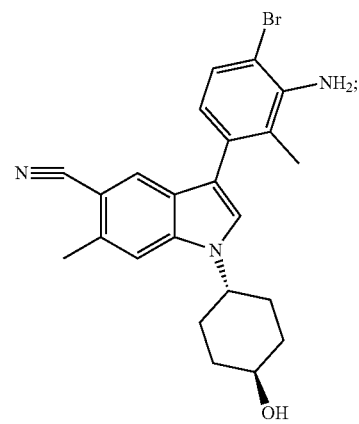
324
-continued
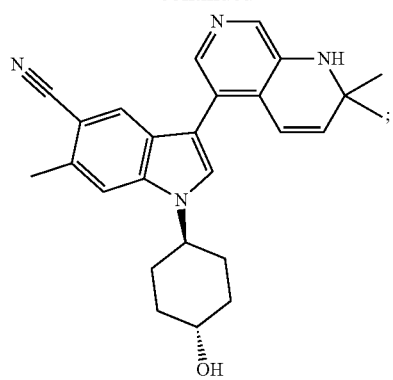
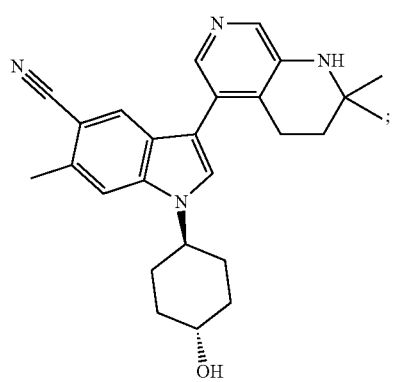
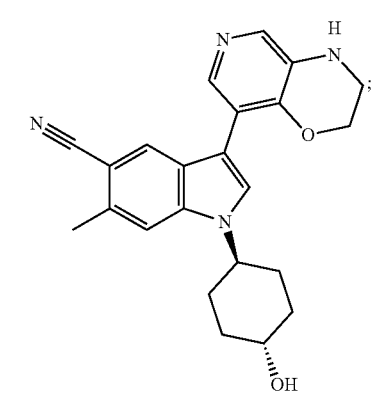
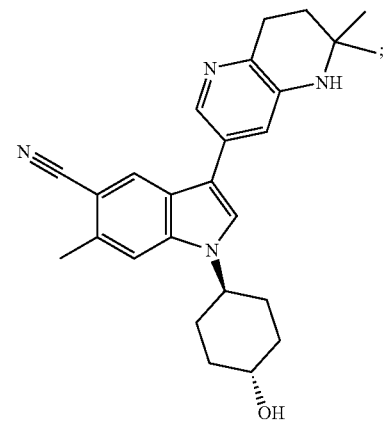

-continued
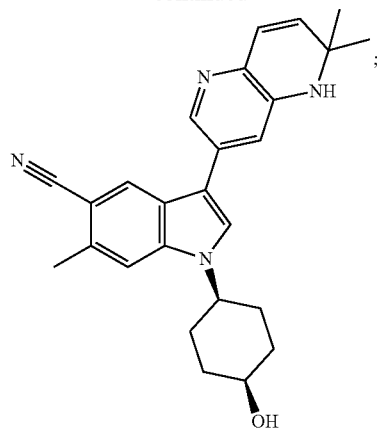
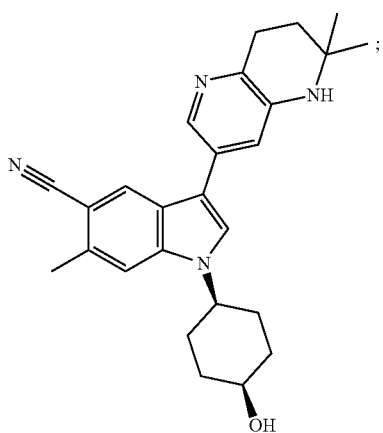
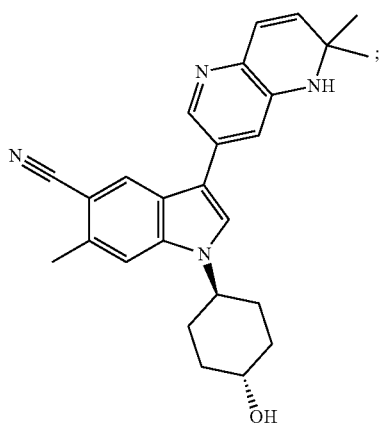
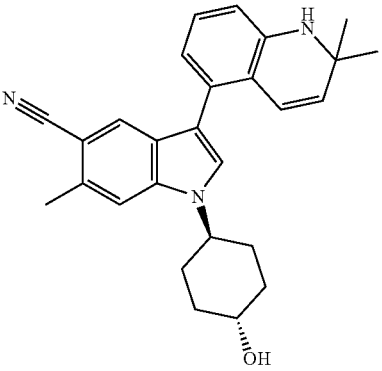
-continued
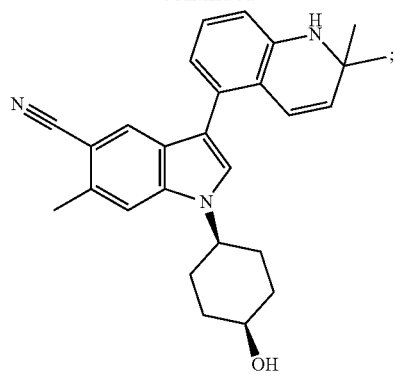
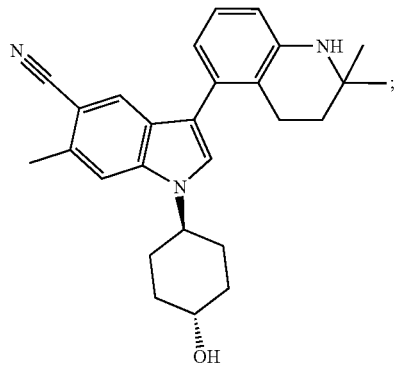
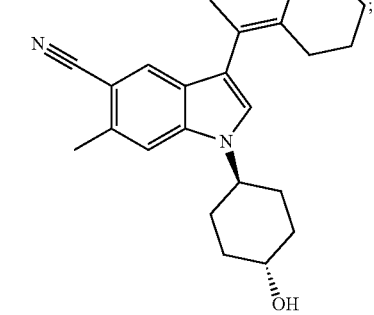
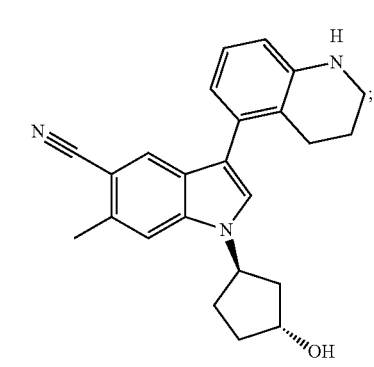

327
-continued
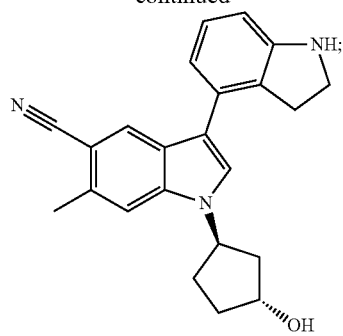
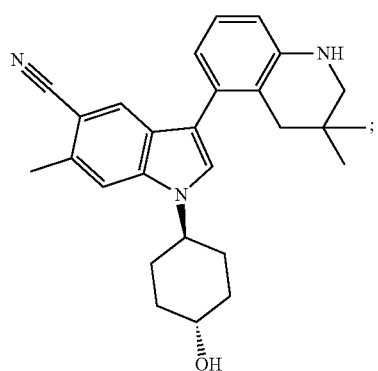
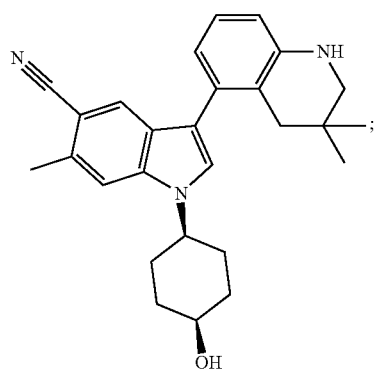
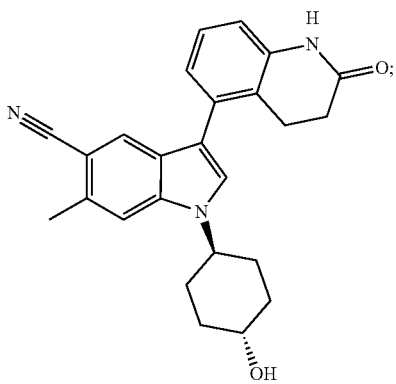
328
-continued
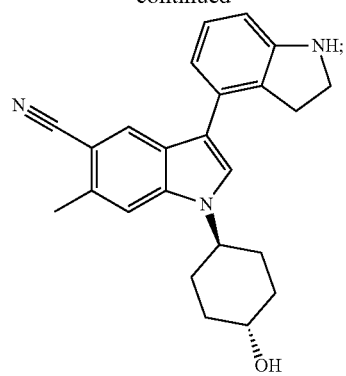
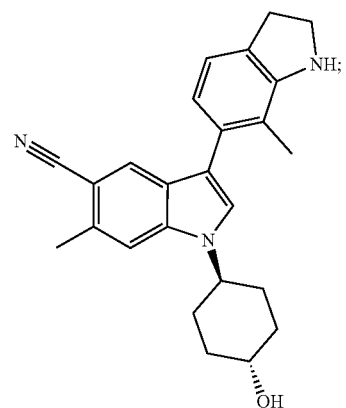
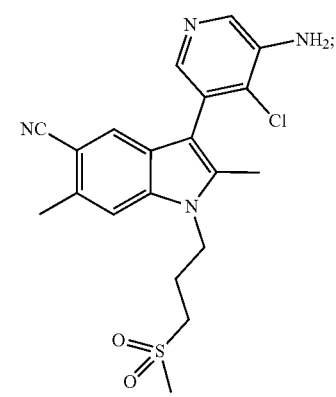
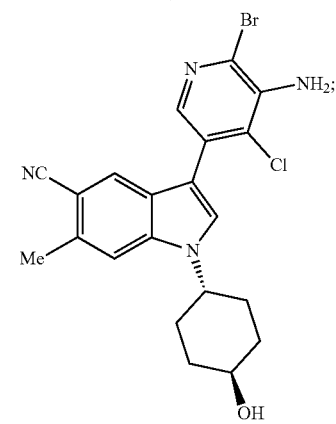

329
-continued
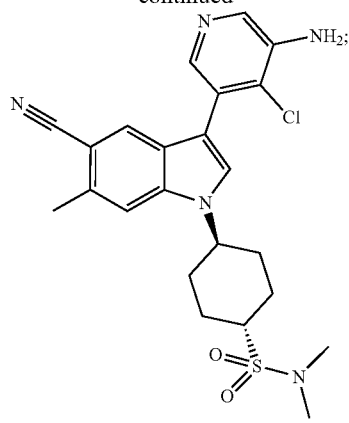
330
-continued
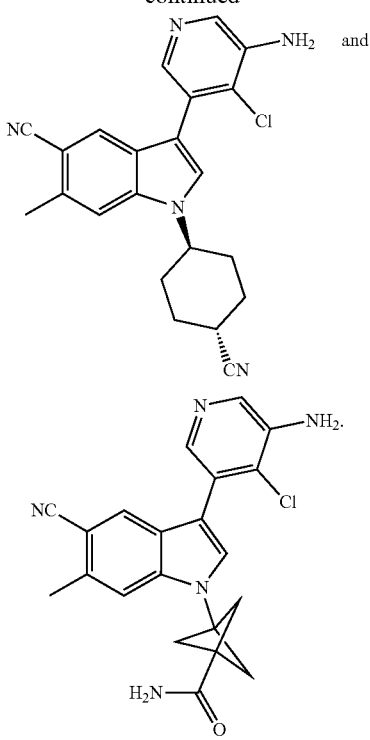
10. The compound of claim 1, or a pharmaceutically acceptable salt, wherein the compound is selected from:
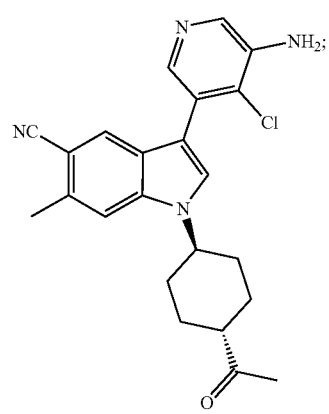
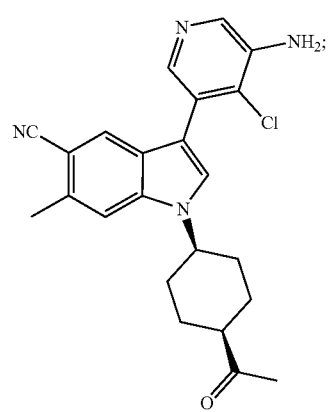

331
-continued
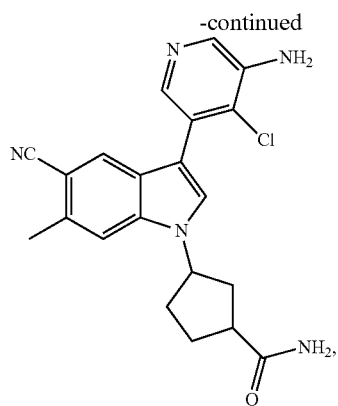
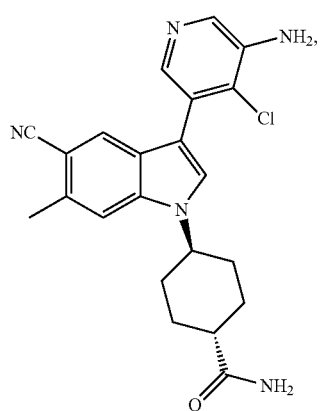
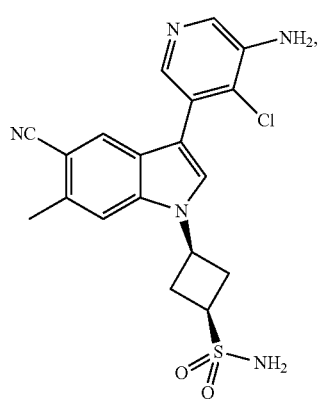
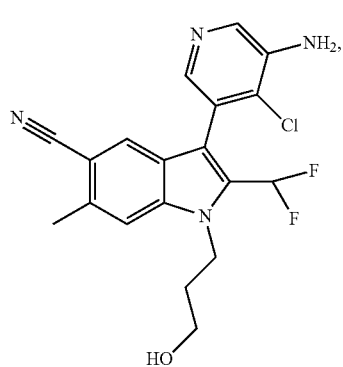
332
-continued
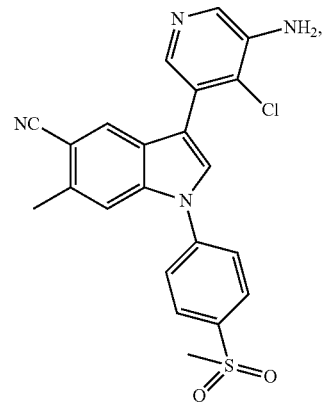
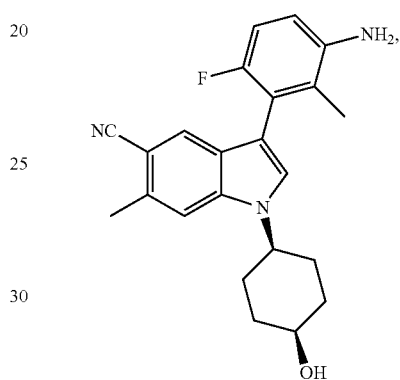
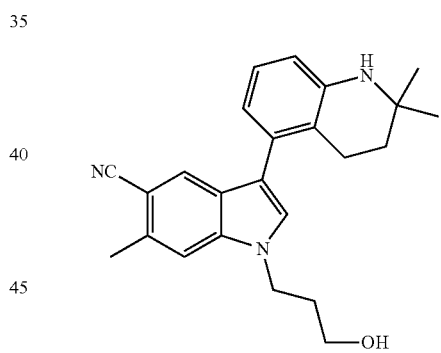
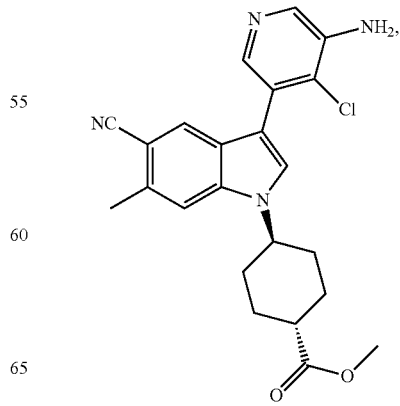

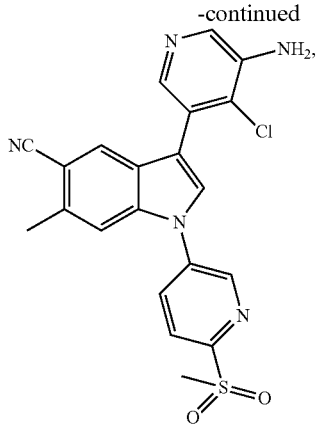
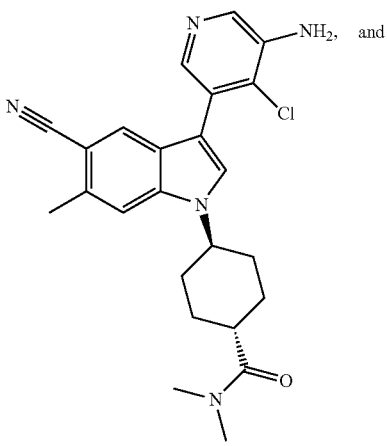
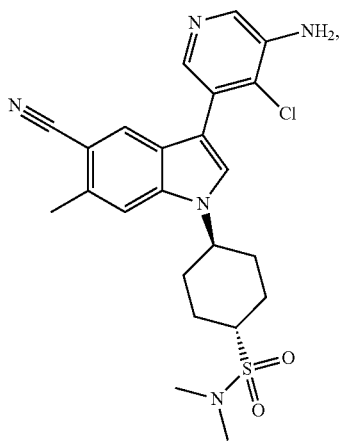
11. A compound, or a pharmaceutically acceptable salt, wherein the compound is selected from:
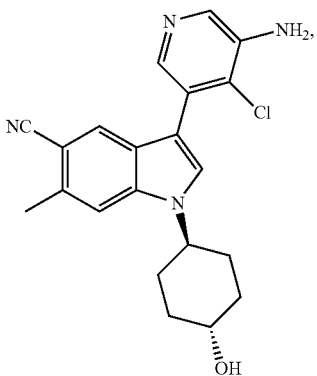

335
-continued
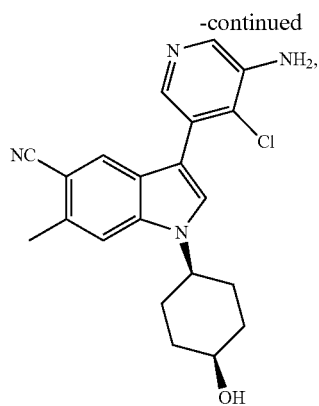
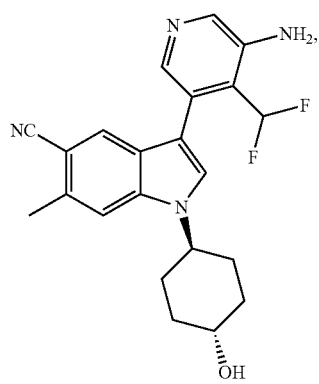
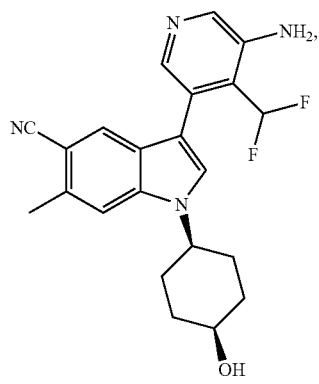
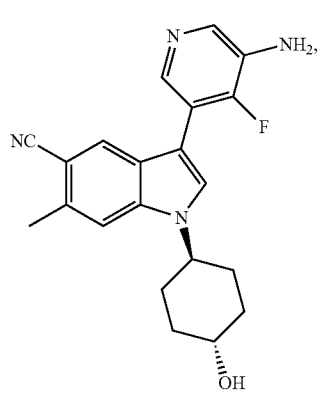
336
-continued
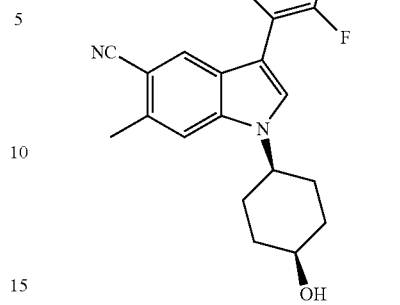
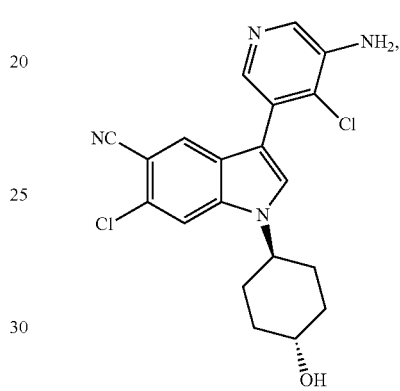
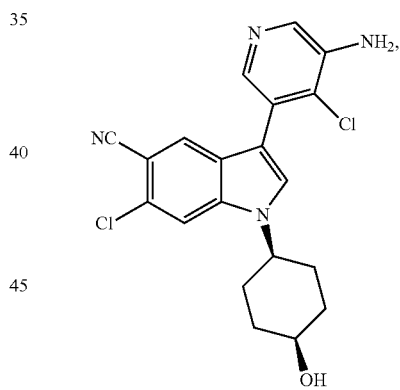
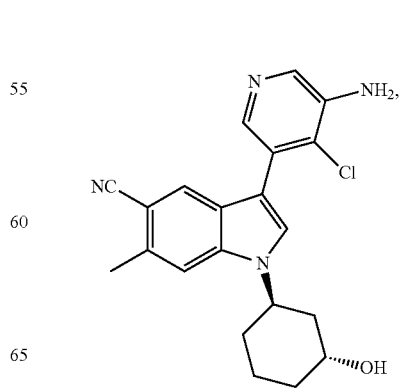

337
-continued
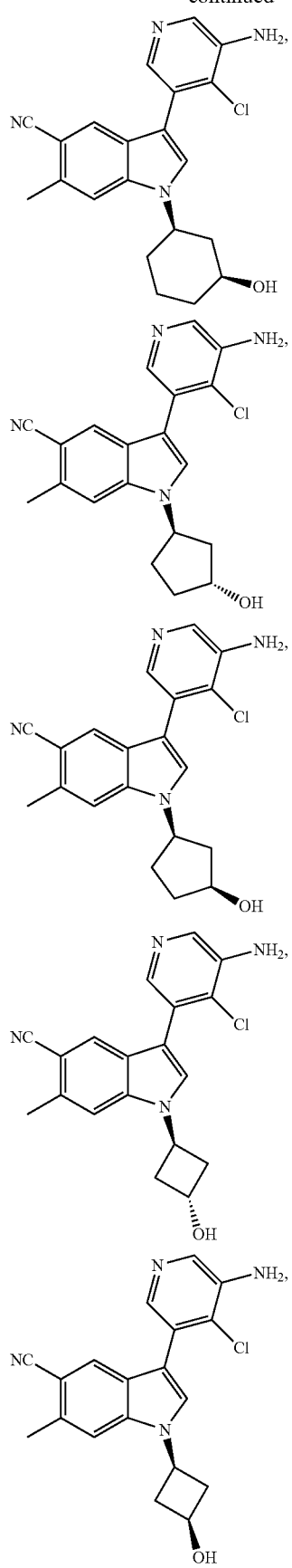
338
-continued
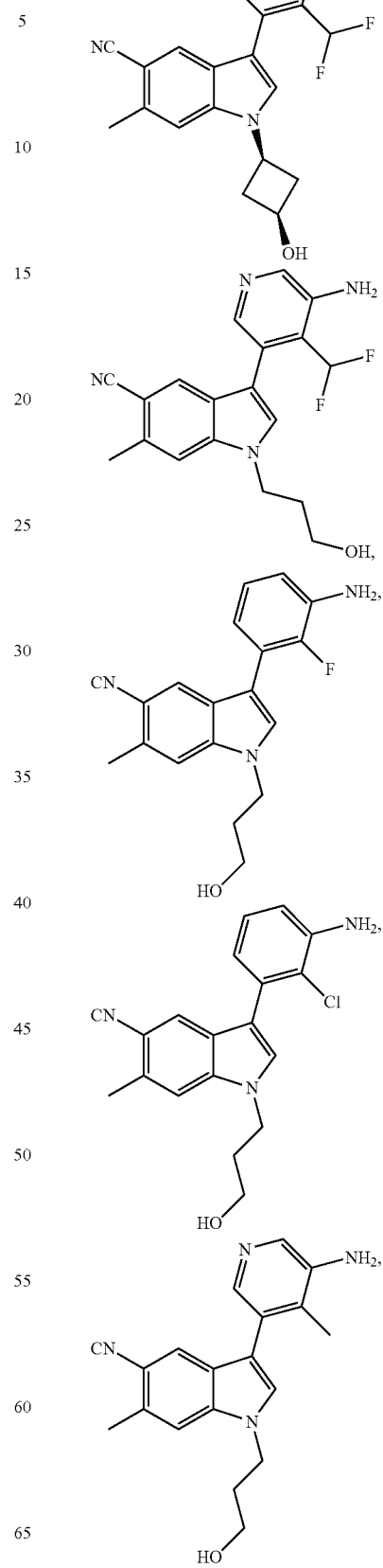

-continued

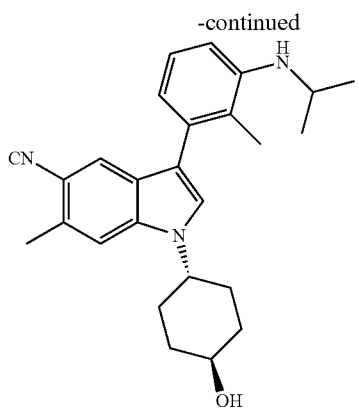

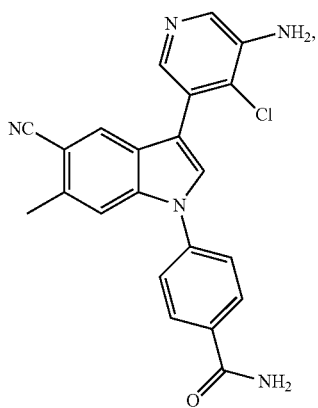

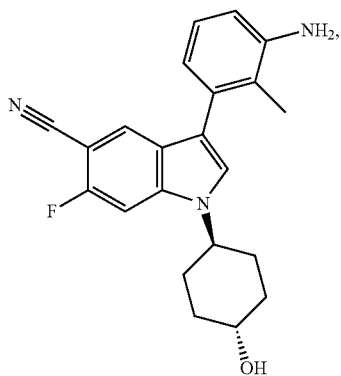

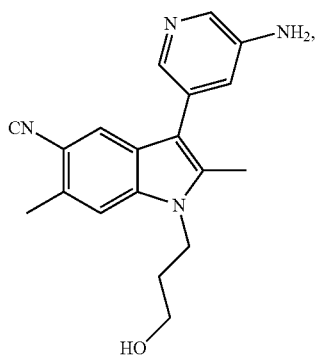

-continued

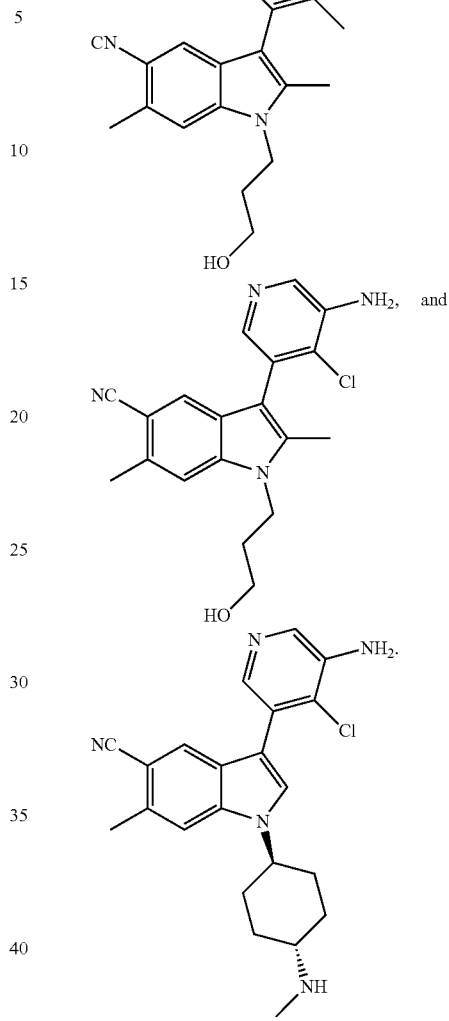

12. A pharmaceutical composition, comprising one or more pharmaceutically acceptable carriers and a compound or a pharmaceutically acceptable salt thereof, according to claim 1.

13. The pharmaceutical composition of claim 12, further comprising at least one additional therapeutic agent.

14. The pharmaceutical composition of claim 12, wherein the at least one additional therapeutic agent is selected from other anti-cancer agents, immunomodulators, anti-allergic agents, anti-emetics, pain relievers, cytoprotective agents, and combinations thereof.

15. A method for therapeutically treating a disease or disorder mediated by lysine (K)-specific demethylase 1A, comprising the step of administering to a subject in need of such treatment a therapeutically effective amount of a compound or a pharmaceutically acceptable salt thereof, according to claim 1.

16. The method of claim 15 wherein the disease or disorder is selected from B cell lymphoma, acute myeloid leukemia, gastric cancer, hepatocellular carcinoma, prostate cancer, breast carcinoma, neuroblastoma, glioblastoma, nasopharyngeal carcinoma, colon cancer, gallbladder cancer, esophageal cancer, head and neck cancer, lung cancer, ovarian cancer, pancreatic cancer, endometrial carcinoma and soft tissue sarcomas, Ewing's sarcoma, liver fibrosis, and sickle cell disease.

17. A compound according to claim 1, or a pharmaceutically acceptable salt thereof, for use in the therapeutic treatment of a disease or disorder mediated by lysine (K)-specific demethylase 1A.

18. The compound of claim 16, wherein the disease or disorder is selected from B cell lymphoma, acute myeloid leukemia, gastric cancer, hepatocellular carcinoma, prostate cancer, breast carcinoma, neuroblastoma, glioblastoma, nasopharyngeal carcinoma, colon cancer, gallbladder cancer, esophageal cancer, head and neck cancer, lung cancer, ovarian cancer, pancreatic cancer, endometrial carcinoma and soft tissue sarcomas, Ewing's sarcoma, liver fibrosis, and sickle cell disease.

* * * * *